United States Patent
Zhang et al.

(10) Patent No.: US 11,999,728 B2
(45) Date of Patent: Jun. 4, 2024

(54) ESTROGEN RECEPTOR MODULATORS

(71) Applicant: Recurium IP Holdings, LLC, San Diego, CA (US)

(72) Inventors: Guobao Zhang, San Diego, CA (US); Peter Qinhua Huang, San Diego, CA (US); Kevin Duane Bunker, Escondido, CA (US); Sayee Gajanan Hegde, San Diego, CA (US)

(73) Assignee: RECURIUM IP HOLDINGS, LLC, San Diego, CA (US)

( * ) Notice: Subject to any disclaimer, the term of this patent is extended or adjusted under 35 U.S.C. 154(b) by 0 days.

(21) Appl. No.: 17/657,841

(22) Filed: Apr. 4, 2022

(65) Prior Publication Data
US 2022/0235050 A1    Jul. 28, 2022

Related U.S. Application Data

(62) Division of application No. 17/645,119, filed on Dec. 20, 2021, now Pat. No. 11,339,162.

(60) Provisional application No. 63/265,052, filed on Dec. 7, 2021, provisional application No. 63/164,095, filed on Mar. 22, 2021, provisional application No. 63/130,123, filed on Dec. 23, 2020.

(51) Int. Cl.
*C07D 471/04* (2006.01)
*A61P 35/00* (2006.01)

(52) U.S. Cl.
CPC .......... *C07D 471/04* (2013.01); *A61P 35/00* (2018.01)

(58) Field of Classification Search
CPC ............................. C07D 471/04; A61P 35/00
USPC ..................................... 514/210.21
See application file for complete search history.

(56) References Cited

U.S. PATENT DOCUMENTS

| | | |
|---|---|---|
| 6,177,443 B1 | 1/2001 | Madsen et al. |
| 6,492,358 B2 | 12/2002 | Sui et al. |
| 6,720,330 B2 | 4/2004 | Hay et al. |
| 6,864,253 B2 | 3/2005 | Sui et al. |
| 6,933,303 B2 | 8/2005 | Mjalli et al. |
| 7,601,840 B2 | 10/2009 | Moon et al. |
| 7,964,726 B2 | 6/2011 | Ohmoto et al. |
| 8,076,352 B2 | 12/2011 | Cao et al. |
| 8,367,694 B2 | 2/2013 | Moon et al. |
| 8,372,860 B2 | 2/2013 | Moon et al. |
| 8,476,293 B2 | 7/2013 | Ohmoto et al. |
| 8,697,662 B2 | 4/2014 | Cao et al. |
| 8,703,726 B2 | 4/2014 | Cao et al. |
| 10,807,994 B2 | 10/2020 | Chakravarty et al. |
| 10,954,234 B2 | 3/2021 | Chung et al. |
| 11,339,162 B1* | 5/2022 | Zhang ................ A61P 35/00 |
| 2010/0158858 A1 | 6/2010 | Cao et al. |
| 2010/0184799 A1 | 7/2010 | Du et al. |
| 2012/0129841 A1 | 5/2012 | Cao et al. |
| 2012/0135089 A1 | 5/2012 | Stockwell et al. |
| 2012/0157401 A1 | 6/2012 | Cao et al. |
| 2012/0157402 A1 | 6/2012 | Cao et al. |
| 2012/0202801 A1 | 8/2012 | Cao et al. |
| 2013/0171103 A1 | 7/2013 | David et al. |
| 2013/0172320 A1 | 7/2013 | Chakravarty et al. |
| 2014/0235660 A1 | 8/2014 | Burks et al. |
| 2015/0105415 A1 | 4/2015 | Ohmoto et al. |

FOREIGN PATENT DOCUMENTS

| | | |
|---|---|---|
| CN | 109867659 A | 11/2019 |
| WO | WO 2006/058088 | 6/2006 |
| WO | WO 2007/002051 | 1/2007 |
| WO | WO 2008/002490 | 1/2008 |
| WO | WO 2010/138758 | 12/2010 |
| WO | WO 2011/156518 | 12/2011 |
| WO | WO 2013/090829 | 6/2013 |
| WO | WO 2013/090836 | 6/2013 |

(Continued)

OTHER PUBLICATIONS

Garner, F. et al., "RAD1901: a novel, orally bioavailable selective estrogen receptor degrader that demonstrates antitumor activity in breast cancer xenograft models" Anti-Cancer Drugs 26(9), 948-956 (2015).

De Savi, C. et al., "Optimization of a Novel Binding Motif to (E)-3-(3,5-Difluoro-4-((1R,3R)2-(2-fluoro-2-methylpropyl)-3-methyl-2,3,4,9-tetrahydro-1H-pyrido[3,4b]indol-1-yl)phenyl)acrylic Acid (AZD9496), a Potent and Orally Bioavailable Selective Estrogen Receptor Downregulator and Antagonist", J. Med. Chem. 58, 8128-8140 (2015).

(Continued)

*Primary Examiner* — Niloofar Rahmani
(74) *Attorney, Agent, or Firm* — Knobbe, Martens, Olson & Bear, LLP

(57) ABSTRACT

Compounds of Formula (I) are estrogen receptor alpha modulators, where the variables in Formula (I) are described in the disclosure. Such compounds, as well as pharmaceutically acceptable salts and compositions thereof, are useful for treating diseases or conditions that are estrogen receptor alpha dependent and/or estrogen receptor alpha mediated, including conditions characterized by excessive cellular proliferation, such as cancer.

18 Claims, 1 Drawing Sheet

Formula (I)

(56) References Cited

FOREIGN PATENT DOCUMENTS

| WO | WO 2013/142266 | 9/2013 |
| WO | WO 2014/151899 | 9/2014 |
| WO | WO 2014/191726 | 12/2014 |
| WO | WO 2015/082990 | 6/2015 |
| WO | WO 2015/197861 | 12/2015 |
| WO | WO 2016/069949 | 5/2016 |
| WO | WO 2016/097072 | 6/2016 |
| WO | WO 2017/059139 | 4/2017 |
| WO | WO 2017/172957 | 10/2017 |
| WO | WO 2017/216279 | 12/2017 |
| WO | WO 2018/130123 | 7/2018 |
| WO | WO 2018/130124 | 7/2018 |
| WO | WO 2019/223715 | 11/2019 |
| WO | WO 2019/245974 | 12/2019 |
| WO | WO 2020/037203 | 2/2020 |
| WO | WO 2021/026153 | 2/2021 |
| WO | WO 2021/091819 | 5/2021 |
| WO | WO 2021/216671 | 10/2021 |

OTHER PUBLICATIONS

Lai, A. et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", J. Med. Chem. 58, 4888-4904 (2015).

Scott, James S., et al., "Discovery of AZD9833, a Potent and Orally Bioavailable Selective Estrogen Receptor Degrader and Antagonist", J. Med. Chem., Sep. 10, 2020, 63, 14530-14559.

International Search Report and Written Opinion dated Mar. 4, 2022, issued in corresponding PCT Application PCT/US2021/072983.

\* cited by examiner

ESTROGEN RECEPTOR MODULATORS

INCORPORATION BY REFERENCE TO PRIORITY APPLICATIONS

This application is a divisional of U.S. application Ser. No. 17/645,119, filed Dec. 20, 2021, which claims priority to U.S. Provisional Application Ser. No. 63/130,123, filed Dec. 23, 2020; U.S. Provisional Application Ser. No. 63/164,095, filed Mar. 22, 2021; and U.S. Provisional Application Ser. No. 63/265,052, filed Dec. 7, 2021. The disclosures of each of the aforementioned applications are hereby incorporated herein by reference in their entireties.

BACKGROUND

Field

The present application relates to compounds that are estrogen receptor alpha modulators and methods of using them to treat conditions characterized by excessive cellular proliferation, such as cancer.

Description

Many cancer cells express estrogen receptors (ERs) and have growth characteristics that are modulated by estrogen. A number of breast cancer drug therapies have been developed that target ERs. In many cases the drugs are selective estrogen receptor modulators (SERMs) or selective estrogen receptor degraders (SERDs) that have agonistic and/or antagonistic effects on ERs. For example, fulvestrant is a drug that is used for the treatment of metastatic breast cancer. It has antagonistic effects on ER-alpha and is considered a SERD. Fulvestrant has the following chemical structure:

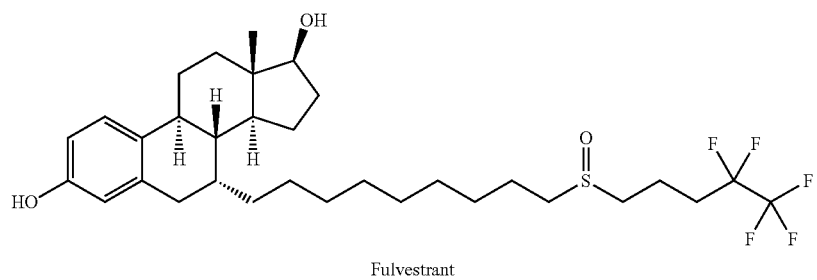

Fulvestrant

A number of other SERMs and SERDs are also known. See, e.g., WO 2017/172957. However, there remains a long-felt need for well tolerated orally dosed SERDs or SERMs that are useful in the study and the treatment of proliferative disorders, such as breast cancer, that have growth characteristics that are modulated by estrogen, especially breast cancer with brain metastasis.

SUMMARY

Various embodiments provide a compound of Formula (I), or a pharmaceutically acceptable salt thereof, having the structure:

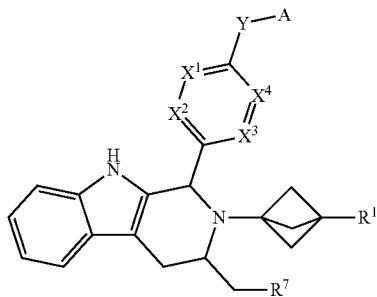

wherein:
each $X^1$, $X^2$, $X^3$ and $X^4$ is independently N or $CR^2$;
Y is a bond, alkenyl (such as $C_{1-6}$ alkenyl or $C_{1-3}$ alkenyl), —O(CR$^3$R$^4$)$_m$—, or —NH(CR$^5$R$^6$)$_n$—;
$R^1$ is selected from H, F, OH, CN, alkyl (such as $C_{1-6}$ alkyl or $C_{1-3}$ alkyl), haloalkyl (such as $C_{1-6}$ haloalkyl or $C_{1-3}$ haloalkyl), alkoxy (such as $C_{1-6}$ alkoxy or $C_{1-3}$ alkoxy), amide, or hydroxyalkyl (such as $C_{1-6}$ hydroxyalkyl or $C_{1-3}$ hydroxyalkyl);
each $R^2$, $R^3$, $R^4$, $R^5$ and $R^6$ is independently H, halogen (such as F, Cl or Br), alkoxy (such as $C_{1-6}$ alkoxy or $C_{1-3}$ alkoxy), or alkyl (such as $C_{1-6}$ alkyl or $C_{1-3}$ alkyl);
$R^7$ is H or halogen (such as F, Cl or Br);
m and n are each 0, 1 or 2; and
A is a heterocyclyl (such as azetidinyl or pyrrolidinyl) optionally substituted with 1 or more substituents selected from halogen, CN, OH, alkyl (such as $C_{1-6}$ alkyl or $C_{1-3}$ alkyl), alkenyl (such as $C_{1-6}$ alkenyl or $C_{1-3}$ alkenyl), alkynyl (such as $C_{1-6}$ alkynyl or $C_{1-3}$ alkynyl), cycloalkyl (such as $C_{3-6}$ cycloalkyl), haloalkyl (such as $C_{1-6}$ haloalkyl or $C_{1-3}$ haloalkyl), haloalkylamino (such as $C_{1-6}$ haloalkylamino or $C_{1-3}$ haloalkylamino), haloalkoxy (such as $C_{1-6}$ haloalkoxy or $C_{1-3}$ haloalkoxy), hydroxyalkyl (such as $C_{1-6}$ hydroxyalkyl or $C_{1-3}$ hydroxyalkyl), or cyanoalkyl (such as $C_{1-6}$ cyanoalkyl or $C_{1-3}$ cyanoalkyl).

Various embodiments provide a pharmaceutical composition comprising an effective amount of the compound of Formula (I), or a pharmaceutically acceptable salt thereof, and a pharmaceutically acceptable carrier, diluent, excipient or combination thereof.

Various embodiments provide a method of treatment, comprising
identifying a subject that is in need of treatment for a disease or condition that is estrogen receptor alpha dependent and/or estrogen receptor alpha mediated; and administering to said subject an effective amount of a compound of Formula (I) or a pharmaceutically acceptable salt thereof, or a pharmaceutical composition comprising a compound of Formula (I) or a pharmaceutically acceptable salt thereof.

These and other embodiments are described in greater detail below.

DETAILED DESCRIPTION

Definitions

Figure 1:
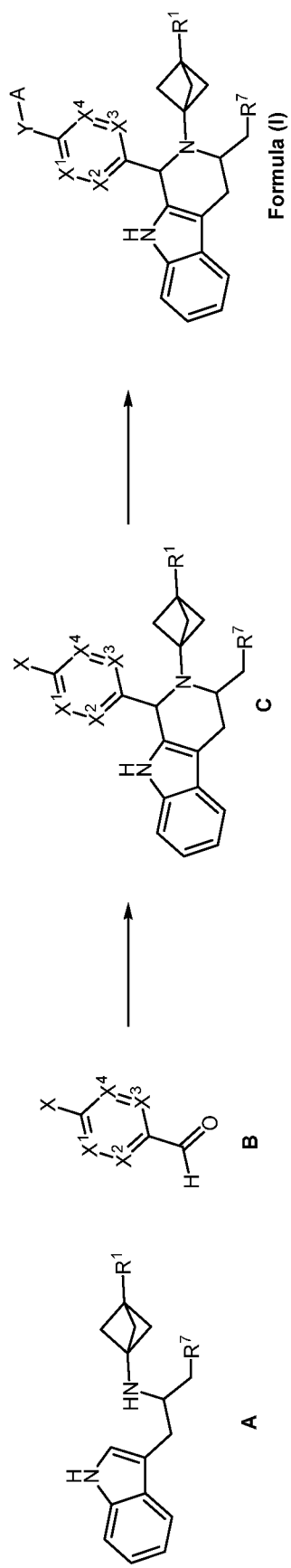
FIG. 1 illustrates a general reaction scheme for preparing compounds of the Formula (I).
Figure 2:
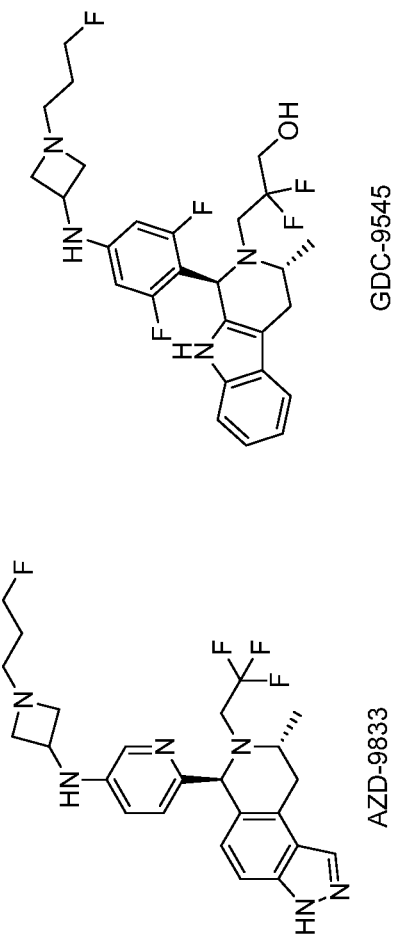
FIG. 2 shows the chemical structures of AZD-9833 and GDC-9545.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

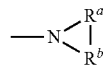

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted. For example, a "haloalkyl" is an alkyl group in which one or more hydrogen atoms have been substituted with one or more halogen atoms. Likewise, a "hydroxyalkyl" group is an alkyl group in which one or more hydrogen atoms have been substituted with one or more hydroxy groups. Likewise, a "cyanoalkyl" group is an alkyl group in which one or more hydrogen atoms have been substituted with one or more cyano groups.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl, and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 6 to 10 atoms in the ring(s) or 6 to 8 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicylylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, "lower alkylene groups" are straight-chained —$CH_2$-tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group and/or by substituting both hydrogens on the same carbon with a cycloalkyl group (e.g., 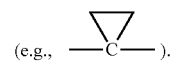 ).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—$NO_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —$NH_2$ group.

A "mono-substituted amino" group refers to a "—NHR" group in which R can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—N$R_A R_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, when a chemical group or unit includes an asterisk (*), that asterisk indicates a point of attachment of the group or unit to another structure.

As used herein, "linking groups" are chemical groups that are indicated as having multiple open valencies for connecting to two or more other groups. For example, lower alkylene groups of the general formula —$(CH_2)_n$— where n is in the range of 1 to 10, are examples of linking groups that are described elsewhere herein as connecting molecular fragments via their terminal carbon atoms. Other examples of linking groups include —$(CH_2)_nO$—, —$(CH_2)_nNH$—, —$(CH_2)_nN(C_1$-$C_6$alkyl)-, and —$(CH_2)_nS$—, wherein each n is 0, 1, 2, 3, 4, 5, 6, 7, 8, 9, or 10. Those skilled in the art will recognize that n can be zero for some linking groups such as —$(CH_2)_nO$—, in which case the linking group is simply —O—. Those skilled in the art will also recognize that reference herein to an asymmetrical linking group will be understood as a reference to all orientations of that group (unless stated otherwise). For example, reference herein to —$(CH_2)_nO$— will be understood as a reference to both —$(CH_2)_nO$— and —O—$(CH_2)_n$—.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as Cl—).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to compounds of the Formula (I), or pharmaceutically acceptable salts thereof.

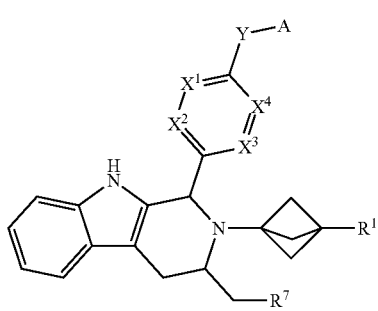

In various embodiments, compounds of Formula (I) are useful for ameliorating, treating and/or diagnosing a disease or condition that is estrogen receptor dependent and/or estrogen receptor mediated. In an embodiment, the disease is cancer. In an embodiment, the cancer is a metastatic cancer. In an embodiment, the cancer is breast cancer. In an embodiment, the breast cancer is a metastatic breast cancer that has metastasized to at least one organ selected from brain, liver, bone and lung. In an embodiment, the metastatic breast cancer is a breast cancer that has metastasized to brain. In an embodiment, compounds of Formula (I) are selective estrogen receptor modulators (SERMs). In an embodiment, compounds of Formula (I) are selective estrogen receptor degraders (SERDs). Additional details regarding various uses and methods of treatment are described elsewhere herein.

In various embodiments, the variables $X^1$, $X^2$, $X^3$ and $X^4$ in Formula (I) are each independently N or $CR^2$. In an embodiment, $X^1$ is N; and $X^2$, $X^3$ and $X^4$ are each $CR^2$. In an embodiment, $X^2$ is N; and $X^1$, $X^3$ and $X^4$ are each $CR^2$. In an embodiment, $X^1$ and $X^2$ are each N; and $X^3$ and $X^4$ are each $CR^2$. In an embodiment, $X^1$ and $X^3$ are each N; and $X^2$ and $X^4$ are each $CR^2$.

In various embodiments, the variable Y in Formula (I) is a bond, alkenyl (such as $C_{1-6}$ alkenyl or $C_{1-3}$ alkenyl), —O($CR^3R^4$)$_m$—, or —NH($CR^5R^6$)$_n$—. In an embodiment, Y is a bond. In an embodiment, Y is alkenyl. For example, in an embodiment, Y is a $C_{1-6}$ alkenyl (e.g., $C_{1-3}$ alkenyl). In an embodiment, Y is —O($CR^3R^4$)$_m$—, where m is 0, 1 or 2. In an embodiment, Y is —NH($CR^5R^6$)$_n$—, where n is 0, 1 or 2.

In various embodiments, the variable $R^1$ in Formula (I) is selected from H, F, OH, CN, alkyl (such as $C_{1-6}$ alkyl or $C_{1-3}$ alkyl), haloalkyl (such as $C_{1-6}$ haloalkyl or $C_{1-3}$ haloalkyl), alkoxy (such as $C_{1-6}$ alkoxy or $C_{1-3}$ alkoxy), amide, or hydroxyalkyl (such as $C_{1-6}$ hydroxyalkyl or $C_{1-3}$ hydroxyalkyl). In an embodiment, $R^1$ is H. In an embodiment, $R^1$ is F. In an embodiment, $R^1$ is OH. In an embodiment, $R^1$ is CN. In an embodiment, $R^1$ is alkyl (such as $C_{1-6}$ alkyl or $C_{1-3}$ alkyl). In an embodiment, $R^1$ is haloalkyl (such as $C_{1-6}$ haloalkyl or $C_{1-3}$ haloalkyl). In an embodiment, $R^1$ is alkoxy (such as $C_{1-6}$ alkoxy or $C_{1-3}$ alkoxy, e.g., methoxy). In an embodiment, $R^1$ is amide. In an embodiment, $R^1$ is hydroxyalkyl (such as $C_{1-6}$ hydroxyalkyl or $C_{1-3}$ hydroxyalkyl).

In various embodiments the variables $R^2$, $R^3$, $R^4$, $R^5$ and $R^6$ in Formula (I) are each independently H, halogen (such as F, Cl or Br), alkoxy (such as $C_{1-6}$ alkoxy or $C_{1-3}$ alkoxy), or alkyl (such as $C_{1-6}$ alkyl or $C_{1-3}$ alkyl). In an embodiment, $R^2$ is H. In an embodiment, $R^2$ is halogen (such as F, Cl or Br). In an embodiment, $R^2$ is alkoxy. For example, in an embodiment, $R^2$ is $C_{1-6}$ alkoxy (e.g., $C_{1-3}$ alkoxy). In an embodiment, $R^2$ is alkyl (such as $C_{1-6}$ alkyl or $C_{1-3}$ alkyl). In an embodiment, at least one of $R^3$ and $R^4$ is H. In an embodiment, $R^3$ is halogen (such as F, Cl or Br) and $R^4$ is H. In an embodiment, $R^3$ is alkyl (such as $C_{1-6}$ alkyl or $C_{1-3}$ alkyl) and $R^4$ is H. In an embodiment, at least one of $R^5$ and $R^6$ is H. In an embodiment, $R^5$ is halogen (such as F, Cl or Br) and $R^6$ is H. In an embodiment, $R^5$ is alkyl (such as $C_{1-6}$ alkyl or $C_{1-3}$ alkyl) and $R^6$ is H. In an embodiment, $R^7$ is H. In another embodiment, $R^7$ is halogen (such as F, Cl or Br).

In various embodiments, the variable A in Formula (I) is a heterocyclyl (such as azetidinyl or pyrrolidinyl) that is optionally substituted with 1 or more substituents selected from halogen, CN, OH, alkyl (such as $C_{1-6}$ alkyl or $C_{1-3}$ alkyl), alkenyl (such as $C_{1-6}$ alkenyl or $C_{1-3}$ alkenyl), alkynyl (such as $C_{1-6}$ alkynyl or $C_{1-3}$ alkynyl), cycloalkyl (such as $C_{3-6}$ cycloalkyl, e.g., cyclopropyl), haloalkyl (such as $C_{1-6}$ haloalkyl or $C_{1-3}$ haloalkyl), haloalkylamino (such as $C_{1-6}$ haloalkylamino or $C_{1-3}$ haloalkylamino), haloalkoxy (such as $C_{1-6}$ haloalkoxy or $C_{1-3}$ haloalkoxy), hydroxyalkyl (such as $C_{1-6}$ hydroxyalkyl or $C_{1-3}$ hydroxyalkyl), or cyanoalkyl (such as $C_{1-6}$ cyanoalkyl or $C_{1-3}$ cyanoalkyl). In an embodiment, A is an unsubstituted 3-6 membered N-containing heterocyclyl. In an embodiment, A is unsubstituted azetidinyl. In an embodiment, A is unsubstituted pyrrolidinyl.

In various embodiment, the variable A in Formula (I) is a 3-6 membered N-containing heterocyclyl (such as azetidinyl or pyrrolidinyl) that is substituted with F, CN, $C_{1-3}$ alkyl, $C_{3-6}$ cycloalkyl, $C_{1-3}$ fluoroalkyl, $C_{1-3}$ fluoroalkylamino, $C_{1-3}$ fluoroalkoxy, $C_{1-3}$ hydroxyalkyl, or $C_{1-3}$ cyanoalkyl. In an embodiment, A is substituted with F. For example, in an embodiment, A is azetidinyl substituted with F or pyrrolidinyl substituted with F. In an embodiment, A is substituted with CN. For example, in an embodiment, A is azetidinyl substituted with CN or pyrrolidinyl substituted with CN. In an embodiment, A is substituted with $C_{1-3}$ alkyl. For example, in an embodiment, A is azetidinyl substituted with $C_{1-3}$ alkyl or pyrrolidinyl substituted with $C_{1-3}$ alkyl. In an embodiment, A is substituted with $C_{3-6}$ cycloalkyl. For example, in an embodiment, A is azetidinyl substituted with $C_{3-6}$ cycloalkyl (such as cyclopropyl). In an embodiment, A is substituted with $C_{1-3}$ fluoroalkyl. For example, in an embodiment, A is azetidinyl substituted with $C_{1-3}$ fluoroalkyl or pyrrolidinyl substituted with $C_{1-3}$ fluoroalkyl. In an embodiment, A is substituted with $C_{1-3}$ fluoroalkylamino. For example, in an embodiment, A is azetidinyl substituted with $C_{1-3}$ fluoroalkylamino. In an embodiment, A is substituted with $C_{1-3}$ fluoroalkoxy. For example, in an embodiment, A is azetidinyl substituted with $C_{1-3}$ fluoroalkoxy. In an embodiment, A is substituted with $C_{1-3}$ hydroxyalkyl. For example, in an embodiment, A is azetidinyl substituted with $C_{1-3}$ hydroxyalkyl or pyrrolidinyl substituted with $C_{1-3}$ hydroxyalkyl. In an embodiment, A is substituted with $C_{1-3}$ cyanoalkyl. For example, in an embodiment, A is azetidinyl substituted with $C_{1-3}$ cyanoalkyl or pyrrolidinyl substituted with $C_{1-3}$ cyanoalkyl.

In various embodiments, the compound of formula (I) is a compound as described in Table 1 herein.

Methods of Making

Compounds of the Formula (I), or pharmaceutically acceptable salts thereof, can be made in various ways by those skilled using known techniques as guided by the detailed teachings provided herein. For example, in an embodiment, compounds of the Formula (I) are prepared in accordance with the general reaction scheme summarized in FIG. 1 and described in the Examples below. The variables in the generic chemical structures shown in FIG. 1 are as described elsewhere herein with respect to the Formula (I).

Uses and Methods of Treatment

As described herein, one or more compounds of Formula (I), or pharmaceutically acceptable salts thereof, or a pharmaceutical composition as described herein, can be used to inhibit the growth of a cell. In an embodiment, the cell is identified as having an estrogen receptor that mediates a growth characteristic of the cell. Growth of a cell can be inhibited by contacting the cell with an effective amount of at least one of the compounds described herein, or pharmaceutically acceptable salts thereof, or a pharmaceutical composition as described elsewhere herein. Such contacting of the one or more compounds, or pharmaceutically acceptable salts thereof, can take place in various ways and locations, including without limitation away from a living subject (e.g., in a laboratory, diagnostic and/or analytical setting) or in proximity to a living subject (e.g., within or on an exterior portion of an animal, e.g., a human). For example, an embodiment provides a method of treating a subject, comprising identifying a subject that is in need of treatment for a disease or condition that is estrogen receptor dependent and/or estrogen receptor mediated (such as a cancer) and administering to said subject an effective amount of one or more compounds of Formula (I), or a pharmaceutically acceptable salt thereof, or a pharmaceutical composition, as described elsewhere herein. Another embodiment provides a use of one or more compounds of Formula (I), or a pharmaceutically acceptable salt thereof, or a pharmaceutical composition (as described elsewhere herein), in the manufacture of a medicament for the treatment of a disease or condition that is estrogen receptor alpha dependent and/or estrogen receptor alpha mediated (such as cancer).

Non-limiting examples of diseases or conditions that are estrogen receptor alpha dependent and/or estrogen alpha receptor mediated and thus suitable for treatment using the compounds, compositions and methods described herein include breast cancers and gynecological cancers. For example, such diseases or conditions may include one or more of the following cancers: breast cancer, endometrial cancer, ovarian cancer and cervical cancer. An embodiment provides a use of one or more compounds of Formula (I), or a pharmaceutically acceptable salt thereof, or a pharmaceutical composition (as described elsewhere herein), in the treatment (or in the manufacture of a medicament for the treatment) of breast cancers and gynecological cancers, including for example one or more of the following: breast cancer, endometrial cancer, ovarian cancer and cervical cancer. In various embodiments, the compound, pharmaceutically acceptable salt or pharmaceutical composition is for use in a method of treatment (or in the manufacture of a medicament for the treatment) of a metastatic cancer, such as a metastatic breast cancer. In various embodiments of such treatment methods and uses, the metastatic breast cancer is a breast cancer that has metastasized to at least one organ selected from brain, liver, bone and lung. In an embodiment, the metastatic breast cancer is a breast cancer that has metastasized to brain. In an embodiment, the metastatic breast cancer is a breast cancer that has metastasized to liver. In an embodiment, the metastatic breast cancer is a breast cancer that has metastasized to bone. In an embodiment, the metastatic breast cancer is a breast cancer that has metastasized to lung.

As described herein, compounds of Formula (I), or a pharmaceutically acceptable salt thereof, or a pharmaceutical composition as described elsewhere herein, can be administered to such subjects by a variety of methods. In any of the uses or methods described herein, administration can be by various routes known to those skilled in the art, including without limitation oral, intravenous, intramuscular, topical, subcutaneous, systemic, and/or intraperitoneal administration to a subject in need thereof.

As used herein, the terms "treat," "treating," "treatment," "therapeutic," and "therapy" do not necessarily mean total cure or abolition of the estrogen receptor dependent and/or estrogen receptor mediated disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the estrogen receptor dependent and/or estrogen receptor mediated disease or condition, or prolong the survival of the subject being treated This response may occur in a tissue, system, animal or human and includes alleviation of the signs or symptoms of the estrogen receptor dependent and/or estrogen receptor mediated disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The amount of the compound of Formula (I), or a pharmaceutically acceptable salt thereof, required for use in treatment will vary not only with the particular compound or salt selected but also with the route of administration, the nature and/or symptoms of the estrogen receptor dependent and/or estrogen receptor mediated disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive estrogen receptor dependent and/or estrogen receptor mediated diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 500 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of Formula (I), or pharmaceutically acceptable salts thereof, can be determined by comparing their in vitro activity, and in vivo activity in animal models. Such comparison can be done by comparison against an established drug, such as fulvestrant.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the estrogen receptor dependent and/or estrogen receptor mediated disease or condition to be treated and to the route of administration. The severity of the estrogen receptor dependent and/or estrogen receptor mediated disease or condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as antioxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

EXAMPLES

Additional embodiments are described in further detail in the following examples, which are not in any way intended to limit the scope of the claims.

Compounds

The compounds of Formula (I) illustrated in Table 1 can be prepared in various ways, using techniques known to those skilled in the art as guided by the detailed teachings provided herein. For example, the compounds of Formula (I) illustrated in Table 1 can be prepared in accordance with the general reaction scheme illustrated in FIG. 1 as described in the general procedures below. Those skilled in the art will understand that Formula (I) and a number of structures shown in Table 1 are not stereospecific and/or are depicted as having unfilled valencies, and thus are generic to isotopic and/or stereochemical variants, including racemates, diastereomers, enantiomers and/or deuterated versions, which can be prepared in accordance with the guidance provided herein.

General Procedures:

Step 1: Intermediate A was prepared according to procedure described in patent publication WO 2017172957 A1. Pictet-Spengler reaction was carried out in similar fashion as described in patent publication WO 2017172957 A1. Briefly, intermediate A and aldehyde B in toluene were mixed with various amount of acid. The reaction was stirred at various temperature from 90° C. to 130° C. for 3-12 hours.

Step 2: The second step was carried out by Pd- or Cu-catalyzed Ullman, Buchwald reaction, or by Mitsunobu or alkylation reactions as described in patent publication WO 2016097072.

TABLE 1

| No. | Compound Structure |
|---|---|
| 1 | 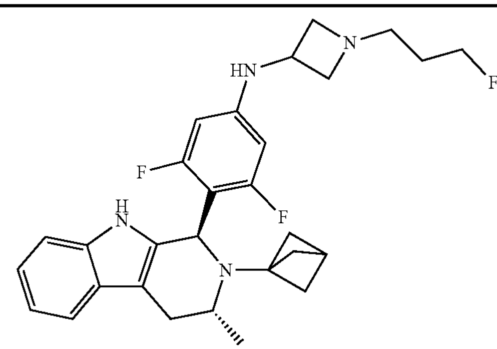 |
| 2 | 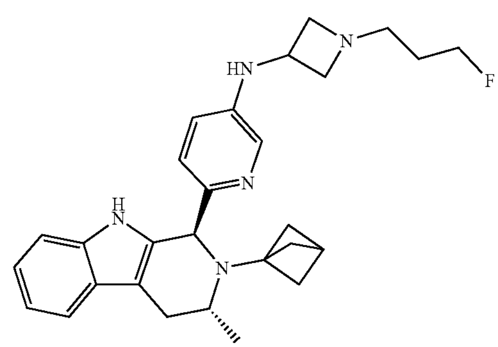 [SMILES: C[C@@H]1Cc2c([nH]c3ccccc23)[C@@H](c2ccc(NC3CN(CCCF)C3)cn2)N1C12CC(C1)C2] |

TABLE 1-continued
| No. | Compound Structure |
|---|---|
| 3 | 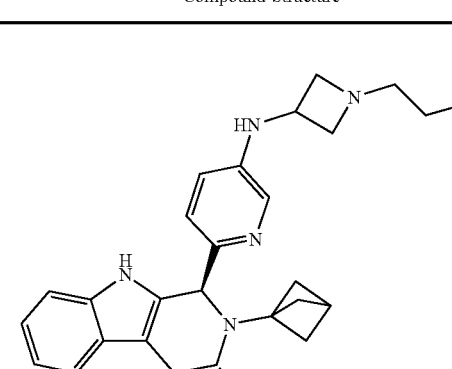 |
| 4 | 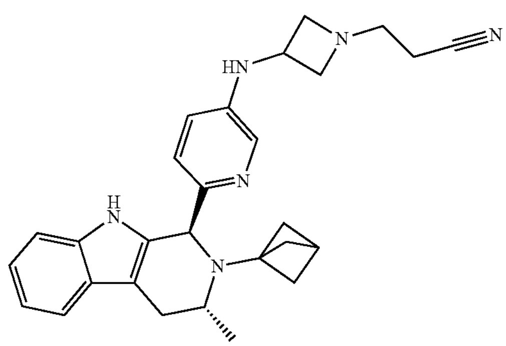 [SMILES: C[C@@H]1Cc2c([nH]c3ccccc23)[C@@H](c2ccc(NC3CN(CCC#N)C3)cn2)N1C12CC(C1)C2] |
| 5 | 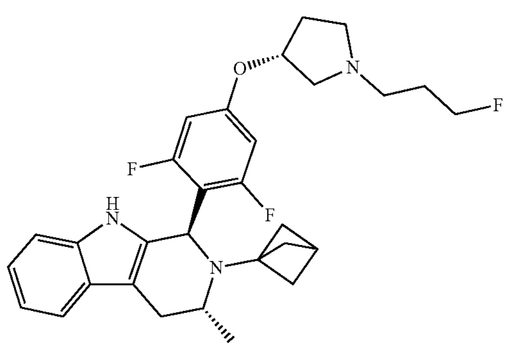 [SMILES: C[C@@H]1Cc2c([nH]c3ccccc23)[C@@H](c2c(F)cc(O[C@@H]3CCN(CCCF)C3)cc2F)N1C12CC(C1)C2] |
| 6 | 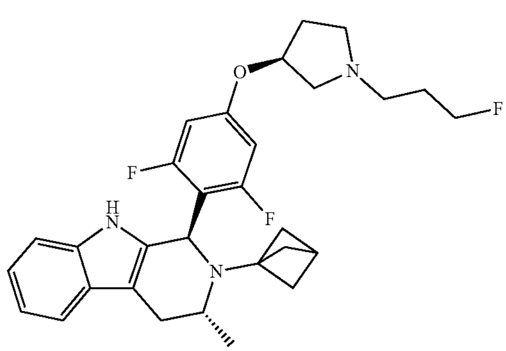 [SMILES: C[C@@H]1Cc2c([nH]c3ccccc23)[C@@H](c2c(F)cc(O[C@H]3CCN(CCCF)C3)cc2F)N1C12CC(C1)C2] |
TABLE 1-continued
| No. | Compound Structure |
|---|---|
| 7 | 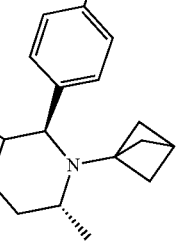 |
| 8 | 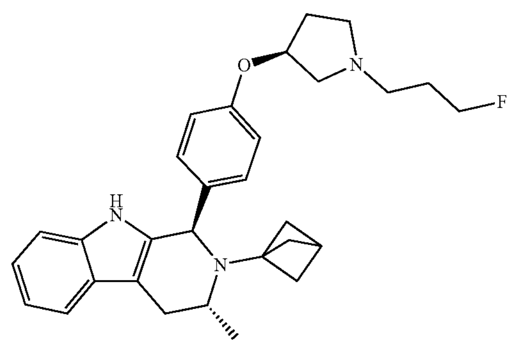 [SMILES: C[C@@H]1Cc2c([nH]c3ccccc23)[C@@H](c2ccc(O[C@H]3CCN(CCCF)C3)cc2)N1C12CC(C1)C2] |
| 9 | 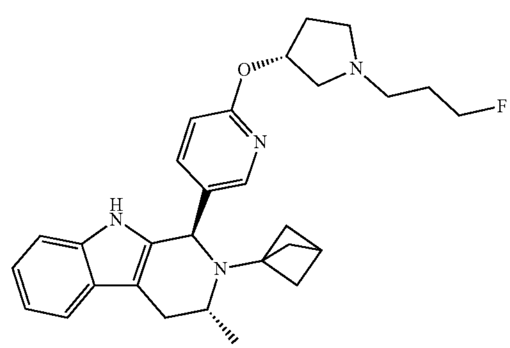 [SMILES: C[C@@H]1Cc2c([nH]c3ccccc23)[C@@H](c2ccc(O[C@@H]3CCN(CCCF)C3)nc2)N1C12CC(C1)C2] |
| 10 | 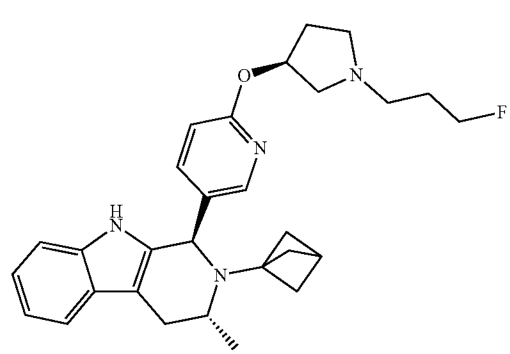 [SMILES: C[C@@H]1Cc2c([nH]c3ccccc23)[C@@H](c2ccc(O[C@H]3CCN(CCCF)C3)nc2)N1C12CC(C1)C2] |

TABLE 1-continued
| No. | Compound Structure |
|---|---|
| 11 | 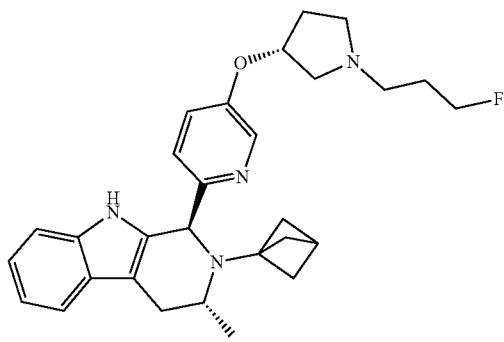 |
| 12 | 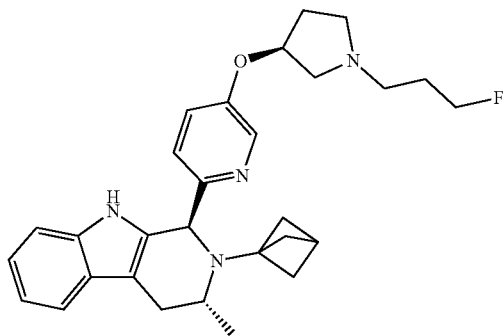 [SMILES: C[C@@H]1Cc2c([nH]c3ccccc23)[C@@H](c2ccc(O[C@H]3CCN(CCCF)C3)cn2)N1C12CC(C1)C2] |
| 13 | 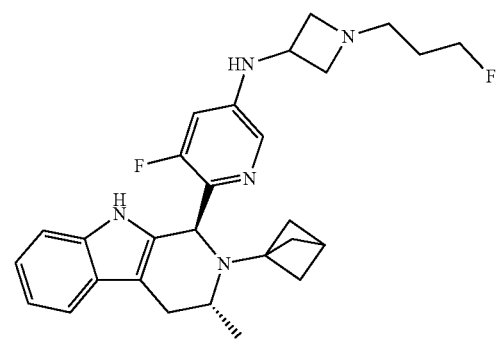 [SMILES: C[C@@H]1Cc2c([nH]c3ccccc23)[C@@H](c2ncc(NC3CN(CCCF)C3)cc2F)N1C12CC(C1)C2] |
| 14 | 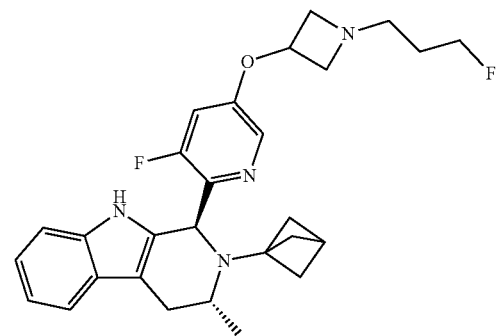 [SMILES: C[C@@H]1Cc2c([nH]c3ccccc23)[C@@H](c2ncc(OC3CN(CCCF)C3)cc2F)N1C12CC(C1)C2] |
TABLE 1-continued
| No. | Compound Structure |
|---|---|
| 15 | 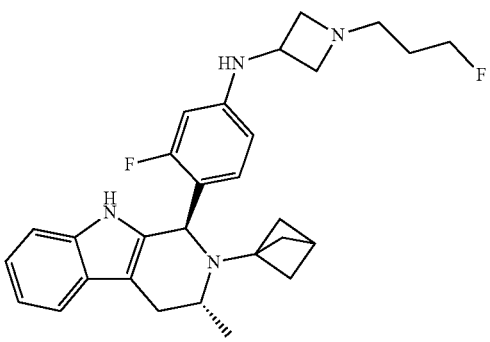 [SMILES: C[C@@H]1Cc2c([nH]c3ccccc23)[C@@H](c2ccc(NC3CN(CCCF)C3)cc2F)N1C12CC(C1)C2] |
| 16 | 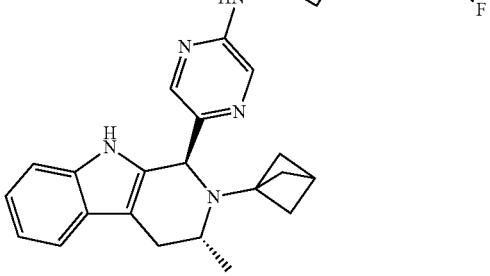 |
| 17 | 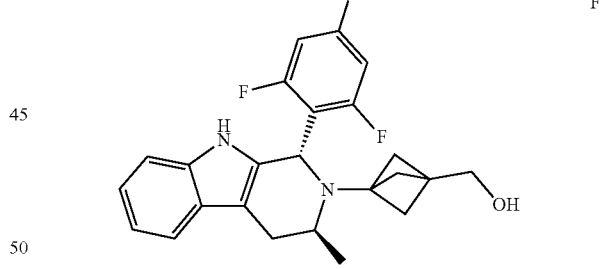 |
| 18 | 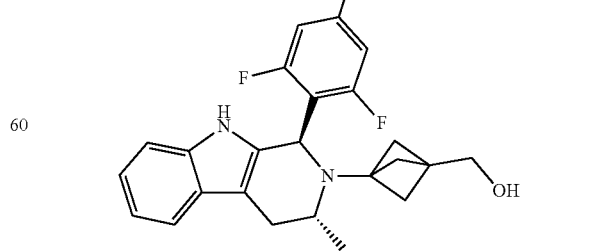 |

TABLE 1-continued
| No. | Compound Structure |
|---|---|
| 19 | 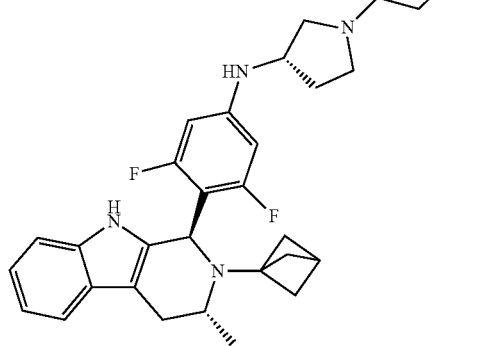 |
| 20 | 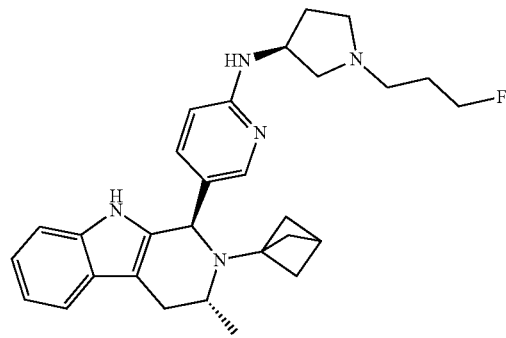 [SMILES: C[C@@H]1Cc2c([nH]c3ccccc23)[C@@H](c2ccc(N[C@H]3CCN(CCCF)C3)nc2)N1C12CC(C1)C2] |
| 21 | 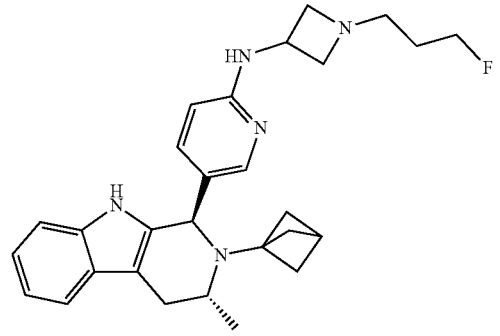 [SMILES: C[C@@H]1Cc2c([nH]c3ccccc23)[C@@H](c2ccc(NC3CN(CCCF)C3)nc2)N1C12CC(C1)C2] |
| 22 | 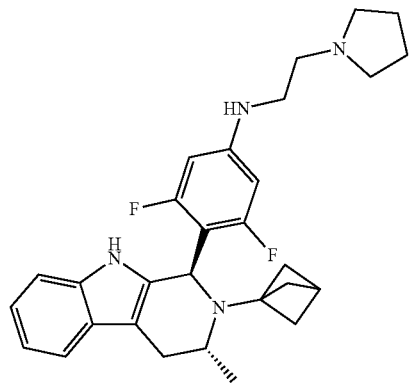 [SMILES: C[C@@H]1Cc2c([nH]c3ccccc23)[C@@H](c2c(F)cc(NCCN3CCCC3)cc2F)N1C12CC(C1)C2] |
| 23 | 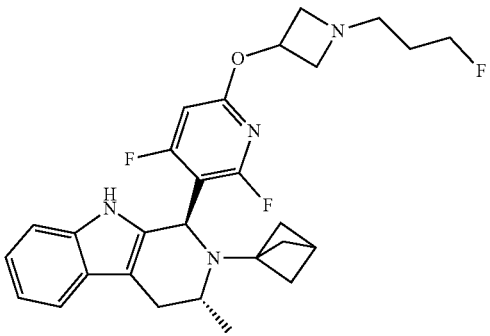 [SMILES: C[C@@H]1Cc2c([nH]c3ccccc23)[C@@H](c2c(F)cc(OC3CN(CCCF)C3)nc2F)N1C12CC(C1)C2] |
| 24 | 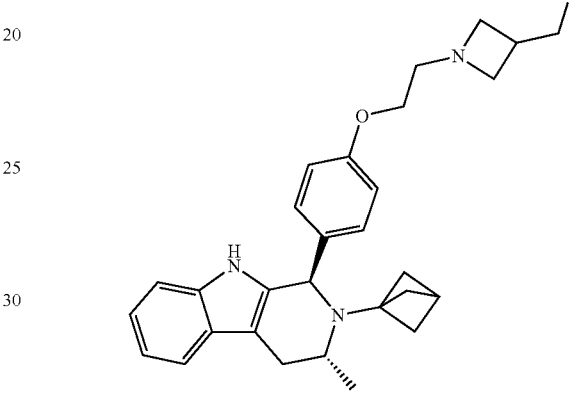 |
| 25 | 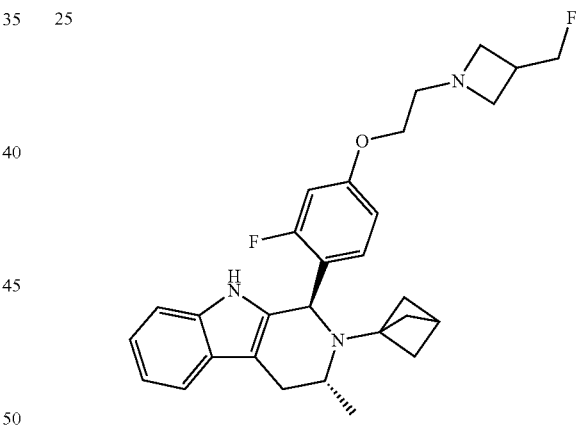 |
| 26 | 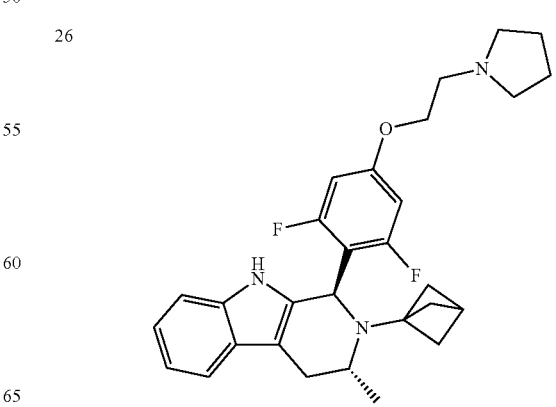 |

TABLE 1-continued
| No. | Compound Structure |
|---|---|
| 27 | 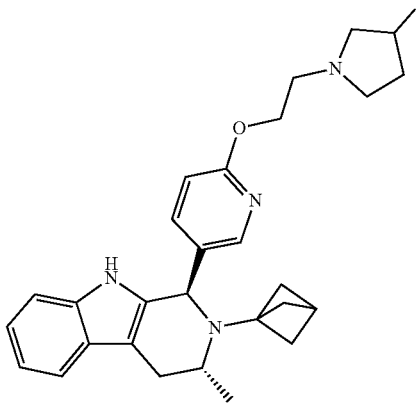 |
| 28 | 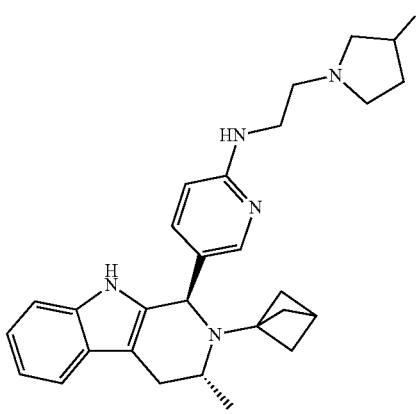 |
| 29 | 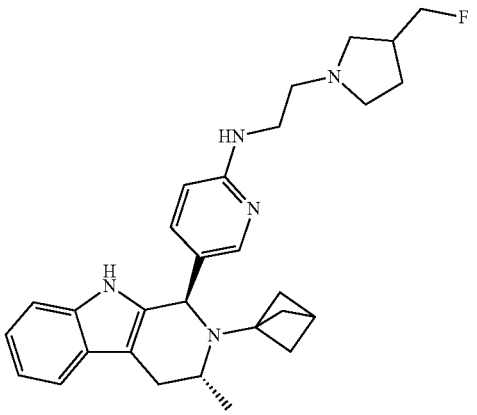 [SMILES: C[C@@H]1Cc2c([nH]c3ccccc23)[C@@H](c2ccc(NCCN3CCC(CF)C3)nc2)N1C12CC(C1)C2] |
| 30 | 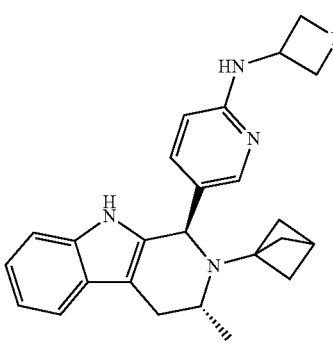 |
| 31 | 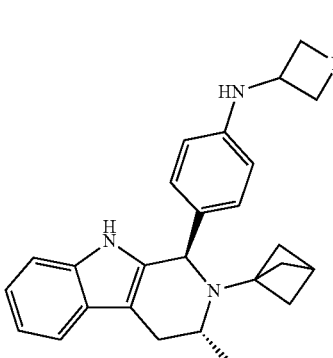 |
| 32 | 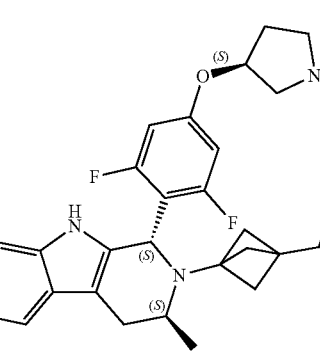 |
| 33 | 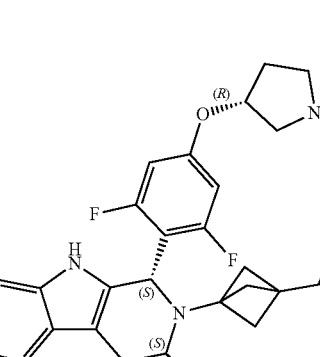 |

TABLE 1-continued
| No. | Compound Structure |
|---|---|
| 34 | 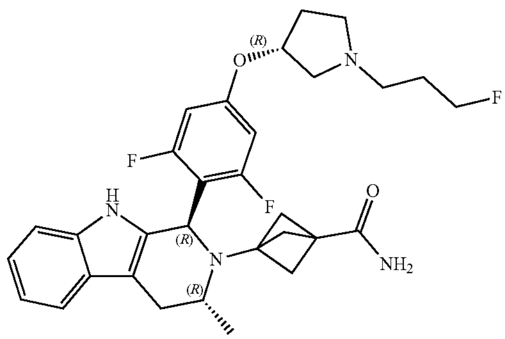 |
| 35 | 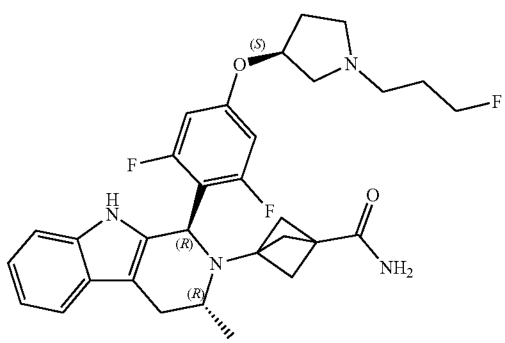 |
| 36 | 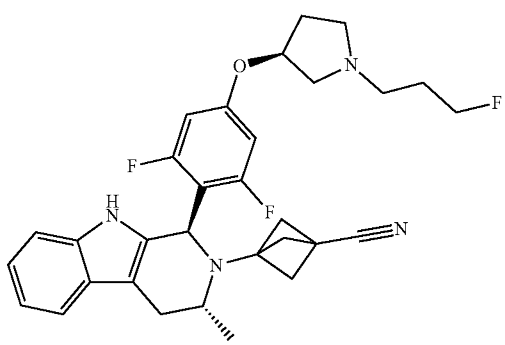 [SMILES: C[C@@H]1Cc2c([nH]c3ccccc23)[C@@H](c2c(F)cc(O[C@H]3CCN(CCCF)C3)cc2F)N1C12CC(C#N)(C1)C2] |
| 37 | 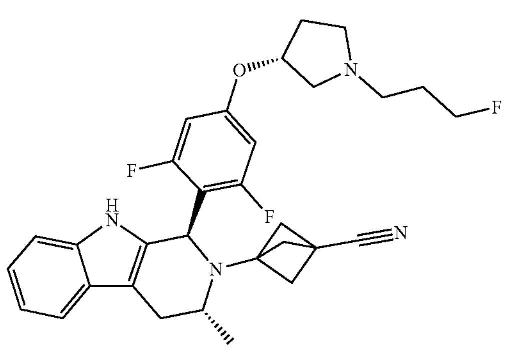 [SMILES: C[C@@H]1Cc2c([nH]c3ccccc23)[C@@H](c2c(F)cc(O[C@@H]3CCN(CCCF)C3)cc2F)N1C12CC(C#N)(C1)C2] |
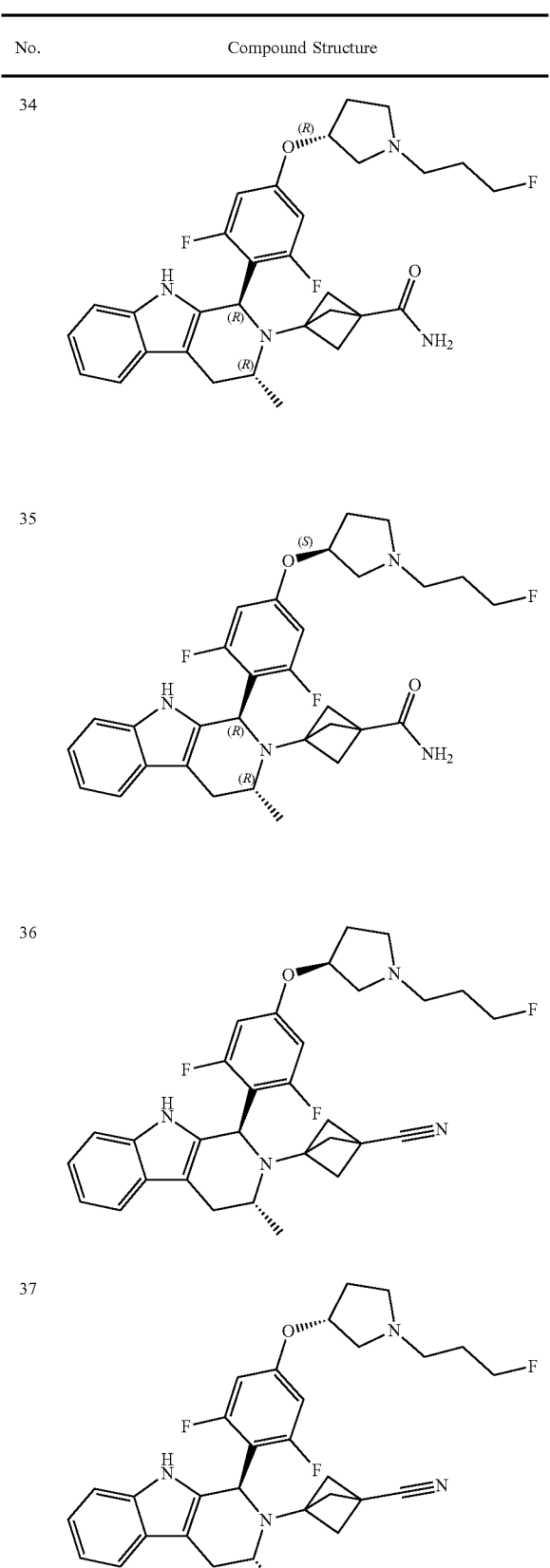
TABLE 1-continued
| No. | Compound Structure |
|---|---|
| 38 | 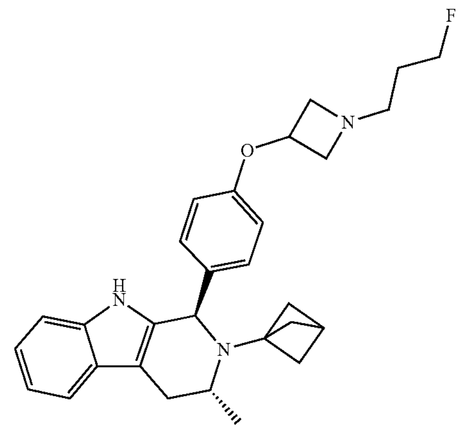 [SMILES: C[C@@H]1Cc2c([nH]c3ccccc23)[C@@H](c2ccc(OC3CN(CCCF)C3)cc2)N1C12CC(C1)C2] |
| 39 | 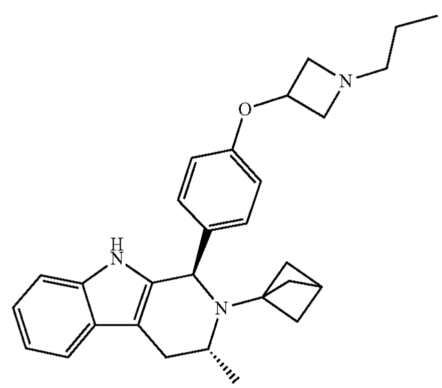 [SMILES: CCCN1CC(Oc2ccc([C@@H]3c4[nH]c5ccccc5c4C[C@@H](C)N3C34CC(C3)C4)cc2)C1] |
| 40 | 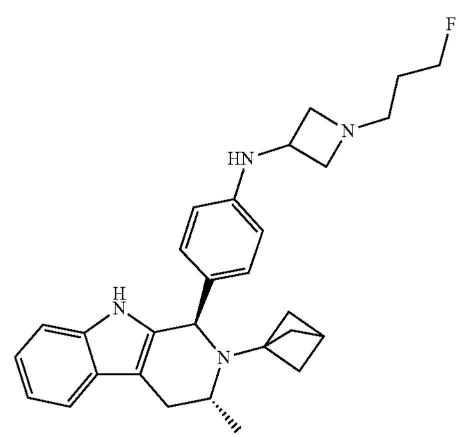 [SMILES: C[C@@H]1Cc2c([nH]c3ccccc23)[C@@H](c2ccc(NC3CN(CCCF)C3)cc2)N1C12CC(C1)C2] |
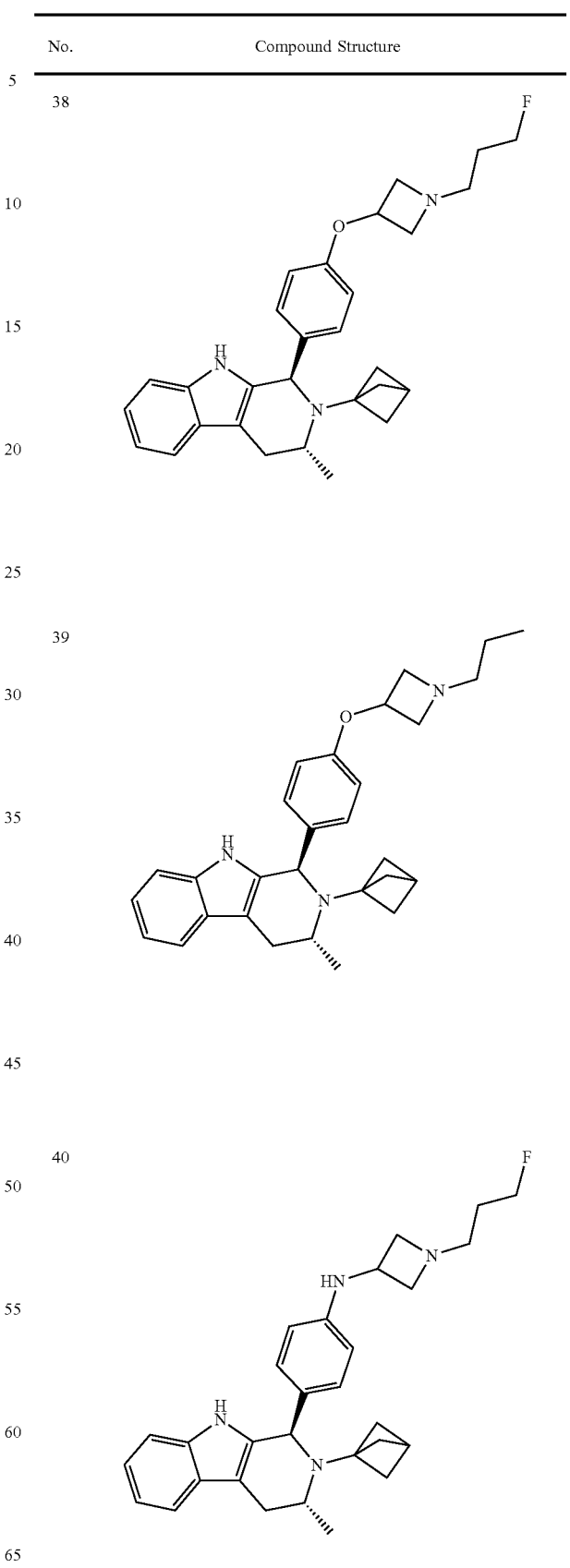

TABLE 1-continued
| No. | Compound Structure |
|---|---|
| 41 | 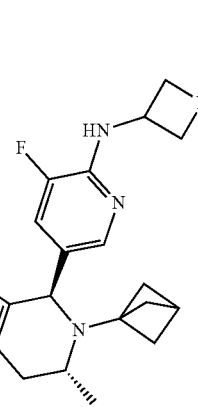 |
| 42 | 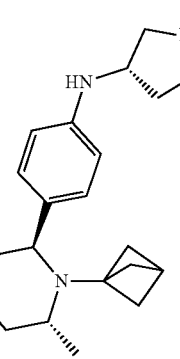 |
| 43 | 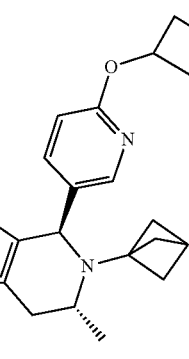 |
| 44 | 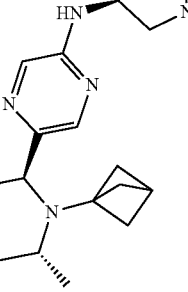 |
| 45 | 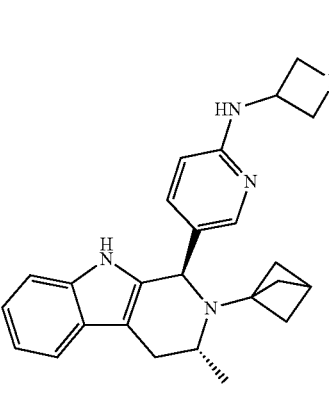 |
| 46 | 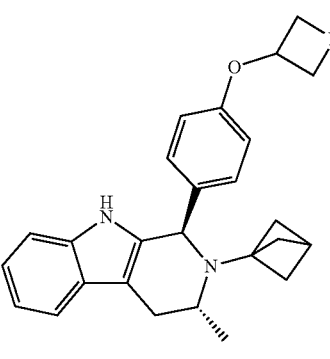 |
| 47 | 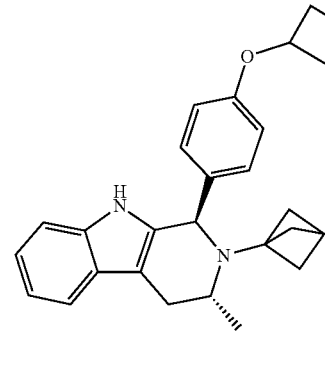 |
| 48 | 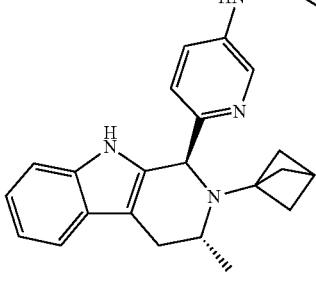 |

TABLE 1-continued

| No. | Compound Structure |
|-----|--------------------|
| 49  | 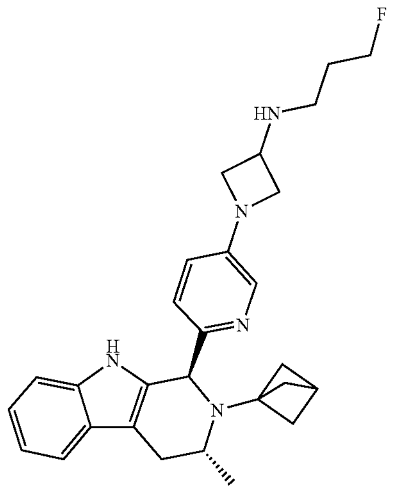 [SMILES: C[C@@H]1Cc2c([nH]c3ccccc23)[C@@H](c2ccc(N3CC(NCCCF)C3)cn2)N1C12CC(C1)C2]                   |
| 50  | 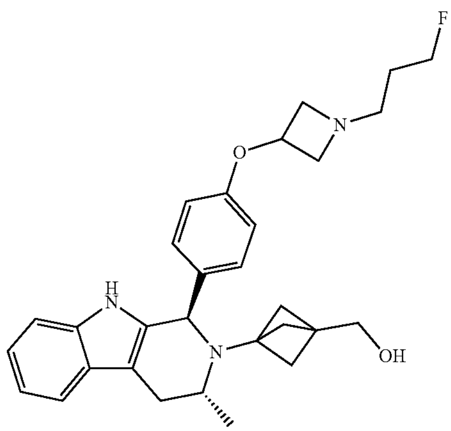 [SMILES: C[C@@H]1Cc2c([nH]c3ccccc23)[C@@H](c2ccc(OC3CN(CCCF)C3)cc2)N1C12CC(CO)(C1)C2]                   |
| 51  | 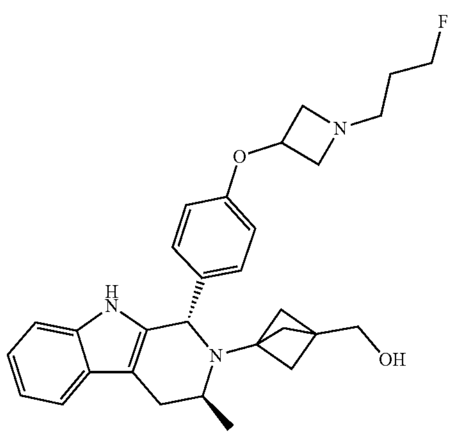 [SMILES: C[C@H]1Cc2c([nH]c3ccccc23)[C@H](c2ccc(OC3CN(CCCF)C3)cc2)N1C12CC(CO)(C1)C2]                   |
| 52  | 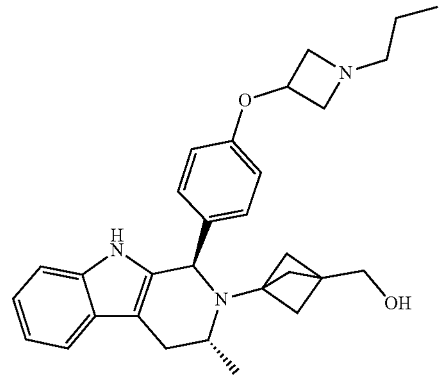 [SMILES: CCCN1CC(Oc2ccc([C@@H]3c4[nH]c5ccccc5c4C[C@@H](C)N3C34CC(CO)(C3)C4)cc2)C1]                   |
| 53  | 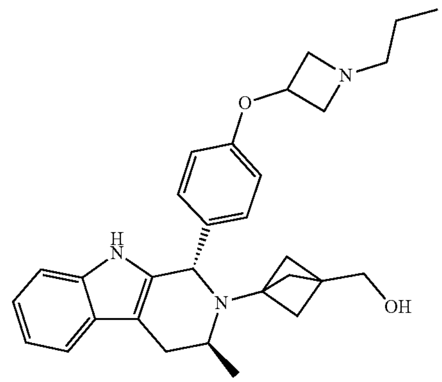 [SMILES: CCCN1CC(Oc2ccc([C@H]3c4[nH]c5ccccc5c4C[C@H](C)N3C34CC(CO)(C3)C4)cc2)C1]                   |
| 54  | 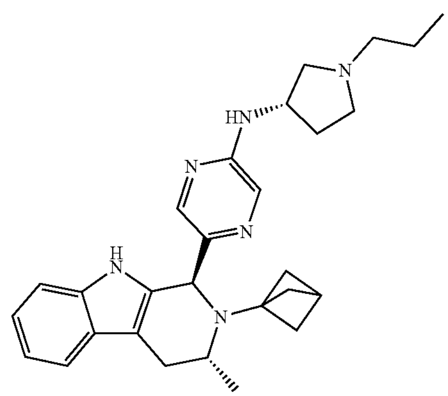 [SMILES: CCCN1CC[C@H](Nc2cnc([C@@H]3c4[nH]c5ccccc5c4C[C@@H](C)N3C34CC(C3)C4)cn2)C1]                   |
| 55  | 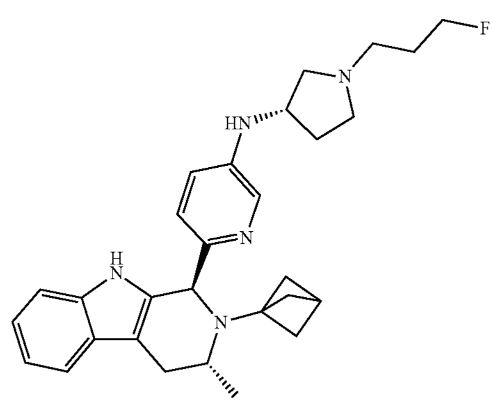 [SMILES: C[C@@H]1Cc2c([nH]c3ccccc23)[C@@H](c2ccc(N[C@H]3CCN(CCCF)C3)cn2)N1C12CC(C1)C2]                   |

TABLE 1-continued
| No. | Compound Structure |
|---|---|
| 56 | 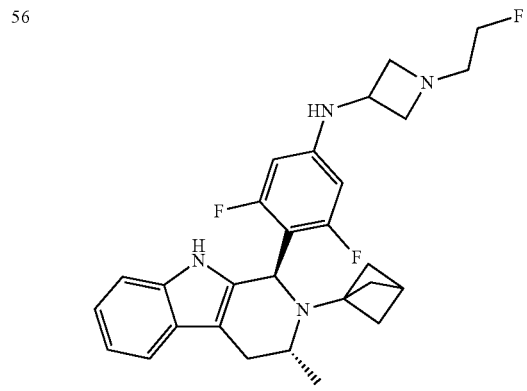 |
| 57 | 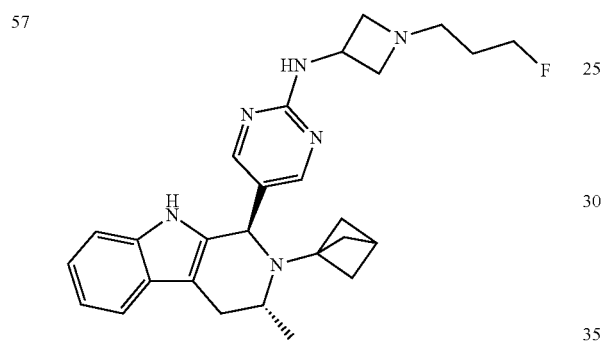 |
| 58 | 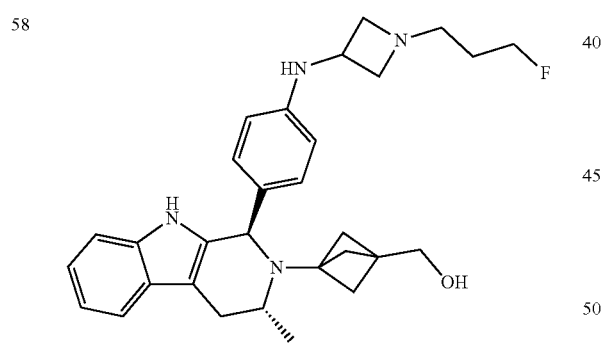 |
| 59 | 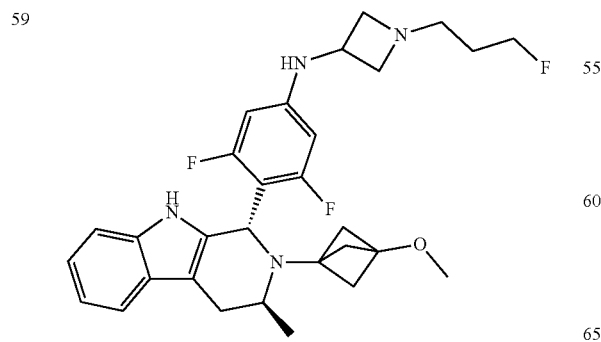 |
TABLE 1-continued
| No. | Compound Structure |
|---|---|
| 60 | 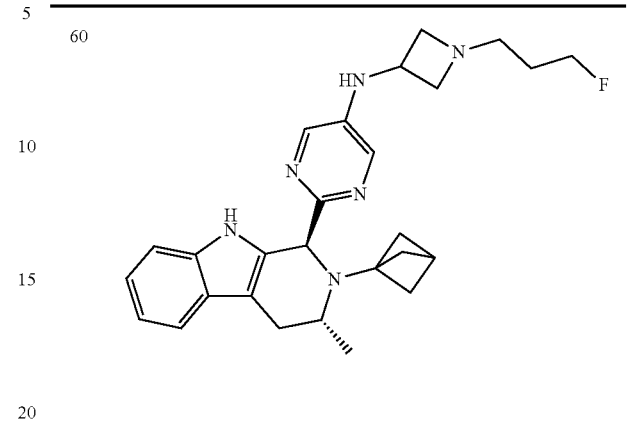 |
| 61 | 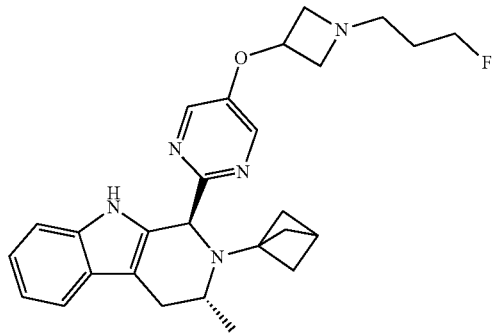 [SMILES: C[C@@H]1Cc2c([nH]c3ccccc23)[C@@H](c2ncc(OC3CN(CCCF)C3)cn2)N1C12CC(C1)C2] |
| 62 | 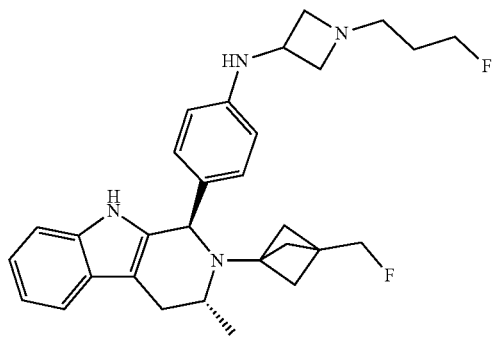 [SMILES: C[C@@H]1Cc2c([nH]c3ccccc23)[C@@H](c2ccc(NC3CN(CCCF)C3)cc2)N1C12CC(CF)(C1)C2] |
| 63 | 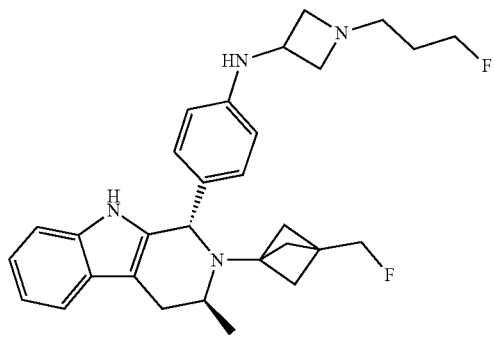 [SMILES: C[C@H]1Cc2c([nH]c3ccccc23)[C@H](c2ccc(NC3CN(CCCF)C3)cc2)N1C12CC(CF)(C1)C2] |

TABLE 1-continued
| No. | Compound Structure |
|---|---|
| 64 | 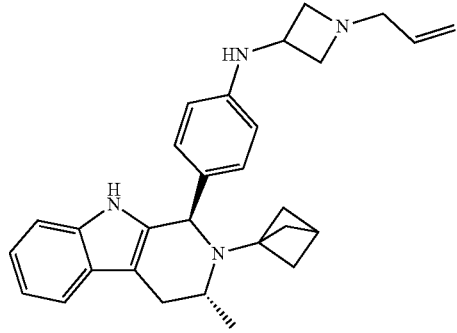 [SMILES: C=CCN1CC(Nc2ccc([C@@H]3c4[nH]c5ccccc5c4C[C@@H](C)N3C34CC(C3)C4)cc2)C1] |
| 65 | 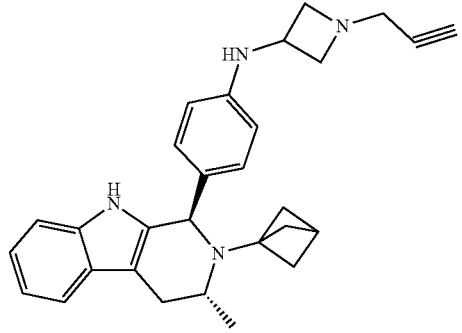 |
| 66 | 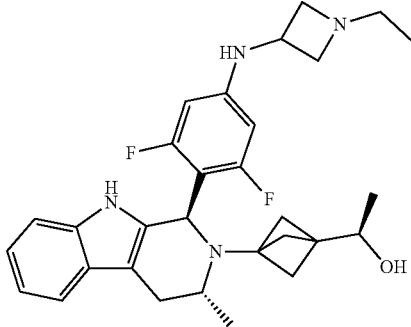 |
| 67 | 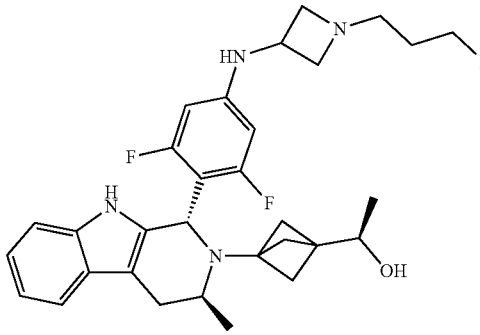 |
| 68 | 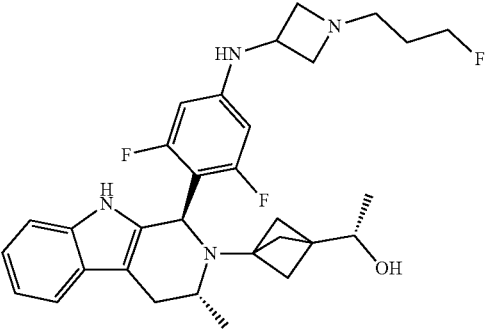 [SMILES: C[C@@H]1Cc2c([nH]c3ccccc23)[C@@H](c2c(F)cc(NC3CN(CCCF)C3)cc2F)N1C12CC([C@H](C)O)(C1)C2] |
| 69 | 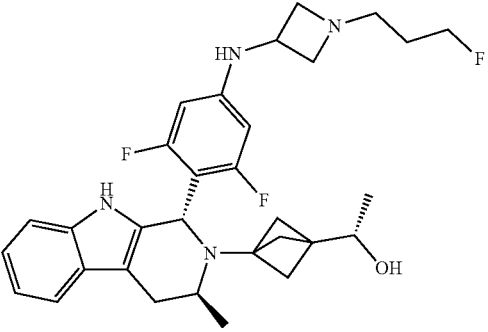 [SMILES: C[C@H](O)C12CC(N3[C@@H](c4c(F)cc(NC5CN(CCCF)C5)cc4F)c4[nH]c5ccccc5c4C[C@@H]3C)(C1)C2] |
| 70 | 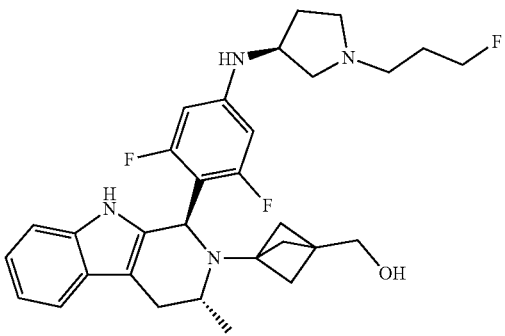 [SMILES: C[C@@H]1Cc2c([nH]c3ccccc23)[C@@H](c2c(F)cc(N[C@H]3CCN(CCCF)C3)cc2F)N1C12CC(CO)(C1)C2] |
| 71 | 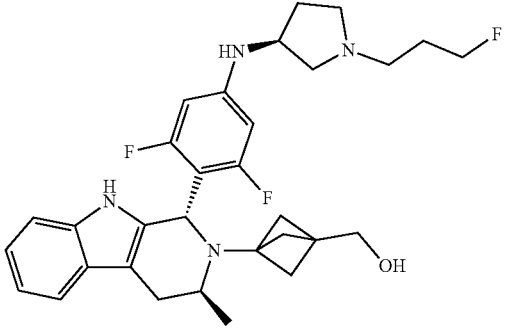 [SMILES: C[C@H]1Cc2c([nH]c3ccccc23)[C@H](c2c(F)cc(N[C@H]3CCN(CCCF)C3)cc2F)N1C12CC(CO)(C1)C2] |

TABLE 1-continued

| No. | Compound Structure |
|---|---|
| 72 | 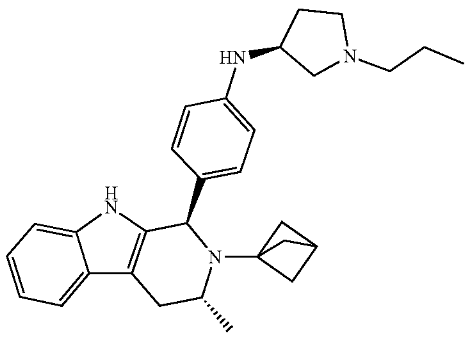 [SMILES: CCCN1CC[C@H](Nc2ccc([C@@H]3c4[nH]c5ccccc5c4C[C@@H](C)N3C34CC(C3)C4)cc2)C1] |
| 73 | 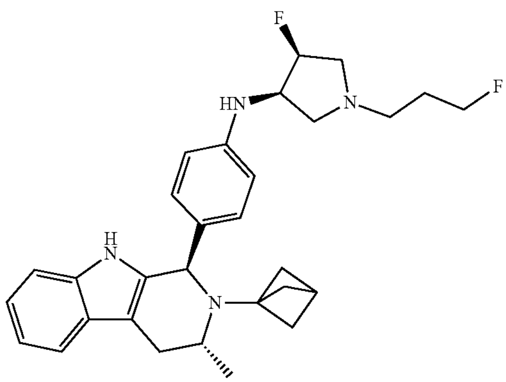 [SMILES: C[C@@H]1Cc2c([nH]c3ccccc23)[C@@H](c2ccc(N[C@@H]3CN(CCCF)C[C@@H]3F)cc2)N1C12CC(C1)C2] |
| 74 | 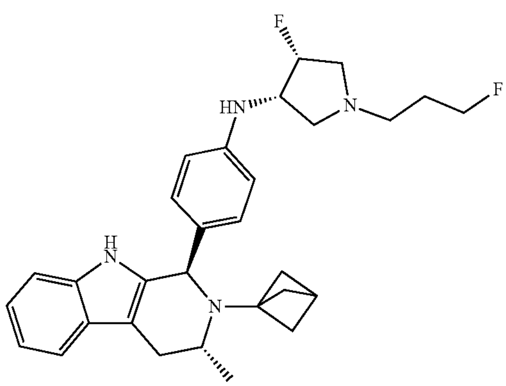 [SMILES: C[C@@H]1Cc2c([nH]c3ccccc23)[C@@H](c2ccc(N[C@H]3CN(CCCF)C[C@H]3F)cc2)N1C12CC(C1)C2] |
| 75 | 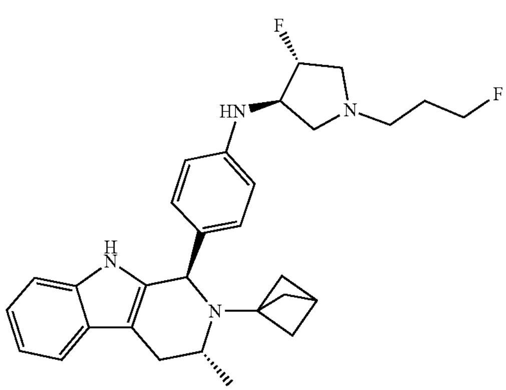 [SMILES: C[C@@H]1Cc2c([nH]c3ccccc23)[C@@H](c2ccc(N[C@@H]3CN(CCCF)C[C@H]3F)cc2)N1C12CC(C1)C2] |
| 76 | |
| 77 | |
| 78 | |
| 79 | |

TABLE 1-continued
| No. | Compound Structure |
|---|---|
| 80 | |
| 81 | |
| 82 | |
| 83 | |
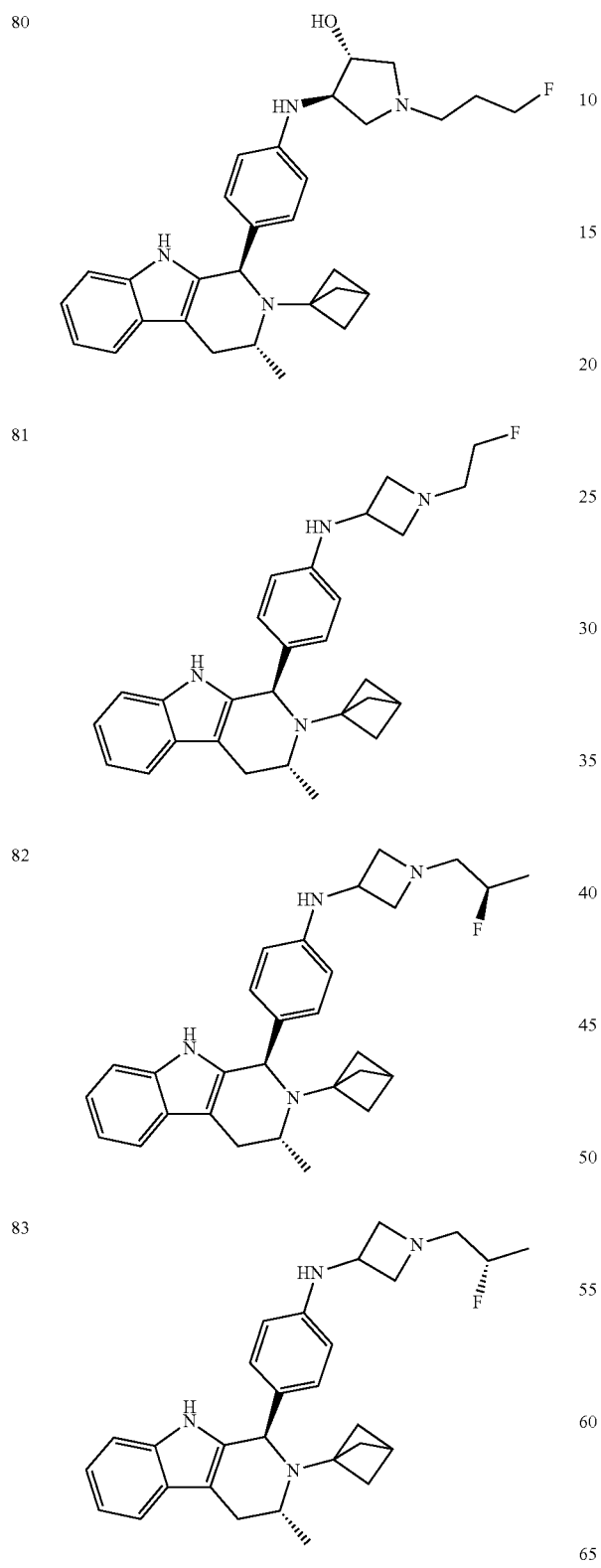
TABLE 1-continued
| No. | Compound Structure |
|---|---|
| 84 | 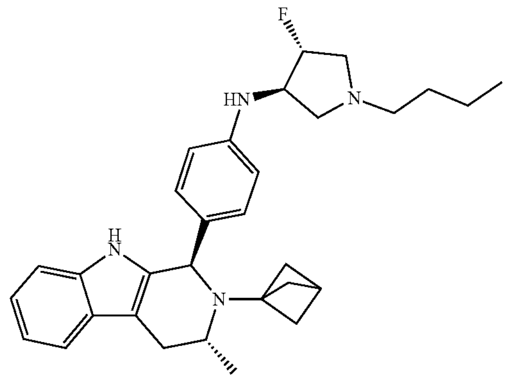 [SMILES: CCCCN1C[C@@H](F)[C@H](Nc2ccc([C@@H]3c4[nH]c5ccccc5c4C[C@@H](C)N3C34CC(C3)C4)cc2)C1] |
| 85 | 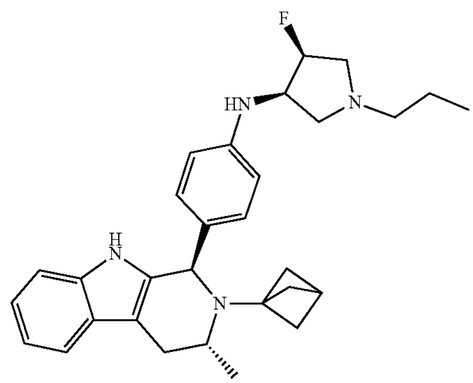 [SMILES: CCCN1C[C@H](F)[C@H](Nc2ccc([C@@H]3c4[nH]c5ccccc5c4C[C@@H](C)N3C34CC(C3)C4)cc2)C1] |
| 86 | 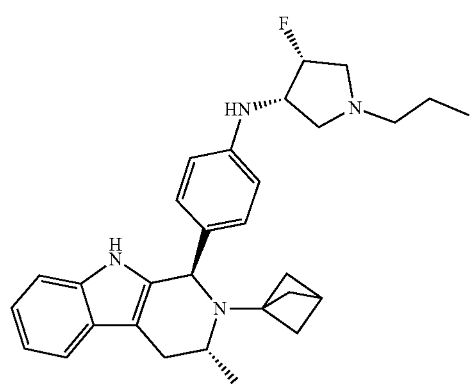 [SMILES: CCCN1C[C@@H](F)[C@@H](Nc2ccc([C@@H]3c4[nH]c5ccccc5c4C[C@@H](C)N3C34CC(C3)C4)cc2)C1] |
| 87 | 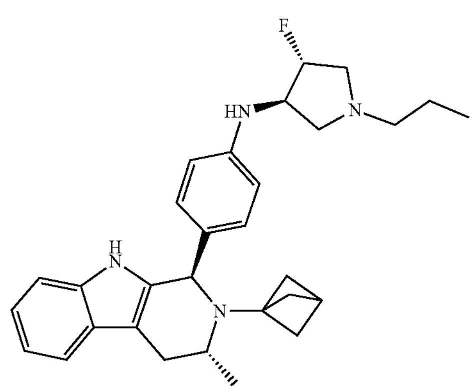 [SMILES: CCCN1C[C@@H](F)[C@H](Nc2ccc([C@@H]3c4[nH]c5ccccc5c4C[C@@H](C)N3C34CC(C3)C4)cc2)C1] |
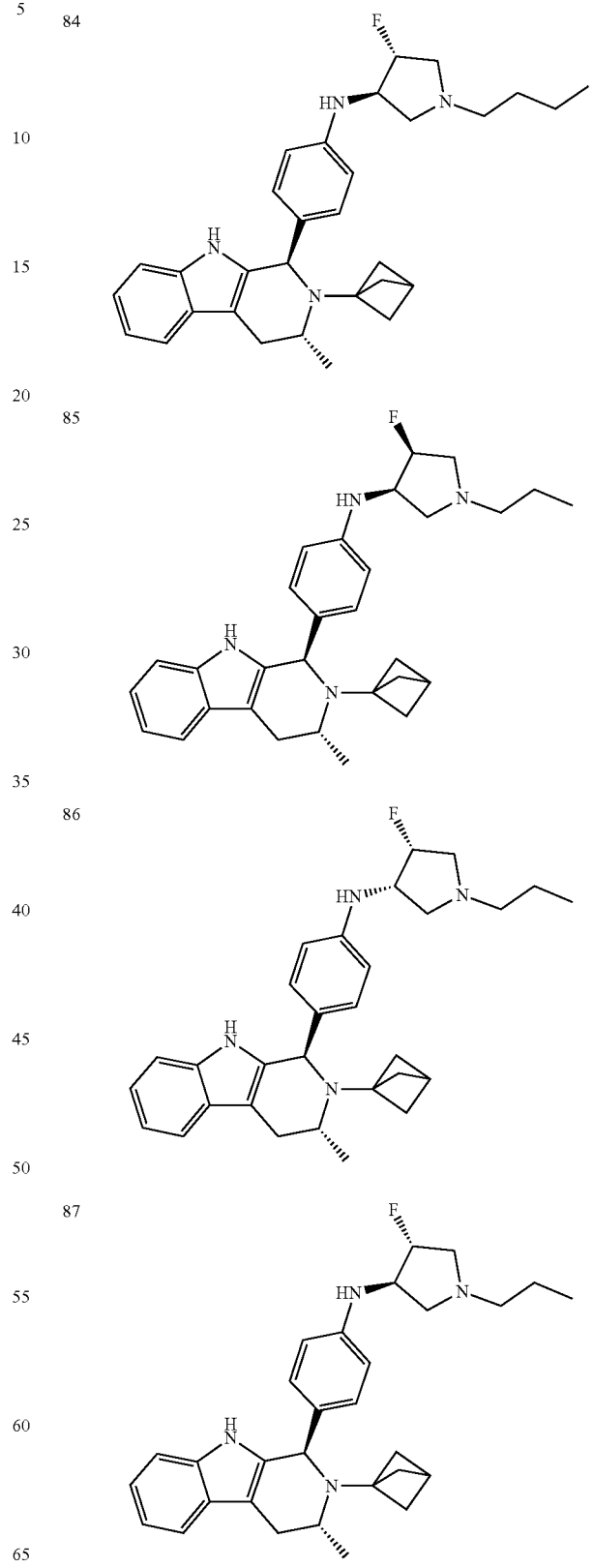

TABLE 1-continued
| No. | Compound Structure |
|---|---|
| 88 | 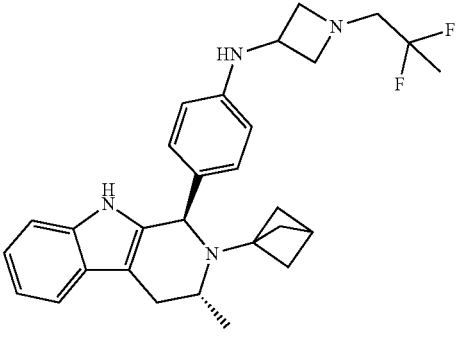 [SMILES: C[C@@H]1Cc2c([nH]c3ccccc23)[C@@H](c2ccc(NC3CN(CC(C)(F)F)C3)cc2)N1C12CC(C1)C2] |
| 89 | 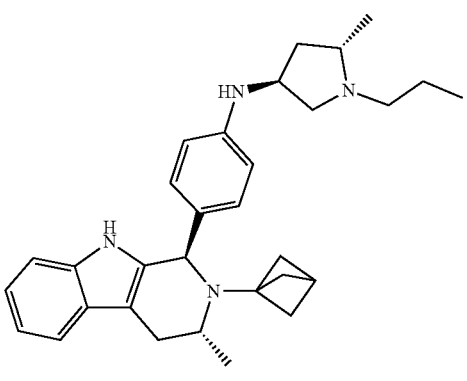 [SMILES: CCCN1C[C@@H](Nc2ccc([C@@H]3c4[nH]c5ccccc5c4C[C@@H](C)N3C34CC(C3)C4)cc2)C[C@@H]1C] |
| 90 | 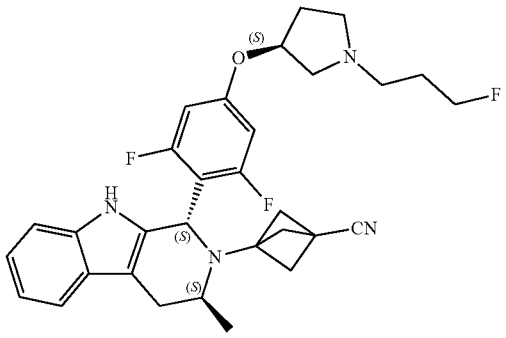 |
| 91 | 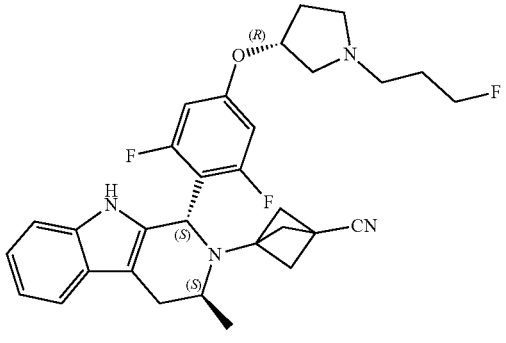 |
| 92 | 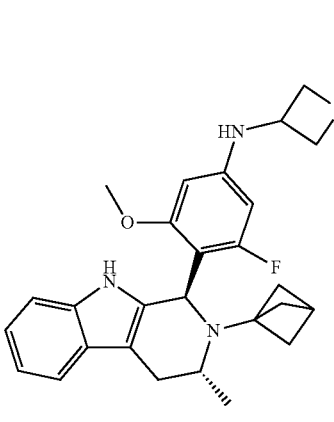 |
| 93 | 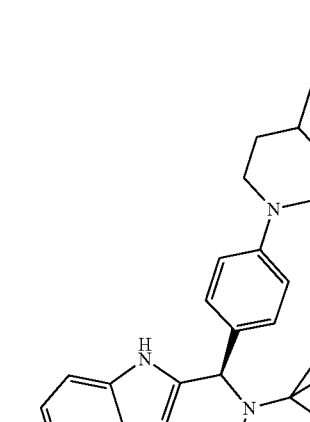 |
| 94 | 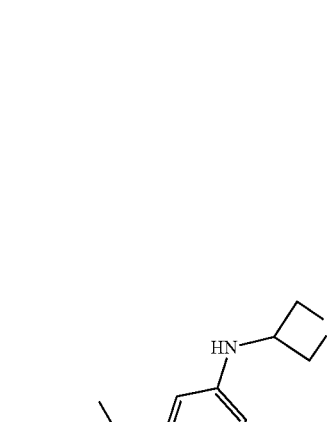 |

TABLE 1-continued

| No. | Compound Structure |
|---|---|
| 95 | |
| 96 | |

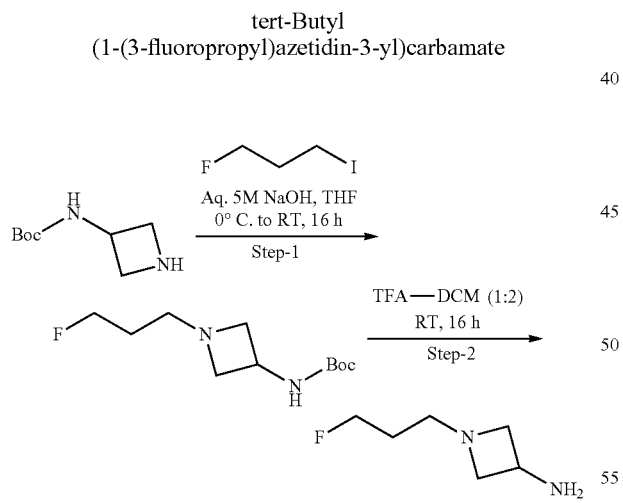

Intermediate 1 tert-Butyl (1-(3-fluoropropyl)azetidin-3-yl)carbamate

Step 1: Aq. 5 M NaOH (3.5 mL, 17.43 mmol) was added to an ice cooled stirred solution of tert-butyl azetidin-3-ylcarbamate (1 g, 5.81 mmol) in THF (10 mL) followed by addition of 1-fluoro-3-iodopropane (1.20 g, 6.39 mmol) at 0 TC. Then reaction mixture was stirred at room temperature (RT) for 16 h. After completion of the reaction, it was diluted with water (50 mL) and extracted into 10% MeOH in DCM (3×50 mL). The organic layer was collected, dried over Na₂SO₄, filtered and evaporated. The crude product was purified by silica gel column chromatography to yield 809 mg (3.48 mmol, 60%) of tert-butyl (1-(3-fluoropropyl)azetidin-3-yl)carbamate. ¹H NMR (400 MHz, DMSO-d6) δ 7.27 (d, J=7.2 Hz, 1H), 4.48 (t, J=6.0 Hz, 1H), 4.36 (t, J=6.0 Hz, 1H), 4.01-3.99 (q, 1H), 3.45 (t, J=6.8 Hz, 2H), 2.72 (t, J=6.8 Hz, 2H), 2.40 (t, J=6.8 Hz, 2H), 1.66-1.56 (m, 2H), 1.37 (s, 9H).

Step 2: To a stirred solution of tert-butyl (1-(3-fluoropropyl)azetidin-3-yl)carbamate (809 mg, 3.48 mmol) in DCM (6 mL) was added TFA (3 mL) at 0° C. Then reaction mixture was stirred at room temperature for 16 h. After completion of the reaction, it was evaporated, then dissolved in 10% MeOH in DCM. K₂CO₃ (4.8 g, 34.8 mmol) was then added at 0° C. and stirred for 20 min and then filtered. The filtrate was concentrated to yield 322 mg (2.44 mmol, 70%) of 1-(3-fluoropropyl)azetidin-3-amine. ¹H NMR (400 MHz, DMSO-d₆) δ 4.48 (t, J=6.0 Hz, 1H), 4.36 (t, J=6.0 Hz, 1H), 3.47-3.43 (m, 2H), 3.34-3.31 (q, 1H), 2.50-2.46 (m, 3H), 2.38 (t, J=5.6 Hz, 2H), 1.65-1.55 (m, 2H).

Example 1

N-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)-1-(3-fluoropropyl)azetidin-3-amine (Compound 1)

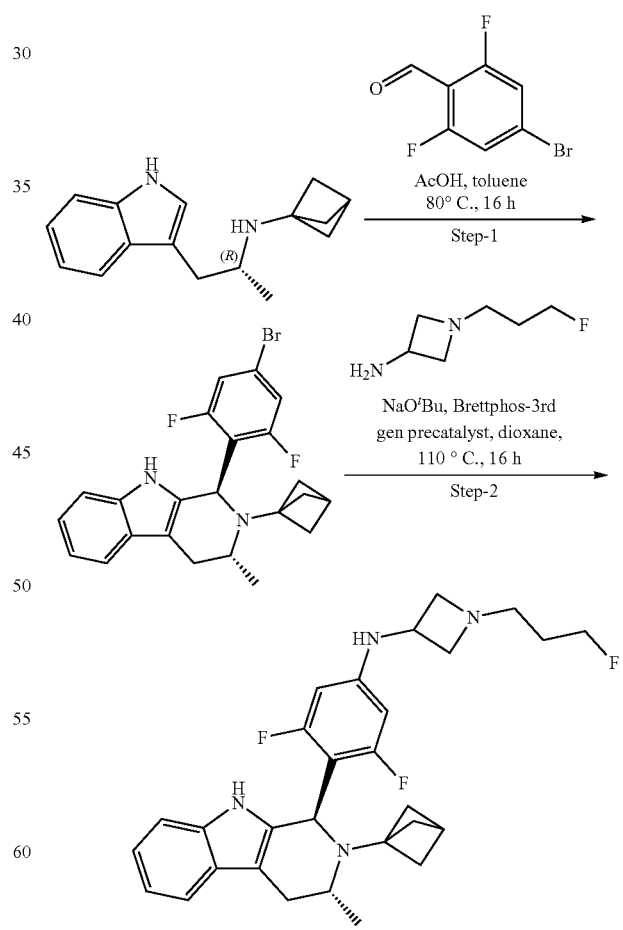

Step 1. To a stirred solution of (R)—N-(1-(1H-indol-3-yl)propan-2-yl) bicyclo [1.1.1] pentan-1-amine (1 g, 4.16 mmol) in toluene (10 mL) was added 4-bromo-2,6-difluorobenzaldehyde (1.01 g, 4.58 mmol) followed by AcOH (0.36 mL, 6.24 mmol) and stirred at 80° C. for 16 h. After completion of the reaction, reaction mixture was cooled to room temperature. The reaction mixture was diluted with water (50 mL) and extracted with EtOAc (2×50 mL). The combined organic layers were dried over Na$_2$SO$_4$, filtered and evaporated to get semi-pure crude. Thus obtained crude product was purified by silica gel column chromatography by eluting with 10-15% EtOAc in petroleum ether to afford (1R,3R)-2-(bicyclo[1.1.1]pentan-1-yl)-1-(4-bromo-2,6-difluorophenyl)-3-methyl-2,3,4,9-tetrahydro-1H-pyrido[3,4-b]indole (700 mg 1.57 mmol, 38% yield). MS (ESI) m/z 443.1 [M+H]$^+$; $^1$H NMR (400 MHz, DMSO-d$_6$) δ 10.52 (s, 1H), 7.41-7.37 (t, J=8.8 Hz, 3H), 7.17 (d, J=8.0 Hz, 1H), 7.01-6.91 (m, 2H), 5.29 (s, 1H), 4.03-4.01 (m, 1H), 2.96-2.92 (m, 1H), 2.58-2.54 (m, 1H), 2.25 (s, 1H), 1.77 (d, J=9.2 Hz, 3H), 1.57 (d, J=9.2 Hz, 3H), 1.07 (d, J=6.4 Hz, 3H).

Step 2. To a stirred solution of (1R,3R)-2-(bicyclo[1.1.1]pentan-1-yl)-1-(4-bromo-2,6-difluorophenyl)-3-methyl-2,3,4,9-tetrahydro-1H-pyrido[3,4-b]indole (500 mg, 1.12 mmol) in 1,4-dioxane (10 mL) was added 1-(3-fluoropropyl)azetidin-3-amine (223.6 mg, 1.69 mmol) and NaOt-Bu (188.2 mg, 1.96 mmol) and reaction mixture was degassed under argon for 30 min. Later Brettphos-3rd gen precatalyst (30.45 mg, 0.03 mmol) was added and the reaction mixture was again degassed for 30 min. It was then heated at 110° C. for 16 h. After completion of the reaction, it was cooled to room temperature and filtered through a bed of celite. The filtrate was diluted with water (50 mL) and extracted with EtOAc (2×50 mL). The combined organic layers were dried over Na$_2$SO$_4$, filtered and evaporated. The crude product was purified by RP prep-HPLC to afford N-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)-1-(3-fluoropropyl)azetidin-3-amine (158 mg, 0.31 mmol, 28% yield) (Compound 1). MS (ESI) m/z 495.2 [M+H]$^+$; $^1$H NMR (400 MHz, DMSO-d$_6$) δ 10.42 (s, 1H), 7.34 (d, J=7.6 Hz, 1H), 7.17 (d, J=8.0 Hz, 1H), 6.97-6.89 (m, 2H), 6.62 (d, J=6.8 Hz, 1H), 6.09 (d, J=12.0 Hz, 2H) 5.14 (s, 1H), 4.50 (t, J=6 Hz, 1H), 4.38 (t, J=6.4 Hz, 1H), 3.94-3.90 (m, 1H), 3.63-3.55 (m, 3H), 2.90 (dd, J=14.8, 3.6 Hz, 1H), 2.72 (t, J=6.0 Hz, 2H), 2.50-2.49 (m, 1H), 2.45 (t, J=7.2 Hz, 2H), 2.22 (s, 1H), 1.76 (d, J=8.8 Hz, 3H), 1.69-1.57 (m, 5H), 1.04 (d, J=6.4 Hz, 3H).

Example 2

6-((1S,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyridin-3-amine (Compound 2)

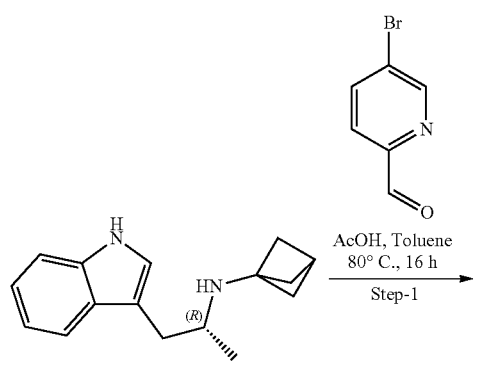

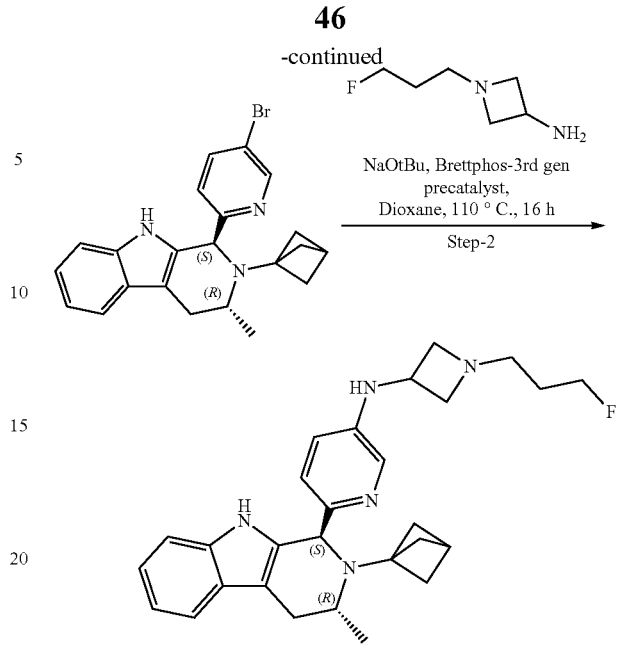

Step 1: To a stirred solution of (R)—N-(1-(1H-indol-3-yl)propan-2-yl)bicyclo[1.1.1]pentan-1-amine (500 mg, 2.07 mmol) in toluene (10 mL) were added 5-bromopicolinaldehyde (424.5 mg, 2.28 mmol) followed by AcOH (0.18 mL, 3.10 mmol) and the resulting mixture was stirred at 90° C. for 16 h. After completion of the reaction, it was cooled to room temperature. The reaction mixture was diluted with water (50 mL) and extracted into EtOAc (2×50 mL). The combined organic layer was collected, dried over Na$_2$SO$_4$, filtered and evaporated. The crude product was purified by silica gel column chromatography to yield 400 mg (0.98 mmol, 47%) of (1S,3R)-2-(bicyclo[1.1.1]pentan-1-yl)-1-(5-bromopyridin-2-yl)-3-methyl-2,3,4,9-tetrahydro-1H-pyrido[3,4-b]indole. MS (ESI) m/z 408.40 [M+H]$^+$; $^1$H NMR (400 MHz, CDCl$_3$) δ 8.56 (d, J=2.0 Hz, 1H), 7.98 (s, 1H), 7.69-7.66 (dd, J=8.4, 2.4 Hz, 1H), 7.49-7.47 (m, 2H), 7.24-7.22 (m, 1H), 7.12-7.05 (m, 2H), 5.07 (s, 1H), 3.67-3.69 (m, 1H), 3.51 (d, J=6.0 Hz, 1H), 3.12-3.06 (dd, J=8.4, 2.0 Hz, 1H), 2.66 (d, J=7.6 Hz, 1H), 2.28 (s, 1H), 1.81 (d, J=8.4 Hz, 3H), 1.63 (d, J=7.6 Hz, 3H), 1.18 (d, J=6.4 Hz, 3H).

Step 2: To a solution of (1S,3R)-2-(bicyclo[1.1.1]pentan-1-yl)-1-(5-bromopyridin-2-yl)-3-methyl-2,3,4,9-tetrahydro-1H-pyrido[3,4-b]indole (400 mg, 0.98 mmol) in 1,4-dioxane (10 mL) were added 1-(3-fluoropropyl)azetidin-3-amine (194 mg, 1.47 mmol), NaOt-Bu (188.2 mg, 1.96 mmol) and reaction mixture was degassed under argon for 30 min. Next Brettphos-3rd gen precatalyst (44.39 mg, 0.05 mmol) was added and the reaction mixture was again degassed for 30 min. It was then heated to 110° C. for 16 h. After completion of the reaction, it was cooled to room temperature and filtered through a bed of celite. The filtrate was diluted with water (50 mL) and extracted with EtOAc (2×50 mL). The combined organic layer was collected, dried over Na$_2$SO$_4$, filtered and evaporated. The crude product was purified by RP prep-HPLC to yield 112.8 mg (0.24 mmol, 25%) of 6-((1S,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyridin-3-amine (Compound 2). MS (ESI) m/z 460.57 [M+H]$^+$; $^1$H NMR (400 MHz, DMSO-d$_6$) δ 10.16 (s, 1H), 7.82 (d, J=2.4 Hz, 1H), 7.35 (d, J=7.2 Hz, 1H), 7.17 (d, J=7.6 Hz, 1H), 6.97-6.88 (m, 3H), 6.80-6.77 (dd, J=8.4, 2.4 Hz, 1H), 6.19 (d, J=7.2 Hz, 1H), 4.86 (s, 1H), 4.50 (t, J=6.0 Hz, 1H), 4.39 (t, J=6.0 Hz, 1H), 3.97-3.92 (m, 1H), 3.68 (br, 2H), 3.52 (br, 1H), 2.96-2.92 (dd, J=7.2, 2.0 Hz, 1H), 2.75 (q, 2H), 2.61-2.44 (m, 3H), 2.20 (s, 1H), 1.73 (d, J=8.4 Hz, 3H), 1.71-1.61 (m, 2H), 1.50 (d, J=7.2 Hz, 3H), 1.08 (d, J=7.6 Hz, 3H).

Example 3

(1S,3R)-2-(bicyclo[1.1.1]pentan-1-yl)-1-(5-((1-(3-fluoropropyl)azetidin-3-yl)oxy)pyridin-2-yl)-3-methyl-2,3,4,9-tetrahydro-1H-pyrido[3,4-b]indole (Compound 3)

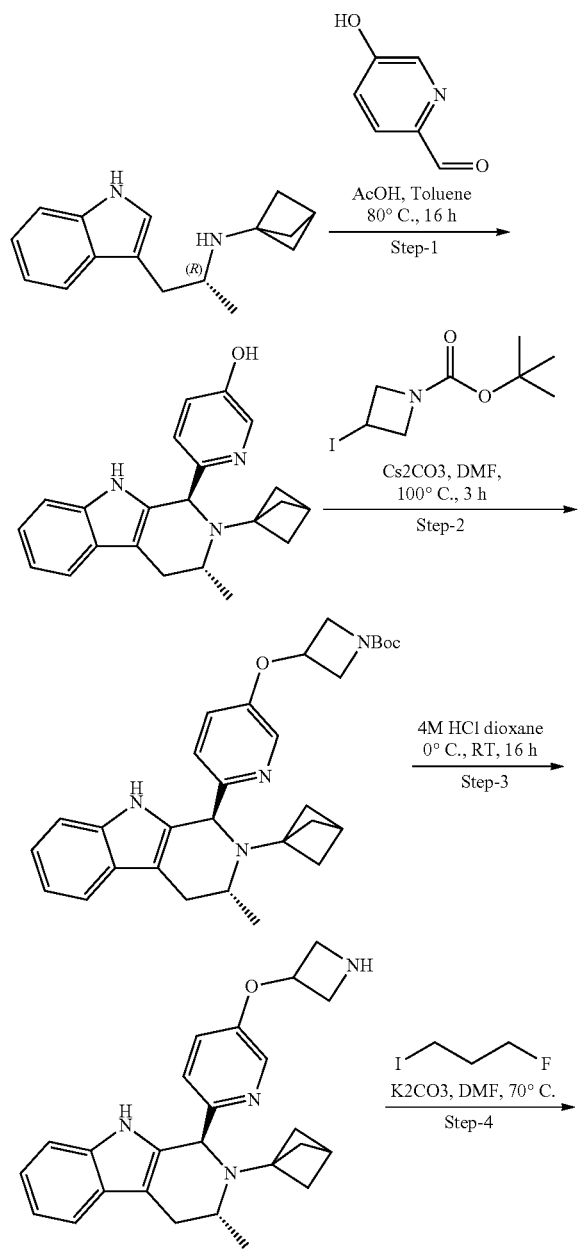

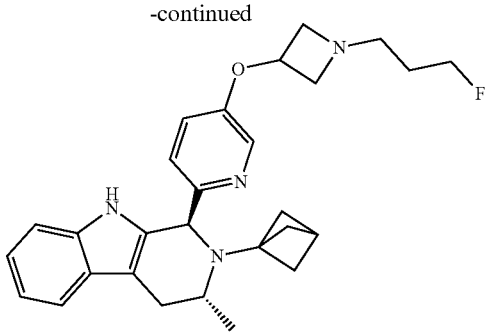

Step 1: To a stirred solution of (R)—N-(1-(1H-indol-3-yl)propan-2-yl)bicyclo[1.1.1]pentan-1-amine (1 gm, 4.16 mmol) in toluene (10 mL) were added 5-hydroxypicolinaldehyde (561.38 mg, 4.56 mmol) followed by AcOH (0.36 mL, 6.24 mmol) and the resulting reaction mixture was stirred at 80° C. for 16 h. After completion of the reaction, it was cooled to room temperature. The reaction mixture was diluted with water (50 mL) and extracted with EtOAc (2×50 mL). The combined organic layer was collected, dried over $Na_2SO_4$, filtered and evaporated. The crude product was purified by silica gel column chromatography to yield 220 mg (0.63 mmol, 15%) of 6-((1S,3R)-2-(bicyclo[1.1.1]pentan-1-yl)-3-methyl-2,3,4,9-tetrahydro-1H-pyrido[3,4-b]indol-1-yl)pyridin-3-ol. MS (ESI) m/z 345.42 [M+H]$^+$; $^1$H NMR (400 MHz, $CDCl_3$) δ 7.50-7.48 (m, 1H), 7.25-7.15 (m, 3H), 7.10-7.05 (m, 2H), 6.74 (d, J=8.4 Hz, 2H), 4.82 (s, 1H), 3.67-3.63 (m, 1H), 3.49 (s, 1H), 3.14-3.09 (m, 1H), 2.62-2.58 (m, 1H), 2.21 (s, 1H), 1.83-1.76 (m, 3H), 1.59-1.57 (m, 5H), 1.22 (d, J=3.6 Hz, 3H).

Step 2: To a solution of 6-((1S,3R)-2-(bicyclo[1.1.1]pentan-1-yl)-3-methyl-2,3,4,9-tetrahydro-1H-pyrido[3,4-b]indol-1-yl)pyridin-3-ol (220 mg, 0.63 mmol) in DMF (4 mL) were added tert-butyl 3-iodoazetidine-1-carboxylate (216.35 mg, 0.76 mmol), $Cs_2CO_3$ (307.89 mg, 0.94 mmol) at room temperature. It was then heated to 100° C. for 3 h. After completion of the reaction, it was cooled to room temperature. The reaction was diluted with water (30 mL) and extracted with EtOAc (2×30 mL). The combined organic layer was collected, dried over $Na_2SO_4$, filtered and evaporated. The crude product was purified by silica gel column chromatography to yield 155 mg (0.31 mmol, 49%) of tert-butyl 3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)oxy)azetidine-1-carboxylate. MS (ESI) m/z 501.55 [M+H]$^+$; $^1$H NMR (400 MHz, DMSO-$d_6$) δ 10.2 (s, 1H), 8.14 (d, J=2.4 Hz, 1H), 7.38 (d, J=7.6 Hz, 1H), 7.24-7.18 (m, 3H), 6.99-6.90 (m, 2H), 5.74 (s, 1H), 5.05-4.97 (m, 2H), 4.30 (s, 2H), 4.19-4.15 (m, 1H), 3.82-3.78 (m, 3H), 3.27-3.16 (m, 2H), 2.99-2.94 (m, 2H), 2.61-2.58 (m, 2H), 2.21 (s, 1H), 1.72 (d, J=8.8 Hz, 3H), 1.51 (d, J=9.2 Hz, 3H), 1.38 (s, 9H), 1.21 (s, 2H), 1.11 (d, J=3.6 Hz, 3H).

Step 3: To a solution of tert-butyl 3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)oxy)azetidine-1-carboxylate (155 mg, 0.31 mmol) in 1,4-dioxane (2 mL) were added 4M HCl in 1,4-dioxane (2 ml) at 0° C. It was then stirred at room temperature for 16 h. After completion of the reaction, it was directly evaporated. The crude product was triturated with diethyl ether to yield 200 mg (0.49 mmol, quantitative yield) of (1S,3R)-1-(5-(azetidin-3-yloxy)pyridin-2-yl)-2-(bicyclo[1.1.1]pentan-1-yl)-3-methyl-2,3,4,9-tetrahydro-1H-pyrido[3,4-b]indole. MS (ESI) m/z 403.79

[M+H]⁺; ¹H NMR (400 MHz, DMSO-d₆) δ 10.7 (s, 1H), 9.78-9.61 (m, 2H), 8.31 (d, J=2.4 Hz, 1H), 7.86 (s, 1H), 7.55 (d, J=6.8 Hz, 1H), 7.48 (d, J=7.6 Hz, 1H), 7.25 (d, J=8 Hz, 1H), 7.09 (t, J=7.2 Hz, 1H), 7.01 (t, J=7.2 Hz, 1H), 5.96 (s, 1H), 5.21 (m, 1H), 4.47 (m, 2H), 4.24 (s, 2H), 3.56 (s, 2H), 3.40-3.30 (m, 3H), 2.87 (d, J=15.6 Hz, 1H), 2.21-2.07 (m, 4H), 1.81 (s, 3H), 1.47 (d, J=5.6 Hz, 3H), 1.09 (t, J=6.8 Hz, 3H).

Step 4: To a solution of (1S,3R)-1-(5-(azetidin-3-yloxy)pyridin-2-yl)-2-(bicyclo[1.1.1]pentan-1-yl)-3-methyl-2,3,4,9-tetrahydro-1H-pyrido[3,4-b]indole (200 mg, 0.49 mmol) in DMF (3 mL) were added 1-fluoro-3-iodopropane (103.25 mg, 0.54 mmol), and K₂CO₃ (203 mg, 1.49 mmol) at room temperature. The reaction mixture was stirred for 16 h at 70° C. After completion of the reaction, it was cooled to room temperature. The reaction was diluted with water (5 mL) and extracted with EtOAc (2×15 mL). The combined organic layer was collected, dried over Na₂SO₄, filtered and evaporated. The crude product was purified by RP prep-HPLC to yield 62 mg (0.13 mmol, 27%) of (1S,3R)-2-(bicyclo[1.1.1]pentan-1-yl)-1-(5-((1-(3-fluoropropyl)azetidin-3-yl)oxy)pyridin-2-yl)-3-methyl-2,3,4,9-tetrahydro-1H-pyrido[3,4-b]indole (Compound 3). MS (ESI) m/z 461.42 [M+H]⁺; ¹H NMR (400 MHz, DMSO-d₆) δ 10.2 (s, 1H), 8.14 (d, J=2.4 Hz, 1H), 7.37 (d, J=7.6 Hz, 1H), 7.21-7.15 (m, 3H), 6.98-6.89 (m, 2H), 4.96 (s, 1H), 4.83 (m, 1H), 4.50 (t, J=6 Hz, 1H), 4.39 (t, J=6 Hz, 1H), 3.72-3.73 (m, 2H), 3.57-3.54 (m, 1H), 2.97-2.93 (m, 3H), 2.61-2.56 (m, 3H), 2.21 (s, 1H), 1.73-1.52 (m, 5H), 1.51 (d, J=9.2 Hz, 3H), 1.30 (d, J=9.2 Hz, 3H).

Example 4

3-(3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)amino)azetidin-1-yl)propanenitrile (Compound 4)

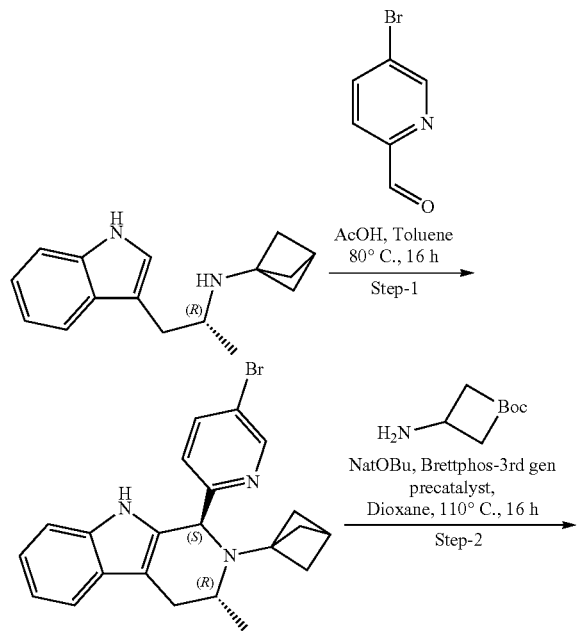

Step 1: To a stirred solution of (R)—N-(1-(1H-indol-3-yl)propan-2-yl)bicyclo[1.1.1]pentan-1-amine (5 g, 20.82 mmol) in toluene (50 mL) were added 5-bromopicolinaldehyde (3.75 g, 22.84 mmol) followed by AcOH (1.8 mL, 16.24 mmol). The resulting mixture was stirred at 80° C. for 16 h. After completion of the reaction, reaction mixture was cooled to room temperature. The reaction mixture was diluted with water (100 mL) and extracted with EtOAc (2×100 mL). The combined organic layers were dried over Na₂SO₄, filtered and evaporated. The crude product was purified by silica gel column chromatography by eluting with 10-20% ethyl acetate in pet.ether to afford (1S,3R)-2-(bicyclo[1.1.1]pentan-1-yl)-1-(5-bromopyridin-2-yl)-3-methyl-2,3,4,9-tetrahydro-1H-pyrido[3,4-b]indole (4.3 g, 10.53 mmol, 50%). MS (ESI) m/z 408.3 [M+H]⁺. ¹H NMR (400 MHz, DMSO-d₆) δ 10.3 (s, 1H), 8.67 (d, J=2 Hz, 1H), 7.92-7.89 (dd, J=6.8, 2.4 Hz, 1H). 7.38 (d, J=7.2 Hz, 1H), 7.29 (d, J=8.4 Hz, 1H), 7.15 (d, J=8.0 Hz, 1H), 6.98-6.92 (m, 2H), 4.98 (s, 1H), 4.01-3.96 (m, 1H), 3.58-3.59 (m, 1H), 3.16 (d, J=5.6 Hz, 2H), 3.02-2.97 (dd, J=14 HZ, 1H), 2.63-2.57 (m, 1H), 2.23 (s, 1H). 1.74 (d, J=8.4 Hz, 3H), 1.51 (d, J=9.2 Hz, 3H), 1.01 (d, J=6.4 Hz, 3H).

Step 2: To a solution of (1S,3R)-2-(bicyclo[1.1.1]pentan-1-yl)-1-(5-bromopyridin-2-yl)-3-methyl-2,3,4,9-tetrahydro-1H-pyrido[3,4-b]indole (4.3 g, 10.53 mmol) in dioxane (45 mL) were added NaO'Bu (4.0 g, 41.62 mmol), Boc azetidine (1.82 g, 10.59 mmol), Brettphos-3rd gen precatalyst (289.3 mg, 0.31 mmol) and the reaction mixture was degassed using argon for 15 min. The reaction mixture was heated at 110° C. for 16 h. After completion of the reaction, it cooled to room temperature. The reaction was filtered through celite pad. The filtrate was collected, dried over Na$_2$SO$_4$, filtered and evaporated to afford tert-butyl 3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)amino)azetidine-1-carboxylate (1.1 g, 2.20 mmol, 20%). MS (ESI) m/z 500.54 [M+H]$^+$; $^1$H NMR (400 MHz, DMSO-d$_6$) δ 10.17 (s, 1H), 7.82 (d, J=2.4 Hz, 1H), 7.36 (d, J=7.6 Hz, 1H), 7.18 (d, J=7.6 Hz, 1H), 6.97-6.88 (m, 3H), 6.80-6.78 (dd, J=2.8, 8.8 Hz, 1H), 6.41 (d, J=5.6 Hz, 1H), 4.88 (s, 1H), 4.16-4.02 (m, 3H), 3.61-3.54 (m, 3H), 2.93 (dd, J=4.0, 6.8 Hz, 1H), 2.48 (dd, J=4.0, 6.8 Hz, 1H), 2.20 (s, 1H), 1.73 (d, J=8.4 Hz, 3H), 1.52 (d, J=9.2 Hz, 3H), 1.48 (s, 9H), 1.50 (d, J=6.8 Hz, 3H).

Step 3: To a stirred solution of tert-butyl 3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)amino)azetidine-1-carboxylate (1.1 g, 2.20 mmol) in dioxane (10 mL) were added 4M HCl in dioxane (15 ml, 5.56 mmol) dropwise at 0° C. The reaction mixture was stirred at room temperature for 16 h. After completion of the reaction, the reaction mixture was evaporated and washed with diethyl ether (25 mL) followed by pentane (25 mL) to afford N-(azetidin-3-yl)-6-((1S,3R)-2-(bicyclo[1.1.1]pentan-1-yl)-3-methyl-2,3,4,9-tetrahydro-1H-pyrido[3,4-b]indol-1-yl)pyridin-3-amine (1.5 g, 3.44 mmol, quantitative yield). MS (ESI) m/z 400.30 [M+H]$^+$.

Step 4: To a stirred solution of 3-(3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)amino)azetidin-1-yl)propanenitrile (0.45 g, 1.12 mmol) in DMF (10 mL) were added 3-iodopropanenitrile (0.22 g, 1.23 mmol) followed by DIPEA (1.9 g, 13.92 mmol). Then the resulting reaction mixture was stirred at room temperature for 16 h. After completion of the reaction, reaction mixture was diluted with cold water (50 mL) and extracted with EtOAc (2×50 mL). The combined organic layers were dried over Na$_2$SO$_4$, filtered and evaporated. The crude product was purified by RP prep-HPLC to afford 3-(3-((6-((1S,3R)-2-(bicyclo[1.1.1]pentan-1-yl)-3-methyl-2,3,4,9-tetrahydro-1H-pyrido[3,4-b]indol-1-yl)pyridin-3-yl)amino)azetidin-1-yl)propanenitrile (Compound 4) (133.2 mg, 0.29 mmol, 22%). MS (ESI) m/z 453.85 [M+H]$^+$, $^1$H NMR (400 MHz, DMSO-d$_6$) δ 10.34 (s, 1H), 7.82 (d, J=2.4 Hz, 1H), 7.35 (d, J=7.6 Hz, 1H), 7.17 (d, J=7.6 Hz, 1H), 6.97-6.88 (m, 3H), 6.81-6.78 (dd, J=2.4, 7.6 Hz, 1H), 6.21 (d, J=6.8 Hz, 1H), 4.86 (s, 1H), 4.01-3.96 (m, 1H), 3.67-3.7 (m, 2H), 3.57-3.53 (m, 1H), 2.96-2.92 (dd, J=4, 6.8 Hz, 1H), 2.85-2.81 (m, 2H), 2.63-2.54 (m, 5H), 2.20 (s, 1H), 1.72 (d, J=8.4 Hz, 3H), 1.52 (d, J=9.2 Hz, 3H), 1.09 (d, J=6.8 Hz, 3H).

Intermediate 2

1-(3-fluoropropyl)pyrrolidin-3-ol

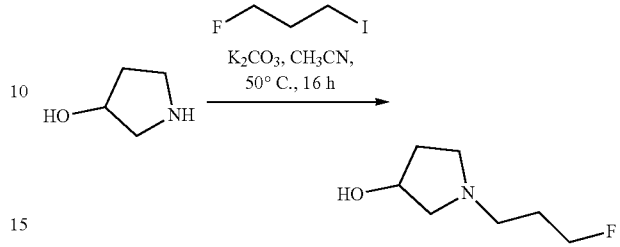

To a stirred solution of pyrrolidin-3-ol (5.0 g, 57.39 mmol) in acetonitrile (50 mL) were added potassium carbonate (23.8 g, 172.17 mmol) followed by 1-fluoro-3-iodopropane (9.7 g, 68.86 mmol), and the resulting reaction mixture was stirred at 50° C. for 16 h. The reaction mixture was diluted with water (50 mL) and extracted with EtOAc (2×50 mL). The combined organic layers were dried over Na$_2$SO$_4$, filtered and evaporated. The crude product was purified by silica gel column chromatography by eluting with 40-45% EtOAc in pet ether to afford 1-(3-fluoropropyl)pyrrolidin-3-ol (3.8 g, 25.81 mmol, 52% yield). $^1$H NMR (400 MHz, DMSO-d$_6$) δ 4.66-4.64 (m, 1H), 4.53 (t, J=6 Hz, 1H), 4.41 (t, J=6.0 Hz, 1H), 4.19-4.16 (m, 1H), 2.71-2.67 (m, 1H), 2.54-2.50 (m, 1H), 2.47-2.41 (m, 3H), 2.29-2.26 (m, 1H), 1.99-1.94 (m, 1H), 1.83-1.73 (m, 2H), 1.54-1.52 (m, 1H.)

Example 5

(1R,3R)-2-(bicyclo[1.1.1]pentan-1-yl)-1-(2,6-difluoro-4-(((S)-1-(3-fluoropropyl)pyrrolidin-3-yl)oxy)phenyl)-3-methyl-2,3,4,9-tetrahydro-1H-pyrido[3,4-b]indole (Compound 5)

Example 6

(1R,3R)-2-(bicyclo[1.1.1]pentan-1-yl)-1-(2,6-difluoro-4-(((R)-1-(3-fluoropropyl)pyrrolidin-3-yl)oxy)phenyl)-3-methyl-2,3,4,9-tetrahydro-1H-pyrido[3,4-b]indole (Compound 6)

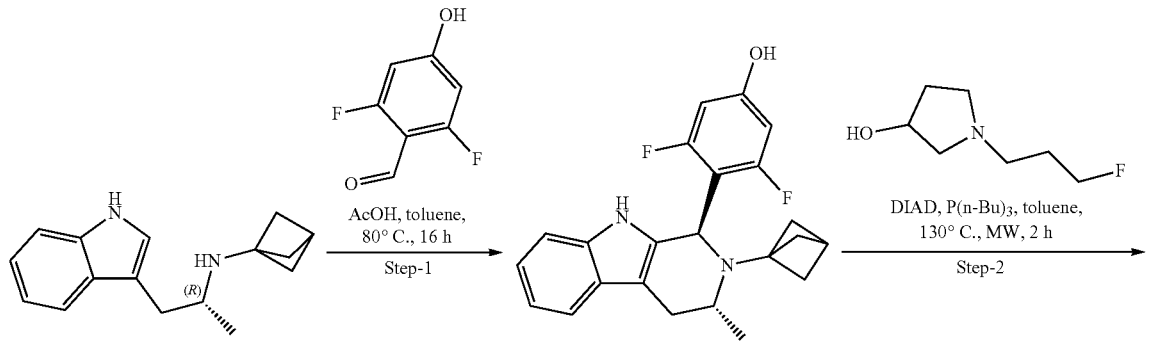

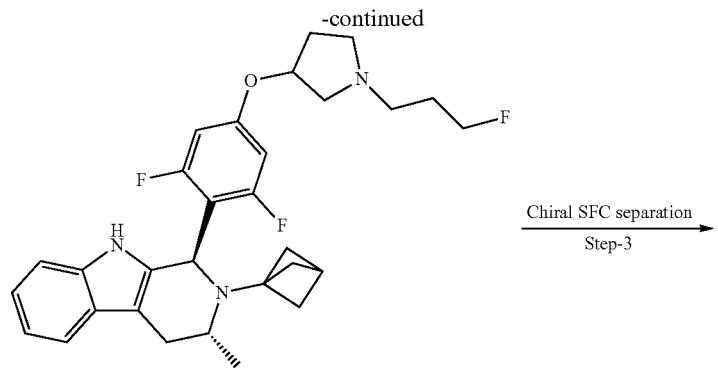

Chiral SFC separation
Step-3

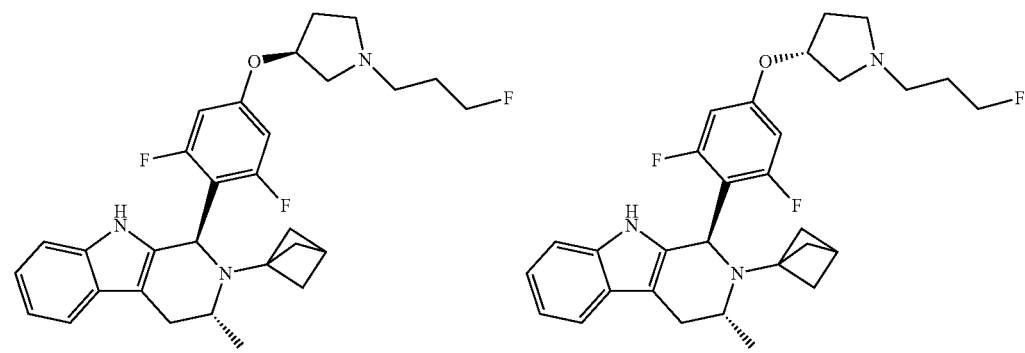

Step 1: To a stirred solution of (R)—N-(1-(1H-indol-3-yl)propan-2-yl)bicyclo[1.1.1]pentan-1-amine (1 g, 4.16 mmol) in toluene (10 mL) were added 2,6-difluoro-4-hydroxybenzaldehyde (1.01 g, 4.58 mmol) followed by AcOH (0.36 mL, 6.24 mmol), and the resulting reaction mixture was stirred at 80° C. for 16 h. After completion of the reaction, reaction mixture was cooled to room temperature, diluted with water (50 mL) and extracted with EtOAc (2×50 mL). The combined organic layers were dried over $Na_2SO_4$, filtered and evaporated to get semi-pure crude. Thus obtained crude product was purified by silica gel column chromatography by eluting with 10-15% EtOAc in pet ether to afford 4-((1R,3R)-2-(bicyclo[1.1.1]pentan-1-yl)-3-methyl-2,3,4,9-tetrahydro-1H-pyrido[3,4-b]indol-1-yl)-3,5-difluorophenol (1.0 g, 2.63 mmol, 63% yield). MS (ESI) m/z 381.41 [M+H]$^+$; $^1$H NMR (400 MHz, CDCl$_3$) δ 7.49 (s, 2H), 7.26-7.09 (m, 3H), 6.27 (d, J=10.0 Hz, 1H), 5.34 (s, 1H), 3.73 (br, s, 1H), 3.48 (s, 1H), 3.13-3.08 (m, 1H), 2.65-2.59 (m, 1H), 2.26 (s, 1H), 1.87 (d, J=8.8 Hz, 3H), 1.68 (d, J=9.2 Hz, 3H), 1.26 (s, 1H), 1.18 (d, J=6.4 Hz, 3H).

Step 2: To a solution of 4-((1R,3R)-2-(bicyclo[1.1.1]pentan-1-yl)-3-methyl-2,3,4,9-tetrahydro-1H-pyrido[3,4-b]indol-1-yl)-3,5-difluorophenol (1.2 g, 3.15 mmol) in toluene (12 mL) were added 1-(3-fluoropropyl)pyrrolidin-3-ol (557.08 mg, 3.78 mmol), tri-n-butylphosphine (1.27 g, 6.31 mmol) and diisopropyl azodicarboxylate (1.24 mL, 6.31 mmol) at 0° C. The resulting reaction mixture was then heated to 130° C. and stirred for 2 h under microwave irradiation. After completion of the reaction, the reaction mixture was cooled to room temperature and filtered through a bed of celite. The filtrate was diluted with water (15 mL) and extracted with EtOAc (2×15 mL). The combined organic layer was collected, dried over $Na_2SO_4$, filtered and evaporated. The crude product was purified by RP prep-HPLC to afford (1R,3R)-2-(bicyclo[1.1.1]pentan-1-yl)-1-(2,6-difluoro-4-((1-(3-fluoropropyl)pyrrolidin-3-yl)oxy)phenyl)-3-methyl-2,3,4,9-tetrahydro-1H-pyrido[3,4-b]indole (240 mg, 0.47 mmol, 15%). MS (ESI) m/z 510.46 [M+H]$^+$; $^1$H NMR (400 MHz, DMSO-d$_6$) δ 10.52 (s, 1H), 7.36 (d, J=7.6 Hz, 1H), 7.17 (d, J=8.0 Hz, 1H), 6.99-6.90 (m, 2H), 6.59 (d, J=11.2 Hz, 2H), 5.23 (s, 1H), 4.88 (s, 1H), 4.55-4.51 (m, 1H), 4.43-4.4 (m, 1H), 3.59-3.58 (m, 1H), 2.94-2.90 (m, 1H), 2.83-2.80 (m, 1H), 2.70-2.60 (m, 3H), 2.38-2.24 (m, 3H), 1.85-1.75 (m, 6H), 1.57 (d, J=9.2 Hz, 3H), 1.07 (d, J=6.8 Hz, 3H).

Step 3: (1R,3R)-2-(bicyclo[1.1.1]pentan-1-yl)-1-(2,6-difluoro-4-((1-(3-fluoropropyl)pyrrolidin-3-yl)oxy)phenyl)-3-methyl-2,3,4,9-tetrahydro-1H-pyrido[3,4-b]indole (240 mg, 0.47 mmol,) was purified by chiral SFC to afford Peak 1 (Compound 5, 80 mg) and Peak 2 (Compound 6, 75 mg). Compound 5: MS (ESI) m/z 510.56 [M+H]$^+$; $^1$H NMR (400 MHz, DMSO-d$_6$) δ 10.47 (s, 1H), 7.36 (d, J=7.6 Hz, 1H), 7.18 (d, J=8 Hz, 1H), 6.90-6.99 (m, 2H), 6.59 (d, J=11.2 Hz, 2H), 5.23 (s, 1H), 4.86 (s, 1H), 4.55-4.52 (m, 1H), 4.40-4.43 (m, 1H), 3.60 (s, 1H), 2.90-2.94 (m, 1H), 2.83-2.80 (m, 1H), 2.79-2.67 (m, 3H), 2.49-2.47 (m, 2H), 2.42-2.24 (m, 3H), 1.85-1.78 (m, 6H), 1.75 (d, J=7.6 Hz, 3H), 1.07 (d, J=6.4 Hz, 3H). Compound 6: MS (ESI) m/z 510.56 [M+H]$^+$; $^1$H NMR (400 MHz, DMSO-d$_6$) δ 10.47 (s, 1H), 7.38 (d, J=7.6 Hz, 1H), 7.17 (d, J=7.6 Hz, 1H), 6.90-6.99 (m, 2H), 6.59 (d, J=11.2 Hz, 2H), 5.23 (s, 1H), 4.88 (s, 1H), 4.52-4.55 (m, 1H), 4.40-4.43 (m, 1H), 3.59 (s, 1H), 2.91-2.96 (m, 1H), 2.84-2.82 (m, 1H), 2.71-2.82 (m, 2H), 2.50-2.48 (m, 3H), 2.40-2.25 (m, 3H), 1.87-1.72 (m, 6H), 1.58 (d, J=9.4 Hz, 3H), 1.07 (d, J=6.4 Hz, 3H). The absolute stereochemistry was arbitrarily assigned for Compound 5 and Compound 6.

Example 7

(1R,3R)-2-(bicyclo[1.1.1]pentan-1-yl)-1-(4-(((R)-1-(3-fluoropropyl)pyrrolidin-3-yl)oxy)phenyl)-3-methyl-2,3,4,9-tetrahydro-1H-pyrido[3,4-b]indole (Compound 7)

Example 8

(1R,3R)-2-(bicyclo[1.1.1]pentan-1-yl)-1-(4-(((S)-1-(3-fluoropropyl)pyrrolidin-3-yl)oxy)phenyl)-3-methyl-2,3,4,9-tetrahydro-1H-pyrido[3,4-b]indole (Compound 8)

Example 9

(1R,3R)-2-(bicyclo[1.1.1]pentan-1-yl)-1-(6-(((R)-1-(3-fluoropropyl)pyrrolidin-3-yl)oxy)pyridin-3-yl)-3-methyl-2,3,4,9-tetrahydro-1H-pyrido[3,4-b]indole (Compound 9)

Example 10

(1R,3R)-2-(bicyclo[1.1.1]pentan-1-yl)-1-(6-(((S)-1-(3-fluoropropyl)pyrrolidin-3-yl)oxy)pyridin-3-yl)-3-methyl-2,3,4,9-tetrahydro-1H-pyrido[3,4-b]indole (Compound 10)

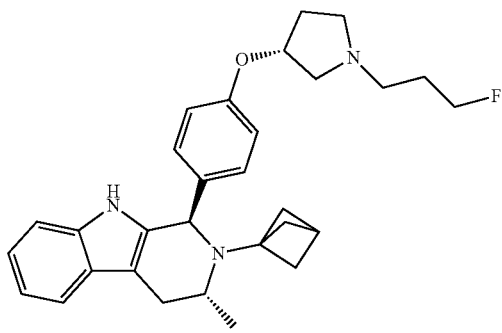

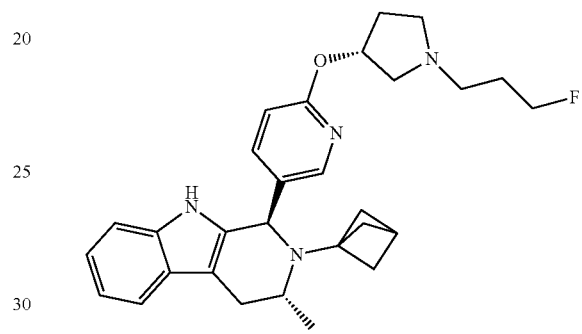

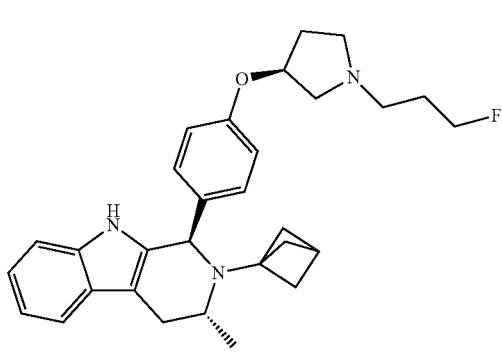

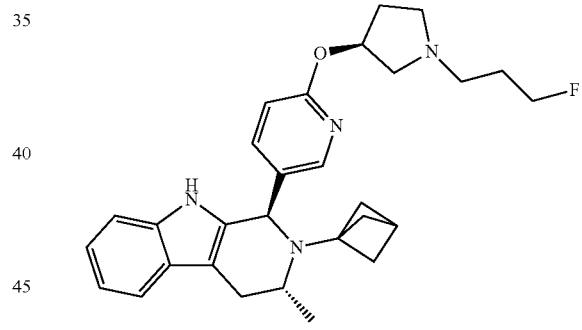

Compounds 7 and 8 were prepared following a procedure analogous to that described for Examples 5 and 6 above. Compound 7: MS (ESI) m/z 474.58 [M+H]$^+$; 1H NMR (400 MHz, DMSO-d$_6$) δ 10.29 (s, 1H), 7.42 (d, J=7.6 Hz, 1H), 7.21 (d, J=8.4 Hz, 3H), 7.04-6.95 (m, 2H), 6.82 (d, J=8.4 Hz, 2H), 4.87 (s, 1H), 4.84 (s, 1H), 4.54-4.40 (dt, J1=12 Hz, J2=5.6 Hz, 2H), 3.58-3.45 (m, 1H), 3.01-2.91 (m, 2H), 2.72-2.60 (m, 3H), 2.52-2.48 (m, 3H), 2.28-2.21 (m, 2H), 1.87-1.73 (m, 6H), 1.56 (d, J=9.2 Hz, 3H), 1.10 (d, J=6.8 Hz, 3H). Compound 8: MS (ESI) m/z 474.58 [M+H]$^+$; $^1$H NMR (400 MHz, DMSO-d$_6$) δ 10.3 (s, 1H), 7.37 (d, J=7.6 Hz, 1H), 7.18 (t, J=8.4 Hz, 3H), 6.99-6.90 (m, 2H), 6.79 (d, J=8.4 Hz, 2H), 4.87 (s, 1H), 4.81 (s, 1H), 4.54-4.40 (m, 2H), 3.45-3.31 (m, 1H), 2.98-2.91 (m, 2H), 2.72-2.60 (m, 3H), 2.52-2.48 (m, 3H), 2.20 (s, 2H), 1.83-1.71 (m, 6H), 1.59 (d, J=9.2 Hz, 3H), 1.10 (d, J=6.8 Hz, 3H). The absolute stereochemistry was arbitrarily assigned for Compound 7 and Compound 8.

Compounds 9 and 10 were prepared following a procedure analogous to that described for Examples 5 and 6. Compound 9: MS (ESI) m/z 475.49 [M+H]$^+$; $^1$H NMR (400 MHz, DMSO-d$_6$) δ 10.31 (s, 1H), 8.09 (s, 1H), 7.49 (d, J=8.4 Hz, 1H), 7.38 (d, J=7.6 Hz, 1H), 7.19 (d, J=7.6 Hz, 1H), 7.00-6.90 (m, 2H), 6.69 (d, J=8.4 Hz, 1H), 5.35 (s, 1H), 4.91 (s, 1H), 4.53-4.39 (m, 2H), 3.51-3.49 (m, 1H), 2.94-2.82 (m, 2H), 2.70-2.55 (m, 3H), 2.50-2.41 (m, 3H), 2.27-2.23 (m, 2H), 1.84-1.73 (m, 6H), 1.58 (d, J=9.2 Hz, 3H), 1.01 (d, J=6.4 Hz, 3H). Compound 10: MS (ESI) m/z 475.49 [M+H]$^+$; $^1$H NMR (400 MHz, DMSO-d$_6$) δ 10.31 (s, 1H), 8.09 (s, 1H), 7.49 (d, J=8.4 Hz, 1H), 7.38 (d, J=7.6 Hz, 1H), 7.19 (d, J=7.6 Hz, 1H), 7.00-6.90 (m, 2H), 6.69 (d, J=8.4 Hz, 1H), 5.35 (s, 1H), 4.91 (s, 1H), 4.53-4.39 (m, 2H), 3.51-3.48 (m, 1H), 2.94-2.82 (m, 2H), 2.70-2.55 (m, 3H), 2.50-2.41 (m, 3H), 2.27-2.23 (m, 2H), 1.85-1.73 (m, 6H), 1.58-1.55 (m, 3H), 1.01 (d, J=6.4 Hz, 3H). The absolute stereochemistry was arbitrarily assigned for Compound 9 and Compound 10.

Example 11

(1S,3R)-2-(bicyclo[1.1.1]pentan-1-yl)-1-(5-(((R)-1-(3-fluoropropyl)pyrrolidin-3-yl)oxy)pyridin-2-yl)-3-methyl-2,3,4,9-tetrahydro-1H-pyrido[3,4-b]indole (Compound 11)

Example 12

(1S,3R)-2-(bicyclo[1.1.1]pentan-1-yl)-1-(5-(((S)-1-(3-fluoropropyl)pyrrolidin-3-yl)oxy)pyridin-2-yl)-3-methyl-2,3,4,9-tetrahydro-1H-pyrido[3,4-b]indole (Compound 12)

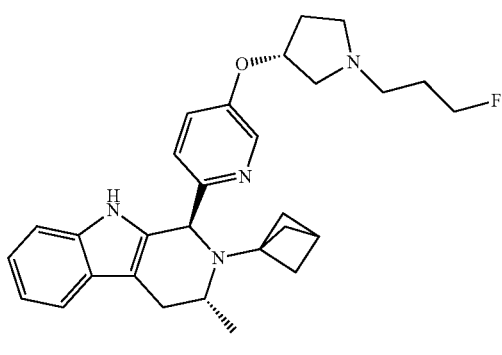

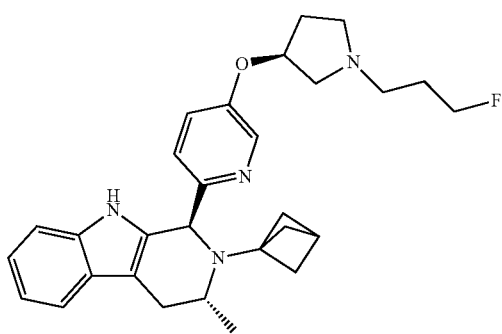

Compounds 11 and 12 were prepared following a procedure analogous to that described for Examples 5 and 6. Compound 11: MS (ESI) m/z 475.49 [M+H]+; 1H NMR (400 MHz, DMSO-d6) δ 10.31 (s, 1H), 8.17 (d, J=2 Hz, 1H), 7.37 (d, J=7.6 Hz, 1H), 7.24-7.17 (m, 3H), 6.98-6.89 (m, 2H), 4.95 (s, 1H), 4.90 (s, 1H), 4.53-4.39 (m, 2H), 3.51-3.49 (m, 1H), 2.94-2.82 (m, 2H), 2.70-2.55 (m, 3H), 2.50-2.41 (m, 3H), 2.27-2.23 (m, 2H), 1.84-1.73 (m, 6H), 1.58 (d, J=9.2 Hz, 3H), 1.01 (d, J=6.4 Hz, 3H). Compound 12: MS (ESI) m/z 475.45 [M+H]+; 1H NMR (400 MHz, DMSO-d6) δ 10.31 (s, 1H), 8.17 (d, J=2 Hz, 1H), 7.37 (d, J=7.6 Hz, 1H), 7.24-7.17 (m, 3H), 6.98-6.89 (m, 2H), 4.95 (s, 1H), 4.90 (s, 1H), 4.54-4.39 (m, 2H), 3.51-3.49 (m, 1H), 2.94-2.82 (m, 2H), 2.70-2.55 (m, 3H), 2.50-2.41 (m, 3H), 2.27-2.23 (m, 2H), 1.84-1.73 (m, 6H), 1.58 (d, J=9.2 Hz, 3H), 1.01 (d, J=6.4 Hz, 3H). The absolute stereochemistry was arbitrarily assigned for Compound 11 and Compound 12.

Example 13

6-((1S,3R)-2-(bicyclo[1.1.1]pentan-1-yl)-3-methyl-2,3,4,9-tetrahydro-1H-pyrido[3,4-b]indol-1-yl)-5-fluoro-N-(1-(3-fluoropropyl)azetidin-3-yl)pyridin-3-amine (Compound 13)

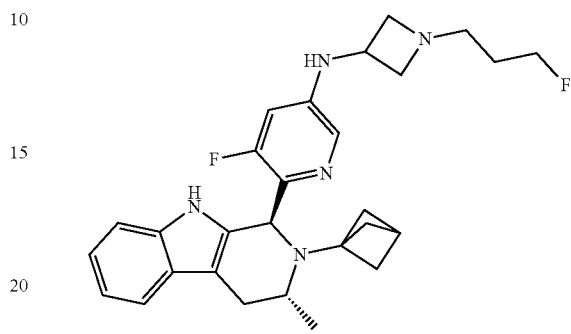

Compound 13 was prepared following a procedure analogous to that described for Example 1. MS (ESI) m/z 478.39 [M+H]+; 1H NMR (400 MHz, DMSO-d6), δ 10.35 (s, 1H), 7.61 (s, 1H), 7.36 (d, J=7.6 Hz, 1H), 7.16 (d, J=8.0 Hz, 1H), 6.98-6.89 (m, 2H), 6.68 (dd, J=12.8 Hz, 2 Hz, 1H), 6.60 (d, J=6.8 Hz, 1H), 5.2 (s, 1H), 4.51 (t, J=6 Hz, 1H), 4.39 (t, J=6 Hz, 1H), 3.95-3.97 (m, 1H), 3.63 (t, J=6.8 Hz, 2H), 3.52-3.54 (m, 1H), 2.72-2.79 (m, 3H), 2.59-2.57 (m, 1H), 2.46-2.44 (m, 2H), 2.23 (s, 1H), 1.75 (d, J=8.4 Hz, 3H), 1.69-1.60 (m, 5H), 1.13 (d, J=7.2 Hz, 3H). 19F NMR (400 MHz, DMSO-d6) δ−124.52 (d, J=12.0 Hz, 1F) −217.68-218.07 (m, 1F).

Example 14

(1S,3R)-2-(bicyclo[1.1.1]pentan-1-yl)-1-(3-fluoro-5-((1-(3-fluoropropyl)azetidin-3-yl)oxy)pyridin-2-yl)-3-methyl-2,3,4,9-tetrahydro-1H-pyrido[3,4-b]indole (Compound 14)

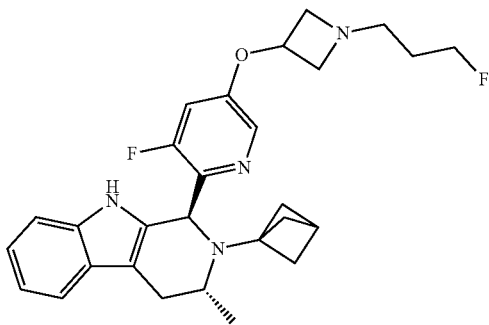 [SMILES: C[C@@H]1Cc2c([nH]c3ccccc23)[C@@H](c2ncc(OC3CN(CCCF)C3)cc2F)N1C12CC(C1)C2]

Compound 14 was prepared following a procedure analogous to that described for Example 3. MS (ESI) m/z 479.45 [M+H]+, 1H NMR (400 MHz, DMSO-d6) δ 10.4 (s, 1H), 7.95 (d, J=2.0 Hz, 1H), 7.38 (d, J=7.6 Hz, 1H), 7.29-7.26 (dd, J=12.0, 2.4 Hz, 1H), 7.17 (d, J=7.6 Hz, 1H), 6.90-7.00 (m, 2H), 5.31 (s, 1H), 4.86 (q, 1H), 4.50 (t, J=6.0 Hz, 1H), 4.39 (t, J=6.0 Hz, 1H), 3.72-3.73 (m, 2H), 3.57-3.54 (m, 1H), 2.97-2.93 (m, 2H), 2.61-2.56 (dd, J=7.6, 1.6 Hz, 1H), 2.52-2.49 (m, 3H), 2.25 (s, 1H), 1.78-1.70 (d, J=9.6 Hz, 3H), 1.69-1.61 (m, 5H), 1.14 (d, 3H).

Example 15

N-(4-((1R,3R)-2-(bicyclo[1.1.1]pentan-1-yl)-3-methyl-2,3,4,9-tetrahydro-1H-pyrido[3,4-b]indol-1-yl)-3-fluorophenyl)-1-(3-fluoropropyl)azetidin-3-amine (Compound 15)

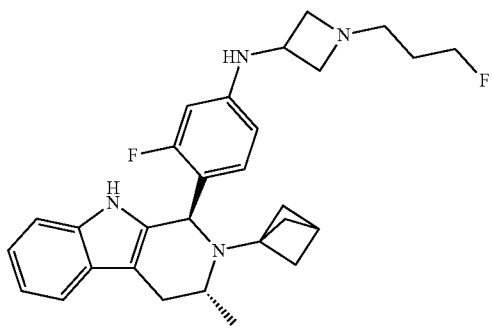 [SMILES: C[C@@H]1Cc2c([nH]c3ccccc23)[C@@H](c2ccc(NC3CN(CCCF)C3)cc2F)N1C12CC(C1)C2]

Compound 15 was prepared following a procedure analogous to that described for Example 1. MS (ESI) m/z 477.4 [M+H]$^+$; $^1$H NMR (400 MHz, DMSO-d$_6$) δ 10.35 (s, 1H), 7.40 (d, J=15.2 Hz, 1H), 7.22 (d, J=19.6 Hz, 1H), 7.032-6.9 (m, 2H), 6.62 (t, J=8.8 Hz, 1H), 6.30-6.15 (m, 3H) 5.14 (s, 1H), 4.50 (t, J=6 Hz, 1H), 4.38 (t, J=6 Hz, 1H), 3.93-3.86 (m, 1H), 3.62 (s, 1H), 3.47-3.44 (m, 1H), 2.89-2.84 (m, 1H), 2.73-2.67 (m, 2H), 2.45 (s, 2H), 2.21 (s, 1H), 1.75-1.59 (m, 8H), 1.23 (d, J=6.4 Hz, 3H), $^{19}$F NMR (400 MHz, DMSO-d$_6$) δ−118.73 (s, 1F), −217.62-218.01 (m, 1F).

Example 16

5-((1S,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyrazin-2-amine (Compound 16)

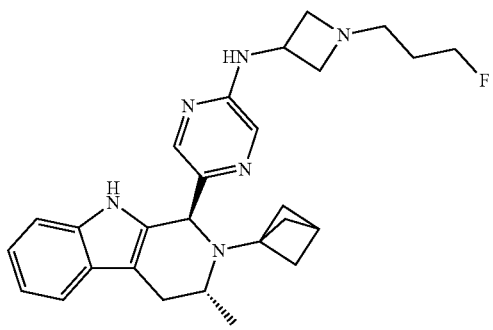 [SMILES: C[C@@H]1Cc2c([nH]c3ccccc23)[C@@H](c2cnc(NC3CN(CCCF)C3)cn2)N1C12CC(C1)C2]

Compound 16 was prepared following a procedure analogous to that described for Example 1. MS (ESI) m/z 461.08 [M+H]$^+$; $^1$H NMR (400 MHz, DMSO-d$_6$) δ 10.03 (s, 1H), 7.83 (d, J=14.8 Hz, 2H), 7.38 (t, J=7.6 Hz, 2H), 7.18 (d, J=8 Hz, 1H), 6.99-6.89 (m, 2H), 4.9 (s, 1H), 4.51-4.37 (m, 2H), 4.31-4.29 (m, 1H), 3.59-3.32 (m, 3H), 2.90-2.81 (m, 1H), 2.79-2.75 (m, 2H), 2.58-2.54 (m, 1H), 2.44-2.5 (m, 2H), 2.23 (s, 1H), 1.75-1.55 (m, 8H), 1.11 (d, J=6.4 Hz, 3H), $^{19}$F NMR (400 MHz, DMSO-d$_6$) δ−218.32-217.93 (m, 1F).

Intermediates 3A, 3B (S)-(3-((1-(1H-indol-3-yl)propan-2-yl)amino)bicyclo[1.1.1]pentan-1-yl)methanol (R)-(3-((1-(1H-indol-3-yl)propan-2-yl)amino)bicyclo[1.1.1]pentan-1-yl)methanol

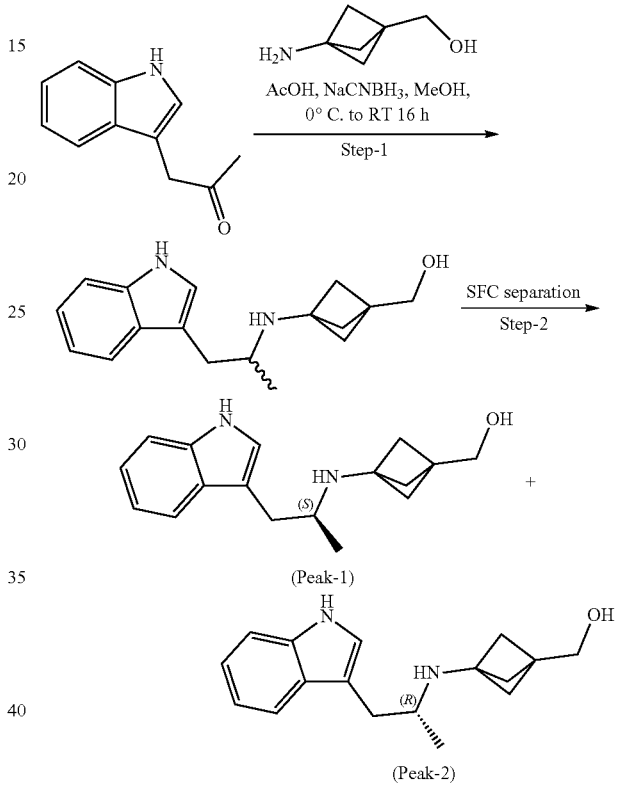

Step 1: To a stirred solution of 1-(1H-indol-3-yl)propan-2-one (6 g, 34.68 mmol) in MeOH (50 mL) was added (3-aminobicyclo[1.1.1]pentan-1-yl)methanol (1.01 g, 4.58 mmol) followed by AcOH (4.35 mL, 69.36 mmol). The reaction mixture was stirred at room temperature for 3 h. Then NaCNBH$_3$ (1.01 g, 4.58 mmol) was added, and reaction mixture was stirred at room temperature for 16 h. After completion of the reaction, the reaction mixture was cooled to room temperature. The reaction mixture was diluted with water (50 mL) and extracted with EtOAc (2×50 mL). The combined organic layers were dried over Na$_2$SO$_4$, filtered and evaporated to get semi-pure crude. Thus obtained crude product was purified by silica gel column chromatography by eluting with 10-15% EtOAc in pet ether to afford (3-((1-(1H-indol-3-yl)propan-2-yl)amino)bicyclo[1.1.1]pentan-1-yl)methanol (5 g 18.5 mmol, 53% yield). MS (ESI) m/z 271.67 [M+H]$^+$; $^1$H NMR (400 MHz, DMSO-d$_6$) δ 10.88 (s, 1H), 7.48 (d, J=7.2 Hz, 1H), 7.31 (d, J=4.0 Hz, 1H), 7.10 (d, J=2.0 Hz, 1H), 7.04 (t, J=16.4 Hz, 1H), 6.94 (t, J=15.8 Hz, 1H), 4.38 (t, J=5.6 Hz, 1H), 4.04 (q, 1H), 3.41 (d, J=8.0 Hz, 1H), 2.98-2.95 (m, 1H), 2.84-2.79 (dd, J=14.0, 5.2 Hz, 1H), 2.55 (m, 1H), 1.61 (m, 5H), 0.94 (d, J=6.4 Hz, 3H).

Step 2: (3-((1-(1H-indol-3-yl)propan-2-yl)amino)bicyclo[1.1.1]pentan-1-yl)methanol (3, racemic) (5 g, 18.55 mmol,) was purified by chiral SFC to afford (S)-(3-((1-(1H-indol-3-yl)propan-2-yl)amino)bicyclo[1.1.1]pentan-1-yl)methanol (Intermediate 3A, peak-1) (2 g, 9.25 mmol, 33% yield) and (R)-(3-((1-(1H-indol-3-yl)propan-2-yl)amino)bicyclo[1.1.1]pentan-1-yl)methanol (Intermediate 3B, peak-2) (2.05 g, 9.27 mmol, 34% yield). Intermediate 3A: MS (ESI) m/z 271.67 [M+H]$^+$; $^1$H NMR (400 MHz, DMSO-d$_6$) δ 10.77 (s, 1H), 7.48 (d, J=7.6 Hz, 1H), 7.32 (d, J=8.0 Hz, 1H), 7.10 (d, J=2.0 Hz, 1H), 7.04 (t, J=7.6 Hz, 1H), 6.98 (t, J=8.4 Hz, 1H), 4.38 (t, J=5.6 Hz, 1H), 4.04 (q, 1H), 3.44 (d, J=5.2 Hz, 2H), 3.17 (d, J=5.2 Hz, 2H), 2.98-2.94 (m, 1H), 2.84-2.79 (dd, J=14.0, 5.2 Hz, 1H), 2.55 (m, 1H), 2.04 (br, 1H) 1.62 (m, 6H), 0.94 (d, J=6.4 Hz, 3H). Intermediate 3B: MS (ESI) m/z 271.67 [M+H]$^+$; $^1$H NMR (400 MHz, DMSO-d$_6$) δ 10.78 (s, 1H), 7.48 (d, J=7.6 Hz, 1H), 7.31 (d, J=8.0 Hz, 1H), 7.10 (d, J=2.0 Hz, 1H), 7.04 (t, J=7.6 Hz, 1H), 6.98 (t, J=8.4 Hz, 1H), 4.38 (t, J=5.6 Hz, 1H), 4.04 (q, 1H), 3.41 (d, J=5.2 Hz, 2H), 3.17 (d, J=5.2 Hz, 2H), 2.98-2.95 (m, 1H), 2.84-2.79 (dd, J=14.0, 5.2 Hz, 1H), 2.55 (m, 1H), 2.04 (br, 1H) 1.61 (m, 6H), 0.94 (d, J=6.4 Hz, 3H). The absolute stereochemistry was arbitrarily assigned for Intermediate 3A and Intermediate 3B.

Example 17

(3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 17)

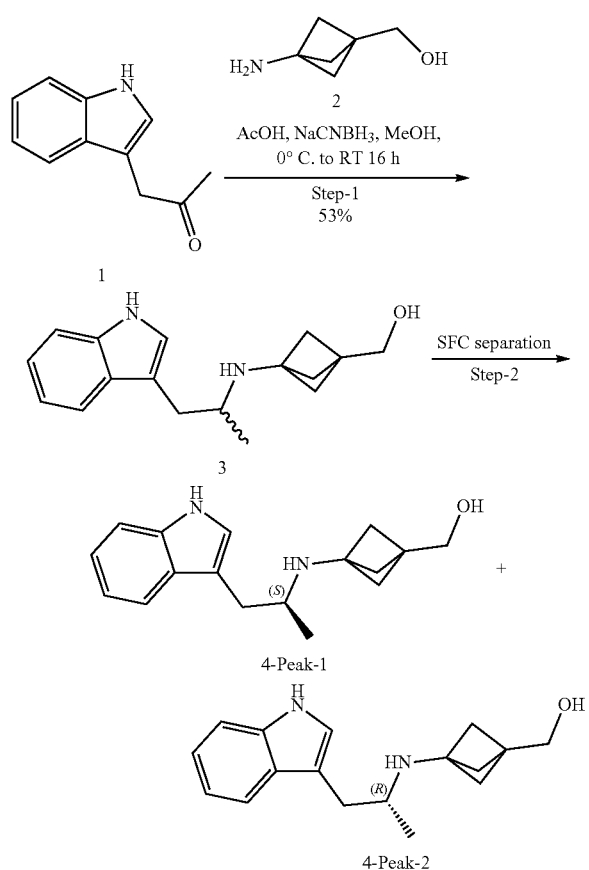

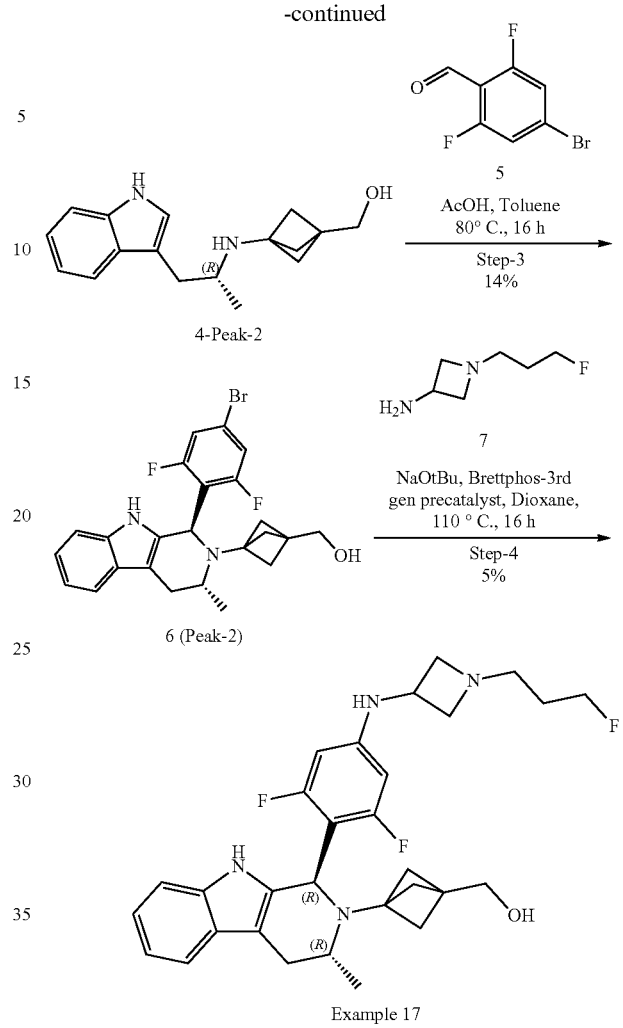

Example 17

Step 1: To a stirred solution of 1-(1H-indol-3-yl)propan-2-one (1) (6 g, 34.68 mmol) in MeOH (60 mL) was added (3-aminobicyclo[1.1.1]pentan-1-yl)methanol (2) (3.95 g, 34.64 mmol) followed by AcOH (4.35 mL, 69.36 mmol), and the reaction mixture was stirred at room temperature for 3 h. NaCNBH$_3$ (4.35 g, 69.22 mmol) was then added and reaction mixture was stirred at room temperature for 16 h. After completion of the reaction, reaction mixture was cooled to room temperature. The reaction mixture was diluted with water (50 mL) and extracted with EtOAc (2×50 mL). The combined organic layers were dried over Na$_2$SO$_4$, filtered and evaporated to get semi-pure crude. Thus obtained crude product was purified by silica gel column chromatography by eluting with 10-15% MeOH in DCM to afford (3-((1-(1H-indol-3-yl)propan-2-yl)amino)bicyclo[1.1.1]pentan-1-yl)methanol (3) (5 g 18.5 mmol, 53% yield). MS (ESI) m/z 271.67 [M+1]$^+$; $^1$H NMR (400 MHz, DMSO-d$_6$) δ 10.88 (s, 1H), 7.48 (d, J=7.2 Hz, 1H), 7.31 (d, J=4.0 Hz, 1H), 7.10 (d, J=2.0 Hz, 1H), 7.04 (t, J=16.4 Hz, 1H), 6.94 (t, J=15.8 Hz, 1H), 4.38 (t, J=5.6 Hz, 1H), 4.04 (q, 1H), 3.41 (d, J=8.0 Hz, 1H), 2.98-2.95 (m, 1H), 2.84-2.79 (dd, J=14.0, 5.2 Hz, 1H), 2.55 (m, 1H), 1.61 (m, 5H), 0.94 (d, J=6.4 Hz, 3H).

Step 2: (3-((1-(1H-indol-3-yl)propan-2-yl)amino)bicyclo[1.1.1]pentan-1-yl)methanol (3, racemic) (5 g, 18.55 mmol,) was purified by chiral SFC to afford (S)-(3-((1-(1H-indol- 3-yl)propan-2-yl)amino)bicyclo[1.1.1]pentan-1-yl)methanol (4 peak-1) (2 g, 9.25 mmol, 33% yield) and (R)-(3-((1-(1H-indol-3-yl)propan-2-yl)amino)bicyclo[1.1.1]pentan-1-yl)methanol (4 peak-2) (2.05 g, 9.27 mmol, 34% yield). 4 peak-1: MS (ESI) m/z 269.43 [M−H]⁻; ¹H NMR (400 MHz, DMSO-d₆) δ 10.77 (s, 1H), 7.48 (d, J=7.6 Hz, 1H), 7.32 (d, J=8.0 Hz, 1H), 7.10 (d, J=2.0 Hz, 1H), 7.04 (t, J=7.6 Hz, 1H), 6.98 (t, J=8.4 Hz, 1H), 4.38 (t, J=5.6 Hz, 1H), 4.04 (q, 1H), 3.44 (d, J=5.2 Hz, 2H), 3.17 (d, J=5.2 Hz, 2H), 2.98-2.94 (m, 1H), 2.84-2.79 (dd, J=14.0, 5.2 Hz, 1H), 2.55 (m, 1H), 2.04 (br, 1H) 1.62 (m, 6H), 0.94 (d, J=6.4 Hz, 3H). 4 peak-2: MS (ESI) m/z 269.38 [M−H]⁻; ¹H NMR (400 MHz, DMSO-d₆) δ 10.78 (s, 1H), 7.48 (d, J=7.6 Hz, 1H), 7.31 (d, J=8.0 Hz, 1H), 7.10 (d, J=2.0 Hz, 1H), 7.04 (t, J=7.6 Hz, 1H), 6.98 (t, J=8.4 Hz, 1H), 4.38 (t, J=5.6 Hz, 1H), 4.04 (q, 1H), 3.41 (d, J=5.2 Hz, 2H), 3.17 (d, J=5.2 Hz, 2H), 2.98-2.95 (m, 1H), 2.84-2.79 (dd, J=14.0, 5.2 Hz, 1H), 2.55 (m, 1H), 2.04 (br, 1H) 1.61 (m, 6H), 0.94 (d, J=6.4 Hz, 3H). The absolute stereochemistry was arbitrarily assigned for Intermediate 4 peak-1 and Intermediate 4 peak-2.

Step 3: To a stirred solution of (3-((1-(1H-indol-3-yl)propan-2-yl)amino)bicyclo[1.1.1]pentan-1-yl)methanol (4 peak-2) (2 g, 18.55 mmol) in toluene 20 mL) was added 4-bromo-2,6-difluorobenzaldehyde (5) (2.05 g, 9.36 mmol) followed by AcOH (0.7 mL, 12.24 mmol). The reaction mixture was stirred at 80° C. for 16 h. After completion of the reaction, the reaction mixture was cooled to room temperature. The reaction mixture was diluted with water (50 mL) and extracted with EtOAc (2×50 mL). The combined organic layers were dried over Na₂SO₄, filtered and evaporated to get semi-pure crude. Thus obtained crude product was purified by silica gel column chromatography by eluting with 10-15% EtOAc in pet ether to afford (3-((1R,3R)-1-(4-bromo-2,6-difluorophenyl)-3-methyl-1,3,4,9-tetrahydro-2H-pyrido[3,4-b]indol-2-yl)bicyclo[1.1.1]pentan-1-yl)methanol (6 peak-2) (500 mg 1.05 mmol, 14.28% yield). MS (ESI) m/z 473.34 [M+1]⁻; ¹H NMR (400 MHz, DMSO-d₆) δ 10.51 (s, 1H), 7.41-7.37 (m, 3H), 7.17 (d, J=8.0 Hz, 1H), 7.01-6.91 (m, 2H), 5.28 (s, 1H), 4.38 (t, J=5.4 Hz, 1H), 3.63 (m, 1H), 3.38 (d, J=6.4 Hz, 2H), 2.98-2.92 (dd, J=6.4, 2.4 Hz, 1H), 2.56-2.53 (m, 3H), 1.63 (d, J=9.2 Hz, 3H), 1.23 (d, J=8.8 Hz, 3H).

Step 4: To a stirred solution of (3-((1R,3R)-1-(4-bromo-2,6-difluorophenyl)-3-methyl-1,3,4,9-tetrahydro-2H-pyrido[3,4-b]indol-2-yl)bicyclo[1.1.1]pentan-1-yl)methanol (6 peak-2) (500 mg, 1.05 mmol) in 1,4-dioxane (10 mL) were added 1-(3-fluoropropyl)azetidin-3-amine (7) (223.6 mg, 1.69 mmol) and NaOt-Bu (188.2 mg, 1.96 mmol), and the reaction mixture was degassed under argon for 30 min. Later Brettphos-3rd gen precatalyst (30.45 mg, 0.03 mmol) was added and the reaction mixture was again degassed for 30 min. It was then heated at 110° C. for 16 h. After completion of the reaction, it was cooled to room temperature and filtered through a bed of celite. The filtrate was diluted with water (50 mL) and extracted with EtOAc (2×50 mL). The combined organic layers were dried over Na₂SO₄, filtered and evaporated. The crude product was purified by RP prep-HPLC to afford (3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 17) (61 mg, 0.11 mmol, 10% yield). MS (ESI) m/z 525.33 [M−H]⁺; ¹H NMR (400 MHz, DMSO-d₆) δ 10.38 (s, 1H), 7.34 (d, J=7.6 Hz, 1H), 7.17 (d, J=7.6 Hz, 1H), 6.98-6.90 (m, 2H), 6.74 (br, 1H), 6.12 (d, J=12.4 Hz, 1H), 5.13 (s, 1H), 4.54 (t, J=5.4 Hz, 1H), 4.49-4.37 (m, 2H), 3.95 (q, 1H), 3.64-3.57 (br, 4H), 3.35-3.31 (m, 2H), 2.94-2.89 (dd, J=6.4, 2.4 Hz, 1H), 1.75 (br, 2H), 1.60 (d, J=8.8 Hz, 3H), 1.44 (d, J=8.8 Hz, 3H), 1.06 (d, J=8.8 Hz, 3H).

Example 18

(3-((1S,3S)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 18)

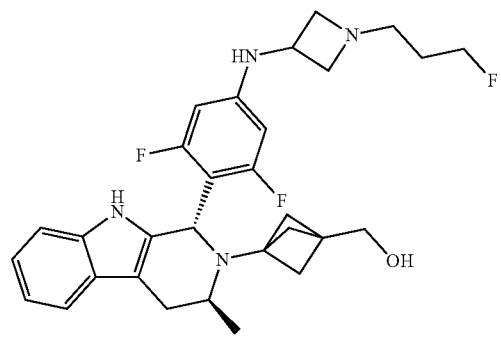 [SMILES: C[C@H]1Cc2c([nH]c3ccccc23)[C@H](c2c(F)cc(NC3CN(CCCF)C3)cc2F)N1C12CC(CO)(C1)C2]

Compound 18 was prepared following a procedure analogous to that described for Example 17 using intermediate 4 peak-1 in step 3. Compound 18: MS (ESI) m/z 525.33 [M+H]⁺; ¹H NMR (400 MHz, DMSO-d₆) δ 10.38 (s, 1H), 7.34 (d, J=7.6 Hz, 1H), 7.17 (d, J=7.6 Hz, 1H), 6.98-6.90 (m, 2H), 6.74 (br, 1H), 6.12 (d, J=12.4 Hz, 1H), 5.13 (s, 1H), 4.54 (t, J=5.4 Hz, 1H), 4.49-4.37 (m, 2H), 3.95 (q, 1H), 3.64-3.57 (br, 4H), 3.35-3.31 (m, 2H), 2.94-2.89 (dd, J=6.4, 2.4 Hz, 1H), 1.75 (br, 2H), 1.60 (d, J=8.8 Hz, 3H), 1.44 (d, J=8.8 Hz, 3H), 1.06 (d, J=8.8 Hz, 3H). The absolute stereochemistry was arbitrarily assigned for Compound 17 and Compound 18.

Intermediate 4

(S)-1-(3-fluoropropyl)pyrrolidin-3-amine

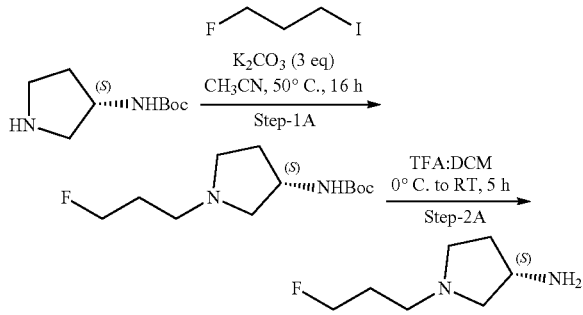

Step 1: To a stirred solution of tert-butyl (S)-pyrrolidin-3-ylcarbamate (2 g, 10.73 mmol) in ACN (20.0 mL) were added K₂CO₃ (4.44 g, 32.19 mmol) and 1-fluoro-3-iodopropane (2.42 g, 12.87 mmol) at RT. The reaction mixture was heated to 50° C. for 16 h. After completion of the reaction, it was diluted with water (50 mL) and extracted with 10% MeOH in DCM (3×50 mL). The organic layer was collected, dried over Na₂SO₄, filtered and evaporated. The crude product was purified by silica gel column chromatography to yield 1.6 g (6.49 mmol, 61%) of tert-butyl (S)-(1-(3-fluoropropyl)pyrrolidin-3-yl)carbamate. ¹H NMR (400 MHz, DMSO-d6) δ 6.95 (d, J=6.0 Hz, 1H), 4.53 (t, J=6.0 Hz, 1H), 4.41 (t, J=6.0 Hz, 1H), 3.89-3.91 (m, 1H), 2.75-2.69 (m, 1H), 2.50-2.46 (m, 2H), 2.27 (s, 1H), 2.03-1.98 (m, 1H), 1.83-1.74 (m, 2H), 1.58-1.55 (m, 1H), 1.45 (s, 9H).

Step 2: To a stirred solution of tert-butyl (S)-(1-(3-fluoropropyl)pyrrolidin-3-yl)carbamate (1.6 g, 6.49 mmol) in DCM (16 mL) was added TFA (4 mL) at 0° C. The reaction mixture was stirred at room temperature for 16 h. After completion of the reaction, it was evaporated, then the residue was dissolved in 10% MeOH in DCM. K₂CO₃ (8.95 g, 64.9 mmol) was then add at 0° C. and the mixture was stirred for 50 min and then filtered. The filtrate was concentrated to yield 900 mg (6.15 mmol, 95%) of (S)-1-(3-fluoropropyl)pyrrolidin-3-amine. ¹H NMR (400 MHz, DMSO-d₆) δ 4.52 (t, J=6.0 Hz, 1H), 4.40 (t, J=6.0 Hz, 1H), 3.32-3.29 (m, 1H), 2.65-2.61 (m, 1H), 2.52-2.37 (m, 4H), 2.07 (m, 1H), 1.98-1.95 (m, 1H) 1.83-1.73 (m, 2H), 1.36-1.34 (m, 1H).

Example 19

(S)—N-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)-1-(3-fluoropropyl)pyrrolidin-3-amine (Compound 19)

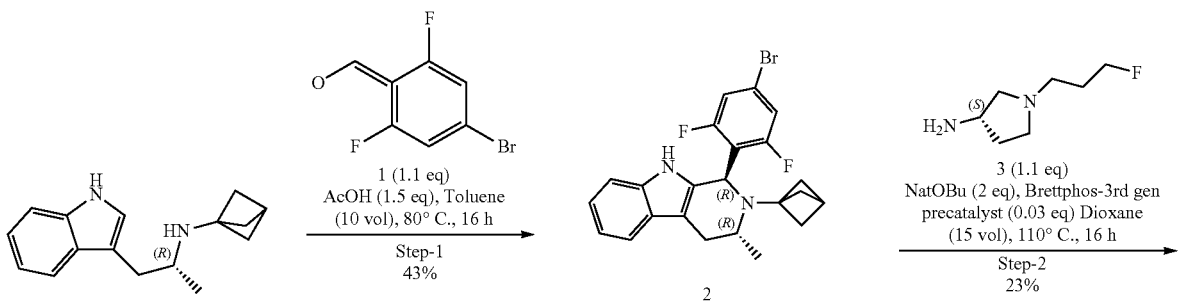

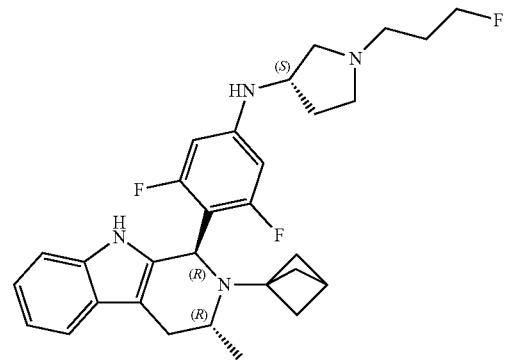

Compound 19

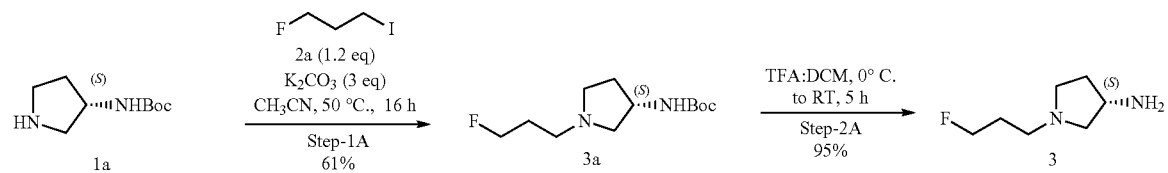

Step 1A: To a stirred solution of tert-butyl (S)-pyrrolidin-3-ylcarbamate (2 g, 10.73 mmol) in ACN (20.0 mL) were added $K_2CO_3$ (4.44 g, 32.19 mmol) and 1-fluoro-3-iodopropane (2.42 g, 12.87 mmol) at RT. The reaction mixture was heated to 50° C. for 16 h. After completion of the reaction, it was diluted with water (50 mL) and extracted with 10% MeOH in DCM (3×50 mL). The organic layer was collected, dried over $Na_2SO_4$, filtered and evaporated. The crude product was purified by silica gel column chromatography to yield 1.6 g (6.49 mmol, 61%) of tert-butyl (S)-(1-(3-fluoropropyl)pyrrolidin-3-yl)carbamate (3a). $^1$H NMR (400 MHz, DMSO-$d_6$) δ 6.95 (d, J=6.0 Hz, 1H), 4.53 (t, J=6.0 Hz, 1H), 4.41 (t, J=6.0 Hz, 1H), 3.89-3.91 (m, 1H), 2.75-2.69 (m, 1H), 2.50-2.46 (m, 2H), 2.27 (s, 1H), 2.03-1.98 (m, 1H), 1.83-1.74 (m, 2H), 1.58-1.55 (m, 1H), 1.45 (s, 9H).

Step 2A: To a stirred solution of tert-butyl (S)-(1-(3-fluoropropyl)pyrrolidin-3-yl)carbamate (3a) (1.6 g, 6.49 mmol) in DCM (16 mL) was added TFA (4 mL) at 0° C. Then the reaction mixture was stirred at room temperature for 16 h. After completion of the reaction, it was evaporated, then dissolved in 10% MeOH in DCM. $K_2CO_3$ (8.95 g, 64.9 mmol) was then added at 0° C. and the mixture was stirred for 50 min and then filtered. The filtrate was concentrated to yield 900 mg (6.15 mmol, 95%) of (S)-1-(3-fluoropropyl)pyrrolidin-3-amine (3). $^1$H NMR (400 MHz, DMSO-$d_6$) δ 4.52 (t, J=6.0 Hz, 1H), 4.40 (t, J=6.0 Hz, 1H), 3.32-3.29 (m, 1H), 2.65-2.61 (m, 1H), 2.52-2.37 (m, 4H), 2.07 (m, 1H), 1.98-1.95 (m, 1H) 1.83-1.73 (m, 2H), 1.36-1.34 (m, 1H).

Step 1: To a stirred solution of (R)—N-(1-(1H-indol-3-yl)propan-2-yl)bicyclo[1.1.1]pentan-1-amine (400 mg, 1.66 mmol) in toluene (8 mL) was added 4-bromo-2,6-difluorobenzaldehyde (1) (424.5 mg, 1.83 mmol) followed by AcOH (0.14 mL, 2.49 mmol). The reaction mixture was stirred at 90° C. for 16 h. After completion of the reaction, it was cooled to room temperature. The reaction mixture was diluted with water (50 mL) and extracted with EtOAc (2×50 mL). The combined organic layer was collected, dried over $Na_2SO_4$, filtered and evaporated. The crude product was purified by silica gel column chromatography to yield 310 mg (0.69 mmol, 47%) of (1R,3R)-2-(bicyclo[1.1.1]pentan-1-yl)-1-(4-bromo-2,6-difluorophenyl)-3-methyl-2,3,4,9-tetrahydro-1H-pyrido[3,4-b]indole (2). MS (ESI) m/z 443.36 [M+1]$^+$; $^1$H NMR (400 MHz, DMSO-$d_6$) δ 10.52 (s, 1H), 7.41-7.37 (m, 3H), 7.17 (d, J=8.0 Hz, 1H), 7.01-6.92 (m, 2H), 5.29 (s, 1H), 3.59-3.62 (m, 1H), 2.92-2.97 (m, 1H), 2.50-2.58 (m, 1H), 2.23-2.25 (d, J=17.6 Hz, 1H), 1.78 (d, J=9.2 Hz, 3H), 1.57 (d, J=9.2 Hz, 3H), 1.07 (d, J=6.4 Hz, 3H).

Step 2: To a solution of (1R,3R)-2-(bicyclo[1.1.1]pentan-1-yl)-1-(4-bromo-2,6-difluorophenyl)-3-methyl-2,3,4,9-tetrahydro-1H-pyrido[3,4-b]indole (2) (310 mg, 0.69 mmol) in 1,4-dioxane (8 mL) were added (S)-1-(3-fluoropropyl)pyrrolidin-3-amine (3) (113 mg, 0.76 mmol), NaOt-Bu (133 mg, 1.38 mmol). The reaction mixture was degassed under argon for 30 min. Next Brettphos-3rd gen precatalyst (18.75 mg, 0.02 mmol) was added and the reaction mixture was again degassed for 30 min. It was then heated to 110° C. for 16 h. After completion of the reaction, it was cooled to room temperature and filtered through a bed of celite. The filtrate was diluted with water (50 mL) and extracted with EtOAc (2×50 mL). The combined organic layer was collected, dried over $Na_2SO_4$, filtered and evaporated. The crude product was purified by RP prep-HPLC to yield 62 mg (0.12 mmol, 23%) of (S)—N-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)-1-(3-fluoropropyl)pyrrolidin-3-amine (Compound 19). MS (ESI) m/z 508.97 [M+1]$^+$; $^1$H NMR (400 MHz, DMSO-$d_6$) δ 10.42 (s, 1H), 7.34 (d, J=7.2 Hz, 1H), 7.17 (d, J=7.6 Hz, 1H), 6.89-6.98 (m, 2H), 6.32 (d, J=6.4 Hz, 1H), 6.12 (d, J=12 Hz, 2H), 5.14 (s, 1H), 4.54 (t, J=6 Hz, 1H), 4.42 (t, J=6 Hz, 1H), 3.83 (m, 1H), 3.57 (s, 1H), 2.89-2.90 (m, 1H), 2.75-2.77 (m, 1H), 2.61-2.50 (m, 1H), 2.44-2.32 (m, 5H), 2.23-2.34 (m, 2H), 1.76-1.84 (m, 5H), 1.52-1.60 (m, 4H), 1.06 (d, J=6.4 Hz, 3H).

Example 20

5-((1R,3R)-2-(bicyclo[1.1.1]pentan-1-yl)-3-methyl-2,3,4,9-tetrahydro-1H-pyrido[3,4-b]indol-1-yl)-N—((S)-1-(3-fluoropropyl)pyrrolidin-3-yl)pyridin-2-amine (Compound 20)

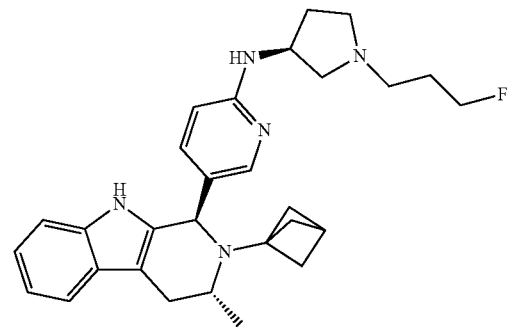 [SMILES: C[C@@H]1Cc2c([nH]c3ccccc23)[C@@H](c2ccc(N[C@H]3CCN(CCCF)C3)nc2)N1C12CC(C1)C2]

Compound 20 was prepared following a procedure analogous to that described for Example 1. MS (ESI) m/z 474.2 [M+H]$^+$; $^1$H NMR (400 MHz, DMSO-$d_6$) δ 10.3 (s, 1H), 7.88 (d, J=1.6 Hz, 1H), 7.36 (d, J=7.6 Hz, 1H), 7.19-7.13 (m, 2H), 6.98-6.89 (m, 2H), 6.53 (d, J=6.8 Hz, 1H), 6.38 (d, J=8.8 Hz, 1H), 4.82 (s, 1H), 4.53 (t, J=6 Hz, 1H), 4.42 (t, J=6 Hz, 1H), 4.25 (s, 1H), 3.51-3.47 (m, 1H), 2.95-2.90 (m, 1H), 2.77 (m, 1H), 2.59-2.50 (m, 1H), 2.45-2.22 (m, 5H), 2.16 (s, 2H), 1.83-1.73 (m, 5H), 1.59 (d, J=9.2 Hz, 4H), 1.09 (d, J=6.4 Hz, 3H).

Example 21

5-((1R,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyridin-2-amine (Compound 21)

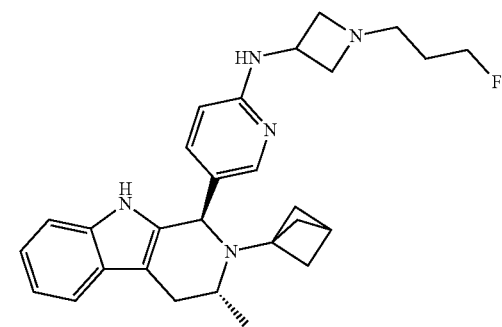 [SMILES: C[C@@H]1Cc2c([nH]c3ccccc23)[C@@H](c2ccc(NC3CN(CCCF)C3)nc2)N1C12CC(C1)C2]

Compound 21 was prepared following a procedure analogous to that described for Example 1. MS (ESI) m/z 460.59 [M+H]$^+$; $^1$H NMR (400 MHz, DMSO-$d_6$) δ 10.42 (s, 1H), 7.90 (d, J=1.25 Hz, 1H), 7.36 (d, J=7.6 Hz, 1H), 7.18-7.15 (dd, J=8.4, 2.8 Hz, 2H), 6.96-6.91 (m, 2H), 6.84 (d, J=6.8 Hz, 1H), 6.36 (d, J=8.4 Hz, 1H), 4.82 (s, 1H), 4.52 (t, J=6.0 Hz, 1H), 4.39-4.34 (m, 2H), 3.58 (t, J=6.8 Hz, 2H), 3.32 (m, 1H), 2.92-2.90 (dd, J=8.4, 2.4 Hz, 1H), 2.74 (q, 2H), 2.56-2.42 (m, 3H), 2.22 (s, 1H), 1.75 (d, J=8.4 Hz, 3H), 1.66 (m, 5H), 1.07 (d, J=6.4 Hz, 3H).

Example 22

4-((1R,3R)-2-(bicyclo[1.1.1]pentan-1-yl)-3-methyl-2,3,4,9-tetrahydro-1H-pyrido[3,4-b]indol-1-yl)-3,5-difluoro-N-(2-(pyrrolidin-1-yl)ethyl)aniline (Compound 22)

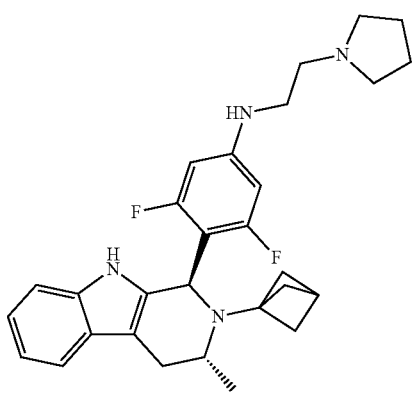 [SMILES: C[C@@H]1Cc2c([nH]c3ccccc23)[C@@H](c2c(F)cc(NCCN3CCCC3)cc2F)N1C12CC(C1)C2]

Compound 22 was prepared following a procedure analogous to that described for Example 1. MS (ESI) m/z 477.26 [M+H]+; 1H NMR (400 MHz, DMSO-d6) δ 10.42 (s, 1H), 7.34 (d, J=7.6 Hz, 1H), 7.17 (d, J=8.0 Hz, 1H), 6.97-6.89 (m, 2H), 6.16 (d, J=12.4 Hz, 2H), 6.08 (t, J=5.2 Hz, 1H), 5.14 (s, 1H), 3.60-3.56 (m, 1H), 3.17-3.07 (m, 2H), 2.93-2.88 (m, 1H), 2.56 (t, J=13.2 Hz, 2H), 2.50-2.46 (m, 5H), 2.25 (s, 1H), 1.77 (d, J=8.8 Hz, 3H), 1.68-1.58 (m, 7H), 1.06 (d, J=6.4 Hz, 3H).

Example 23

(1R,3R)-2-(bicyclo[1.1.1]pentan-1-yl)-1-(2,6-difluoro-4-((1-(3-fluoropropyl)azetidin-3-yl)oxy)phenyl)-3-methyl-2,3,4,9-tetrahydro-1H-pyrido[3,4-b]indole (Compound 23)

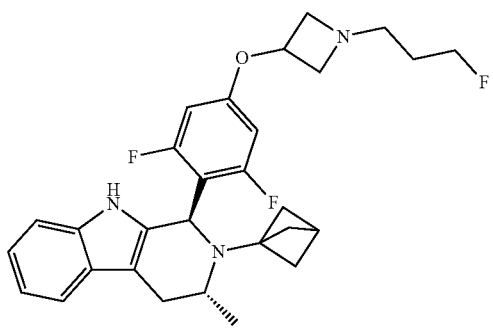 [SMILES: C[C@@H]1Cc2c([nH]c3ccccc23)[C@@H](c2c(F)cc(OC3CN(CCCF)C3)cc2F)N1C12CC(C1)C2]

Compound 23 was prepared following a procedure described for Example 3. MS (ESI) m/z 496.61 [M+H]+; 1H NMR (400 MHz, DMSO-d6) δ 10.40 (s, 1H), 7.37 (d, J=7.6 Hz, 1H), 7.17 (d, J=8.0 Hz, 1H), 7.00-6.90 (m, 2H), 6.62 (d, J=10.8 Hz, 1H), 5.25 (s, 1H), 4.98 (q, 1H), 4.56 (t, J=6.0 Hz, 1H), 4.44 (t, J=6.0 Hz, 1H), 3.61-3.57 (m, 2H), 2.97-2.94 (dd, J=7.6, 1.6 Hz, 1H), 2.57-2.49 (m, 1H), 2.24 (s, 1H), 1.82 (br, 2H), 1.78-1.70 (d, J=9.6 Hz, 3H), 1.59-1.56 (m, 3H), 1.07 (d, J=6.8 Hz, 3H).

Example 24

(1R,3R)-2-(bicyclo[1.1.1]pentan-1-yl)-1-(4-(2-(3-(fluoromethyl)azetidin-1-yl)ethoxy)phenyl)-3-methyl-2,3,4,9-tetrahydro-1H-pyrido[3,4-b]indole (Compound 24)

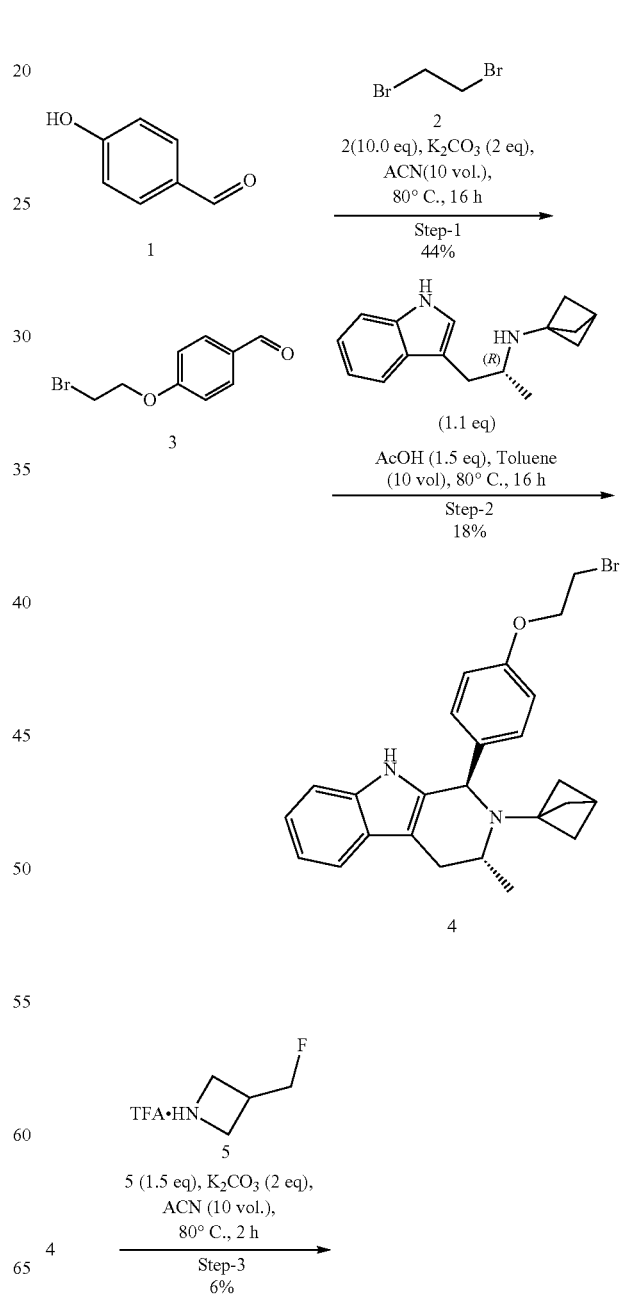

-continued

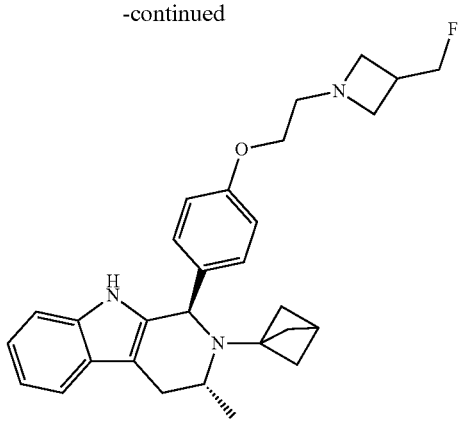

Step 1: To a solution of 4-hydroxybenzaldehyde (1) (5.0 g, 40.983 mmol) in ACN (50 mL) were added 1,2-dibromoethane (2) (77.1 g, 409.83 mmol) and $K_2CO_3$ (11.3 g, 81.96 mmol) at room temperature. The reaction mixture was stirred at 80° C. 16 h. Progress of the reaction was monitored by TLC and LCMS. After completion, the reaction mixture was cooled to room temperature. The reaction mixture was concentrated under reduced pressure. The residue was diluted with water (50 mL) and extracted with EtOAc (2×75 mL). The combined organic layer was collected, dried over $Na_2SO_4$, filtered and evaporated. The crude product was purified by silica gel column chromatography by eluting with 8-7% EA/PE to afford 4-(2-bromoethoxy)benzaldehyde (3) (2.2 g, 17.90 mmol, 44%). MS (ESI) m/z 231.04 [M+H]$^+$; $^1$H NMR (400 MHz, CDCl3) δ 9.90 (s, 1H), 7.86-7.84 (dd, J=7.6, 1.6 Hz, 2H), 7.02 (d, J=8.8 Hz, 2H), 4.38 (t, J=4.4 Hz, 2H), 3.67 (t, J=4.4 Hz, 2H).

Step 2: To a stirred solution of 4-(2-bromoethoxy)benzaldehyde (3) (500 mg, 2.183 mmol) in toluene (10 mL) was added AcOH (0.22 mL, 3.275 mmol) followed by (R)—N-(1-(1H-indol-3-yl)propan-2-yl)bicyclo[1.1.1]pentan-1-amine (786 mg, 3.275 mmol). The reaction mixture was stirred at 80° C. for 16 h. After completion of the reaction, the reaction mixture was cooled to room temperature. The reaction mixture was diluted with water (50 mL) and extracted with EtOAc (2×50 mL). The combined organic layers were washed with aqueous sat. $NaHCO_3$ solution followed by brine solution and dried over $Na_2SO_4$, filtered and evaporated. The crude product was purified by silica gel column chromatography by eluting with 10-15% EA to afford (1R,3R)-2-(bicyclo[1.1.1]pentan-1-yl)-1-(4-(2-bromoethoxy)phenyl)-3-methyl-2,3,4,9-tetrahydro-1H-pyrido[3,4-b]indole (4) (180 mg, 398 mmol, 18%). MS (ESI) m/z 497.08 [M+H]$^+$; $^1$H NMR (400 MHz, DMSO-d$_6$) δ 7.45 (d, J=7.6 Hz, 1H), 7.34-6.92 (m, 6H), 6.84 (d, J=8.4 Hz, 1H), 5.23 (s, 1H), 4.80 (s, 1H), 4.24 (br, 2H), 3.66 (br, 3H), 3.11 (dd, 1H), 2.60 (dd, 1H), 2.21 (s, 1H), 1.76 (d, 2H), 1.56 (d, 3H), 1.22 (m, 6H).

Step 3: To a solution of (1R,3R)-2-(bicyclo[1.1.1]pentan-1-yl)-1-(4-(2-bromoethoxy)phenyl)-3-methyl-2,3,4,9-tetrahydro-1H-pyrido[3,4-b]indole (4) (180 mg, 0.4 mmol) in ACN (3 mL) were added 2,2,2-trifluoro-1-(3-(fluoromethyl)-1$^4$-azetidin-1-yl)ethan-1-one (5) (111 mg, 0.6 mmol) and $K_2CO_3$ (110 mg, 0.8 mmol) at room temperature. The reaction mixture was stirred at 80° C. for 2 h. After completion of the reaction, it was cooled to room temperature. The reaction was diluted with water (5 mL) and extracted with EtOAc (2×10 mL). The combined organic layer was collected, dried over $Na_2SO_4$, filtered and evaporated. The crude product was purified by RP prep-HPLC to afford (1R,3R)-2-(bicyclo[1.1.1]pentan-1-yl)-1-(4-(2-(3-(fluoromethyl)azetidin-1-yl)ethoxy)phenyl)-3-methyl-2,3,4,9-tetrahydro-1H-pyrido[3,4-b]indole (Compound 24) (10.9 mg, 23.72 mmol, 6%). MS (ESI) m/z 458.3 [M+H]$^-$; $^1$H NMR (400 MHz, DMSO-d$_6$) δ 10.26 (s, 1H), 7.37 (d, J=7.6 Hz, 1H), 7.19-7.17 (m, 3H), 6.99-6.9 (m, 2H), 6.81 (d, J=8.4 Hz, 2H), 4.86 (s, 1H), 4.55 (d, J=4.4 Hz, 1H), 4.43 (d, J=4.0 Hz, 1H), 3.87 (t, J=5.6 Hz, 2H), 3.47 (q, 1H), 3.58 (br, 2H), 3.04 (t, J=7.6 Hz, 2H), 2.81 (dd, J=7.6, 1.6 Hz, 1H), 2.73 (t, J=8.4 Hz, 3H), 2.55 (m, 1H), 2.20 (s, 1H), 1.73 (d, J=9.6 Hz, 3H), 1.57 (d, J=9.2 Hz, 3H), 1.10 (d, J=6.4 Hz, 3H).

Example 25

(1R,3R)-2-(bicyclo[1.1.1]pentan-1-yl)-1-(2-fluoro-4-(2-(3-(fluoromethyl)azetidin-1-yl)ethoxy)phenyl)-3-methyl-2,3,4,9-tetrahydro-1H-pyrido[3,4-b]indole (Compound 25)

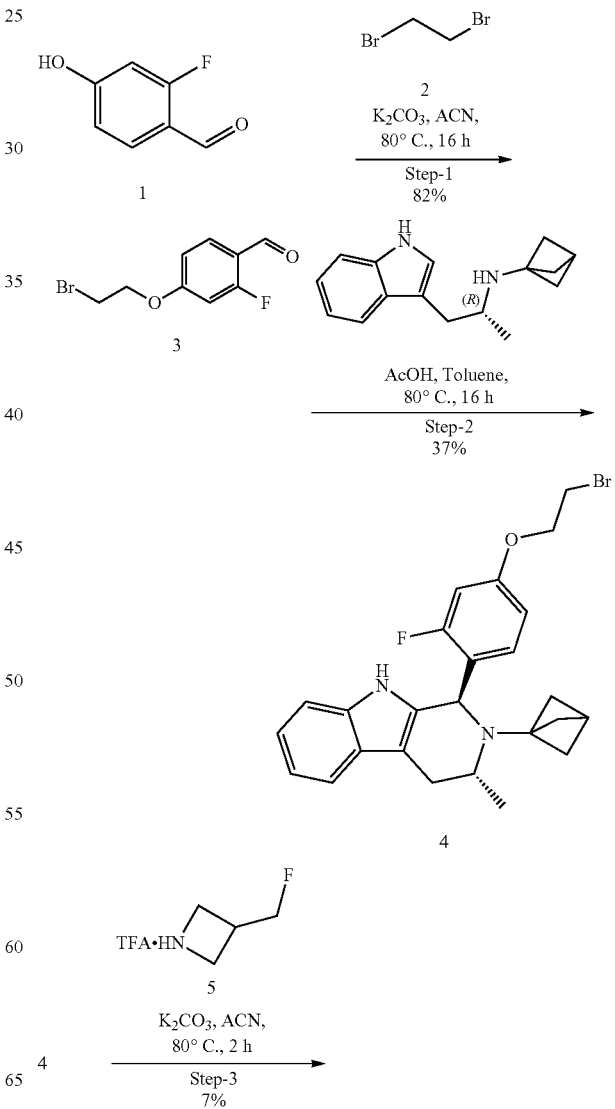

-continued

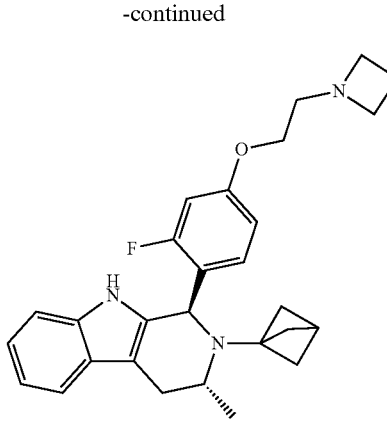

Step 1: To a stirred solution of 2-fluoro-4-hydroxybenzaldehyde (2.0 g, 14.27 mmol) in acetonitrile (20 mL) was added potassium carbonate (3.93 g, 28.54 mmol) followed by 1,2-dibromoethane (12.31 ml, 14.22 mmol), and the resulting reaction mixture was stirred at 80° C. for 16 h. The reaction mixture was diluted with water (50 mL) and extracted with EtOAc (2×50 mL). The combined organic layers were dried over $Na_2SO_4$, filtered and evaporated. The crude product was purified by silica gel column chromatography by eluting with 40-45% EtOAc in pet ether to afford 4-(2-bromoethoxy)-2-fluorobenzaldehyde (3) (2.9 g, 11.73 mmol, Yield=82%). MS (ESI) m/z 247.05 [M+H]+, $^1$H NMR (400 MHz, DMSO-$d_6$) δ 10.22 (s, 1H), 7.84 (t, J=16.8 Hz, 1H), 6.81-6.78 (m, 1H), 6.68-6.48 (m, 1H), 4.35 (t, J=12.4 Hz, 2H), 3.66 (t, J=12.4 Hz, 2H).

Step 2: To a stirred solution of (R)—N-(1-(1H-indol-3-yl)propan-2-yl)bicyclo[1.1.1]pentan-1-amine (500 mg, 2.08 mmol) in toluene (5 mL) were added 4-(2-bromoethoxy)-2-fluorobenzaldehyde (3) (462.56 mg, 1.87 mmol) followed by AcOH (0.8 mL, 3.12 mmol). The reaction mixture was stirred at 80° C. for 16 h. After completion of the reaction, the reaction mixture was cooled to room temperature. The reaction mixture was diluted with water (100 mL) and extracted into EtOAc (2×100 mL). The combined organic layers were dried over $Na_2SO_4$, filtered and evaporated. The crude product was purified by silica gel column chromatography by eluting with 5-7% MeOH in DCM to afford (1R,3R)-2-(bicyclo[1.1.1]pentan-1-yl)-1-(4-(2-bromoethoxy)-2-fluorophenyl)-3-methyl-2,3,4,9-tetrahydro-1H-pyrido[3,4-b]indole (4) (350 mg, 0.74 mmol, Yield=37%). MS (ESI) m/z 469.18 [M+H]+; $^1$H NMR (400 MHz, DMSO-$d_6$) δ 7.49 (d, J=7.2 Hz, 1H), 7.39 (s, 1H), 7.21-7.15 (m, 2H), 7.12-7.07 (m, 2H), 6.67-6.63 (m, 1H), 6.58-6.55 (m, 1H), 5.29 (s, 1H), 4.27-4.23 (m, 2H), 3.66-3.60 (m, 3H), 3.11-3.06 (m, 1H), 2.64-2.60 (m, 1H), 1.85 (s, 1H), 1.81 (d, J=9.2 Hz, 3H), 1.64 (d, J=9.2 Hz, 3H), 1.17 (d, J=6.8 Hz, 3H).

Step 3: To a stirred solution of (1R,3R)-2-(bicyclo[1.1.1]pentan-1-yl)-1-(4-(2-bromoethoxy)-2-fluorophenyl)-3-methyl-2,3,4,9-tetrahydro-1H-pyrido[3,4-b]indole (300 mg, 0.63 mmol) in acetonitrile (5 mL) was added potassium carbonate (176.39 mg, 1.27 mmol) followed by the addition of 3-(fluoromethyl)azetidine (175.89 mg, 0.94 mmol). The resulting reaction mixture was stirred at 80° C. for 2 h. The reaction mixture was diluted with water (50 mL) and extracted with EtOAc (2×50 mL). The combined organic layer was collected, dried over $Na_2SO_4$, filtered and evaporated. The crude product was purified by RP prep-HPLC to yield 16 mg (0.033 mmol, Yield=7%) of (1R,3R)-2-(bicyclo[1.1.1]pentan-1-yl)-1-(2-fluoro-4-(2-(3-(fluoromethyl)azetidin-1-yl)ethoxy)phenyl)-3-methyl-2,3,4,9-tetrahydro-1H-pyrido[3,4-b]indole (Compound 25). MS (ESI) m/z 476.27 [M−H]−; $^1$H NMR (400 MHz, DMSO-$d_6$) δ 10.38 (s, 1H), 7.39 (d, J=7.6 Hz, 1H), 7.18 (d, J=8 Hz, 1H), 7.00-6.91 (m, 2H), 6.86-6.77 (m, 2H), 6.61-6.58 (m, 1H), 5.22 (s, 1H), 4.55 (d, J=6.4 Hz, 1H), 4.43 (d, J=6 Hz, 1H), 3.89 (t, J=12 Hz, 2H), 3.47-3.43 (m, 1H), 3.31-3.28 (m, 3H), 3.00-2.87 (m, 3H), 2.74-2.66 (m, 3H), 2.61-2.50 (m, 1H), 2.22 (s, 1H), 1.75 (d, J=9.2 Hz, 3H), 1.63 (d, J=9.2 Hz, 3H), 1.12 (d, J=6.8 Hz, 3H).

Example 26

(1R,3R)-2-(bicyclo[1.1.1]pentan-1-yl)-1-(2,6-difluoro-4-(2-(pyrrolidin-1-yl)ethoxy)phenyl)-3-methyl-2,3,4,9-tetrahydro-1H-pyrido[3,4-b]indole (Compound 26)

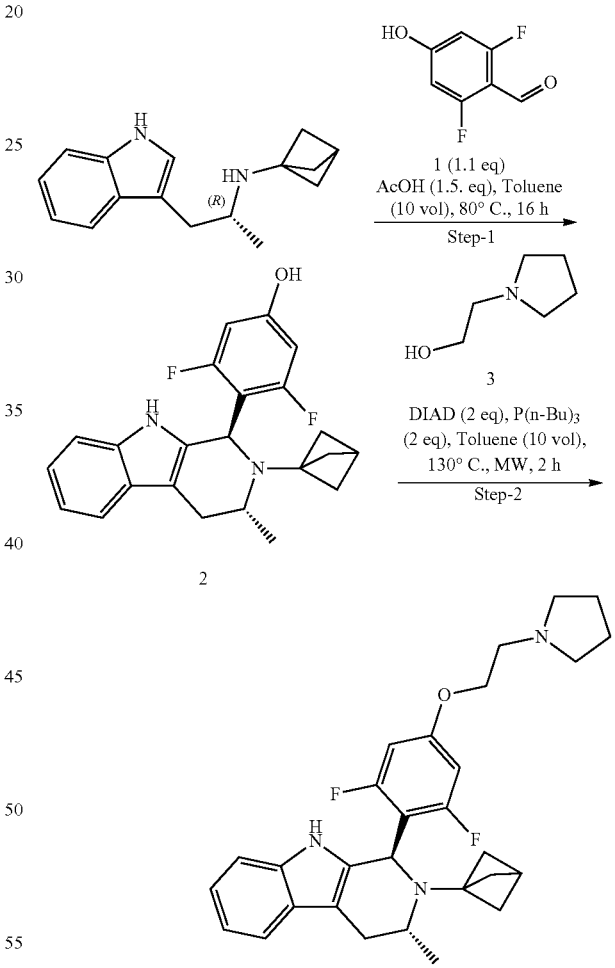

Step 1: To a stirred solution of (R)—N-(1-(1H-indol-3-yl)propan-2-yl)bicyclo[1.1.1]pentan-1-amine (500 mg, 2.07 mmol) in toluene (10 mL) was added 2,6-difluoro-4-hydroxybenzaldehyde (1) (327.8 mg, 2.07 mmol) followed by AcOH (0.25 mL, 3.52 mmol). The resulting reaction mixture was stirred at 80° C. for 16 h. After completion of the reaction, reaction mixture was cooled to room temperature, diluted with water (50 mL) and extracted with EtOAc (2×40 mL). The combined organic layers were dried over $Na_2SO_4$, filtered and evaporated to get semi-pure crude. Thus obtained crude product was purified by silica gel column chromatography by eluting with 10-15% EtOAc in pet ether to afford 4-((1R,3R)-2-(bicyclo[1.1.1]pentan-1-yl)-3-methyl-2,3,4,9-tetrahydro-1H-pyrido[3,4-b]indol-1-yl)-3,5-difluorophenol (2) (330 mg, 0.86 mmol, 42% yield). MS (ESI) m/z 381.68 [M+1]$^+$; $^1$H NMR (400 MHz, DMSO-d$_6$) δ 10.43 (s, 1H), 10.26 (s, 1H), 7.35 (d, J=7.6 Hz, 1H), 7.16 (d, J=6.8 Hz, 1H), 6.99-6.90 (m, 2H), 6.38 (d, J=11.2 Hz, 2H), 5.22 (s, 1H), 3.62 (br, 1H), 2.88 (dd, 1H), 2.51 (m, 1H), 2.23 (s, 1H), 1.75 (d, J=8.0 Hz, 3H), 1.58 (d, J=8.0 Hz, 3H), 1.08 (d, J=8.4 Hz, 3H).

Step 2: To a solution of 4-((1R,3R)-2-(bicyclo[1.1.1]pentan-1-yl)-3-methyl-2,3,4,9-tetrahydro-1H-pyrido[3,4-b]indol-1-yl)-3,5-difluorophenol (2) (330 mg, 0.86 mmol) in toluene (5 mL) were added 2-(pyrrolidin-1-yl)ethan-1-ol (3) (420 mg, 0.95 mmol), tri-n-butylphosphine (347.99 mg, 1.72 mmol) and diisopropyl azodicarboxylate (0.34 mL, 1.72 mmol) at 0° C. The resulting reaction mixture was then heated to 130° C. for 2 h under microwave irradiation. After completion of the reaction, the reaction mixture was cooled to room temperature and filtered through a bed of celite. The filtrate was diluted with water (15 mL) and extracted with EtOAc (2×15 mL). The combined organic layer was collected, dried over Na$_2$SO$_4$, filtered and evaporated. The crude product was purified by RP prep-HPLC to afford (1R,3R)-2-(bicyclo[1.1.1]pentan-1-yl)-1-(2,6-difluoro-4-(2-(pyrrolidin-1-yl)ethoxy)phenyl)-3-methyl-2,3,4,9-tetrahydro-1H-pyrido[3,4-b]indole (Compound 26) (60.4 mg, 0.12 mmol, 14.58%). MS (ESI) m/z 477.90 [M+H]$^+$; $^1$H NMR (400 MHz, DMSO-d$_6$) δ 10.52 (s, 1H), 7.36 (d, J=7.6 Hz, 1H), 7.17 (d, J=8.0 Hz, 1H), 6.99-6.90 (m, 2H), 6.59 (d, J=11.2 Hz, 2H), 5.23 (s, 1H), 4.07 (t, J=6.0 Hz, 2H), 3.58 (q, 1H), 2.92 (dd, J=11.4, 2.8 Hz, 1H), 2.77 (t, J=6.8 Hz, 2H), 2.67-2.49 (m, 5H), 2.24 (s, 1H), 1.78-1.76 (d, 3H), 1.68 (m, 4H), 1.57 (d, J=8.8 Hz, 3H), 1.07 (d, J=6.8 Hz, 3H).

Example 27

(1R,3R)-2-(bicyclo[1.1.1]pentan-1-yl)-1-(6-(2-(3-fluoropyrrolidin-1-yl)ethoxy)pyridin-3-yl)-3-methyl-2,3,4,9-tetrahydro-1H-pyrido[3,4-b]indole (Compound 27)

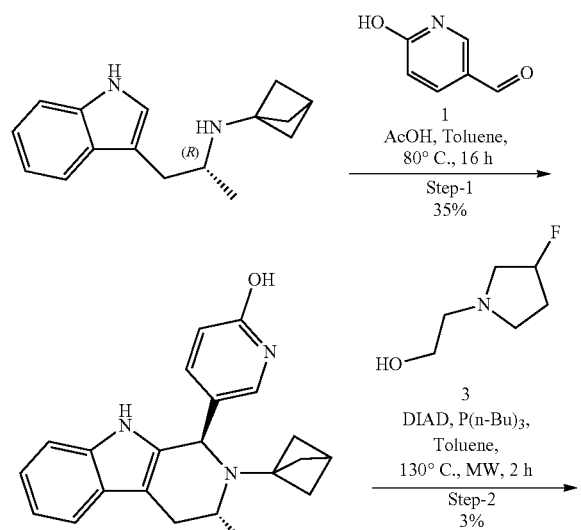

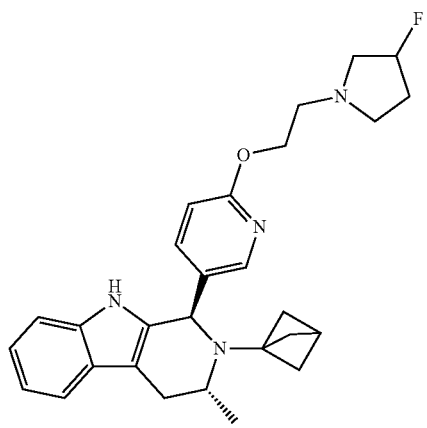

Compound 27

Step 1: To a stirred solution of (R)—N-(1-(1H-indol-3-yl)propan-2-yl)bicyclo[1.1.1]pentan-1-amine (5 g, 20.82 mmol) in toluene (50 mL) was added 6-hydroxynicotinaldehyde (1) (2.81 g, 18.68 mmol) followed by AcOH (1.8 mL, 16.24 mmol). The reaction mixture was stirred at 80° C. for 16 h. After completion of the reaction, the reaction mixture was cooled to room temperature. The reaction mixture was diluted with water (100 mL) and extracted with EtOAc (2×100 mL). The combined organic layers were dried over Na$_2$SO$_4$, filtered and evaporated. The crude product was purified by silica gel column chromatography by eluting with 5-7% MeOH in DCM to afford 5-((1R,3R)-2-(bicyclo[1.1.1]pentan-1-yl)-3-methyl-2,3,4,9-tetrahydro-1H-pyrido[3,4-b]indol-1-yl)pyridin-2-ol (2) (2.5 g, 13.8 mmol, 35%). MS (ESI) m/z 346.40 [M+1]$^+$; $^1$H NMR (400 MHz, DMSO-d$_6$) δ 11.47 (s, 1H), 10.42 (s, 1H), 7.37 (d, J=7.6 Hz, 1H), 7.24-7.20 (m, 3H), 6.24 (d, J=9.6 Hz, 1H), 5.74 (s, 1H), 4.72 (s, 1H), 4.15-4.11 (m, 1H), 3.17 (d, J=5.2 Hz, 4H), 2.27 (s, 1H), 1.79 (t, J=15.6 Hz, 3H), 1.68 (d, J=9.2 Hz, 3H), 1.08 (d, J=6.4 Hz, 3H).

Step 2: To a stirred solution of 5-((1R,3R)-2-(bicyclo[1.1.1]pentan-1-yl)-3-methyl-2,3,4,9-tetrahydro-1H-pyrido[3,4-b]indol-1-yl)pyridin-2-ol (2) (500 mg, 1.44 mmol) in toluene (5 mL) were added 2-(3-fluoropyrrolidin-1-yl)ethan-1-ol (3) (319.1 mg, 2.17 mmol) followed by DIAD (0.28 ml, 1.13 mmol) and P(n-Bu)$_3$ (0.35 ml, 1.13 mmol). Then the resulting reaction mixture was heated at 130° C. under microwave irradiation for 2 h. After completion of the reaction, the reaction mixture was cooled to room temperature and filtered through a bed of celite. The filtrate was diluted with water (50 mL) and extracted with EtOAc (2×50 mL). Combined organic layers were dried over Na$_2$SO$_4$, filtered and evaporated. The crude product was purified by RP prep-HPLC to afford (1R,3R)-2-(bicyclo[1.1.1]pentan-1-yl)-1-(6-(2-(3-fluoropyrrolidin-1-yl)ethoxy)pyridin-3-yl)-3-methyl-2,3,4,9-tetrahydro-1H-pyrido[3,4-b]indole (Compound 27) (16 mg, 0.034 mmol, 3%). MS (ESI) m/z 459.36 [M−H]$^−$; $^1$H NMR (400 MHz, DMSO-d$_6$) δ 10.35 (s, 1H), 8.11 (d, J=2 Hz, 1H), 7.50-7.48 (m, 1H), 7.6 (d, J=7.6 Hz, 1H), 7.18 (d, J=8 Hz, 1H), 7.00-6.90 (m, 2H), 6.71 (d, J=8.4 Hz, 1H), 5.38-5.10 (m, 1H), 4.91 (s, 1H), 4.33 (t, J=11.6 Hz, 1H), 3.52 (s, 1H), 2.99-2.80 (m, 5H), 2.79-2.61 (m, 2H), 2.37 (d, J=7.2 Hz, 1H), 2.23 (s, 1H), 1.76-1.73 (m, 4H), 1.57 (t, J=9.6 Hz, 3H), 1.23 (s, 1H), 1.10 (d, J=6.8 Hz, 3H).

Intermediate 5

2-(3-fluoropyrrolidin-1-yl)ethan-1-amine

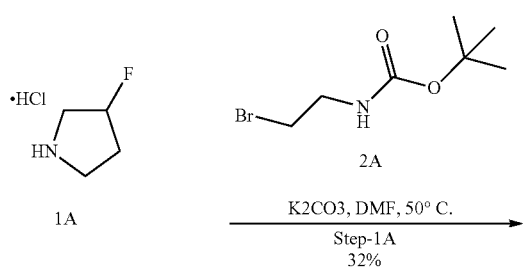

Example 28

5-((1R,3R)-2-(bicyclo[1.1.1]pentan-1-yl)-3-methyl-2,3,4,9-tetrahydro-1H-pyrido[3,4-b]indol-1-yl)-N-(2-(3-fluoropyrrolidin-1-yl)ethyl)pyridin-2-amine (Compound 28)

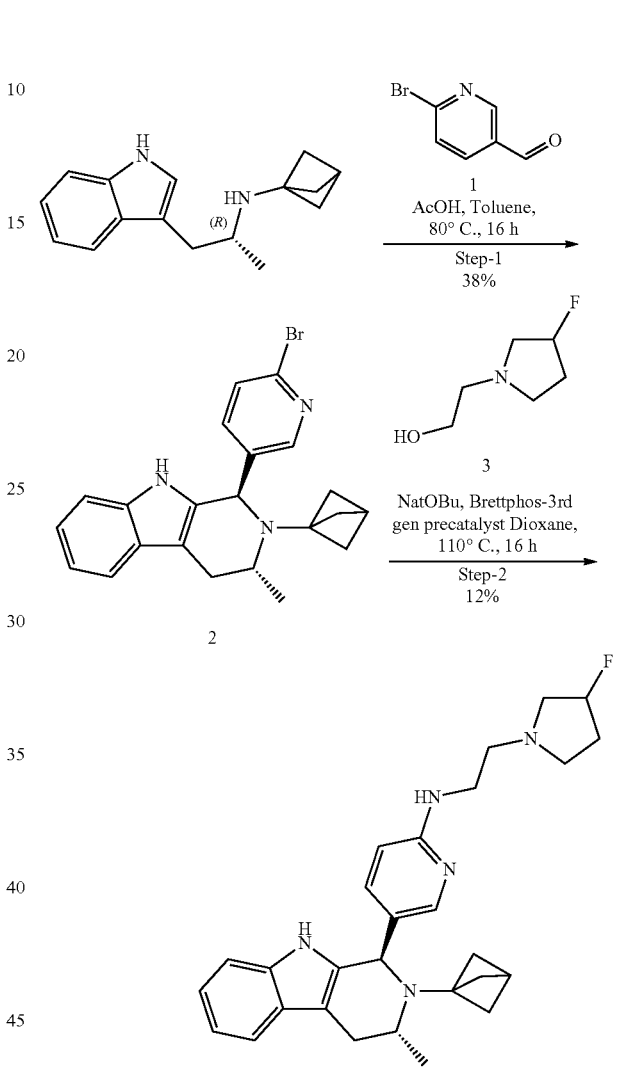

Step 1: To a solution of 3-fluoropyrrolidine (1A) (300 mg, 3.36 mmol) in DMF (5 mL) were added $K_2CO_3$ (929 mg, 6.73 mmol) and tert-butyl (2-bromoethyl)carbamate (2A) (905 mg, 4.04 mmol) at room temperature. The reaction mixture was stirred at 50° C. for 16 h. After completion of the reaction, it was cooled to room temperature. The reaction was diluted with water (10 mL) and extracted with 10% MeOH in DCM (2×20 mL). The combined organic layer was collected, dried over $Na_2SO_4$, filtered and evaporated. The crude product was purified by silica gel column chromatography by eluting with 5-6% MeOH in DCM to afford tert-butyl (2-(3-fluoropyrrolidin-1-yl)ethyl)carbamate (3A) 250 mg (0.60 mmol, 32%). MS (ESI) m/z 233.23 [M+H]$^+$, $^1$H NMR (400 MHz, DMSO-d$_6$) δ 6.69 (s, 1H), 5.23 (t, J=6.8 Hz, 1H), 5.09 (t, J=7.2 Hz, 1H), 3.04-2.99 (q, 4H), 2.86-2.77 (m, 4H), 2.64-2.43 (m, 6H), 2.33-2.16 (q, 2H), 2.18-2.04 (m, 2H), 1.88-1.76 (m, 2H), 1.37 (s, 9H).

Step 2: To a solution of tert-butyl (2-(3-fluoropyrrolidin-1-yl)ethyl)carbamate (3A) (250 mg, 1.07 mmol) in dioxane (4 mL) cooled to 0° C. was added 4M HCl in 1,4-dioxane (4 ml). The reaction mixture was then stirred at room temperature for 3 h. After completion of the reaction, it was evaporated. The residue was dissolved in 10% MeOH in DCM. $K_2CO_3$ (740 mg, 5.36 mmol) was then added at 0° C. and the mixture was stirred for 20 min and then filtered. Filtrate was evaporated to yield 2-(3-fluoropyrrolidin-1-yl)ethan-1-amine (Intermediate 5) (110 mg 0.82 mmol, 77%). MS (ESI) m/z 133.06 [M+H]$^+$; $^1$H NMR (400 MHz, DMSO-d$_6$) δ 8.35-8.26 (d, J=8.0 Hz, 4H), 5.38 (s, 1H), 5.25 (s, 1H), 4.12 (br, 2H), 3.31-2.67 (br, 13H), 2.20-1.91 (br, 4H).

Step 1: To a stirred solution of (1R,3R)-2-(bicyclo[1.1.1]pentan-1-yl)-1-(6-bromo-5-fluoropyridin-3-yl)-3-methyl-2,3,4,9-tetrahydro-1H-pyrido[3,4-b]indole (500 mg, 2.07 mmol) in toluene (5 mL) was added 6-bromonicotinaldehyde (1) (425 mg, 2.28 mmol) followed by AcOH (0.17 mL, 3.11 mmol). The reaction mixture was stirred at 80° C. for 16 h. After completion of the reaction, the reaction mixture was cooled to room temperature. The reaction mixture was diluted with water (20 mL) and extracted with EtOAc (2×20 mL). The combined organic layers were dried over $Na_2SO_4$, filtered and evaporated to get semi-pure crude. Thus obtained crude product was purified by silica gel column chromatography by eluting with 3-6% EtOAc in pet ether to afford (1R,3R)-2-(bicyclo[1.1.1]pentan-1-yl)-1-(6-bromopyridin-3-yl)-3-methyl-2,3,4,9-tetrahydro-1H-pyrido[3,4-b]indole (2) (320 mg 0.98 mmol, 38% yield). MS (ESI) m/z 408.21 [M+1]$^+$; $^1$H NMR (400 MHz, DMSO-d$_6$) δ

10.41 (s, 1H), 8.41 (d, J=2.0 Hz, 1H), 7.60-7.54 (m, 2H), 7.40 (d, J=7.6 Hz, 1H), 7.19 (d, J=8.0 Hz, 1H), 6.98 (t, J=7.6 Hz, 1H), 6.94 (d, J=8.0 Hz, 1H), 5.75 (s, 1H), 4.99 (s, 1H), 3.54-3.52 (q, 1H), 3.01-2.96 (dd, J=15.2, 8.0 Hz, 1H), 2.62-2.57 (dd, J=14.8, 7.6 Hz, 1H), 2.24 (s, 1H), 1.76 (d, J=9.6 Hz, 3H), 1.57 (d, J=9.2 Hz, 3H), 1.10 (d, J=6.8 Hz, 3H).

Step 2: To a stirred solution of (1R,3R)-2-(bicyclo[1.1.1]pentan-1-yl)-1-(6-bromopyridin-3-yl)-3-methyl-2,3,4,9-tetrahydro-1H-pyrido[3,4-b]indole (2) (150 mg, 0.36 mmol) in 1,4-dioxane (8 mL) were added 2-(3-fluoropyrrolidin-1-yl)ethan-1-amine (Intermediate 5) (53 mg, 0.40 mmol) and NaOt-Bu (70.6 mg, 0.73 mmol). The reaction mixture was degassed under argon for 30 min. Later Brettphos-3rd gen pre-catalyst (9.9 mg, 0.011 mmol) was added, and the reaction mixture was again degassed for 30 min. It was then heated at 110° C. for 16 h. After completion of the reaction, it was cooled to room temperature and filtered through a bed of celite. The filtrate was diluted with water (20 mL) and extracted with 10% MeOH in DCM (2×20 mL). The combined organic layers were dried over Na$_2$SO$_4$, filtered and evaporated. The crude product was purified by RP prep-HPLC to afford 5-((1R,3R)-2-(bicyclo[1.1.1]pentan-1-yl)-3-methyl-2,3,4,9-tetrahydro-1H-pyrido[3,4-b]indol-1-yl)-N-(2-(3-fluoropyrrolidin-1-yl)ethyl)pyridin-2-amine (Compound 28) (20.1 mg, 0.043 mmol, 12% yield). MS (ESI) m/z 460.54 [M–H]$^+$; $^1$H NMR (400 MHz, DMSO-d$_6$) δ 10.29 (s, 1H), 7.90 (d, J=2.0 Hz, 1H), 7.36 (d, J=7.6 Hz, 1H), 7.18 (d, J=7.6 Hz, 1H), 7.16-7.13 (dd, J=8.4, 2.4 Hz, 1H), 6.98-6.89 (m, 2H), 6.38 (d, J=8.4 Hz, 1H), 6.34 (t, J=5.6 Hz, 1H), 5.38 and 5.11 (t, 1H), 4.76 (s, 1H), 3.56-3.48 (br, 1H), 3.38 (m, 2H), 2.98-2.76 (m, 2H), 2.56-2.48 (m, 4H), 2.36 (q, 1H), 2.22 (s, 1H), 1.77 (d, J=8.4 Hz, 3H), 1.61 (d, J=7.6 Hz, 3H), 1.09 (d, J=6.4 Hz, 3H)

Example 29

5-((1R,3R)-2-(bicyclo[1.1.1]pentan-1-yl)-3-methyl-2,3,4,9-tetrahydro-1H-pyrido[3,4-b]indol-1-yl)-N-(2-(3-(fluoromethyl)pyrrolidin-1-yl)ethyl)pyridin-2-amine (Compound 29)

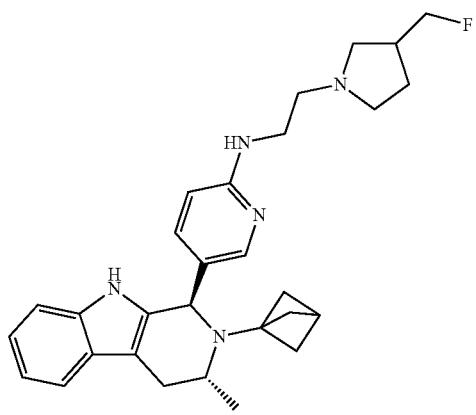 [SMILES: C[C@@H]1Cc2c([nH]c3ccccc23)[C@@H](c2ccc(NCCN3CCC(CF)C3)nc2)N1C12CC(C1)C2]

Compound 29 was prepared following a procedure analogous to that described for Example 1. MS (ESI) m/z 474.43 [M+H]$^+$; $^1$H NMR (400 MHz, DMSO-d6) δ 10.38 (s, 1H), 7.89 (d, J=2.4 Hz, 1H), 7.36 (d, J=7.6 Hz, 1H), 7.19-7.13 (m, 2H), 6.98-6.89 (m, 2H), 6.38 (d, J=8.4 Hz, 1H), 6.31 (d, J=5.2 Hz, 1H), 4.36 (s, 1H), 4.38 (d, J=6.8 Hz, 1H), 4.26 (d, J=6.4 Hz, 1H), 3.54 (t, J=7.4 Hz, 1H), 3.37-3.32 (q, 2H), 2.94-2.85 (dd, J=12.8, 2.8 Hz, 1H), 2.64-2.48 (m, 7H), 2.35 (t, 1H), 2.22 (s, 1H), 1.78 (d, J=8.8 Hz, 3H), 1.64 (d, J=8.4 Hz, 3H), 1.08 (d, J=8.8 Hz, 3H).

Example 30

5-((1R,3R)-2-(bicyclo[1.1.1]pentan-1-yl)-3-methyl-2,3,4,9-tetrahydro-1H-pyrido[3,4-b]indol-1-yl)-N-(1-propylazetidin-3-yl)pyridin-2-amine (Compound 30)

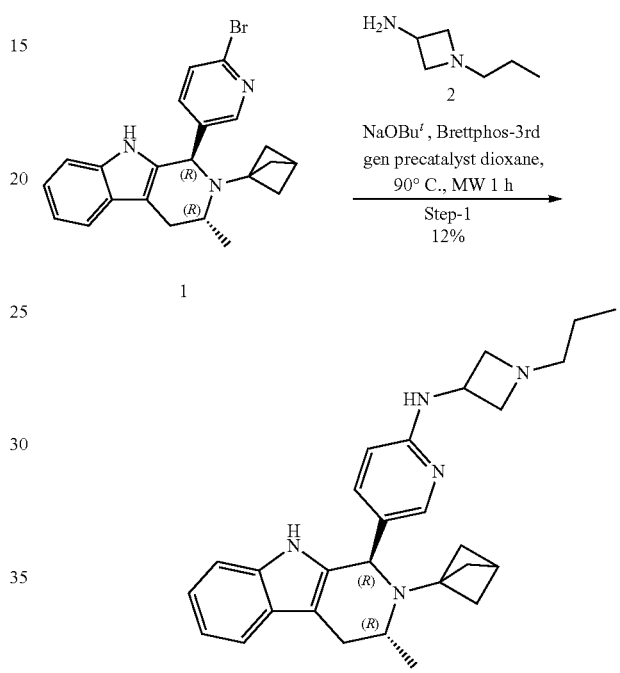

To a solution of (1R,3R)-2-(bicyclo[1.1.1]pentan-1-yl)-1-(6-bromopyridin-3-yl)-3-methyl-2,3,4,9-tetrahydro-1H-pyrido[3,4-b]indole (1) (80 mg, 0.195 mmol) in 1,4-dioxane (1 mL) were added 1-propylazetidin-3-amine (2) (33.5 mg, 0.29 mmol) and NaO$^t$Bu (37.7 mg, 0.39 mmol). The reaction mixture was degassed under argon for 30 min. Next Brettphos-3$^{rd}$ gen pre-catalyst (8.9 mg, 0.009 mmol) was added, and the reaction mixture was again degassed for 30 min. It was then heated to 90° C. under microwave irradiation for 1 h. After completion of the reaction, it was cooled to room temperature and filtered through a bed of celite. The filtrate was diluted with water (20 mL) and extracted with EtOAc (2×20 mL). The combined organic layer was collected, dried over anhydrous Na$_2$SO$_4$, filtered and evaporated to get a crude product which was purified by RP prep-HPLC to yield 5-((1R,3R)-2-(bicyclo[1.1.1]pentan-1-yl)-3-methyl-2,3,4,9-tetrahydro-1H-pyrido[3,4-b]indol-1-yl)-N-(1-propylazetidin-3-yl)pyridin-2-amine (Compound 30) (10.5 mg, 12%). MS (ESI) m/z 442.40 [M+H]$^+$; $^1$H NMR (400 MHz, DMSO-d$_6$) δ 10.28 (s, 1H), 7.89 (d, J=1.6 Hz, 1H), 7.36 (d, J=7.6 Hz, 1H), 7.19-7.15 (m, 2H), 6.98-6.89 (m, 2H), 6.81 (d, J=7.2 Hz, 1H), 6.35 (d, J=8.4 Hz, 1H), 4.76 (s, 1H), 4.38-4.29 (q, 1H), 3.57-3.47 (m, 2H), 2.95-2.90 (dd, J=4.4 Hz, 4.4 Hz, 1H), 2.73-2.66 (m, 3H), 2.56-2.42 (m, 3H), 2.32 (t, J=6.8 Hz, 2H), 1.74 (d, J=9.2 Hz, 3H), 1.58 (d, J=9.2 Hz, 3H), 1.30-1.23 (m, 2H), 1.08 (d, J=6.4 Hz, 3H), 0.82 (t, J=7.6 Hz, 3H).

Example 31

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-propylazetidin-3-amine (Compound 31)

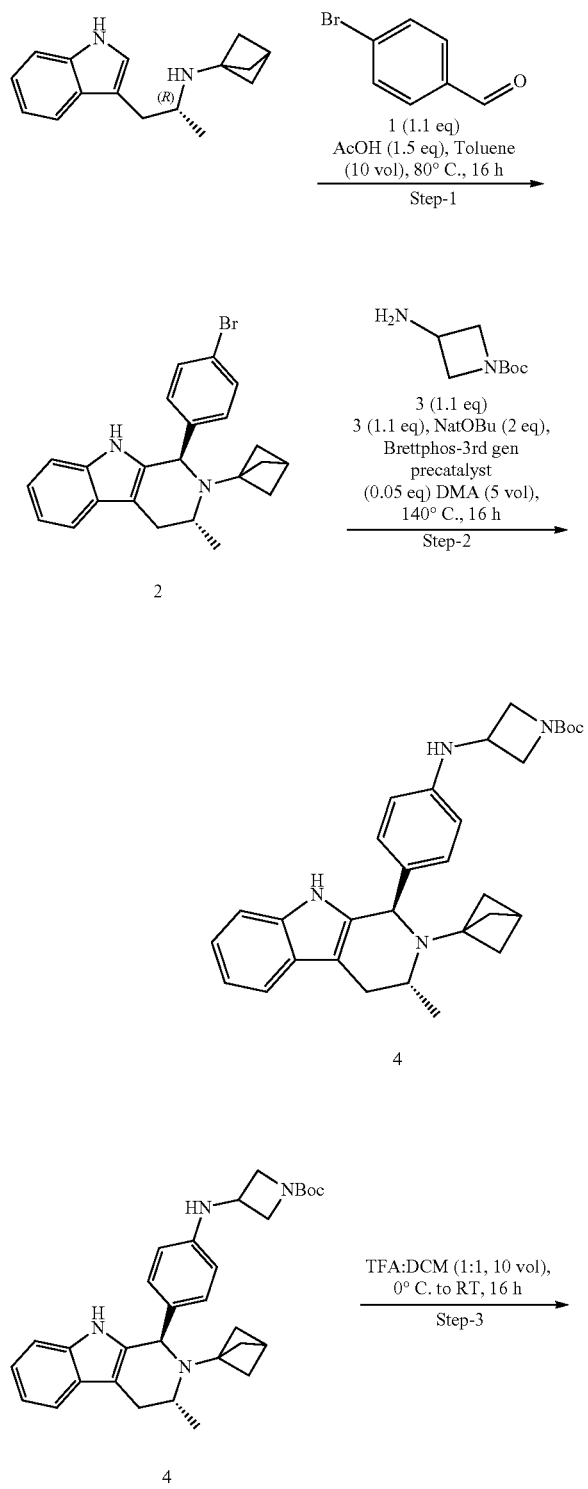

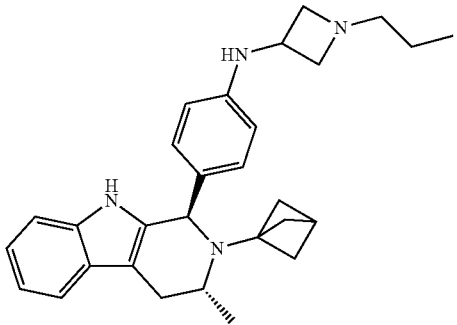 [SMILES: CCCN1CC(Nc2ccc([C@@H]3c4[nH]c5ccccc5c4C[C@@H](C)N3C34CC(C3)C4)cc2)C1]

Step 1: To a stirred solution of (R)—N-(1-(1H-indol-3-yl)propan-2-yl)bicyclo[1.1.1]pentan-1-amine (0.5 g, 2.07 mmol) in toluene (10 mL) was added 4-bromobenzaldehyde (1) (322 mg, 2.28 mmol) followed by AcOH (0.18 mL, 3.1 mmol). The reaction mixture was stirred at 80° C. for 16 h. After completion of the reaction, the reaction mixture was cooled to room temperature. The reaction mixture was diluted with water (100 mL) and extracted with EtOAc (2×100 mL). The combined organic layers were dried over $Na_2SO_4$, filtered and evaporated. The crude product was purified by silica gel column chromatography by eluting with 2% MeOH in DCM to afford (1R,3R)-2-(bicyclo[1.1.1]pentan-1-yl)-1-(4-bromophenyl)-3-methyl-2,3,4,9-tetrahydro-1H-pyrido[3,4-b]indole (2) (233 mg, 0.64 mmol, 31%). MS (ESI) m/z 407.3 [M+1]$^+$; $^1$H NMR (400 MHz, DMSO-$d_6$) δ 10.53 (s, 1H), 7.84 (d, J=1.6 Hz, 1H), 7.48 (d, J=8.4 Hz, 2H), 7.38 (d, J=7.6 Hz, 1H), 7.28 (d, J=8.0 Hz, 2H), 7.19 (d, J=8.0 Hz, 1H), 6.99-6.91 (m, 2H), 4.91 (s, 1H), 3.46 (q, 1H), 2.92-2.71 (dd, J=8.8, 2.8 Hz, 1H), 2.61-2.50 (m, 1H), 2.22 (s, 1H), 1.77 (d, J=9.2 Hz, 3H), 1.55 (d, J=9.2 Hz, 3H), 1.11 (d, J=6.8 Hz, 3H).

Step 2: To a solution of (1R,3R)-2-(bicyclo[1.1.1]pentan-1-yl)-1-(4-bromophenyl)-3-methyl-2,3,4,9-tetrahydro-1H-pyrido[3,4-b]indole (2) (0.47 g, 1.29 mmol) in DMA (5 mL) were added tert-butyl 3-aminoazetidine-1-carboxylate (3) (438 mg, 1.55 mmol) and NaOt-Bu (188.2 mg, 1.96 mmol). The reaction mixture was degassed under argon for 30 min. Later Brettphos-3rd gen precatalyst (30.45 mg, 0.03 mmol) was added and the reaction mixture was again degassed for 30 min. It was then heated at 110° C. under microwave irradiation for 1 h. After completion of the reaction, it was cooled to room temperature and filtered through a bed of celite. The filtrate was diluted with water (50 mL) and extracted with EtOAc (2×50 mL). The combined organic layers were dried over $Na_2SO_4$, filtered and evaporated. Thus obtained crude product was purified by silica gel column chromatography by eluting with 10-15% EtOAc in pet ether to afford tert-butyl 3-((4-((1R,3R)-2-(bicyclo

[1.1.1]pentan-1-yl)-3-methyl-2,3,4,9-tetrahydro-1H-pyrido[3,4-b]indol-1-yl)phenyl)amino)azetidine-1-carboxylate (4) (343 mg, 0.66 mmol, 51%). MS (ESI) m/z 500.56 [M+H]⁺; ¹H NMR (400 MHz, DMSO-d₆) δ 10.3 (s, 1H), 7.92 (d, J=1.6 Hz, 1H), 7.36 (d, J=7.6 Hz, 1H), 7.23-7.19 (dd, J=8.0, 2.0 Hz, 2H), 7.18 (d, J=7.6 Hz, 1H), 6.99-6.90 (m, 2H), 6.38 (d, J=8.4 Hz, 1H), 4.78 (s, 1H), 4.48 (m, 1H), 4.26-4.06 (m, 2H), 3.67 (br, 2H), 3.50 (br, 1H), 3.18 (d, J=6.8 Hz, 1H), 2.98-2.89 (dd, J=8.4, 2.4 Hz, 1H), 2.58-2.51 (m, 1H), 2.22 (s, 1H), 1.77 (d, J=5.6 Hz, 3H), 1.58 (d, J=9.6 Hz, 3H), 1.39 (s, 9H), 1.22 (d, J=6.8 Hz, 3H).

Step 3: To a solution of tert-butyl 3-((4-(((1R,3R)-2-(bicyclo[1.1.1]pentan-1-yl)-3-methyl-2,3,4,9-tetrahydro-1H-pyrido[3,4-b]indol-1-yl)phenyl)amino)azetidine-1-carboxylate (4) (340 mg, 0.65 mmol) in DCM (2 mL) cooled at 0° C. was added TFA (2 ml) in a dropwise fashion. The reaction mixture was stirred at room temperature for 16 h. After completion of the reaction, it was directly evaporated. Then it was triturated with diethyl ether to yield 260 mg (0.57 mmol, Quantitative yield) of N-(4-((1R,3R)-2-(bicyclo[1.1.1]pentan-1-yl)-3-methyl-2,3,4,9-tetrahydro-1H-pyrido[3,4-b]indol-1-yl)phenyl)azetidin-3-amine (5). MS (ESI) m/z 399.35 [M+H]⁺; ¹H NMR (400 MHz, DMSO-d₆) δ 10.96 (br, 1H), 10.37 (br, 1H), 7.49 (br, 2H), 7.34 (br, 2H), 7.18-6.98 (br, 4H), 6.67-6.58 (br, 2H), 5.70 (br, 1H), 4.36 (br, 1H), 4.25 (br, 1H), 3.38 (q, 3H), 2.98-2.72 (br, 2H), 2.55 (m, 2H), 2.37 (brs, 4H), 1.77 (br, 2H), 1.45 (br, 4H), 1.28 (br, 3H), 1.22-1.03 (br, 5H), 0.84 (m, 1H).

Step 4: To a solution of N-(4-((1R,3R)-2-(bicyclo[1.1.1]pentan-1-yl)-3-methyl-2,3,4,9-tetrahydro-1H-pyrido[3,4-b]indol-1-yl)phenyl)azetidin-3-amine (5) (260 mg, 0.57 mmol) in DMF (3 mL) were added 1-iodopropane (6) (94.4 mg, 0.68 mmol), TEA (236 mg, 1.71 mmol) at room temperature. The reaction mixture was stirred at RT for 16 h. After completion of the reaction, the reaction was diluted with water (5 mL) and extracted with EtOAc (2×15 mL). The combined organic layer was collected, dried over Na₂SO₄, filtered and evaporated. The crude product was purified by RP prep-HPLC to yield 70.4 mg (0.15 mmol, 25%) of N-(4-((1R,3R)-2-(bicyclo[1.1.1]pentan-1-yl)-3-methyl-2,3,4,9-tetrahydro-1H-pyrido[3,4-b]indol-1-yl)phenyl)-1-propylazetidin-3-amine (Compound 31). MS (ESI) m/z 441.08 [M+H]⁻, ¹H NMR (400 MHz, DMSO-d₆) δ 10.26 (s, 1H), 7.35 (d, J=7.6 Hz, 1H), 7.18 (d, J=8.0 Hz, 1H), 6.96 (d, J=8.4 Hz, 2H), 6.94-6.89 (m, 2H), 6.42 (d, J=8.4, Hz, 2H), 5.90 (d, J=6.8 Hz, 1H), 4.76 (s, 1H), 3.88 (q, 1H), 3.61 (m, 2H), 3.49-3.41 (br, 1H), 2.92-2.83 (dd, J=6.8, 2.0 Hz, 1H), 2.68 (m, 2H), 2.58-2.49 (m, 1H), 2.37 (d, J=8.8 Hz, 2H), 2.28 (s, 1H), 1.76-1.71 (d, J=9.6 Hz, 3H), 1.58-1.53 (d, J=8.8 Hz, 3H), 1.31-1.24 (m, 3H), 1.21 (d, J=9.2 Hz, 3H), 0.83 (t, J=7.6 Hz, 3H).

Example 32

3-((1S,3S)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 32)

Example 33

3-((1S,3S)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 33)

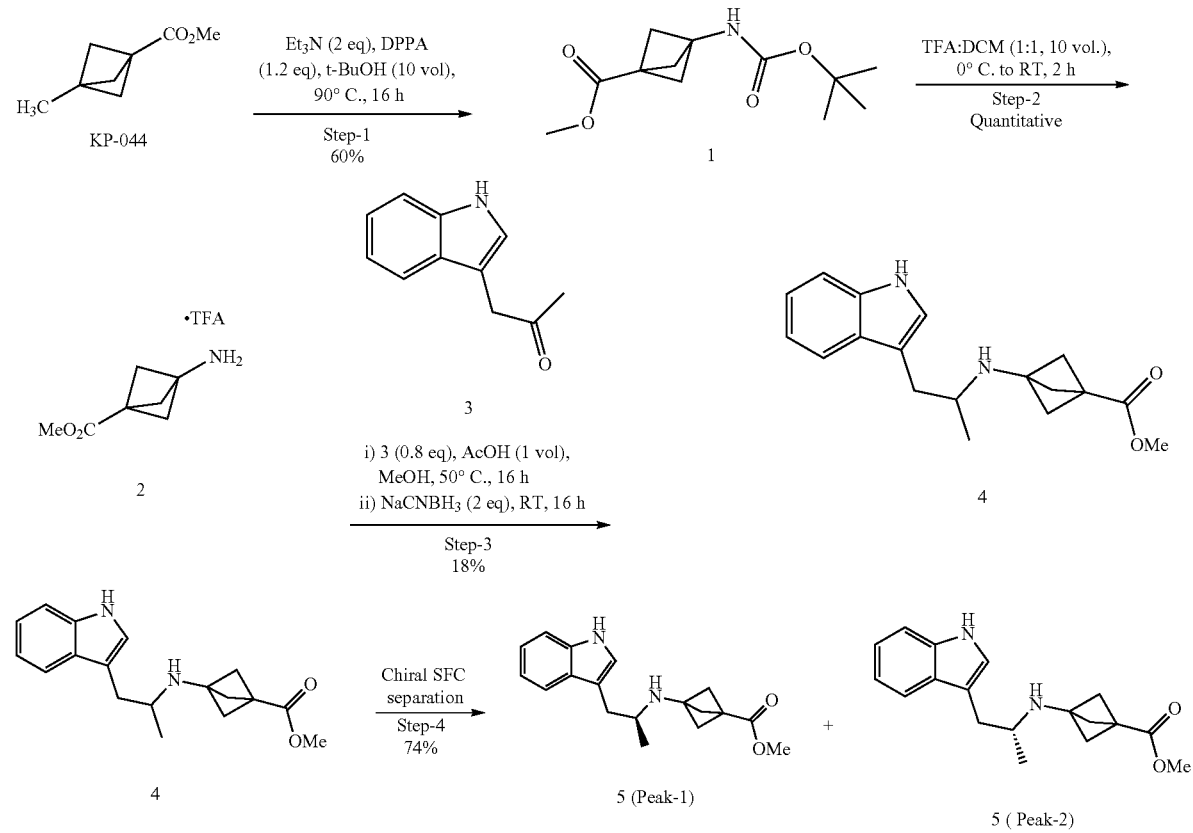

-continued
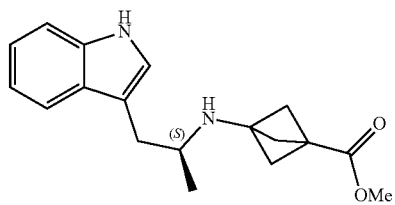
5 (Peak-1)
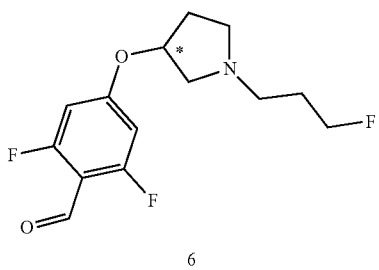
6
6 (1.1 eq), Tartaric acid (1.5 eq), EtOH
(10 vol), 80° C., 16 h
→
Step-6
25%
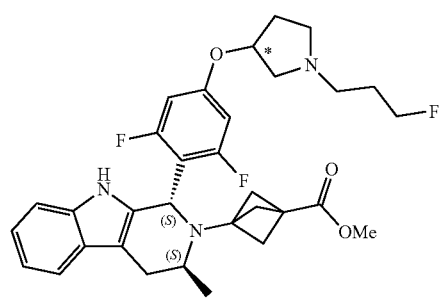
7
NH₃ (7M in MeOH, 20 vol),
MeOH
(10 vol), 0° C. to RT,
sealed tube, 16 h
→
Step-6
Quantitative
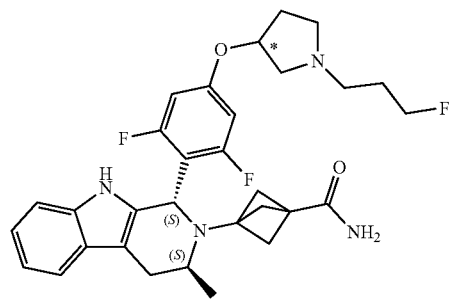
8
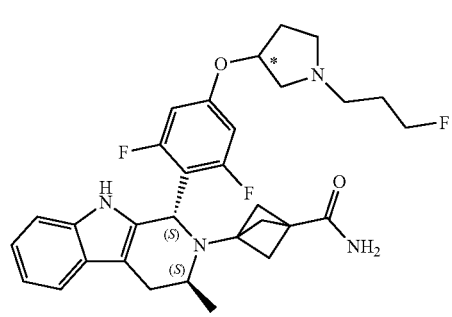
8
Chiral SFC separation
→
Step-7
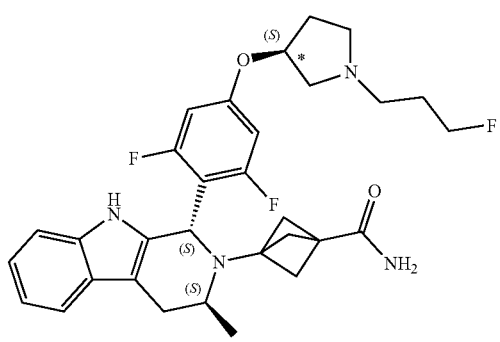
Compound 32
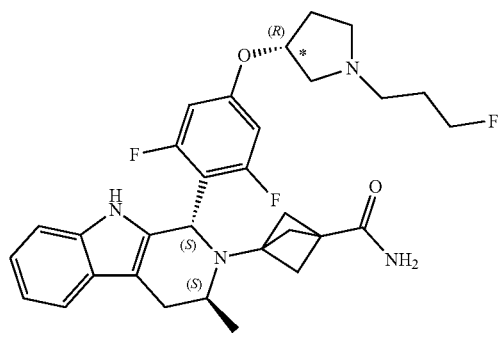
Compound 33

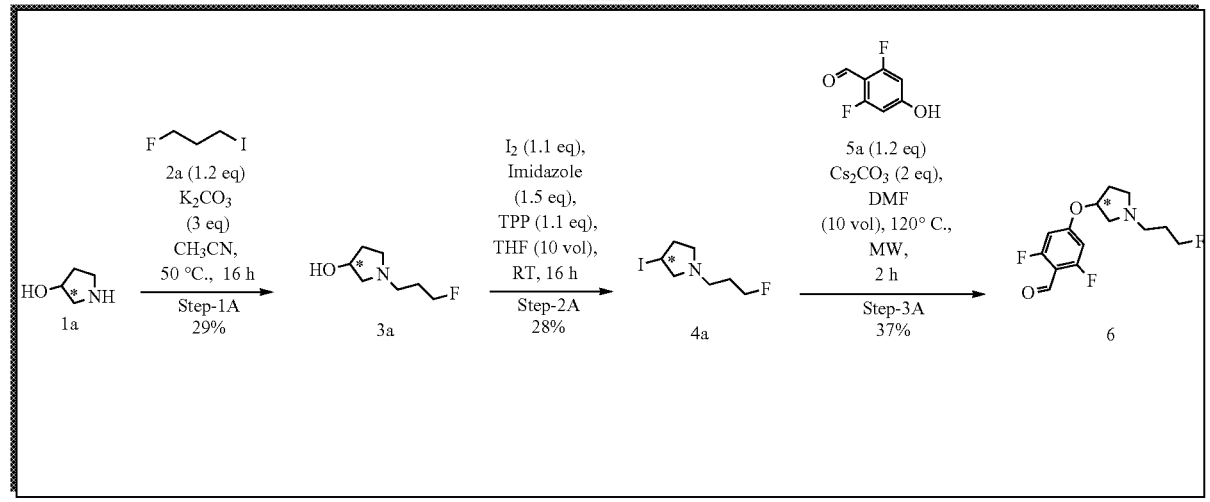

Step 1A: To a stirred solution of pyrrolidin-3-ol (1a) (20 g, 229.56 mmol) in CH₃CN (200 mL) were added 1-fluoro-3-iodopropane (2a) (51.8 g, 275.48 mmol) followed by $K_2CO_3$ (95 g, 688.68 mmol). The reaction was stirred at 50° C. for 16 h. After completion, the reaction mixture was cooled to room temperature, diluted with water (50 mL) and extracted with 10% MeOH/DCM (3×150 mL). The combined organic layers were dried over anhydrous $Na_2SO_4$, filtered and evaporated to afford 1-(3-fluoropropyl)pyrrolidin-3-ol (3a) (10 g, 29% yield). $^1$H NMR (400 MHz, DMSO-$d_6$) δ 4.64 (s, 1H), 4.52 (t, J=8 Hz, 1H), 4.40 (t, J=6.0 Hz, 1H), 4.16-4.15 (m, 1H), 2.65 (m, 1H), 2.51 (t, J=7.6 Hz, 1H), 2.45-2.36 (m, 3H), 2.28-2.25 (dd, J₁=7.2 Hz, J₂=3.36 Hz, 1H), 1.98-1.93 (m, 1H), 1.82-1.72 (m, 2H), 1.51 (bs, 1H).

Step 2A: To a stirred solution of 1-(3-fluoropropyl)pyrrolidin-3-ol (3a) (10 g, 67.94 mmol) in THF (100 mL) were added imidazole (6.94 g, 101.94 mmol) and TPP (19.60 g, 74.73 mmol) followed by iodine (18.97 g, 74.73 mmol). The reaction was stirred at room temperature for 16 h. After completion, the reaction mixture was quenched with saturated sodium thiosulphate (20 mL) and extracted with EtOAc (3×70 mL). The combined organic layers were dried over anhydrous $Na_2SO_4$, filtered and evaporated to get a crude residue. The crude was further purified by silica gel column chromatography (eluting with 10-20% EtOAc in petroleum ether) to afford 1-(3-fluoropropyl)-3-iodopyrrolidine (4a) (5 g, 28% yield). MS (ESI) m/z 258.09 [M+1]⁺; $^1$H NMR (400 MHz, CDCl₃) δ 4.56 (t, J=6 Hz, 1H), 4.59 (t, J=6 Hz, 1H), 4.29-4.25 (m, 1H), 3.18 (q, 1H), 2.93 (m, 1H), 2.70-2.60 (m, 4H), 2.53-2.48 (m, 1H), 2.30-2.26 (m, 1H), 1.93-1.83 (m, 2H).

Step 3A: To a stirred solution of 1-(3-fluoropropyl)-3-iodopyrrolidine (4a) (975 mg, 3.797 mmol) in DMF (10 mL) were added 2,6-difluoro-4-hydroxybenzaldehyde (5a) (0.719 g, 4.55 mmol) followed by $Cs_2CO_3$ (2.47 g, 7.58 mmol). The reaction was stirred at 100° C. for 3 h. After completion, the reaction mixture was cooled to room temperature, diluted with water (15 mL) and extracted with EtOAc (3×20 mL). The combined organic layers were dried over anhydrous $Na_2SO_4$, filtered and evaporated to get a crude residue. The crude was further purified by silica gel column chromatography by eluting with 30-40% EtOAc in petroleum ether to afford 2,6-difluoro-4-((1-(3-fluoropropyl)pyrrolidin-3-yl)oxy)benzaldehyde (6) (400 mg, 37%). MS (ESI) m/z 288.13 [M+1]⁺; $^1$H NMR (400 MHz, DMSO-$d_6$) δ 10.1 (s, 1H), 6.83 (d, J=11.2 Hz, 2H), 5.017-5.010 (m, 1H), 4.53 (t, J=5.6 Hz, 1H), 4.42 (t, J=6 Hz, 1H), 3.38 (s, 1H), 3.38 (s, 1H), 2.83-2.64 (m, 3H), 2.47 (d, J=1.6 Hz, 1H), 2.37-2.32 (m, 2H), 1.86-1.73 (m, 3H).

Step 1: To a stirred solution of 3-(methoxycarbonyl)bicyclo[1.1.1]pentane-1-carboxylic acid (10 g, 58.77 mmol) in t-BuOH (100 mL) were added Et₃N (16.5 mL, 117.53 mmol) followed by diphenyl phosphoryl azide (DPPA) (15.16 mL, 70.52 mmol). The reaction was stirred at room temperature for 2 h and then at 90° C. for 16 h. After completion, the reaction mixture was cooled to room temperature, diluted with water (50 mL) and extracted with EtOAc (3×50 mL). The combined organic layers were dried over anhydrous $Na_2SO_4$, filtered and evaporated to get semi-pure crude. Thus obtained crude product was purified by silica gel column chromatography by eluting with 10-20% EtOAc in petroleum ether to afford methyl 3-((tert-butoxycarbonyl)amino)bicyclo[1.1.1]pentane-1-carboxylate (1) (9.5 g, 60% yield)$^1$H NMR (400 MHz, DMSO-$d_6$) δ 7.62 (s, 1H), 3.59 (s, 3H), 2.12 (s, 6H), 1.37 (s, 9H).

Step 2: To a solution of methyl 3-((tert-butoxycarbonyl)amino)bicyclo[1.1.1]pentane-1-carboxylate (1) (9.5 g, 39.37 mmol) in DCM (95 mL) at 0° C. was added TFA (38 mL, 4 vol.) at 0° C. The reaction was stirred at room temperature for 2 h. After completion of the reaction, it was directly evaporated. The residue was triturated with diethyl ether to afford 11 g (46.18 mmol, quantitative yield) of methyl 3-aminobicyclo[1.1.1]pentane-1-carboxylate.TFA (2). MS (ESI) m/z 240.26 [M+H]⁺; $^1$H NMR (400 MHz, DMSO-$d_6$) δ 8.67 (s, 2H), 3.63 (s, 3H), 2.24 (s, 6H).

Step 3: To a stirred solution of 1-(1H-indol-3-yl)propan-2-one (3) (10.8 g, 62.34 mmol) in MeOH (60 mL) were added methyl 3-aminobicyclo[1.1.1]pentane-1-carboxylate.TFA (2) (11 g, 46.18 mmol) followed by AcOH (11 mL, 1 vol.). The reaction was stirred at room temperature for 3 h. NaCNBH₃ (5.8 g, 92.36 mmol) was then added, and the reaction mixture was stirred at room temperature for 16 h. After completion, the reaction mixture was neutralized by saturated solution of NaHCO₃ and extracted with EtOAc (3×50 mL). The combined organic layers were dried over $Na_2SO_4$, filtered and evaporated to get a crude residue. The crude was further purified by silica gel column chromatography by eluting with 10-15% MeOH in DCM to afford methyl 3-((1-(1H-indol-3-yl)propan-2-yl)amino)bicyclo[1.1.1]pentane-1-carboxylate (4) (2.5 g, 18% yield). MS (ESI) m/z 299.226 [M+1]$^+$; $^1$H NMR (400 MHz, DMSO-d$_6$) δ 10.88 (s, 1H), 7.48 (d, J=8 Hz, 1H), 7.32 (d, J=8.0 Hz, 1H), 7.12 (s, J=0.8 Hz, 1H), 7.04 (t, J=7.2 Hz, 1H), 6.97 (t, J=7.2 Hz, 1H), 4.38 (t, J=5.6 Hz, 1H), 3.58 (s, 3H), 3.165 (d, J=5.2 Hz, 1H), 2.94-2.99 (m, 1H), 2.83-2.78 (dd, J=14.0, 5.2 Hz, 1H), 2.52-2.55 (m, 1H), 2.29 (s, 1H), 1.955-2.00 (m, 6H), 0.94 (d, J=6.4 Hz, 3H).

Step 4: Methyl 3-((1-(1H-indol-3-yl)propan-2-yl)amino)bicyclo[1.1.1]pentane-1-carboxylate (4, racemic) (2.5 g) was purified by chiral SFC to afford methyl (S)-3-((1-(1H-indol-3-yl)propan-2-yl)amino)bicyclo[1.1.1]pentane-1-carboxylate 5 (Peak-1) (1 g, 40% yield) and methyl (R)-3-((1-(1H-indol-3-yl)propan-2-yl)amino)bicyclo[1.1.1]pentane-1-carboxylate 5 (Peak-2) (1.1 g, 44% yield). 5 (Peak-1) MS (ESI) m/z 299.32 [M+1]$^+$; $^1$H NMR (400 MHz, DMSO-d$_6$) δ 10.79 (s, 1H), 7.48 (d, J=8 Hz, 1H), 7.32 (d, J=8.0 Hz, 1H), 7.12 (d, J=2.0 Hz, 1H), 7.04 (t, J=7.2 Hz, 1H), 6.967 (t, J=7.2 Hz, 1H), 3.58 (s, 3H), 3.17 (d, J=5.2 Hz, 1H), 2.96-2.97 (brm, 1H), 2.78-2.83 (dd, J=14 Hz, 5.2 Hz, 1H), 2.50-2.55 (m, 1H), 1.95-2.00 (m, 6H), 0.937 (d, J=6.4 Hz, 3H). 5 (Peak-2): MS (ESI) m/z 299.32 [M+1]$^+$; $^1$H NMR (400 MHz, DMSO-d$_6$) δ 10.79 (s, 1H), 7.48 (d, J=8 Hz, 1H), 7.32 (d, J=8.0 Hz, 1H), 7.12 (d, J=2.0 Hz, 1H), 7.04 (t, J=7.2 Hz, 1H), 6.967 (t, J=7.2 Hz, 1H), 3.58 (s, 3H), 3.17 (d, J=5.2 Hz, 1H), 2.96-2.97 (brm, 1H), 2.78-2.83 (dd, J=14 Hz, 5.2 Hz, 1H), 2.50-2.55 (m, 1H), 1.95-2.00 (m, 6H), 0.937 (d, J=6.4 Hz, 3H). The absolute stereochemistry was arbitrarily assigned for Intermediate 5 (Peak-1) and Intermediate 5 (Peak-2).

Step 5: To a stirred solution of methyl (S)-3-((1-(1H-indol-3-yl)propan-2-yl)amino)bicyclo[1.1.1]pentane-1-carboxylate (5 Peak-1) (1 g, 3.35 mmol) in EtOH (10 mL) were added 2,6-difluoro-4-((1-(3-fluoropropyl)pyrrolidin-3-yl)oxy)benzaldehyde (6) (1.06 g, 3.69 mmol) followed by tartaric acid (0.754 mg, 5.03 mmol). The reaction was stirred at 80° C. for 16 h. After completion of the reaction, the reaction mixture was cooled to room temperature. The reaction mixture was neutralized by saturated solution of NaHCO$_3$ and extracted with EtOAc (3×30 mL). The combined organic layers were dried over Na$_2$SO$_4$, filtered and evaporated to get a crude residue. The crude was purified by silica gel column chromatography by eluting with 30-40% EtOAc in petroleum ether to afford methyl 3-((1S,3S)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxylate (7) (690 mg, 36.27% yield). MS (ESI) m/z 569.45 [M+1]$^+$.

Step 6: To a stirred solution of methyl 3-((1S,3S)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxylate (7) (690 mg, 1.21 mmol) in MeOH (10 mL) was added NH$_3$ (7 M in MeOH (14 mL, 20 vol). The reaction was stirred at room temperature for 16 h. After completion of the reaction, the reaction mixture was concentrated in reduced pressure to get a crude product. The crude was further purified by silica gel column chromatography by eluting with 0-10% MeOH in DCM to afford 3-((1S,3S)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (8) (670 mg, quantitative yield). MS (ESI) m/z 554.221 [M+H]$^+$;

Step 7: 3-((1S,3S)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (8) (0.2 g, 0.361 mmol) was purified by chiral SFC to afford 3-(((1S,3S)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 32) (55 mg, 27.5% yield) 3-(((1S,3S)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 33) (55 mg, 0.099 mmol, 27.5% yield). Compound 32: MS (ESI) m/z 551.36 [M–H]$^-$; $^1$H NMR (400 MHz, DMSO-d$_6$) δ 10.47 (s, 1H), 7.37 (d, J=8 Hz, 1H), 7.14-7.19 (m, 2H), 6.90-7.00 (m, 2H), 6.84 (s, 1H), 6.65 (d, J=11.2 Hz, 1H), 5.21 (s, 1H), 4.98 (s, 1H), 4.42 (t, J=6 Hz, 1H), 4.54 (t, J=6 Hz, 1H), 3.57 (brs, 1H), 2.62-2.93 (m, 2H), 2.29-2.57 (m, 8H), 1.70-1.91 (m, 8H), 1.08 (d, J=6.4 Hz, 3H). Compound 33: MS (ESI) m/z 551.40 [M–H]$^-$; $^1$H NMR (400 MHz, DMSO-d$_6$) δ 10.48 (s, 1H), 7.37 (d, J=8 Hz, 1H), 7.14-7.19 (m, 2H), 6.90-7.00 (m, 2H), 6.84 (s, 1H), 6.65 (d, J=11.2 Hz, 1H), 5.21 (s, 1H), 4.98 (s, 1H), 4.42 (t, J=6 Hz, 1H), 4.54 (t, J=6 Hz, 1H), 3.57 (brs, 1H), 2.62-2.93 (m, 2H), 2.29-2.57 (m, 8H), 1.70-1.91 (m, 8H), 1.07 (d, J=6.4 Hz, 3H). The absolute stereochemistry was arbitrarily assigned for Compound 32 and Compound 33.

Example 34

3-((1R,3R)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 34)

Example 35

3-((1R,3R)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 35)

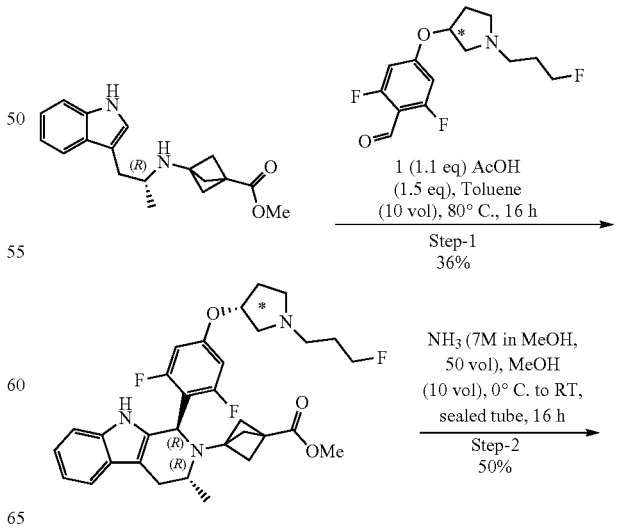

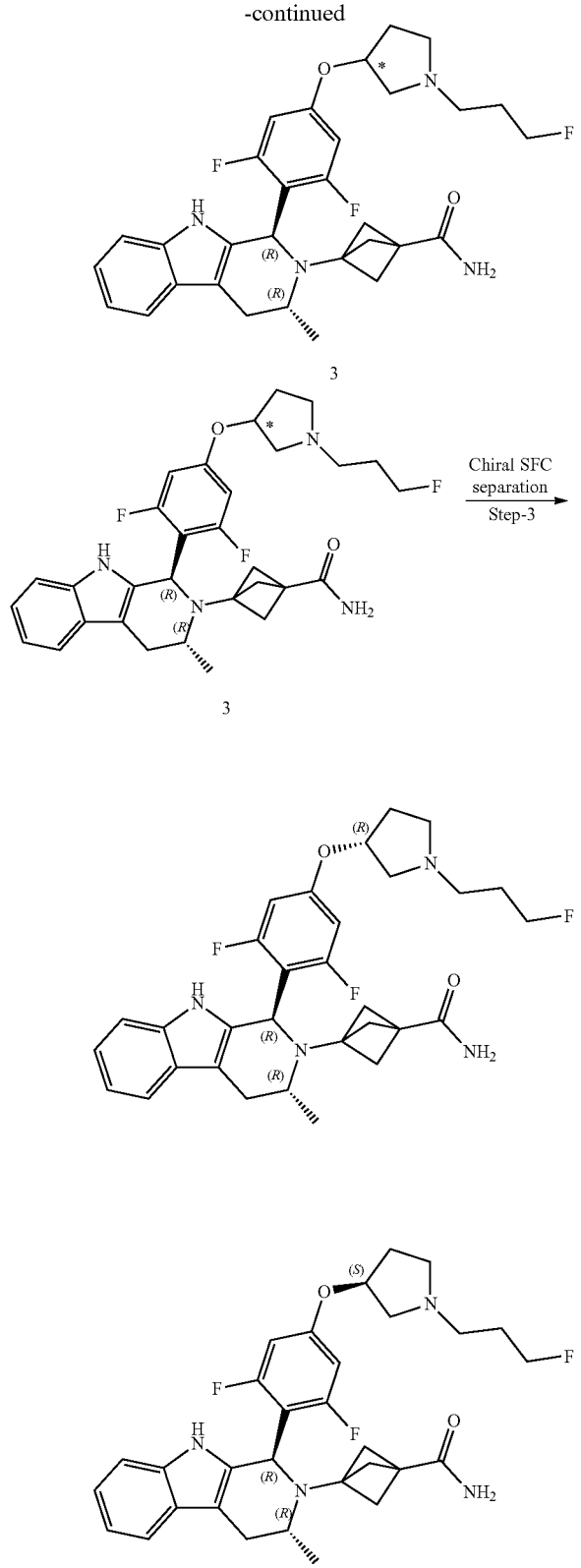

(1.16 g, 4.06 mmol) followed by tartaric acid (0.83 mg, 5.52 mmol). The reaction was stirred at 80° C. for 16 h. After completion of the reaction, the reaction mixture was cooled to room temperature, diluted with water (50 mL) and extracted with EtOAc (2×50 mL). The combined organic layers were dried over anhydrous $Na_2SO_4$, filtered and evaporated to get a crude product. The crude was purified by silica gel column chromatography by eluting with 60-70% EtOAc in petroleum ether to afford methyl 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxylate (2) (750 mg, 36% yield). MS (ESI) m/z 568.94 [M+H]$^+$; $^1$H NMR (400 MHz, DMSO-d6) δ 10.49 (s, 1H), 7.37 (d, J=8 Hz, 1H), 7.18 (d, J=8.0 Hz, 1H), 6.91-7.00 (m, 2H), 6.63 (d, J=11.2 Hz, 2H), 5.22 (s, 1H), 4.88-4.897 (brs, 1H), 4.52-4.9 (m, 1H), 4.4-4.3 (m, 1H), 3.55-3.59 (m, 4H), 2.27-2.94 (m, 8H), 1.98-2.04 (m, 4H), 1.74-1.85 (m, 6H), 1.06 (d, J=6.4 Hz, 3H).

Step 2: To a stirred solution of methyl 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxylate (2) (750 mg, 1.32 mmol) in MeOH (7.5 mL) was added $NH_3$ (7 M in MeOH, 15 mL, 20 vol.). The reaction was stirred at room temperature for 16 h. After completion of the reaction, the reaction mixture was concentrated under reduced pressure to obtain a crude product. The crude was further purified by silica gel column chromatography by eluting with 0-10% MeOH in DCM to afford 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (3) (770 mg, quantitative yield). MS (ESI) m/z 554.11 [M+H]$^+$; $^1$H NMR (400 MHz, DMSO-d$_6$) δ 10.47 (s, 1H), 7.37 (d, J=8 Hz, 1H), 7.15-7.19 (m, 2H), 6.90-7.00 (m, 2H), 6.84 (s, 1H), 6.61 (d, J=11.2 Hz, 2H), 5.21 (s, 1H), 4.98 (brs, 1H), 4.52-4.55 (m, 1H), 4.4-4.43 (m, 1H), 4.07-4.11 (m, 5H), 3.57 (brs, 1H), 3.16-3.17 (m, 14H), 2.37-2.93 (m, 7H), 1.70-1.91 (m, 9H), 1.07 (d, J=6.4 Hz, 3H).

Step 3: 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (3) (0.2 g, 0.361 mmol) was purified by chiral SFC to afford 3-((1R,3R)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 34) (55 mg, 27.5% yield) and 3-((1R,3R)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Compound 35) (55 mg, 27.5% yield). Compound 34: MS (ESI) m/z 551.40 [M−H]$^-$; $^1$H NMR (400 MHz, DMSO-d$_6$) δ 10.47 (s, 1H), 7.37 (d, J=8 Hz, 1H), 7.15-7.19 (m, 2H), 6.90-7.00 (m, 2H), 6.83 (s, 1H), 6.61 (d, J=11.2 Hz, 2H), 5.21 (s, 1H), 4.98 (brs, 1H), 4.47 (dt, J=47.2 Hz, 6 Hz, 2H), 3.57 (brs, 1H), 2.51-2.93 (m, 6H), 2.28-2.48 (m, 4H), 1.70-1.91 (m, 8H), 1.07 (d, J=6.4 Hz, 3H). Compound 35: MS (ESI) m/z 551.40 [M−H]$^-$; $^1$H NMR (400 MHz, DMSO-d$_6$) δ 10.47 (s, 1H), 7.37 (d, J=8 Hz, 1H), 7.15-7.19 (m, 2H), 6.90-7.00 (m, 2H), 6.83 (s, 1H), 6.61 (d, J=11.2 Hz, 2H), 5.21 (s, 1H), 4.98 (brs, 1H), 4.47 (dt, J=47.2 Hz, 6 Hz, 2H), 3.57 (brs, 1H), 2.51-2.93 (m, 6H), 2.28-2.48 (m, 4H), 1.70-1.91 (m, 8H), 1.07 (d, J=6.4 Hz, 3H). The absolute stereochemistry was arbitrarily assigned for Compound 34 and Compound 35.

Step 1: To a stirred solution of methyl (R)-3-((1-(1H-indol-3-yl)propan-2-yl)amino)bicyclo[1.1.1]pentane-1-carboxylate (Int-5, Peak-2 from Example 32 and 33) (1.1 g, 3.68 mmol) in EtOH (11 mL) were added 2,6-difluoro-4-((1-(3-fluoropropyl)pyrrolidin-3-yl)oxy)benzaldehyde (1)

Example 36

3-((1R,3R)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 36)

Example 37

3-((1R,3R)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 37)

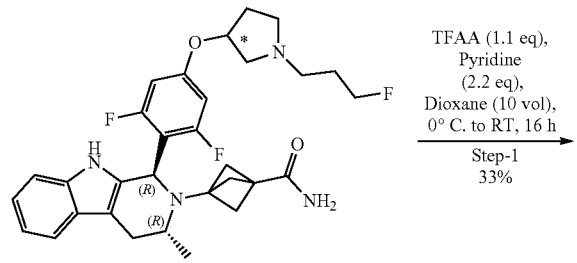

Intermediate 3, Example 34

TFAA (1.1 eq), Pyridine (2.2 eq), Dioxane (10 vol), 0° C. to RT, 16 h
Step-1
33%

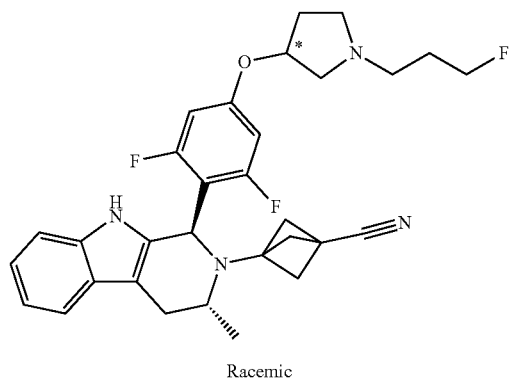

Racemic

Chiral SFC separation
Step-2

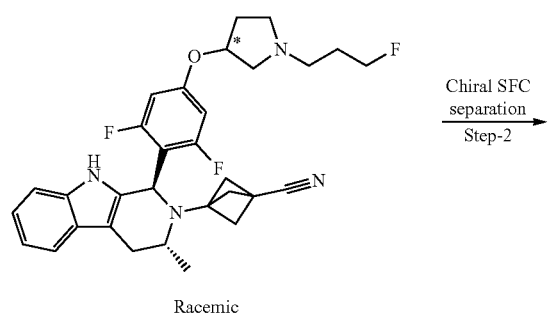

Racemic

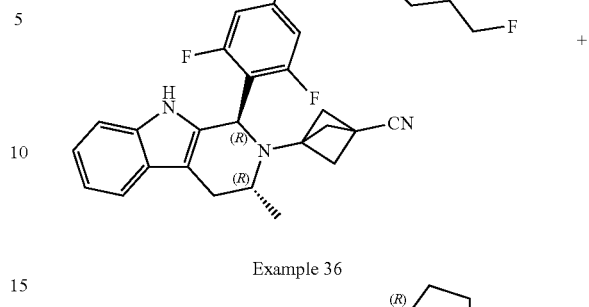

Example 36

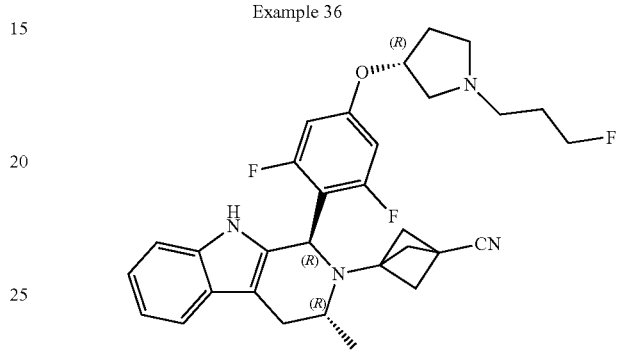

Example 37

Step 1: To a stirred solution of 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carboxamide (Example 34, intermediate 3) (370 mg, 0.67 mmol) in dioxane (37 mL) was added pyridine (0.12 mL, 1.473 mmol) followed by TFAA (0.1 mL, 0.737 mmol). The resulting mixture was stirred at room temperature for 16 h. After completion of the reaction, the reaction mixture was diluted with water (50 mL) and extracted with 10% MeOH/DCM (2×50 mL). The combined organic layers were dried over $Na_2SO_4$, filtered and evaporated to afford the crude product which was purified by reverse phase (RP) prep-HPLC to afford 3-((1R, 3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (120 mg, yield: 33%).

Step 2: 3-((1R,3R)-1-(2,6-difluoro-4-((1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (racemic) (120 mg, 0.22 mmol) was purified by chiral SFC to afford 3-((1R,3R)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 36) (44.6 mg, 0.082 mmol, 36.67% yield) and 3-((1R,3R)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 37) (49.1 g, 0.091 mmol, 41% yield). The stereochemistry of compound 36A (Peak-1) and Compound 36B (Peak-2) were assigned tentatively. Compound 36: MS (ESI) m/z 533.33 [M−H]−; $^1$H NMR (400 MHz, DMSO-$d_6$) δ 10.51 (s, 1H), 7.37 (d, J=7.6 Hz, 1H), 7.18 (d, J=8.0 Hz, 1H), 6.90 (t, J=6.8 Hz, 1H), 6.93 (t, J=7.2 Hz, 1H), 6.62 (d, J=10.8 Hz, 1H), 5.22 (s, 1H), 4.89 (s, 1H), 4.54 (t, J=6 Hz, 1H), 4.42 (t, J=6 Hz, 1H), 3.53 (brs, 1H), 2.91-2.85 (m, 1H), 2.83-2.81 (m, 1H), 2.71-2.49 (m, 3H), 2.50-2.06 (m, 7H), 2.07 (d, J=9.2 Hz, 3H), 1.86-1.74 (m, 3H), 1.07 (d, J=6.4 Hz, 3H). HPLC: 98.05%, LCMS: 99.86% and chiral SFC: 99.90%. Compound 37: MS (ESI) m/z 533.33 [M−H]⁻; ¹H NMR (400 MHz, DMSO-d6) δ 10.51 (s, 1H), 7.37 (d, J=7.6 Hz, 1H), 7.18 (d, J=8.0 Hz, 1H), 6.90 (t, J=6.8 Hz, 1H), 6.93 (t, J=7.2 Hz, 1H), 6.62 (d, J=10.8 Hz, 1H), 5.22 (s, 1H), 4.89 (s, 1H), 4.54 (t, J=6 Hz, 1H), 4.41 (t, J=6 Hz, 1H), 3.53 (brs, 1H), 2.91-2.85 (m, 1H), 2.83-2.81 (m, 1H), 2.71-2.49 (m, 3H), 2.50-2.06 (m, 7H), 2.07 (d, J=9.2 Hz, 3H), 1.86-1.74 (m, 3H), 1.07 (d, J=6.4 Hz, 3H). HPLC: 96.80%, LCMS: 99.05% and chiral SFC: 97.33%. The absolute stereochemistry was arbitrarily assigned for Compound 36 and Compound 37.

Example 38

(1R,3R)-2-(bicyclo[1.1.1]pentan-1-yl)-1-(4-((1-(3-fluoropropyl)azetidin-3-yl)oxy)phenyl)-3-methyl-2,3,4,9-tetrahydro-1H-pyrido[3,4-b]indole (Compound 38)

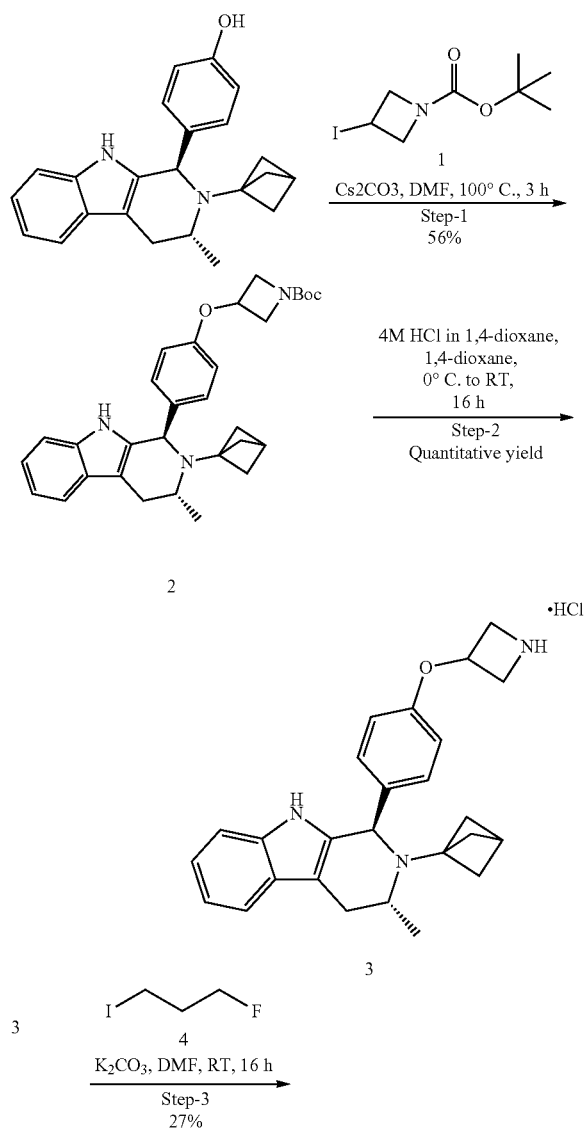

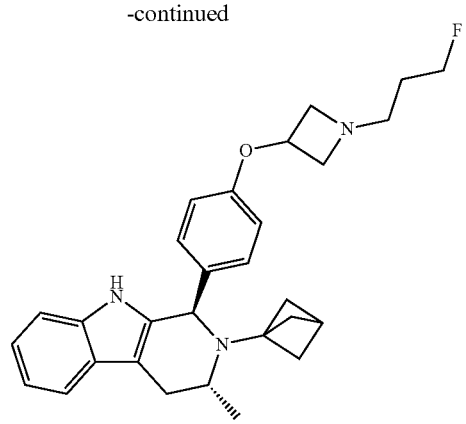

Compound 38

Step 1: To a solution of 4-((1R,3R)-2-(bicyclo[1.1.1] pentan-1-yl)-3-methyl-2,3,4,9-tetrahydro-1H-pyrido[3,4-b] indol-1-yl)phenol (prepared following a procedure analogous to that described for Int-4 from Example 24) (500 mg, 1.45 mmol) in DMF (5 mL) were added Cs₂CO₃ (942 mg, 2.9 mmol) and tert-butyl 3-iodoazetidine-1-carboxylate (1) (492 mg, 1.74 mmol). The resulting mixture was stirred at 100° C. for 3 h. After completion of the reaction, the reaction mixture was cooled to room temperature. The reaction mixture was diluted with water (100 mL) and extracted with EtOAc (2×100 mL). The combined organic layers were dried over Na₂SO₄, filtered and evaporated. The crude product was purified by silica gel column chromatography by eluting with 30% EtOAc in n-pentane to afford tert-butyl 3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenoxy)azetidine-1-carboxylate (2) (406 mg, 0.81 mmol, 56%). MS (ESI) m/z 500.4 [M+H]⁺; ¹H NMR (400 MHz, CDCl₃) δ 7.50-7.48 (dd, J=7.6, 4 Hz, 1H), 7.27-7.19 (m, 1H), 7.11-7.05 (m, 3H), 6.65 (d, J=8.8 Hz, 2H), 4.85 (m, 2H), 4.30-4.25 (q, 2H), 3.97-3.95 (q, 2H), 3.65 (m, 1H), 3.59 (m, 1H), 3.09-3.08 (dd, J=9.3, 2.4 Hz, 1H), 2.5d (d, 1H), 2.21 (s, 1H), 1.76 (d, J=9.6 Hz, 3H), 1.58 (d, J=9.6 Hz, 3H), 1.55 (s, 9H), 1.15 (d, J=6.4 Hz, 3H).

Step 2: To a solution of tert-butyl 3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenoxy)azetidine-1-carboxylate (2) (400 mg, 0.8 mmol) in 1,4-dioxane (2 mL) cooled at 0° C. was added 4M HCl in 1,4-dioxane (2 ml). The reaction mixture was then stirred at room temperature for 16 h. After completion of the reaction, it was directly evaporated. The crude product was triturated with diethyl ether to afford 349 mg (0.8 mmol, Quantitative yield) of (1R,3R)-1-(4-(azetidin-3-yloxy)phenyl)-2-(bicyclo[1.1.1] pentan-1-yl)-3-methyl-2,3,4,9-tetrahydro-1H-pyrido[3,4-b] indole (3). MS (ESI) m/z 400.43 [M+H]⁺.

Step 3: To a solution of (1R,3R)-1-(4-(azetidin-3-yloxy) phenyl)-2-(bicyclo[1.1.1]pentan-1-yl)-3-methyl-2,3,4,9-tetrahydro-1H-pyrido[3,4-b]indole (3) (270 mg, 0.62 mmol) in DMF (3 mL) were added 1-fluoro-3-iodopropane (4) (140 mg, 0.74 mmol) and K₂CO₃ (257 mg, 1.86 mmol) at room temperature. The reaction mixture was stirred at RT for 16 h. After completion of the reaction, the reaction mixture was diluted with water (5 mL) and extracted with EtOAc (2×15 mL). The combined organic layer was collected, dried over Na₂SO₄, filtered and evaporated. The crude product was purified by RP prep-HPLC to yield 74.4 mg (0.16 mmol, 27%) of (1R,3R)-2-(bicyclo[1.1.1]pentan-1-yl)-1-(4-((1-(3-fluoropropyl)azetidin-3-yl)oxy)phenyl)-3-methyl-2,3,4,9-tetrahydro-1H-pyrido[3,4-b]indole (Compound 38). MS (ESI) m/z 458.33 [M+H]$^+$; $^1$H NMR (400 MHz, DMSO-d$_6$) δ 10.4 (s, 1H), 7.37 (d, J=7.6 Hz, 1H), 7.20-7.17 (m, 3H), 7.00-6.90 (m, 2H), 6.74 (d, J=8.8 Hz, 1H), 2.74 (s, 1H), 4.73 (q, 1H), 4.48 (t, J=6.0 Hz, 1H), 4.38 (t, J=6.0 Hz, 1H), 3.72-3.69 (m, 2H), 3.44 (q, 1H), 2.93-2.89 (m, 3H), 2.58-2.49 (m, 3H), 2.20 (s, 1H), 1.74-1.58 (m, 8H), 1.10 (d, J=6.8 Hz, 3H).

Example 39

(1R,3R)-2-(bicyclo[1.1.1]pentan-1-yl)-3-methyl-1-(4-((1-propylazetidin-3-yl)oxy)phenyl)-2,3,4,9-tetrahydro-1H-pyrido[3,4-b]indole (Compound 39)

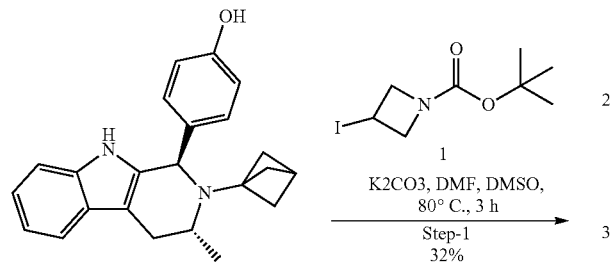

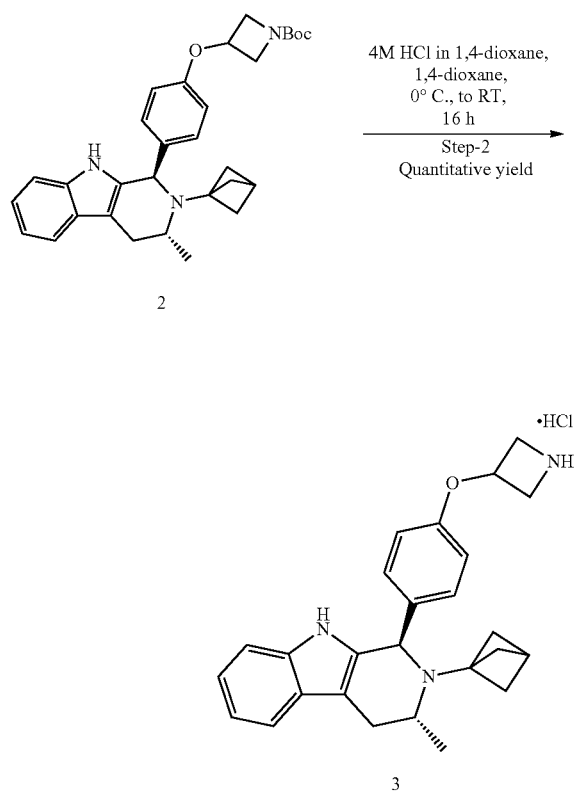

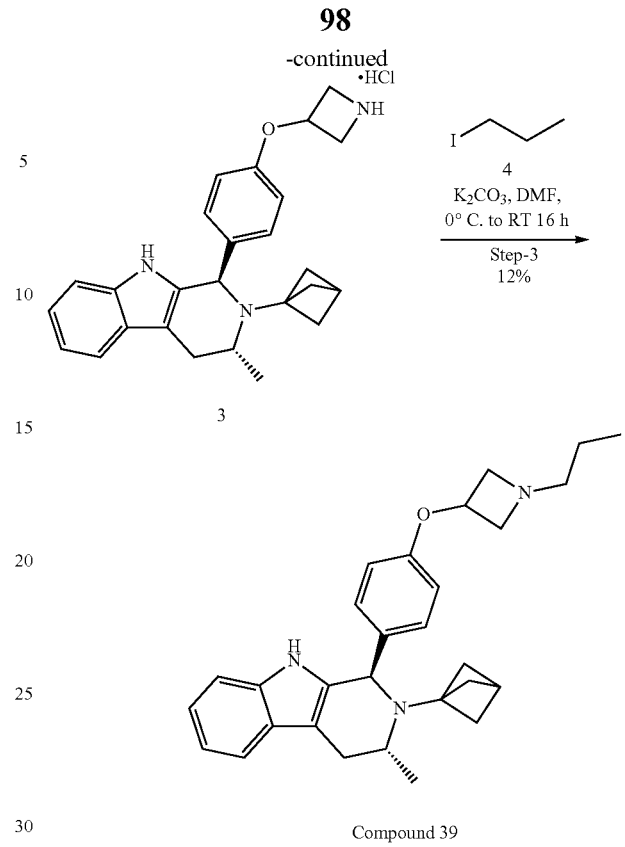

Compound 39

Step 1: To a stirred solution of 4-((1R,3R)-2-(bicyclo[1.1.1]pentan-1-yl)-3-methyl-2,3,4,9-tetrahydro-1H-pyrido[3,4-b]indol-1-yl)phenol (Example 24, Intermediate-4) (1 g, 2.89 mmol) in DMF (5 mL) and DMSO (0.5 mL) was added K$_2$CO$_3$ (799 mg, 5.79 mmol) followed by tert-butyl 3-iodo-azetidine-1-carboxylate (1) (899 mg, 3.17 mmol). The reaction mixture was stirred at 80° C. for 3 h. After completion of the reaction, the reaction mixture was cooled to room temperature. The reaction mixture was diluted with water (50 mL) and extracted with EtOAc (2×50 mL). The combined organic layers were dried over Na$_2$SO$_4$, filtered and evaporated to get semi-pure crude. Thus obtained crude product was purified by silica gel column chromatography by eluting with 20-25% EtOAc in pet ether to afford tert-butyl 3-(4-((1R,3R)-2-(bicyclo[1.1.1]pentan-1-yl)-3-methyl-2,3,4,9-tetrahydro-1H-pyrido[3,4-b]indol-1-yl)phenoxy)azetidine-1-carboxylate (2) (460 mg, 0.92 mmol, 32% yield). MS (ESI) m/z 500.82 [M+1]$^+$; $^1$H NMR (400 MHz, CDCl$_3$) δ 7.50-7.48 (m, 1H), 7.27-7.22 (m, 2H), 7.17-7.17 (m, 1H), 7.09-7.06 (m, 2H), 6.65 (d, J=8.8 Hz, 2H), 4.86-4.83 (m, 2H), 4.30-4.18 (m, 2H), 4.06-3.95 (m, 2H), 3.66 (br, 1H), 3.16-3.12 (dd, J=8.4, 2.2 Hz, 1H), 2.67-2.56 (d, J=8.8, Hz, 1H), 2.21 (s, 1H), 1.78 (d, J=8.8 Hz, 3H), 1.58 (d, J=9.2 Hz, 6H), 1.48 (s, 9H), 1.18 (d, J=6.8 Hz, 3H).

Step 2: To a stirred solution of tert-butyl 3-(4-((1R,3R)-2-(bicyclo[1.1.1]pentan-1-yl)-3-methyl-2,3,4,9-tetrahydro-1H-pyrido[3,4-b]indol-1-yl)phenoxy)azetidine-1-carboxylate (2) (400 mg, 1.12 mmol) in 1,4-dioxane (2 mL) was added 4M HCl in 1,4-dioxane (2 mL) drop-wise at 0° C. The reaction mixture was stirred at room temperature for 16 h. After completion of the reaction, it was evaporated under reduced pressure to yield a crude. The crude product was purified by silica gel column chromatography by eluting with 20-25% EtOAc in pet ether to afford (1R,3R)-1-(4-(azetidin-3-yloxy)phenyl)-2-(bicyclo[1.1.1]pentan-1-yl)-3- methyl-2,3,4,9-tetrahydro-1H-pyrido[3,4-b]indole (3) (348 mg, 0.69 mmol, quantitative yield). MS (ESI) m/z 400.36 [M−H]+; 1H NMR (400 MHz, DMSO-d6) δ 11.77-11.66 (br, 1H), 11.04-10.85 (br, 1H). 10.34-10.31 (br, 1H). 9.64-9.43 (br, 3H), 7.75-6.95 (br, 14H), 5.58 (br, 2H), 5.25 (br, 2H), 4.60 (br, 3H), 3.96 (br, 6H), 2.70 (br, 2H), 2.28 (br, 6H), 1.64 (br, 3H), 1.44 (br, 6H).

Step 3: To a stirred solution of (1R,3R)-1-(4-(azetidin-3-yloxy)phenyl)-2-(bicyclo[1.1.1]pentan-1-yl)-3-methyl-2,3, 4,9-tetrahydro-1H-pyrido[3,4-b]indole hydrochloride (3) (200 mg, 0.46 mmol) in DMF (1 mL) were added K2CO3 (187 mg, 1.38 mmol) and 1-iodopropane (4) (117 mg, 0.69 mmol) at 0° C. The reaction mixture was stirred at room temperature for 16 h. After completion of the reaction, it was diluted with water (50 mL) and extracted with 10% MeOH in DCM (3×50 mL). The organic layer was collected, dried over Na2SO4, filtered and evaporated. The crude product was purified by RP prep-HPLC to afford 25.2 mg (0.06 mmol, 12%) of (1R,3R)-2-(bicyclo[1.1.1]pentan-1-yl)-3-methyl-1-(4-((1-propylazetidin-3-yl)oxy)phenyl)-2,3,4,9-tetrahydro-1H-pyrido[3,4-b]indole (Compound 39). MS (ESI) m/z 442.41 [M+1]+; 1H NMR (400 MHz, DMSO-d6) δ 10.28 (s, 1H), 7.37 (d, J=7.2 Hz, 1H), 7.20-7.17 (m, 3H), 6.11-6.90 (m, 2H), 6.74 (d, J=8.4 Hz, 2H), 4.88 (s, 1H), 4.71 (t, J=6.0 Hz, 1H), 3.69-3.67 (q, 2H), 3.48 (q, 1H), 2.88-2.82 (m, 3H), 2.56-2.50 (m, 1H), 2.38 (q, J=5.6 Hz, 2H), 2.22 (s, 1H), 1.73 (d, J=8.0 Hz, 3H), 1.56 (d, J=9.2 Hz, 3H), 1.31-1.41 (m, 2H), 1.10 (d, J=6.8 Hz, 3H), 0.84 (d, J=7.2 Hz, 3H).

Example 40

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(3-fluoropropyl)azetidin-3-amine (Compound 40)

To a solution of (1R,3R)-2-(bicyclo[1.1.1]pentan-1-yl)-1-(4-bromophenyl)-3-methyl-2,3,4,9-tetrahydro-1H-pyrido[3,4-b]indole (400 mg, 0.98 mmol) (Intermediate 2 from Example 31) in 1,4-dioxane (10 mL) were added 1-(3-fluoropropyl)azetidin-3-amine (3) (194 mg, 1.47 mmol), NaOt-Bu (188.2 mg, 1.96 mmol). The reaction mixture was degassed under argon for 30 min. Next Brettphos-3rd gen pre-catalyst (44.39 mg, 0.05 mmol) was added, and the reaction mixture was again degassed for 30 min. It was then heated to 110° C. for 16 h. After completion of the reaction, it was cooled to room temperature and filtered through a bed of celite. The filtrate was diluted with water (50 mL) and extracted with EtOAc (2×50 mL). The combined organic layer was collected, dried over Na2SO4, filtered and evaporated. The crude product was purified by RP prep-HPLC to yield 128.1 mg (0.27 mmol, 29%) of N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(3-fluoropropyl)azetidin-3-amine (Compound 40). MS (ESI) m/z 457.38 [M+1]−; 1H NMR (400 MHz, DMSO-d6) δ 10.28 (s, 1H), 7.35 (d, J=7.2 Hz, 1H), 7.18 (d, J=8.0 Hz, 1H), 6.98-6.89 (m, 4H), 6.42 (d, J=8.4 Hz, 2H), 5.93 (d, J=6.8 Hz, 1H), 4.52 (s, 1H), 4.49 (t, J=6.0 Hz, 1H), 4.37 (t, J=6.0 Hz, 1H), 3.91-3.89 (m, 1H), 3.62 (q, 2H), 3.45-4.43 (q, 1H), 2.86-2.70 (dd, J=8.4, 2.4 Hz, 1H), 2.74 (q, 2H), 2.58-2.40 (m, 3H), 2.19 (s, 1H), 1.75-1.57 (m, 8H), 1.08 (d, J=6.4 Hz, 3H).

Example 41

5-((1R,3R)-2-(bicyclo[1.1.1]pentan-1-yl)-3-methyl-2,3,4,9-tetrahydro-1H-pyrido[3,4-b]indol-1-yl)-3-fluoro-N-(1-(3-fluoropropyl)azetidin-3-yl)pyridin-2-amine (Compound 41)

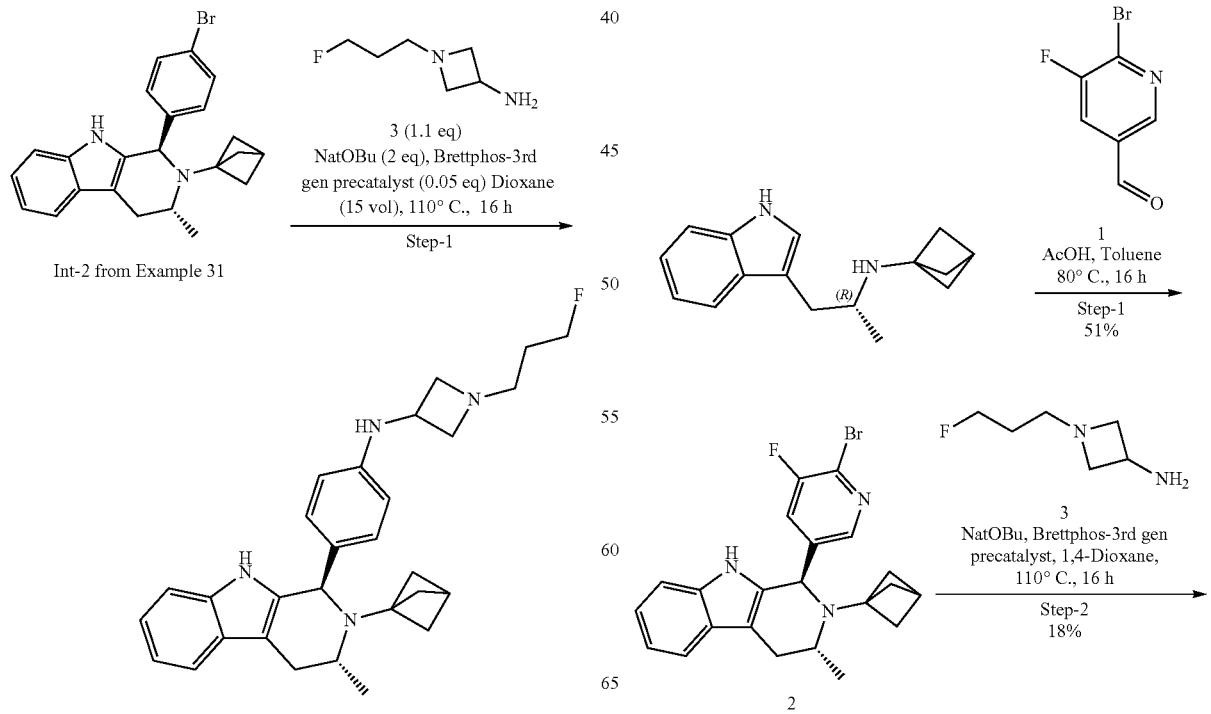

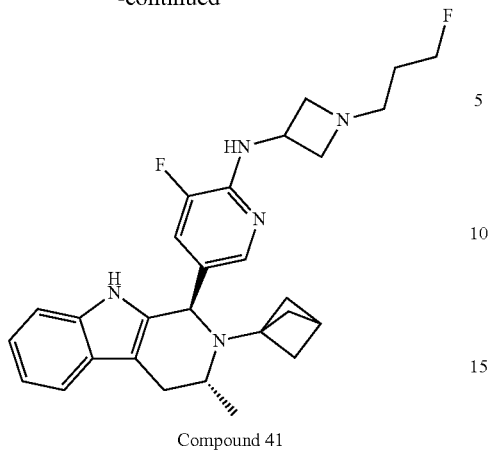

Compound 41

Step 1: To a stirred solution of (1R,3R)-2-(bicyclo[1.1.1] pentan-1-yl)-1-(6-bromo-5-fluoropyridin-3-yl)-3-methyl-2,3,4,9-tetrahydro-1H-pyrido[3,4-b]indole (1 g, 2.08 mmol) in toluene (10 mL) was added 6-bromo-5-fluoronicotinaldehyde (1) (465 mg, 2.28 mmol) followed by AcOH (0.18 mL, 3.12 mmol). The reaction was stirred at 80° C. for 16 h. After completion of the reaction, the reaction mixture was cooled to room temperature. The reaction mixture was diluted with water (30 mL) and extracted with EtOAc (2×30 mL). The combined organic layers were dried over Na$_2$SO$_4$, filtered and evaporated to get semi-pure product. Thus obtained crude product was purified by silica gel column chromatography by eluting with 10-12% EtOAc in pet ether to afford (1R,3R)-2-(bicyclo[1.1.1]pentan-1-yl)-1-(6-bromo-5-fluoropyridin-3-yl)-3-methyl-2,3,4,9-tetrahydro-1H-pyrido[3,4-b]indole (2) (450 mg 1.06 mmol, 51% yield). MS (ESI) m/z 426.17 [M+1]$^+$; $^1$H NMR (400 MHz, DMSO-d$_6$) δ 10.43 (s, 1H), 8.33 (s, 1H), 7.74-7.71 (dd, J=8.8, 1.6 Hz, 1H), 7.40 (d, J=7.6 Hz, 1H), 7.19 (d, J=7.6 Hz, 1H), 7.01 (t, J=7.2 Hz, 1H), 6.94 (d, J=7.6 Hz, 1H), 5.06 (s, 1H), 3.58-3.57 (q, 1H), 3.05-2.96 (dd, J=14.8, 4.8 Hz, 1H), 2.62 (d, J=2.4 Hz, 1H), 2.25 (s, 1H), 1.78 (d, J=9.6 Hz, 3H), 1.58 (d, J=9.2 Hz, 3H), 1.09 (d, J=6.8 Hz, 3H).

Step 2: To a stirred solution of (1R,3R)-2-(bicyclo[1.1.1] pentan-1-yl)-1-(6-bromo-5-fluoropyridin-3-yl)-3-methyl-2,3,4,9-tetrahydro-1H-pyrido[3,4-b]indole (2) (360 mg, 0.84 mmol) in 1,4-dioxane (10 mL) were added 1-(3-fluoropropyl)azetidin-3-amine (3) (223 mg, 1.69 mmol) and NaOt-Bu (162.2 mg, 1.69 mmol). The reaction mixture was degassed under argon for 30 min. Later Brettphos-3rd gen pre-catalyst (38 mg, 0.04 mmol) was added, and the reaction mixture was again degassed for 30 min. It was then heated at 110° C. for 16 h. After completion of the reaction, it was cooled to room temperature and filtered through a bed of celite. The filtrate was diluted with water (50 mL) and extracted with 10% MeOH in DCM (2×50 mL). The combined organic layers were dried over Na$_2$SO$_4$, filtered and evaporated. The crude product was purified by RP prep-HPLC to afford 5-((1R,3R)-2-(bicyclo[1.1.1]pentan-1-yl)-3-methyl-2,3,4,9-tetrahydro-1H-pyrido[3,4-b]indol-1-yl)-3-fluoro-N-(1-(3-fluoropropyl)azetidin-3-yl)pyridin-2-amine (Compound 41) (73.9 mg, 0.15 mmol, 18% yield). MS (ESI) m/z 476.38 [M−H]$^-$; $^1$H NMR (400 MHz, DMSO-d$_6$) δ 10.39 (s, 1H), 7.83 (s, 1H), 7.37 (d, J=7.6 Hz, 1H), 7.17 (d, J=7.6 Hz, 1H), 7.19-6.90 (m, 4H), 4.53 (s, 1H), 4.51-4.47 (q, 2H), 4.39 (t, J=6.0 Hz, 1H), 3.59 (t, J=7.4 Hz, 1H), 3.57-3.51 (q, 2H), 2.94-2.85 (m, 3H), 2.58-2.47 (m, 3H), 2.25 (s, 1H), 1.78 (d, J=8.8 Hz, 3H), 1.68 (m, 2H), 1.54 (d, J=8.8 Hz, 3H), 1.08 (d, J=8.8 Hz, 3H).

Example 42

(S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(3-fluoropropyl)pyrrolidin-3-amine (Compound 42)

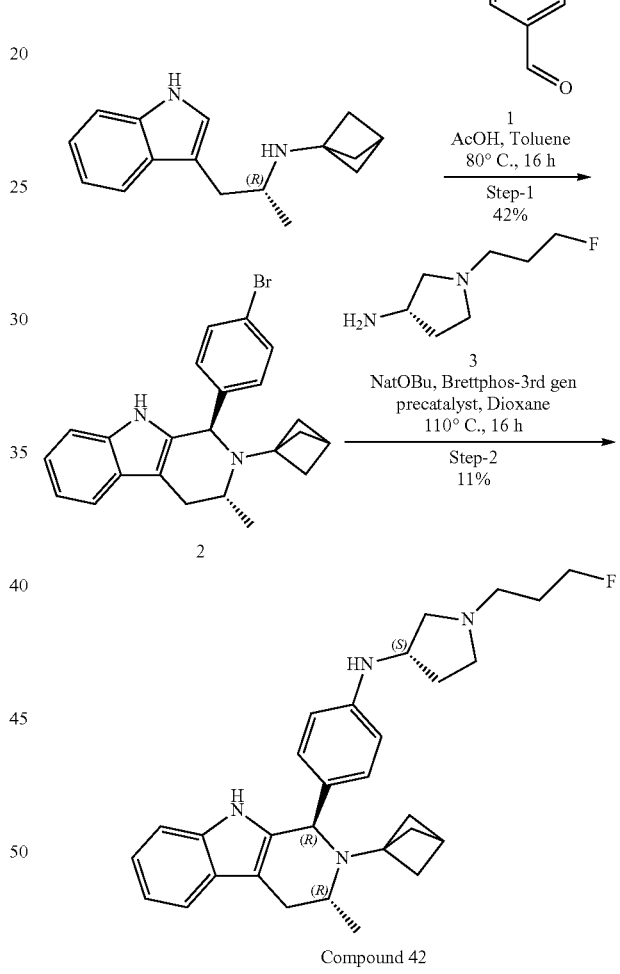

Compound 42

Step 1: To a stirred solution of (1R,3R)-2-(bicyclo[1.1.1] pentan-1-yl)-1-(6-bromo-5-fluoropyridin-3-yl)-3-methyl-2,3,4,9-tetrahydro-1H-pyrido[3,4-b]indole (1 g, 4.16 mmol) in toluene (10 mL) was added 4-bromobenzaldehyde (1) (840 mg, 4.58 mmol) followed by AcOH (0.36 mL, 6.24 mmol). The reaction mixture was stirred at 80° C. for 16 h. After completion of the reaction, the reaction mixture was cooled to room temperature. The reaction mixture was diluted with water (50 mL) and extracted with EtOAc (2×50 mL). Combined organic layers were dried over Na$_2$SO$_4$, filtered and evaporated to get semi-pure crude. Thus obtained crude product was purified by silica gel column chromatography by eluting with 12-15% EtOAc in pet ether to afford (1R,3R)-2-(bicyclo[1.1.1]pentan-1-yl)-1-(4-bromophenyl)-3-methyl-2,3,4,9-tetrahydro-1H-pyrido[3,4-b]indole (2) (709 mg 1.74 mmol, 42% yield). MS (ESI) m/z 407.33 [M+1]$^+$; $^1$H NMR (400 MHz, DMSO-d$_6$) δ 10.42 (s, 1H), 7.84 (d, J=2.0 Hz, 1H), 7.48 (d, J=8.4 Hz, 2H), 7.38 (d, J=7.6 Hz, 1H), 7.28 (d, J=8.0 Hz, 2H), 6.99 (t, J=7.2 Hz, 1H), 6.93 (t, J=7.6 Hz, 1H), 4.91 (s, 1H), 3.46 (q, 1H), 2.92-2.91 (dd, J=8.8, 1.6 Hz, 1H), 2.55 (d, J=2.4 Hz, 1H), 2.22 (s, 1H), 1.76 (d, J=9.6 Hz, 3H), 1.58 (d, J=9.2 Hz, 3H), 1.10 (d, J=6.8 Hz, 3H).

Step 2: To a stirred solution of (1R,3R)-2-(bicyclo[1.1.1]pentan-1-yl)-1-(4-bromophenyl)-3-methyl-2,3,4,9-tetrahydro-1H-pyrido[3,4-b]indole (2) (150 mg, 0.37 mmol) in 1,4-dioxane (5 mL) were added (S)-1-(3-fluoropropyl)pyrrolidin-3-amine (3) (108 mg, 0.74 mmol) and NaOt-Bu (71 mg, 0.74 mmol). The reaction mixture was degassed under argon for 30 min. Later Brettphos-3rd gen pre-catalyst (16.76 mg, 0.02 mmol) was added, and the reaction mixture was again degassed for 15 min. It was then heated at 110° C. for 16 h. After completion of the reaction, it was cooled to room temperature and filtered through a bed of celite. The filtrate was diluted with water (50 mL) and extracted with 10% MeOH in DCM (2×50 mL). The combined organic layers were dried over Na$_2$SO$_4$, filtered and evaporated. The crude product was purified by RP prep-HPLC to afford (S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(3-fluoropropyl)pyrrolidin-3-amine (Compound 42) (19.5 mg, 0.04 mmol, 11% yield). MS (ESI) m/z 473.57 [M–H]$^+$; $^1$H NMR (400 MHz, DMSO-d$_6$) δ 10.23 (s, 1H), 7.50 (d, J=7.6 Hz, 1H), 7.19 (d, J=8.0 Hz, 1H), 6.97-6.89 (m, 4H), 6.46 (d, J=8.0 Hz, 2H), 5.59 (d, J=6.8 Hz, 1H), 4.78 (s, 1H), 4.53 (t, J=6.0 Hz, 1H), 4.43 (t, J=7.4 Hz, 1H), 3.84 (q, 1H), 3.49 (q, 1H), 2.94-2.91 (dd, J=6.8, 1.6 Hz, 1H), 2.78 (t, J=4.4 Hz, 1H), 2.58-2.42 (m, 5H), 2.38 (br, 1H), 2.19 (s, 1H), 2.19 (br, 1H), 1.78 (d, J=8.4 Hz, 3H), 1.56 (d, J=7.6 Hz, 3H), 1.09 (d, J=6.8 Hz, 3H).

Example 43

(1R,3R)-2-(bicyclo[1.1.1]pentan-1-yl)-3-methyl-1-(6-(((1-propylazetidin-3-yl)oxy)pyridin-3-yl)-2,3,4,9-tetrahydro-1H-pyrido[3,4-b]indole (Compound 43)

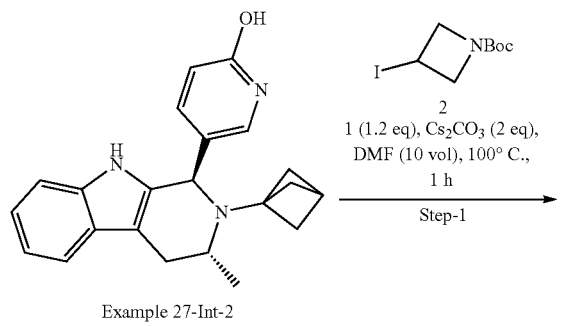

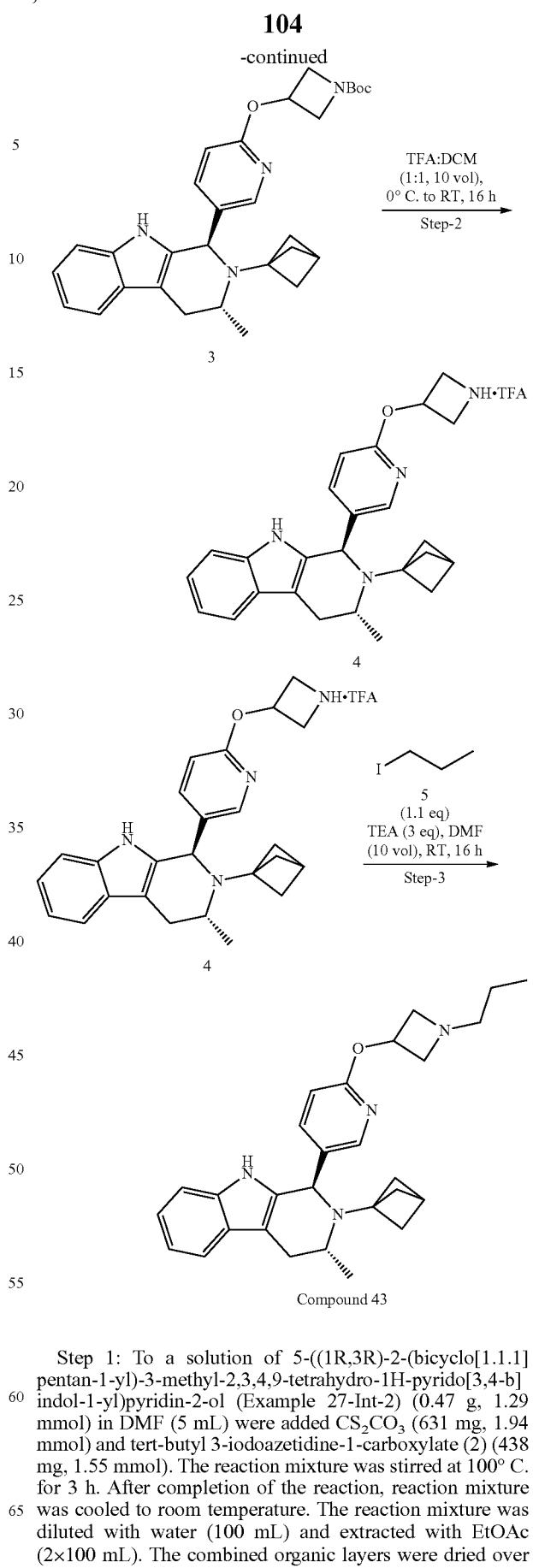

Step 1: To a solution of 5-((1R,3R)-2-(bicyclo[1.1.1]pentan-1-yl)-3-methyl-2,3,4,9-tetrahydro-1H-pyrido[3,4-b]indol-1-yl)pyridin-2-ol (Example 27-Int-2) (0.47 g, 1.29 mmol) in DMF (5 mL) were added CS$_2$CO$_3$ (631 mg, 1.94 mmol) and tert-butyl 3-iodoazetidine-1-carboxylate (2) (438 mg, 1.55 mmol). The reaction mixture was stirred at 100° C. for 3 h. After completion of the reaction, reaction mixture was cooled to room temperature. The reaction mixture was diluted with water (100 mL) and extracted with EtOAc (2×100 mL). The combined organic layers were dried over Na$_2$SO$_4$, filtered and evaporated. The crude product was purified by silica gel column chromatography by eluting with 50% EtOAc in pet-ether to afford tert-butyl 3-((5-((1R,3R)-2-(bicyclo[1.1.1]pentan-1-yl)-3-methyl-2,3,4,9-tetrahydro-1H-pyrido[3,4-b]indol-1-yl)pyridin-2-yl)oxy)azetidine-1-carboxylate (3) (343 mg, 0.66 mmol, 51%). MS (ESI) m/z 501.6 [M+H]$^+$; $^1$H NMR (400 MHz, DMSO-d$_6$) δ 10.37 (s, 1H), 8.10 (d, J=2.0 Hz, 1H), 7.57-7.54 (dd, J=8.4, 2.0 Hz, 1H), 7.38 (d, J=7.6 Hz, 1H), 7.19 (d, J=8.0 Hz, 1H), 6.99-6.91 (m, 2H), 6.79 (d, J=8.4 Hz, 1H), 5.28 (br, 1H), 4.93 (s, 1H), 4.62-4.58 (br, 2H), 4.26 (br, 2H), 4.08 (br, 1H), 3.77 (br, 2H), 3.52 (br, 1H), 2.97 (dd, J=8.4, 2.4 Hz, 1H), 2.61-2.51 (m, 1H), 2.24 (s, 1H), 1.77 (d, J=5.6 Hz, 3H), 1.55 (d, J=9.6 Hz, 3H), 1.39 (s, 9H), 1.22 (d, J=6.8 Hz, 3H).

Step 2: To a solution of tert-butyl 3-((5-((1R,3R)-2-(bicyclo[1.1.1]pentan-1-yl)-3-methyl-2,3,4,9-tetrahydro-1H-pyrido[3,4-b]indol-1-yl)pyridin-2-yl)oxy)azetidine-1-carboxylate (3) (340 mg, 0.65 mmol) in DCM (2 mL) cooled at 0° C. was added TFA (2 ml) dropwise. The reaction mixture was stirred at room temperature for 16 h. After completion of the reaction, it was directly evaporated. The crude product was triturated with diethyl ether to afford 260 mg (0.57 mmol, Quantitative yield) of (1R,3R)-1-(6-(azetidin-3-yloxy)pyridin-3-yl)-2-(bicyclo[1.1.1]pentan-1-yl)-3-methyl-2,3,4,9-tetrahydro-1H-pyrido[3,4-b]indole (4). MS (ESI) m/z 401.3 [M+H]$^+$; $^1$H NMR (400 MHz, DMSO-d$_6$) δ 10.47 (s, 1H), 8.07 (d, J=2.0 Hz, 1H), 7.53-7.51 (dd, J=8.4, 2.4 Hz, 1H), 7.38 (d, J=7.6 Hz, 1H), 7.18 (d, J=8.0 Hz, 1H), 6.99-6.91 (m, 2H), 6.73 (d, J=8.4 Hz, 1H), 5.33-5.30 (t, J=7.2 Hz, 1H), 4.91 (s, 1H), 4.22-4.18 (br, 4H), 4.77 (br, 2H), 3.59-3.48 (br, 8H), 3.18 (s, 10H), 2.98 (dd, J=8.4, 2.4 Hz, 1H), 2.62-2.50 (m, 1H), 2.24 (s, 1H), 1.74 (d, J=5.6 Hz, 3H), 1.55 (d, J=9.6 Hz, 3H), 1.38 (s, 2H), 1.22 (d, J=6.8 Hz, 3H).

Step 3: To a solution of (1R,3R)-1-(6-(azetidin-3-yloxy)pyridin-3-yl)-2-(bicyclo[1.1.1]pentan-1-yl)-3-methyl-2,3,4,9-tetrahydro-1H-pyrido[3,4-b]indole (4) (260 mg, 0.57 mmol) in DMF (3 mL) were added 1-iodopropane (5) (94.4 mg, 0.68 mmol), TEA (236 mg, 1.71 mmol) at room temperature. The reaction mixture was stirred at RT for 16 h. After completion of the reaction, the reaction mixture was diluted with water (5 mL) and extracted with EtOAc (2×15 mL). The combined organic layer was collected, dried over Na$_2$SO$_4$, filtered and evaporated. The crude product was purified by RP prep-HPLC to yield 70.4 mg (0.15 mmol, 25%) of (1R,3R)-2-(bicyclo[1.1.1]pentan-1-yl)-3-methyl-1-(6-((1-propylazetidin-3-yl)oxy)pyridin-3-yl)-2,3,4,9-tetrahydro-1H-pyrido[3,4-b]indole (Compound 43). MS (ESI) m/z 441.38 [M+H]$^-$, $^1$H NMR (400 MHz, DMSO-d$_6$) δ 10.4 (s, 1H), 8.08 (d, J=2 Hz, 1H), 7.53-7.50 (dd, J=8.4, 2.4 Hz, 1H), 7.38 (d, J=7.6 Hz, 1H), 7.18 (d, J=8.0 Hz, 1H), 7.00-6.91 (m, 2H), 6.72 (d, J=8.8, Hz, 1H), 5.09 (t, J=7.2 Hz, 1H), 4.91 (s, 1H), 3.66 (q, 2H), 3.51 (m, 1H), 3.02-2.88 (br, 3H), 2.66-2.52 (m, 1H), 2.36 (q, J=6.8, 2.4 Hz, 2H), 2.23 (s, 1H), 1.78-1.70 (d, J=9.6 Hz, 3H), 1.59-1.55 (d, J=8.8 Hz, 3H), 1.35-1.24 (m, 3H), 1.22 (d, J=9.2 Hz, 3H), 0.83 (t, J=7.6 Hz, 3H).

Example 44

5-((1S,3R)-2-(bicyclo[1.1.1]pentan-1-yl)-3-methyl-2,3,4,9-tetrahydro-1H-pyrido[3,4-b]indol-1-yl)-N—((S)-1-(3-fluoropropyl)pyrrolidin-3-yl)pyrazin-2-amine (Compound 44)

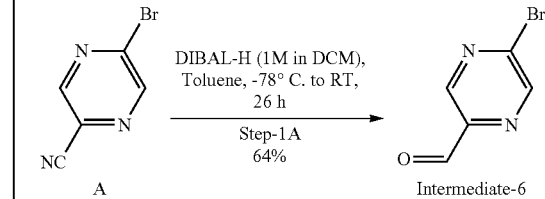

Step 1A: To a solution of 5-bromopyrazine-2-carbonitrile (A) (1.02 g, 5.54 mmol) in toluene (10 mL) cooled at −78° C. was added DIBAL-H (1 M in DCM) (8.3 ml, 8.32 mmol). It was then stirred at room temperature for 26 h. After completion of the reaction, the reaction was diluted with MeOH (4 mL) and stirred for 30 min at room temperature before addition of 10% H$_2$SO$_4$ (55 mL). The resulting solution was stirred for 1.75 h and extracted with EtOAc (100 mL, 50 mL). After solvent was removed at reduced pressure the crude product was purified by silica gel column chromatography to yield 660 mg (1.07 mmol, 64%) of 5-bromopyrazine-2-carbaldehyde (Intermediate 6). $^1$H NMR (400 MHz, CDCl$_3$) δ 10.14 (s, 1H), 8.92 (d, J=1.2 Hz, 1H), 8.85 (d, J=1.2 Hz, 1H).

Step 1: To a stirred solution of (R)—N-(1-(1H-indol-3-yl)propan-2-yl)bicyclo[1.1.1]pentan-1-amine (400 mg, 1.66 mmol) in toluene (10 mL) was added 5-bromopyrazine-2-carbaldehyde (1) (339.2 mg, 1.83 mmol) followed by AcOH (0.16 mL, 2.49 mmol). The reaction was stirred at 90° C. for 16 h. After completion of the reaction, it was cooled to room temperature. The reaction mixture was diluted with water (50 mL) and extracted with EtOAc (2×50 mL). The combined organic layer was collected, dried over Na$_2$SO$_4$, filtered and evaporated. The crude product was purified by silica gel column chromatography to yield 440 mg (1.07 mmol, 51%) of (1S,3R)-2-(bicyclo[1.1.1]pentan-1-yl)-1-(5-bromopyrazin-2-yl)-3-methyl-2,3,4,9-tetrahydro-1H-pyrido[3,4-b]indole (2). MS (ESI) m/z 409.2 [M+1]$^+$; $^1$H NMR (400 MHz, DMSO-d$_6$) δ 10.4 (s, 1H), 8.83 (d, J=1.6 Hz, 1H), 8.42 (d, J=2.4 Hz, 1H), 7.41 (d, J=7.6 Hz, 1H), 7.19 (d, J=8.0 Hz, 1H), 7.06-6.92 (m, 2H), 5.09 (s, 1H), 4.08 (t, J=5.2 Hz, 1H), 3.69-3.66 (m, 1H), 3.19-3.17 (d, 2H), 2.98-2.94 (dd, J=8.4, 2.4 Hz, 1H), 2.88-2.59 (dd, J=9.2, 2.4 Hz, 1H), 1.78 (d, J=7.2 Hz, 3H), 1.57 (d, J=6.8 Hz, 3H), 1.14 (d, J=6.8 Hz, 3H).

Step 2: To a stirred solution of (1S,3R)-2-(bicyclo[1.1.1]pentan-1-yl)-1-(5-bromopyrazin-2-yl)-3-methyl-2,3,4,9-tetrahydro-1H-pyrido[3,4-b]indole (2) (300 mg, 0.73 mmol) in 1,4-dioxane (10 mL) were added (S)-1-(3-fluoropropyl)pyrrolidin-3-amine (3) (213 mg, 1.46 mmol) and NaOt-Bu (140.1 mg, 1.46 mmol). The reaction mixture was degassed under argon for 30 min. Later Brettphos-3rd gen pre-catalyst (33.06 mg, 0.03 mmol) was added, and the reaction mixture was again degassed for 30 min. The reaction mixture was heated at 110° C. for 1 h under microwave irradiation. Progress of reaction was monitored by TLC and LCMS. After completion of the reaction, it was cooled to room temperature and filtered through a bed of celite. The filtrate was diluted with water (50 mL) and extracted with EtOAc (2×50 mL). The combined organic layers were dried over Na$_2$SO$_4$, filtered and evaporated. The crude product was purified by RP prep-HPLC to afford 5-((1S,3R)-2-(bicyclo[1.1.1]pentan-1-yl)-3-methyl-2,3,4,9-tetrahydro-1H-pyrido[3,4-b]indol-1-yl)-N—((S)-1-(3-fluoropropyl)pyrrolidin-3-yl)pyrazin-2-amine (Compound 44) (81 mg, 0.17 mmol, 23% yield). MS (ESI) m/z 475.16 [M–H]$^+$; $^1$H NMR (400 MHz, DMSO-d$_6$) δ 10.28 (s, 1H), 7.87 (d, J=1.2 Hz, 1H), 7.80 (d, J=1.2 Hz, 1H), 7.37 (d, J=7.6 Hz, 1H), 7.18 (d, J=7.6 Hz, 1H), 7.10 (d, J=6.8 Hz, 1H), 6.99-6.88 (m, 2H), 4.89 (s, 1H), 4.53 (t, J=6.0 Hz, 1H), 4.44 (t, J=6.4 Hz, 1H), 4.36 (q, 1H), 3.56 (q, 1H), 2.94-2.91 (dd, J=6.8, 1.6 Hz, 1H), 2.78 (t, J=4.8 Hz, 1H), 2.58-2.42 (m, 5H), 2.38 (br, 1H), 2.23 (s, 1H), 2.18 (br, 2H), 1.88 (m, 2H), 1.78 (d, J=8.4 Hz, 3H), 1.56 (d, J=7.6 Hz, 3H), 1.09 (d, J=6.8 Hz, 3H).

Example 45

2-(3-((5-((1R,3R)-2-(bicyclo[1.1.1]pentan-1-yl)-3-methyl-2,3,4,9-tetrahydro-1H-pyrido[3,4-b]indol-1-yl)pyridin-2-yl)amino)azetidin-1-yl)ethan-1-ol
(Compound 45)

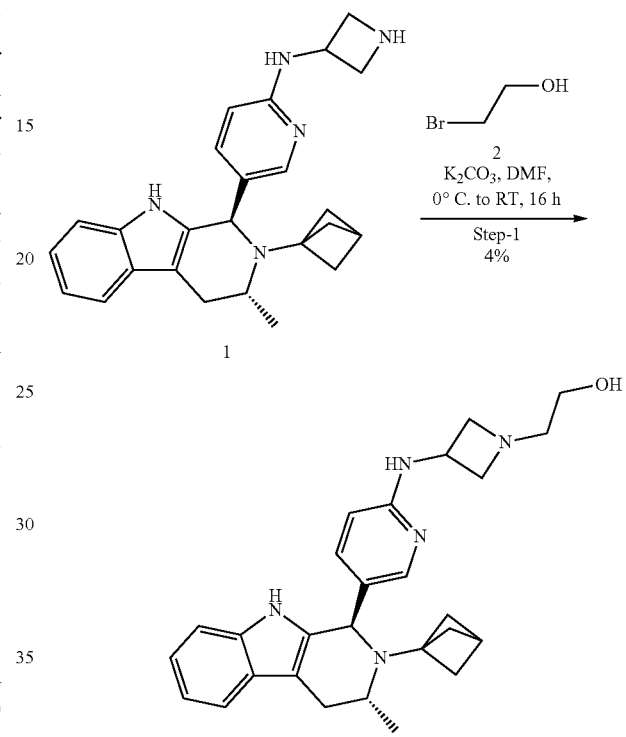

To a solution of N-(4-((1R,3R)-2-(bicyclo[1.1.1]pentan-1-yl)-3-methyl-2,3,4,9-tetrahydro-1H-pyrido[3,4-b]indol-1-yl)phenyl)azetidin-3-amine (1, Example 31-Intermediate 5) (100 mg, 0.25 mmol) in DMF (1 mL) were added K$_2$CO$_3$ (85.6 mg, 0.62 mmol) and 2-bromoethan-1-ol (2) (37.5 mg, 0.3 mmol) at 0° C. The reaction was stirred at RT for 16 h. After completion of the reaction, the reaction was diluted with water (3×5 mL) and extracted with 10% MeOH in DCM (2×15 mL). The combined organic layer was collected, dried over Na$_2$SO$_4$, filtered and evaporated. The crude product was purified by RP prep-HPLC to yield 4.8 mg (0.01 mmol, Yield=4%) of 2-(3-((5-((1R,3R)-2-(bicyclo[1.1.1]pentan-1-yl)-3-methyl-2,3,4,9-tetrahydro-1H-pyrido[3,4-b]indol-1-yl)pyridin-2-yl)amino)azetidin-1-yl)ethan-1-ol (Compound 45). MS (ESI) m/z 444.20 [M+H]$^+$, $^1$H NMR (400 MHz, DMSO-d$_6$) δ 10.27 (s, 1H), 7.89 (d, J=2.0 Hz, 1H), 7.36 (d, J=7.6 Hz, 1H), 7.19-7.15 (m, 2H), 6.89-6.99 (m, 2H), 6.83 (d, J=7.2 Hz, 1H), 6.35 (d, J=8.4 Hz, 1H), 4.78 (s, 1H), 4.34-4.38 (m, 1H), 3.64 (t, J=7.2 Hz, 1H), 3.49-3.52 (m, 1H), 3.37 (t, J=6.4 Hz, 1H), 2.95 (d, J=14.6 Hz, 4.8 Hz, 1H), 2.85 (t, J=7.2 Hz, 2H), 2.53-2.54 (m, 3H), 2.23 (s, 1H), 1.74 (d, J=8.4 Hz, 3H), 1.59 (d, J=9.2 Hz, 3H), 1.08 (d, J=6.8 Hz, 3H).

Example 46

2-(3-(4-((1R,3R)-2-(bicyclo[1.1.1]pentan-1-yl)-3-methyl-2,3,4,9-tetrahydro-1H-pyrido[3,4-b]indol-1-yl)phenoxy)azetidin-1-yl)ethan-1-ol (Compound 46)

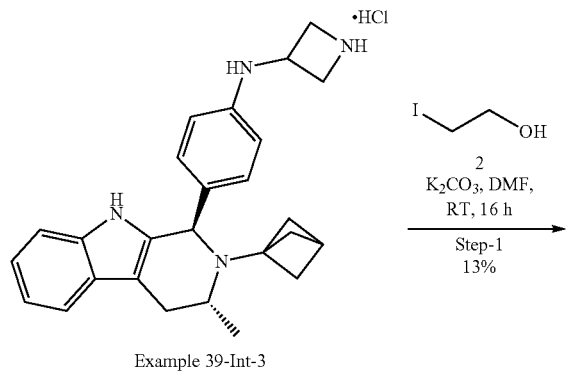

Example 39-Int-3

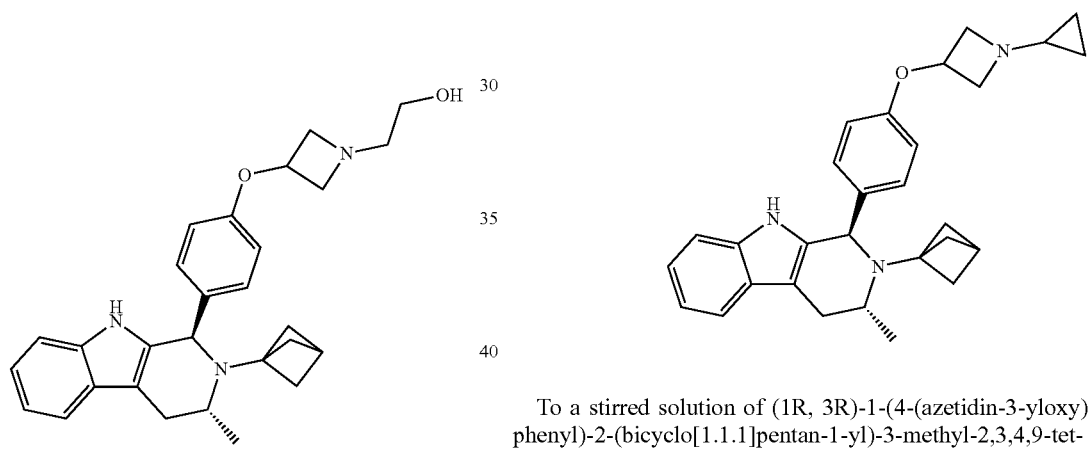

To a solution of (1R,3R)-1-(4-(azetidin-3-yloxy)phenyl)-2-(bicyclo[1.1.1]pentan-1-yl)-3-methyl-2,3,4,9-tetrahydro-1H-pyrido[3,4-b]indole (Example 39-Int-3) (300 mg, 0.69 mmol) in DMF (3 mL) were added K$_2$CO$_3$ (284 mg, 2.06 mmol) and 2-iodoethan-1-ol (1) (106.8 mg, 0.62 mmol) at room temperature. The reaction was stirred at RT for 16 h. After completion of the reaction, it was diluted with water (10 mL) and extracted with 10% MeOH in DCM (2×30 mL). The combined organic layer was collected, dried over Na$_2$SO$_4$, filtered and evaporated. The crude product was purified by RP prep-HPLC to yield 53.3 mg (0.12 mmol, 17%) of 2-(3-(4-((1R,3R)-2-(bicyclo[1.1.1]pentan-1-yl)-3-methyl-2,3,4,9-tetrahydro-1H-pyrido[3,4-b]indol-1-yl)phenoxy)azetidin-1-yl)ethan-1-ol (Compound 46). MS (ESI) m/z 442.41 [M+H]$^-$; $^1$H NMR (400 MHz, DMSO-d$_6$) δ 10.36 (s, 1H), 7.37 (d, J=7.6 Hz, 1H), 7.20-7.17 (m, 3H), 7.00-6.90 (m, 2H), 6.73 (d, J=8.8 Hz, 1H), 4.73 (s, 1H), 4.72 (q, 1H), 4.40 (t, J=6.0 Hz, 1H), 3.78 (q, 1H), 3.46 (q, 1H), 3.38-3.33 (m, 2H), 2.99-2.88 (m, 3H), 2.59-2.49 (m, 6H), 2.20 (s, 1H), 1.78 (d, J=8.4 Hz, 3H), 1.57 (d, J=8.4 Hz, 3H), 1.10 (d, J=6.8 Hz, 3H).

Example 47

(1R,3R)-2-(bicyclo[1.1.1]pentan-1-yl)-1-(4-((1-cyclopropylazetidin-3-yl)oxy)phenyl)-3-methyl-2,3,4,9-tetrahydro-1H-pyrido[3,4-b]indole (Compound 47)

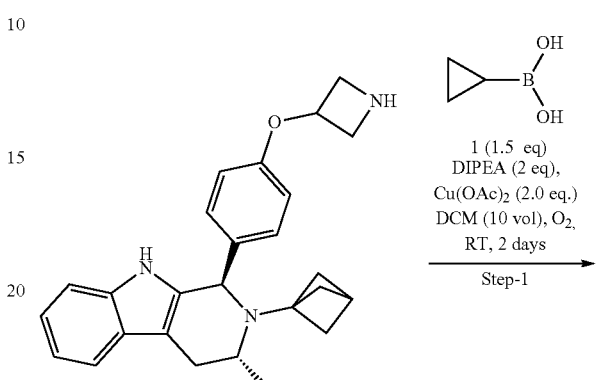

To a stirred solution of (1R, 3R)-1-(4-(azetidin-3-yloxy)phenyl)-2-(bicyclo[1.1.1]pentan-1-yl)-3-methyl-2,3,4,9-tetrahydro-1H-pyrido[3,4-b]indole (Example 39, Int-3) (0.25 g, 0.6257 mmol) in DCM (25 mL) were added cyclopropyl boronic acid (80.6 mg, 0.9386 mmol) followed by DIPEA (0.17 mL, 1.2514 mmol) and Cu(OAc)$_2$ (227.3 mg, 1.2514 mmol). The resulting reaction mixture was stirred at ambient temperature for 2 days under oxygen balloon pressure. After completion of the reaction, reaction mixture was evaporated. The crude product was purified by silica gel column chromatography by eluting with 2-5% MeOH in DCM to afford 120 mg of 68% pure product. The crude was further re-purified by reverse phase HPLC followed by lyophilizing the obtained pure fraction to afford (1R,3R)-2-(bicyclo[1.1.1]pentan-1-yl)-1-(4-bromophenyl)-3-methyl-2,3,4,9-tetrahydro-1H-pyrido[3,4-b]indole (2) (17.0 mg, 0.038 mmol, 6%) (47). MS (ESI) m/z 440.01 [M+1]$^+$; $^1$H NMR (400 MHz, DMSO-d$_6$) δ 10.3 (s, 1H), 7.37 (d, J=7.6 Hz, 1H), 7.20-7.17 (m, 3H), 6.97 (t, J=7.2 Hz, 1H), 6.92 (t, J=7.6 Hz, 1H), 6.74 (d, J=8.4 Hz, 2H), 4.87 (s, 1H), 4.69-4.66 (m, 1H), 3.72-3.68 (m, 2H), 3.45-3.43 (m, 1H), 3.41-3.31 (m, 2H), 2.91-2.87 (m, 1H), 2.59-2.54 (m, 1H), 2.20 (s, 1H), 1.91-1.89 (m, 1H), 1.72 (d, J=9.2 Hz, 3H), 1.59-1.56 (d, J=9.2 Hz, 3H), 1.10 (d, J=13.6 Hz, 3H), 0.34-0.32 (m, 2H), 0.23-0.22 (m, 2H).

Example 48

6-((1S,3R)-2-(bicyclo[1.1.1]pentan-1-yl)-3-methyl-2,3,4,9-tetrahydro-1H-pyrido[3,4-b]indol-1-yl)-N-(1-(prop-2-yn-1-yl)azetidin-3-yl)pyridin-3-amine (Compound 48)

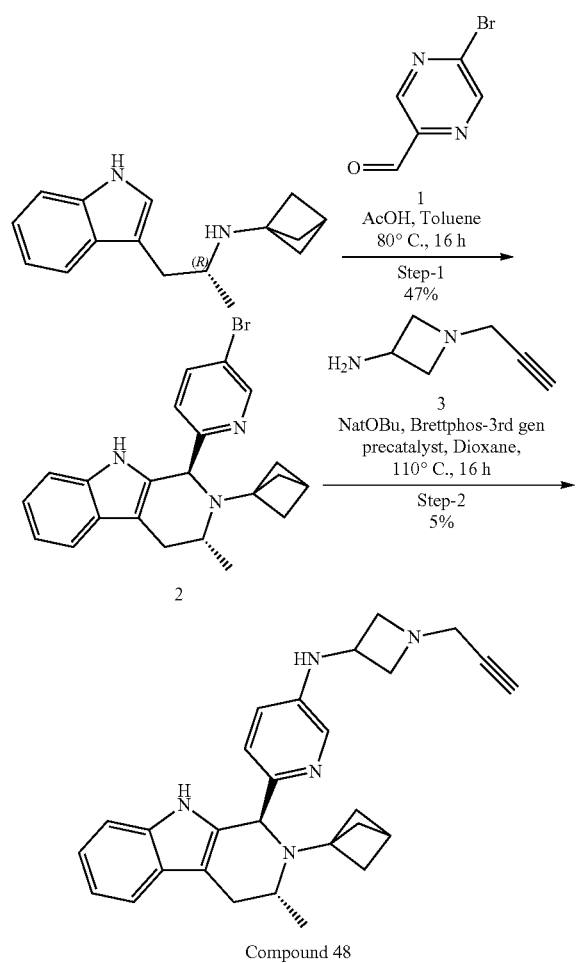

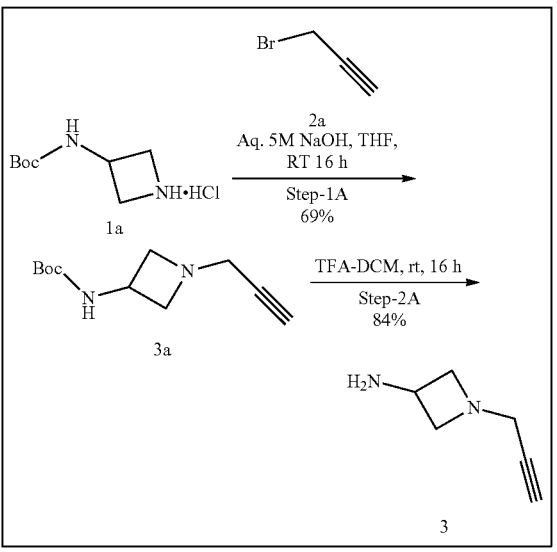

Step 1A: To an ice cooled stirred solution of tert-butyl azetidin-3-ylcarbamate hydrochloride (1a) (1 g, 4.81 mmol) in THF (10 mL) were added aq. 5M NaOH (5.76 mL, 28.84 mmol), followed by 3-bromoprop-1-yne (2a) (624 mg, 5.29 mmol) at 0° C. Then reaction mixture was stirred at room temperature for 16 h. After completion of the reaction, it was diluted with water (50 mL) and extracted with 10% MeOH in DCM (3×50 mL). The organic layer was collected, dried over $Na_2SO_4$, filtered and evaporated. The crude product was purified by silica gel column chromatography to yield 700 mg (3.33 mmol, 69%) of tert-butyl (1-(prop-2-yn-1-yl)azetidin-3-yl)carbamate (3a). $^1$H NMR (400 MHz, DMSO-$d_6$) δ 7.30 (d, J=6.8 Hz, 1H), 4.02-3.95 (m, 1H), 3.39 (t, J=6.8 Hz, 2H), 3.16-3.13 (m 3H), 2.91 (t, J=6.4 Hz, 2H), 1.36 (s, 9H)

Step 2A: To a stirred solution of tert-butyl (1-(prop-2-yn-1-yl)azetidin-3-yl)carbamate (3a) (700 mg, 3.33 mmol) in DCM (6 mL) was added TFA (3 mL) at 0° C. Then reaction mixture was stirred at room temperature for 16 h. After completion of the reaction, it was evaporated. The residue was then dissolved in 10% MeOH in DCM, and $K_2CO_3$ (2.29 g, 16.6 mmol) was added at 0° C. The reaction mixture was stirred for 20 min and then filtered. Filtrate was evaporated to yield 310 mg (2.81 mmol, 84%) of 1-(prop-2-yn-1-yl)azetidin-3-amine (3). MS (ESI) m/z 111.06 [M−H]$^+$; $^1$H NMR (400 MHz, DMSO-$d_6$) δ 3.48-3.22 (m, 2H), 3.18-3.11 (m, 5H), 2.68 (m, 2H), 1.88 (br, 2H).

Step 1: To a stirred solution of (R)—N-(1-(1H-indol-3-yl)propan-2-yl)bicyclo[1.1.1]pentan-1-amine (500 mg, 2.07 mmol) in toluene (10 mL) were added 5-bromopicolinaldehyde (1) (424.5 mg, 2.28 mmol) followed by AcOH (0.18 mL, 3.10 mmol). The reaction was stirred at 90° C. for 16 h. After completion of the reaction, it was cooled to room temperature. The reaction mixture was diluted with water (50 mL) and extracted with EtOAc (2×50 mL). The combined organic layer was collected, dried over $Na_2SO_4$, filtered and evaporated. The crude product was purified by silica gel column chromatography to yield 400 mg (0.98 mmol, 47%) of (1S,3R)-2-(bicyclo[1.1.1]pentan-1-yl)-1-(5-bromopyridin-2-yl)-3-methyl-2,3,4,9-tetrahydro-1H-pyrido[3,4-b]indole (2). MS (ESI) m/z 408.21 [M+1]$^+$; $^1$H NMR (400 MHz, DMSO-$d_6$) δ 10.42 (s, 1H), 8.41 (s, 1H), 7.55-7.51 (m, 2H), 7.42 (d, J=7.6 Hz, 1H), 7.22 (d, J=6.2 Hz, 1H), 6.99-6.92 (m, 2H), 4.99 (s, 1H), 3.54-3.50 (q, 1H), 3.01-2.96 (dd, J=15.2, 8.0 Hz, 1H), 2.62-2.53 (dd, J=14.8, 7.6 Hz, 1H), 2.24 (s, 1H), 1.76 (d, J=9.6 Hz, 3H), 1.58 (d, J=9.2 Hz, 3H), 1.10 (d, J=6.8 Hz, 3H).

Step 2: To a stirred solution of (1S,3R)-2-(bicyclo[1.1.1]pentan-1-yl)-1-(5-bromopyridin-2-yl)-3-methyl-2,3,4,9-tetrahydro-1H-pyrido[3,4-b]indole (2) (500 mg, 1.22 mmol) in 1,4-dioxane (10 mL) were added 1-(prop-2-yn-1-yl)azetidin-3-amine (3) (202 mg, 1.84 mmol) and NaOt-Bu (234 mg, 2.44 mmol). The reaction mixture was degassed under argon for 30 min. Later Brettphos-3rd gen pre-catalyst (55 mg, 0.06 mmol) was added, and the reaction mixture was again degassed for 30 min. It was then heated at 110° C. for 16 h. After completion of the reaction, it was cooled to room temperature and filtered through a bed of celite. The filtrate was diluted with water (50 mL) and extracted with 10% MeOH in DCM (2×50 mL). The combined organic layers were dried over $Na_2SO_4$, filtered and evaporated. The crude product was purified by RP prep-HPLC to afford 6-((1S,3R)-2-(bicyclo[1.1.1]pentan-1-yl)-3-methyl-2,3,4,9-tetrahydro-1H-pyrido[3,4-b]indol-1-yl)-N-(1-(prop-2-yn-1-yl)azetidin-3-yl)pyridin-3-amine (Compound 48) (25.7 mg, 0.06 mmol, 5% yield). MS (ESI) m/z 438.29 [M−H]$^+$; $^1$H NMR (400 MHz, DMSO-$d_6$) δ 10.24 (s, 1H), 7.82 (d, J=2.4

Hz, 1H), 7.35 (d, J=7.6 Hz, 1H), 7.19 (d, J=7.6 Hz, 1H), 6.95 (d, J=8.4 Hz, 1H), 6.93-6.91 (m, 2H), 6.78 (dd, J=8.4, 2.8 Hz, 1H), 6.22 (d, J=6.4 Hz, 1H), 4.86 (s, 1H), 3.94 (q, 1H), 3.59-3.56 (br, 3H), 3.33 (d, J=4.8 Hz, 2H), 3.38 (q, 1H), 2.96-2.91 (m, 3H), 2.58 (m, 1H), 2.58-2.42 (m, 5H), 2.38 (s, 1H), 1.73 (d, J=8.4 Hz, 3H), 1.52 (d, J=7.6 Hz, 3H), 1.09 (d, J=6.4 Hz, 3H).
Example 49
1-(6-((1S,3R)-2-(bicyclo[1.1.1]pentan-1-yl)-3-methyl-2,3,4,9-tetrahydro-1H-pyrido[3,4-b]indol-1-yl)pyridin-3-yl)-N-(3-fluoropropyl)azetidin-3-amine (Compound 49)
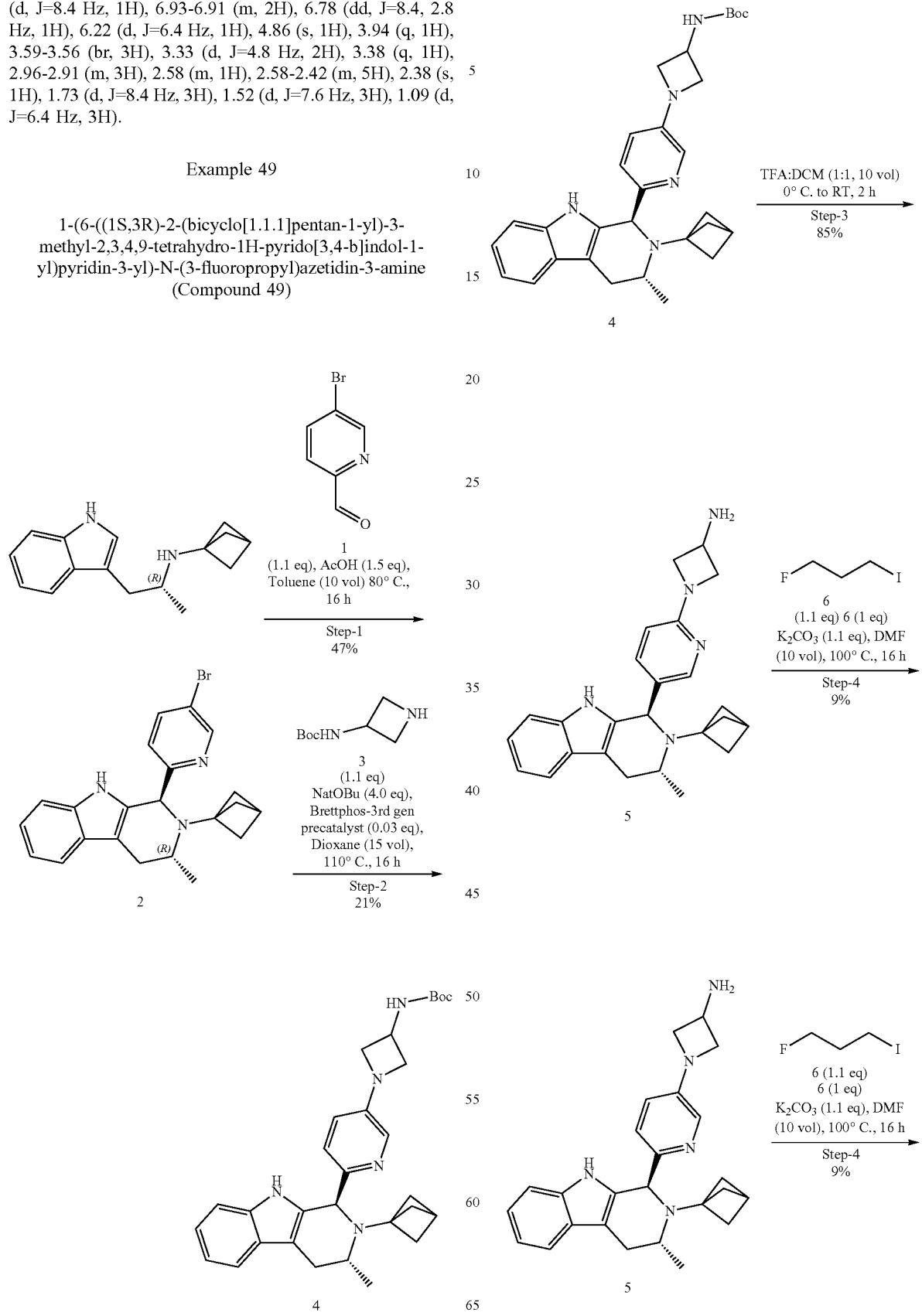

-continued

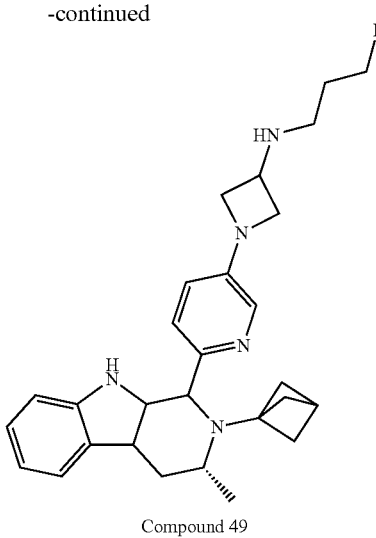

Compound 49

Step 1: To a solution of (R)—N-(1-(1H-indol-3-yl)propan-2-yl)bicyclo[1.1.1]pentan-1-amine (5 g, 20.81 mmol) in toluene (50 mL) were added 5-bromopicolinaldehyde (1) (3.46 g, 18.73 mmol) and acetic acid (1.87 g, 31.22 mmol). The reaction mixture was stirred at 80° C. for 16 h. After completion of the reaction, reaction mixture was cooled to room temperature and then quenched with saturated sodium bicarbonate solution (30 mL) at 0° C. The reaction mixture was diluted with water (150 mL) and extracted with EtOAc (2×100 mL). The combined organic layers were dried over $Na_2SO_4$, filtered and evaporated. The crude product was purified by silica gel column chromatography by eluting with 70% EtOAc in n-pentane to afford (1S,3R)-2-(bicyclo[1.1.1]pentan-1-yl)-1-(5-bromopyridin-2-yl)-3-methyl-2,3,4,9-tetrahydro-1H-pyrido[3,4-b]indole (2) (4 g, 9.82 mmol, yield=47%). MS (ESI) m/z 408.25 $[M+H]^+$, $^1H$ NMR (400 MHz, DMSO-$d_6$) δ 10.32 (s, 1H), 8.66 (d, J=2 Hz, 1H), 7.92-7.89 (dd, J=2.4 Hz, 8.4 Hz, 1H), 7.38 (d, J=7.2 Hz, 1H), 7.29 (d, J=8.4 Hz, 1H), 7.185 (d, J=8 Hz, 1H), 6.99-6.90 (m, 2H), 4.98 (s, 1H), 3.59-3.58 (m, 1H), 3.00-2.97 (m, 1H), 2.63-2.58 (dd, J=2.4 Hz, 14.8 Hz, 1H), 2.23 (s, 1H), 1.75-1.72 (m, 3H), 1.53-1.49 (m, 3H), 1.10 (d, J=6.8 Hz, 3H).

Step 2: A solution of (1S,3R)-2-(bicyclo[1.1.1]pentan-1-yl)-1-(5-bromopyridin-2-yl)-3-methyl-2,3,4,9-tetrahydro-1H-pyrido[3,4-b]indole (2) (3.5 g, 8.57 mmol) and tert-butyl azetidin-3-ylcarbamate (2.21 g, 12.85 mmol) in 1,4-dioxane (20 mL) was degassed with nitrogen for 10 min. NaOtBu (1.64 g, 17.14 mmol) was then added, followed by Brettphos (233 mg, 0.25 mmol). The reaction mixture was again degassed with nitrogen for 10 min and stirred at 110° C. for 16 h. The reaction mixture was cooled to room temperature and filtered through celite bed. Filtrate was diluted with water (200 mL) and extracted with EtOAc (2×200 mL). The combined organic layers were dried over $Na_2SO_4$, filtered and evaporated. The crude product was purified by silica gel column chromatography by eluting with 50% EtOAc in n-pentane to afford tert-butyl(1-(6-(((1S,3R)-2-(bicyclo[1.1.1]pentan-1-yl)-3-methyl-2,3,4,9-tetrahydro-1H-pyrido[3,4-b]indol-1-yl)pyridin-3-yl)azetidin-3-yl)carbamate (4) (900 mg, 2.20 mmol, yield=21%). MS (ESI) m/z 500.90 $[M+H]^+$, $^1H$ NMR (400 MHz, DMSO-$d_6$) δ 10.17 (s, 1H), 7.74 (d, J=2.8 Hz, 1H), 7.54 (d, J=7.2 Hz, 1H), 7.35 (d, J=7.6 Hz, 1H), 7.18 (d, J=8 Hz 1H), 6.97-6.88 (m, 2H), 6.75-6.73 (dd, J=2.8 Hz, 8.4 Hz, 1H), 4.90 (s, 1H), 4.42 (s, 1H), 4.12-4.07 (m, 2H), 3.61-3.54 (m, 3H), 2.98-2.93 (dd, J=4.8 Hz, 15.2 Hz 1H), 2.591-2.54 (dd, J=2.4 Hz, 14.8 Hz, 1H), 2.20 (s, 1H), 1.98 (s, 1H), 1.71 (d, J=8.4 Hz, 3H), 1.50 (d, J=9.2 Hz, 3H), 1.39 (s, 9H), 1.20-1.19 (m, 2H), 1.09 (d, J=6.4 Hz, 3H).

Step 3: To a solution of tert-butyl (1-(6-(((1S,3R)-2-(bicyclo[1.1.1]pentan-1-yl)-3-methyl-2,3,4,9-tetrahydro-1H-pyrido[3,4-b]indol-1-yl)pyridin-3-yl)azetidin-3-yl)carbamate (4) (700 mg, 1.40 mmol) in DCM (3.5 mL) was added trifluoro acetic acid (3.5 mL) at 0° C. The reaction was allowed to stir at RT for 2 h. The reaction mixture was diluted with DCM (50 mL) and quenched with saturated sodium bicarbonate solution (20 mL) and washed with water (20 mL). The organic layer was concentrated to afford 1-(6-(((1S,3R)-2-(bicyclo[1.1.1]pentan-1-yl)-3-methyl-2,3,4,9-tetrahydro-1H-pyrido[3,4-b]indol-1-yl)pyridin-3-yl)azetidin-3-amine (5) (550 mg, 1.37 mmol, yield=85%). MS (ESI) m/z 400.62 $[M+H]^+$. $^1H$ NMR (400 MHz, DMSO-$d_6$) δ 10.16 (s, 1H), 7.74 (d, J=2.4 Hz, 1H), 7.35 (d, J=7.6 Hz, 1H), 7.17 (d, J=8 Hz, 1H), 7.04 (d, J=8.4 Hz 1H), 6.97-6.88 (m, 2H), 6.75-6.72 (dd, J=2.8 Hz, 8.4 Hz, 1H), 5.75 (s, 1H), 4.90 (s, 1H), 4.09-4.05 (m, 2H), 3.86 (t, J=6 Hz, 3H), 3.56 (br, 2H), 3.439 (m, 2H), 2.98-2.94 (dd, J=3.6 Hz, 13.6 Hz 1H), 2.591-2.58 (m, 1H), 2.20 (s, 1H), 1.78-1.71 (m, 1H), 1.50 (d, J=9.2 Hz, 3H), 1.09 (d, J=6.8 Hz, 3H).

Step 4: To a solution of 1-(6-(((1S,3R)-2-(bicyclo[1.1.1]pentan-1-yl)-3-methyl-2,3,4,9-tetrahydro-1H-pyrido[3,4-b]indol-1-yl)pyridin-3-yl)azetidin-3-amine (5) (255 mg, 0.639 mmol) in DMF (2.5 mL) were added 1-fluoro-3-iodopropane (120 mg, 0.639 mmol) followed by potassium carbonate (97 mg, 0.703 mmol). The reaction mixture was heated at 100° C. for 16 h. The reaction mixture was quenched with ice cooled water (30 mL) and extracted with EtOAc (2×80 mL). The organic layer was washed with brine solution (2×50 mL). The combined organic layer was collected, dried over $Na_2SO_4$, filtered and evaporated to yield a crude. The crude was purified by Prep-HPLC to get 1-(6-(((1S,3R)-2-(bicyclo[1.1.1]pentan-1-yl)-3-methyl-2,3,4,9-tetrahydro-1H-pyrido[3,4-b]indol-1-yl)pyridin-3-yl)azetidin-3-amine (Compound 49) (24 mg, 0.052 mmol, yield=9%). MS (ESI) m/z 460.3 $[M+H]^+$; $^1H$ NMR (400 MHz, DMSO-$d_6$) δ 10.4 (s, 1H), 7.735 (d, J=2.8 Hz, 1H), 7.358 (d, J=7.6 Hz, 1H), 7.170 (d, J=7.6 Hz, 1H), 7.04 (d, J=8.8 Hz, 1H), 6.97-6.88 (m, 2H), 6.74-6.71 (dd, J=2.8 Hz, 8.4 Hz, 1H), 4.904 (s, 1H), 4.551 (m, 1H), 4.43 (m, 1H), 4.071 (m, 2H), 3.577 (br, 1H), 3.561 (br, 1H), 3.459 (m, 2H), 2.95 (m, 1H), 2.58-2.54 (m, 2H), 2.203 (s, 1H), 1.79-1.70 (m, 5H), 1.541-1.490 (m, 3H), 1.088 (d, J=6.8 Hz, 3H).

Example 50
(3-((1R,3R)-1-(4-((1-(3-fluoropropyl)azetidin-3-yl)oxy)phenyl)-3-methyl-1,3,4,9-tetrahydro-2H-pyrido[3,4-b]indol-2-yl)bicyclo[1.1.1]pentan-1-yl)methanol (Compound 50)
Example 51
(3-((1S,3S)-1-(4-((1-(3-fluoropropyl)azetidin-3-yl)oxy)phenyl)-3-methyl-1,3,4,9-tetrahydro-2H-pyrido[3,4-b]indol-2-yl)bicyclo[1.1.1]pentan-1-yl)methanol (Compound 51)
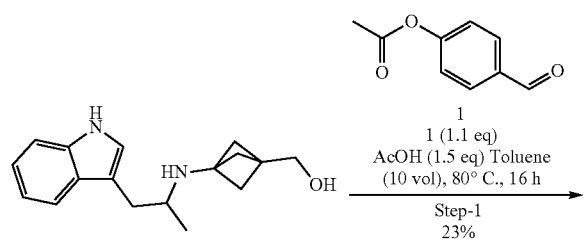

-continued

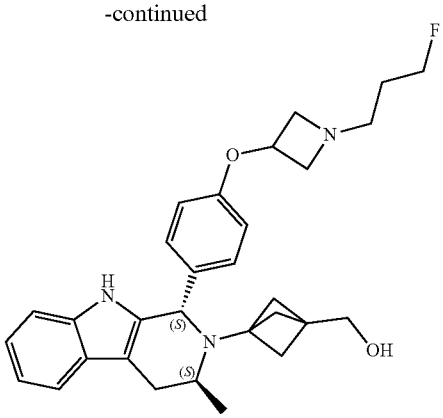

Step 1: To a solution of (3-((1-(1H-indol-3-yl)propan-2-yl)amino)bicyclo[1.1.1]pentan-1-yl)methanol (4.2 g, 15.54 mmol) in toluene (40 mL) were added 4-formylphenyl acetate (1) (1.40 g, 13.99 mmol) and acetic acid (1.87 g, 23.31 mmol). The reaction mixture was stirred at 80° C. for 16 h. After completion of the reaction, the reaction mixture was cooled to room temperature, and was quenched with saturated sodium bicarbonate solution (40 mL) at 0° C. The reaction mixture was diluted with water (100 mL) and extracted with EtOAc (2×100 mL). The combined organic layers were dried over $Na_2SO_4$, filtered and evaporated. The crude product was purified by silica gel column chromatography by eluting with 70% EtOAc in n-pentane to afford 4-((1R)-2-(3-(hydroxymethyl)bicyclo[1.1.1]pentan-1-yl)-3-methyl-2,3,4,9-tetrahydro-1H-pyrido[3,4-b]indol-1-yl)phenyl acetate (2) (1.5 g, 3.60 mmol, Yield=23%). MS (ESI) m/z 415 [M−H]$^+$; $^1$H NMR (400 MHz, DMSO-d$_6$) δ 10.37 (s, 1H), 7.39-7.33 (m, 3H), 7.20 (d, J=8 Hz 1H), 7.05-6.90 (m, 4H), 4.95 (s, 1H), 4.33 (m, 1H), 3.48-3.40 (m, 1H), 2.95-2.87 (m, 1H), 2.61-2.56 (m, 1H), 2.21 (s, 3H), 1.62-1.56 (m, 3H), 1.42 (d, J=9.2 Hz, 3H), 1.23-1.15 (m, 4H).

Step 2: To a solution of 4-((1R)-2-(3-(hydroxymethyl)bicyclo[1.1.1]pentan-1-yl)-3-methyl-2,3,4,9-tetrahydro-1H-pyrido[3,4-b]indol-1-yl)phenyl acetate (1.7 g, 4.08 mmol) in methanol (20 mL) was added $K_2CO_3$ (2) (1.12 g, 8.17 mmol). The reaction mixture was stirred at RT for 16 h. After completion of the reaction, the reaction mixture was diluted with water (50 mL) and extracted with EtOAc (2×70 mL). The combined organic layers were dried over $Na_2SO_4$, filtered and evaporated. The crude product was purified by silica gel column chromatography by eluting with 70% EtOAc in n-pentane to afford 4-((1R)-2-(3-(hydroxyethyl)bicyclo[1.1.1]pentan-1-yl)-3-methyl-2,3,4,9-tetrahydro-1H-pyrido[3,4-b]indol-1-yl)phenol (3) (1 g, 2.67 mmol, Yield=65%). MS (ESI) m/z 375.39 [M+1]$^+$; $^1$H NMR (400 MHz, DMSO-d$_6$)) δ 10.27 (s, 1H), 7.36 (d, J=7.6 Hz, 1H), 7.18 (d, J=8 Hz, 1H), 7.08 (d, J=8.4 Hz, 1H), 6.98-6.89 (m, 2H), 6.66 (d, J=8.4 Hz, 2H), 4.79 (s, 1H), 4.310 (t, 1H), 4.028 (q, J=6.8 Hz, 1H), 3.48-3.31 (m, 2H), 2.94-2.87 (m, 2H), 2.63-2.56 (m, 1H), 1.98 (s, 1H), 1.573 (m, 4H), 1.40 (d, J=9.2 Hz, 3H), 1.23-1.15 (m, 3H), 1.08 (d, J=8 Hz, 3H).

Step 3: To a stirred solution of 4-((1R)-2-(3-(hydroxymethyl)bicyclo[1.1.1]pentan-1-yl)-3-methyl-2,3,4,9-tetrahydro-1H-pyrido[3,4-b]indol-1-yl)phenol (3) (1 g, 2.67 mmol) and tert-butyl 3-iodoazetidine-1-carboxylate (4) (907 mg, 3.20 mmol) in DMF (10 mL) was added $Cs_2CO_3$ (1.74 g, 5.34 mmol). The reaction mixture was stirred at 100° C. for 4 h. After completion of the reaction, the reaction mixture was cooled to room temperature. The reaction mixture was diluted with water (50 mL) and extracted with EtOAc (2×50 mL). The combined organic layers were dried over $Na_2SO_4$, filtered and evaporated to get semi-pure crude. Thus obtained crude product was purified by silica gel column chromatography by eluting with 20-25% EtOAc in pet ether to afford tert-butyl 3-(4-((1R)-2-(3-(hydroxymethyl)bicyclo[1.1.1]pentan-1-yl)-3-methyl-2,3,4,9-tetrahydro-1H-pyrido[3,4-b]indol-1-yl)phenoxy)azetidine-1-carboxylate (5) (1 g, 1.88 mmol, 71% yield) MS (ESI) m/z 530.34 [M+1]$^+$; $^1$H NMR (400 MHz, DMSO-d$_6$)) δ 10.27 (s, 1H), 7.37 (d, J=7.6 Hz, 1H), 7.23-7.18 (m, 3H), 6.97-6.91 (m, 2H), 6.74 (d, J=8 Hz, 2H), 4.94 (br, 1H), 4.85 (s, 1H), 4.33-4.27 (m, 3H), 3.76 (br, 1H), 2.89 (m, 1H), 2.59-2.49 (m, 2H), 1.56 (d, J=8 Hz, 3H), 1.41-1.36 (m, 12H), 1.09 (d, J=4.4 Hz, 3H).

Step 4: To a stirred solution of tert-butyl 3-(4-((1R)-2-(3-(hydroxymethyl)bicyclo[1.1.1]pentan-1-yl)-3-methyl-2,3,4,9-tetrahydro-1H-pyrido[3,4-b]indol-1-yl)phenoxy)azetidine-1-carboxylate (5) (1 g, 1.12 mmol) in DCM (5 mL) was added 4M HCl in 1,4-dioxane (5 mL) drop-wise at RT. The reaction mixture was stirred at room temperature for 3 h. After completion of the reaction, it was evaporated and co-distilled with DCM (2×5 mL) to obtain (3-((1R)-1-(4-(azetidin-3-yloxy)phenyl)-3-methyl-1,3,4,9-tetrahydro-2H-pyrido[3,4-b]indol-2-yl)bicyclo[1.1.1]pentan-1-yl)methanol hydrochloride (6) (800 mg, 1.71 mmol, quantitative yield). MS (ESI) m/z 430.48 [M+H]$^+$.

Step 5: To a stirred solution of ((3-((1R)-1-(4-(azetidin-3-yloxy)phenyl)-3-methyl-1,3,4,9-tetrahydro-2H-pyrido[3,4-b]indol-2-yl)bicyclo[1.1.1]pentan-1-yl)methanol hydrochloride (6) (800 mg, 1.71 mmol) in DMF (10 mL) was added $K_2CO_3$ (711 mg, 5.15 mmol) followed by 1-fluoro-3-iodopropane (7) (484 mg, 2.57 mmol) at RT. The reaction mixture was stirred at room temperature for 16 h. After completion of the reaction, it was diluted with water (50 mL) and extracted with EtOAc (100 mL). The organic layer was washed with brine solution (2×20 mL). The organic layer was collected, dried over $Na_2SO_4$, filtered and evaporated. The crude product was purified by RP prep-HPLC to afford 140 mg (286 mmol, Yield=16%) of (3-((1R)-1-(4-((1-(3-fluoropropyl)azetidin-3-yl)oxy)phenyl)-3-methyl-1,3,4,9-tetrahydro-2H-pyrido[3,4-b]indol-2-yl)bicyclo[1.1.1]pentan-1-yl)methanol (7; Racemic). MS (ESI) m/z 490.52 [M+1]$^+$; $^1$H NMR (400 MHz, DMSO-d$_6$) δ 10.26 (s, 1H), 7.36 (d, J=7.6 Hz, 1H), 7.20-7.18 (dd, J=3.6 Hz, 8.4 Hz, 3H), 6.98-6.89 (m, 2H), 6.74 (d, J=8.8 Hz, 2H), 4.84 (s, 1H), 4.72 (t, J=6.0 Hz, 1H), 4.507 (m, 3H), 4.38 (m, 3H), 4.32 (brs, 1H), 3.71 (m, 3H), 3.47-3.46 (m, 1H), 2.91 (brs, 3H), 1.68-1.54 (m, 5H), 1.40 (d, J=9.2 Hz, 3H), 1.08 (d, J=6.4 Hz, 3H).

Step 6: 140 mg of (3-((1R)-1-(4-((1-(3-fluoropropyl)azetidin-3-yl)oxy)phenyl)-3-methyl-1,3,4,9-tetrahydro-2H-pyrido[3,4-b]indol-2-yl)bicyclo[1.1.1]pentan-1-yl)methanol (7; Racemic) was purified by chiral SFC purification to afford 44.7 mg of (3-((1R,3R)-1-(4-((1-(3-fluoropropyl)azetidin-3-yl)oxy)phenyl)-3-methyl-1,3,4,9-tetrahydro-2H-pyrido[3,4-b]indol-2-yl)bicyclo[1.1.1]pentan-1-yl)methanol (Compound 50), with 96.86% of LCMS purity (chiral HPLC: 99.20%) MS (LCMS) m/z 488.39 [M−H]$^+$. $^1$H NMR (400 MHz, DMSO-d$_6$) δ 10.16 (s, 1H), 7.36 (d, J=7.6 Hz, 1H), 7.20-7.18 (dd, J=3.6 Hz, 8.4 Hz, 3H), 6.98-6.89 (m, 2H), 6.74 (d, J=8.8 Hz, 2H), 4.84 (s, 1H), 4.72 (t, J=6.0 Hz, 1H), 4.52-4.37 (m, 2H), 4.32 (br, 1H), 3.73-3.70 (m, 2H), 3.47-3.46 (m, 1H), 3.317 (s, 2H), 2.92-2.89 (m, 3H), 2.58-2.49 (m, 3H), 1.70-1.57 (m, 5H), 1.40 (d, J=9.2 Hz, 3H), 1.08 (d, J=6.4 Hz, 3H); and 34.7 mg of (3-((1S,3S)-1-(4-((1-(3-fluoropropyl)azetidin-3-yl)oxy)phenyl)-3-methyl-1, 3,4,9-tetrahydro-2H-pyrido[3,4-b]indol-2-yl)bicyclo[1.1.1]pentan-1-yl)methanol (Compound 51), 97.53% of LCMS purity (chiral HPLC: 99.12%). MS (LCMS) m/z 488.35 [M−H]+. 1H NMR (400 MHz, DMSO-d6) δ 10.16 (s, 1H), 7.36 (d, J=7.6 Hz, 1H), 7.20-7.18 (dd, J=3.6 Hz, 8.4 Hz, 3H), 6.98-6.89 (m, 2H), 6.74 (d, J=8.8 Hz, 2H), 4.84 (s, 1H), 4.72 (t, J=6.0 Hz, 1H), 4.52-4.37 (m, 2H), 4.32 (br, 1H), 3.73-3.70 (m, 2H), 3.47-3.46 (m, 1H), 3.317 (s, 2H), 2.92-2.89 (m, 3H), 2.58-2.49 (m, 3H), 1.70-1.57 (m, 5H), 1.40 (d, J=9.2 Hz, 3H), 1.08 (d, J=6.4 Hz, 3H). The stereochemistry of Compound 50 and Compound 51 were assigned tentatively.

Example 52

(3-((1R,3R)-3-methyl-1-(4-((1-propylazetidin-3-yl)oxy)phenyl)-1,3,4,9-tetrahydro-2H-pyrido[3,4-b]indol-2-yl)bicyclo[1.1.1]pentan-1-yl)methanol (Compound 52)

Example 53

(3-((1S,3S)-3-methyl-1-(4-((1-propylazetidin-3-yl)oxy)phenyl)-1,3,4,9-tetrahydro-2H-pyrido[3,4-b]indol-2-yl)bicyclo[1.1.1]pentan-1-yl)methanol (Compound 53)

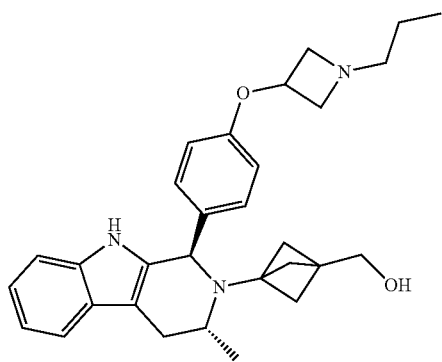

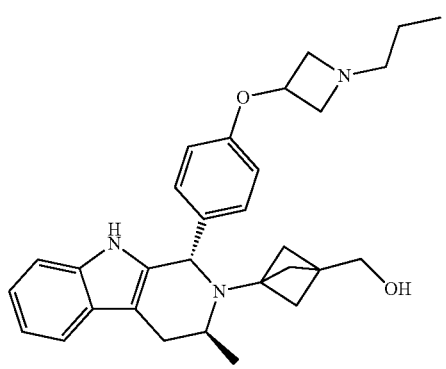

Compounds 52 and 53 were prepared following a procedure analogous to that described for Examples 50 and 51 above. Compound 52: MS (LCMS) m/z 470.43 [M−H]+. 1H NMR (400 MHz, DMSO-d6) δ 10.25 (s, 1H), 7.36 (d, J=7.6 Hz, 1H), 7.18-7.20 (m, 3H), 6.89-6.98 (m, 2H), 6.73 (d, J=8.4 Hz, 2H), 4.84 (s, 1H), 4.72 (t, J=5.6 Hz, 1H), 4.32 (t, J=5.6 Hz, 1H), 3.68-3.71 (m, 2H), 3.47-3.46 (m, 1H), 3.31 (S, 2H), 2.85-2.90 (m, 3H), 2.50-2.53 (m, 1H), 2.38 (t, J=7.2, 2H),1.56 (d, J=9.6 Hz, 3H), 1.40 (d, J=9.2 Hz, 3H), 1.26-1.31 (m, 2H), 1.08 (d, J=6.8 Hz, 3H), 0.83 (t, J=7.4 Hz, 3H). Compound 53: MS (LCMS) m/z 470.43 [M−H]+. 1H NMR (400 MHz, DMSO-d6) δ 10.25 (s, 1H), 7.36 (d, J=7.6 Hz, 1H), 7.20-7.18 (m, 3H), 6.98-6.89 (m, 2H), 6.73 (d, J=12 Hz, 2H), 4.84 (s, 1H), 4.72 (t, J=6.0 Hz, 1H), 4.32 (t, J=5.6 Hz, 1H), 3.71-3.67 (m, 2H), 3.47-3.46 (m, 1H), 2.90-2.85 (m, 3H), 2.57-2.53 (m, 1H), 2.36 (t, J=7.2, 2H),1.56 (d, J=8.8 Hz, 3H), 1.40 (d, J=9.2 Hz, 3H), 1.31-1.26 (m, 2H), 1.08 (d, J=6.4 Hz, 3H), 0.83 (t, J=7.2 Hz, 3H). The absolute stereochemistry was arbitrarily assigned for Compound 52 and Compound 53.

Example 54

5-((1S,3R)-2-(bicyclo[1.1.1]pentan-1-yl)-3-methyl-2,3,4,9-tetrahydro-1H-pyrido[3,4-b]indol-1-yl)-N—((S)-1-propylpyrrolidin-3-yl)pyrazin-2-amine (Compound 54)

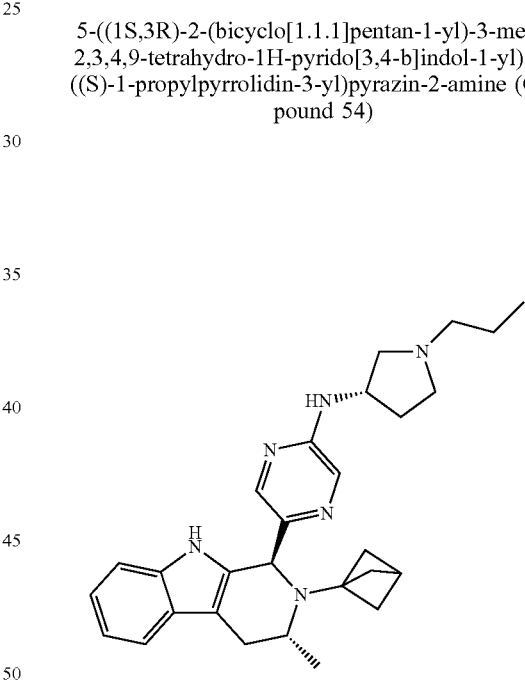

Compound 54 was prepared following a procedure analogous to that described for Example 41. MS (ESI) m/z 457.3 [M+H]+; 1H NMR (400 MHz, DMSO-d6) δ 10.29 (s, 1H), 7.86 (s, 1H), 7.80 (s, 1H), 7.37 (d, J=7.6 Hz, 1H), 7.18 (d, J=7.6 Hz, 1H), 7.09 (d, J=7.6 Hz, 1H), 6.99-6.90 (m, 2H), 4.89 (s, 1H), 4.19 (br, 1H), 3.56 (q, J=7.2, 1.6 Hz, 1H), 2.94-2.91 (dd, J=6.8, 1.6 Hz, 1H), 2.73 (q, J=7.8, 2.4 Hz, 1H), 2.58-2.42 (m, 2H), 2.39 (br, 1H), 2.33 (br, 3H), 2.23 (s, 1H), 2.16 (br, 1H), 1.74 (d, J=8.4 Hz, 3H), 1.56 (d, J=7.6 Hz, 4H), 1.42 (q, J=8.8, 2.4 Hz, 2H), 1.13 (d, J=6.8 Hz, 3H), 0.84 (t, J=7.6 Hz, 3H).

Example 55

6-((1S,3R)-2-(bicyclo[1.1.1]pentan-1-yl)-3-methyl-2,3,4,9-tetrahydro-1H-pyrido[3,4-b]indol-1-yl)-N—((S)-1-(3-fluoropropyl)pyrrolidin-3-yl)pyridin-3-amine (Compound 55)

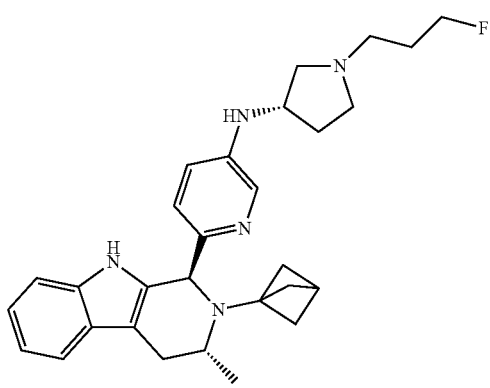 [SMILES: C[C@@H]1Cc2c([nH]c3ccccc23)[C@@H](c2ccc(N[C@H]3CCN(CCCF)C3)cn2)N1C12CC(C1)C2]

Compound 55 was prepared following a procedure analogous to that described for Example 41. MS (ESI) m/z 472.4 [M−H]⁻; ¹H NMR (400 MHz, DMSO-d₆) δ 10.22 (s, 1H), 7.87 (d, J=2.4 Hz, 1H), 7.35 (d, J=7.6 Hz, 1H), 7.18 (d, J=8.0 Hz, 1H), 6.97-6.88 (m, 3H), 6.88-6.80 (dd, J=8.8, 2.8 Hz, 1H), 5.89 (d, J=6.8 Hz, 1H), 4.86 (s, 1H), 4.53 (t, J=6.8 Hz, 1H), 4.44 (t, J=7.2 Hz, 1H), 3.84 (q, 1H), 3.56 (q, 1H), 2.94-2.91 (dd, J=6.8, 1.6 Hz, 1H), 2.78 (t, J=4.8 Hz, 1H), 2.58-2.42 (m, 5H), 2.38 (br, 1H), 2.23 (s, 1H), 2.19 (br, 1H), 1.88-1.76 (m, 2H), 1.78 (d, J=8.4 Hz, 3H), 1.56 (d, J=7.6 Hz, 3H), 1.09 (d, J=6.8 Hz, 3H).

Example 56

N-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)-1-(2-fluoroethyl)azetidin-3-amine (Compound 56)

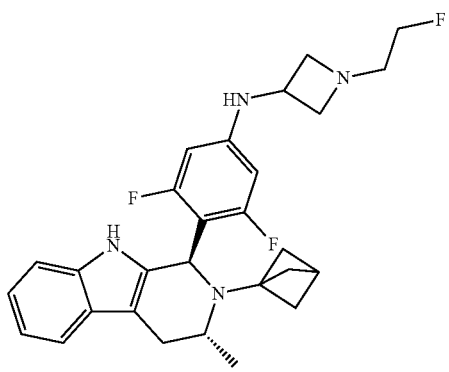 [SMILES: C[C@@H]1Cc2c([nH]c3ccccc23)[C@@H](c2c(F)cc(NC3CN(CCF)C3)cc2F)N1C12CC(C1)C2]

Compound 56 was prepared following a procedure analogous to that described for Example 41. MS (ESI) m/z 479.4 [M+H]⁻; ¹H NMR (400 MHz, DMSO-d₆) δ 10.39 (s, 1H), 7.34 (d, J=7.6 Hz, 1H), 7.17 (d, J=7.6 Hz, 1H), 6.97-6.9 (m, 2H), 6.64 (d, J=6.8 Hz, 1H), 6.09 (d, J=12 Hz, 2H), 5.14 (s, 1H), 4.45 (t, J=7.6 Hz, 1H), 4.36 (t, J=7.6 Hz, 1H), 3.94 (q, 1H), 3.68 (m, 2H), 3.55 (br, 1H), 2.86 (m, 3H), 2.73 (t, J=7.6 Hz, 1H), 2.66 (t, J=7.6 Hz, 1H), 2.22 (s, 1H), 1.77 (d, J=9.6 Hz, 3H), 1.58 (d, J=8.8 Hz, 3H), 1.06 (d, J=9.2 Hz, 3H).

Example 57

5-((1R,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyrimidin-2-amine (Compound 57)

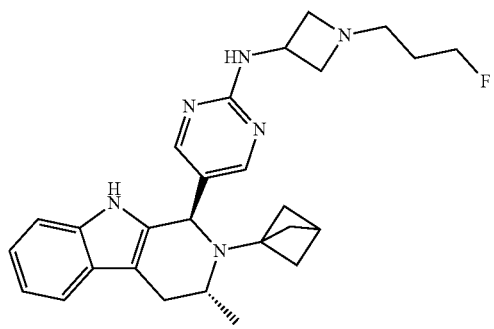 [SMILES: C[C@@H]1Cc2c([nH]c3ccccc23)[C@@H](c2cnc(NC3CN(CCCF)C3)nc2)N1C12CC(C1)C2]

Compound 57 was prepared following a procedure analogous to that described for Example 41. MS (ESI) m/z 460.28 [M+H]⁺; ¹H NMR (400 MHz, DMSO-d₆) δ 10.45 (s, 1H), 8.12 (s, 2H), 7.57 (d, J=6.8 Hz, 1H), 7.38 (d, J=7.6 Hz, 1H), 7.19 (d, J=8.0 Hz, 1H), 6.91-6.99 (m, 2H), 4.79 (s, 1H), 4.39-4.51 (m, 3H), 3.50-3.57 (m, 3H), 2.91 (m, 1H), 2.80-2.83 (m, 2H), 2.50-2.53 (m, 1H), 2.42-2.49 (m, 2H), 2.25 (s, 1H), 1.75-1.77 (m, 3H), 1.60-1.68 (m, 5H), 1.09 (d, J=6.8 Hz, 3H).

Example 58

(3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 58)

Example 59

(3-((1S,3S)-1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 59)

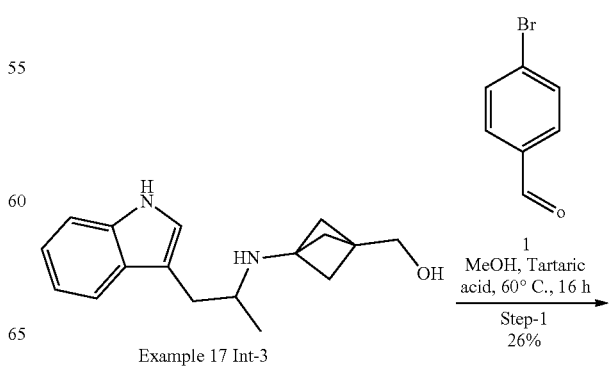

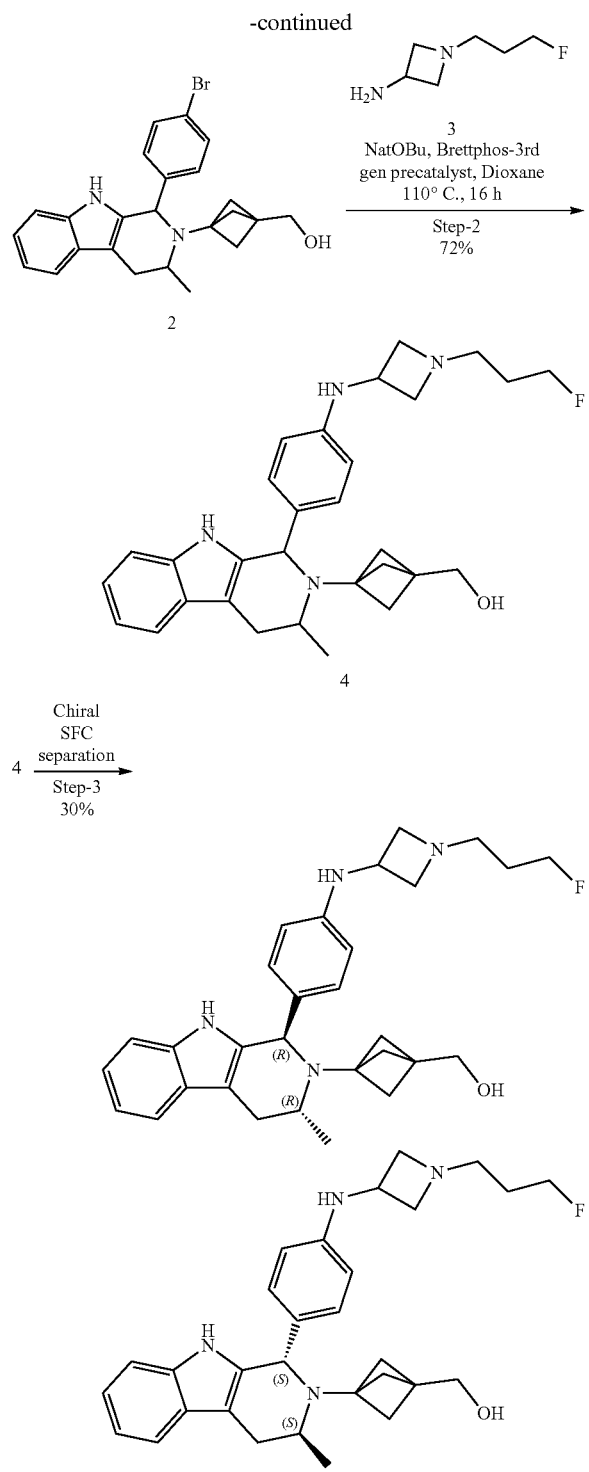

Step 1: To a stirred solution of (3-((1-(1H-indol-3-yl)propan-2-yl)amino)bicyclo[1.1.1]pentan-1-yl)methanol (Example 17 Int-3) (2.1 g, 7.76 mmol) in methanol (10 mL) were added 4-bromobenzaldehyde (1) (1.5 g, 8.10 mmol) followed by tartaric acid (1.66 g, 11.09 mmol). The reaction mixture was stirred at 60° C. for 16 h. After completion of the reaction as monitored by TLC, it was cooled to room temperature. The reaction mixture was diluted with NaHCO₃ solution (50 mL) and extracted with EtOAc (2×50 mL). The combined organic layer was collected, dried over Na₂SO₄, filtered and evaporated. The crude product was purified by silica gel column chromatography to yield 1.1 g (2.51 mmol, 26% Yield) of (3-(1-(4-bromophenyl)-3-methyl-1,3,4,9-tetrahydro-2H-pyrido[3,4-b]indol-2-yl)bicyclo[1.1.1]pentan-1-yl)methanol (2). MS (ESI) m/z 437.1 [M+1]⁺; ¹H NMR (400 MHz, DMSO-d₆) δ 7.49 (d, J=6.4 Hz, 1H), 7.42 (d, J=8.4 Hz, 2H), 7.26 (d, J=7.6 Hz, 1H), 7.21-7.17 (m, 2H), 7.12-7.08 (m, 2H), 5.29 (s, 1H), 4.84 (s, 1H), 4.14-4.09 (m, 1H), 3.67-3.64 (m, 1H), 3.57 (s, 2H), 3.16-3.11 (m, 1H), 2.64-2.60 (m, 1H), 2.17 (s, 1H), 2.04 (s, 2H), 1.71 (t, J=27.2 Hz, 3H), 1.51 (t, J=25.6 Hz, 3H), 1.25 (t, J=14.4 Hz, 2H), 1.15 (d, J=6.8 Hz, 3H).

Step 2: To a solution of (3-(1-(4-bromophenyl)-3-methyl-1,3,4,9-tetrahydro-2H-pyrido[3,4-b]indol-2-yl)bicyclo[1.1.1]pentan-1-yl)methanol (2) (1 g, 2.28 mmol) in 1,4-dioxane (10 mL) were added 1-(3-fluoropropyl)azetidin-3-amine (3) (453.3 mg, 3.42 mmol) and NaOt-Bu (439.4 mg, 4.57 mmol). The reaction mixture was degassed under argon for 30 min. Next Brettphos-3rd gen precatalyst (70 mg, 0.68 mmol) was added and the reaction mixture was again degassed for 30 min before it was heated to 110° C. for 16 h. After completion of the reaction, it was cooled to room temperature and filtered through a bed of celite. The filtrate was diluted with water (50 mL) and extracted with EtOAc (2×50 mL). The combined organic layer was collected, dried over Na₂SO₄, filtered and evaporated. The crude product was purified by RP prep-HPLC to yield 800 mg (1.63 mmol, 72% yield) of (3-(1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (4). MS (ESI) m/z 489.5 [M+H]⁺; ¹H NMR (400 MHz, DMSO-d₆) δ 10.12 (s, 1H), 7.35 (d, J=6.4 Hz, 1H), 7.18 (d, J=8.4 Hz, 2H), 6.99-6.88 (m, 4H), 6.42 (d, J=8.4 Hz, 2H), 5.92 (d, J=6.8 Hz, 1H), 4.84 (s, 1H), 4.40-4.29 (m, 2H), 3.90-3.88 (m, 1H), 3.62 (t, J=12.8 Hz, 2H), 3.48-3.46 (m, 1H), 2.95-2.88 (m, 1H), 2.72-2.69 (m, 2H), 2.50-2.40 (m, 3H), 1.68-1.54 (m, 5H), 1.41 (d, J=9.21 Hz, 3H), 1.08 (d, J=6.8 Hz, 3H).

Step 3: (3-(1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (4, racemic) (364 mg, 0.74 mmol) was purified by chiral SFC to afford (3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 58) (109 mg, 0.29 mmol, 30% yield). MS (ESI) m/z 487.32 [M−H]⁻; ¹H NMR (400 MHz, DMSO-d₆) δ 10.18 (s, 1H), 7.35 (d, J=6.4 Hz, 1H), 7.18 (d, J=8.4 Hz, 2H), 6.99-6.88 (m, 4H), 6.42 (d, J=8.4 Hz, 2H), 5.92 (d, J=6.8 Hz, 1H), 4.74 (s, 1H), 6.50 (t, J=12 Hz, 1H), 4.40-4.29 (m, 2H), 3.90-3.88 (m, 1H), 3.62 (t, J=12.8 Hz, 2H), 3.48-3.46 (m, 1H), 3.31 (s, 2H), 2.95-2.88 (m, 1H), 2.72-2.69 (m, 2H), 2.47-2.40 (m, 2H), 2.50-2.40 (m, 3H), 1.68-1.54 (m, 5H), 1.41 (d, J=9.21 Hz, 3H), 1.08 (d, J=6.8 Hz, 3H), and (3-((1S,3S)-1-(4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)methanol (Compound 59). MS (ESI) m/z 487.32 [M−H]⁻; ¹H NMR (400 MHz, DMSO-d₆) δ 10.18 (s, 1H), 7.35 (d, J=6.4 Hz, 1H), 7.18 (d, J=8.4 Hz, 2H), 6.99-6.88 (m, 4H), 6.42 (d, J=8.4 Hz, 2H), 5.92 (d, J=6.8 Hz, 1H), 4.74 (s, 1H), 6.50 (t, J=12 Hz, 1H), 4.40-4.29 (m, 2H), 3.90-3.88 (m, 1H), 3.62 (t, J=12.8 Hz, 2H), 3.48-3.46 (m, 1H), 3.31 (s, 2H), 2.95-2.88 (m, 1H), 2.72-2.69 (m, 2H), 2.47-2.40 (m, 2H), 2.50-2.40 (m, 3H), 1.68-1.54 (m, 5H), 1.41 (d, J=9.21 Hz, 3H), 1.08 (d, J=6.8 Hz, 3H). The absolute stereochemistry was arbitrarily assigned for Compound 58 and Compound 59.

Example 60

2-((1S,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)pyrimidin-5-amine (Compound 60)

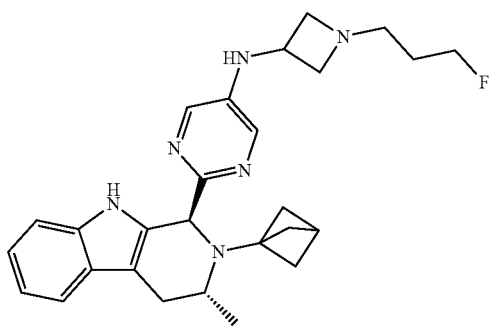 [SMILES: C[C@@H]1Cc2c([nH]c3ccccc23)[C@@H](c2ncc(NC3CN(CCCF)C3)cn2)N1C12CC(C1)C2]

Compound 60 was prepared following a procedure analogous to that described for Example 30. MS (ESI) m/z 459.47 [M−H]−; $^1$H NMR (400 MHz, DMSO-$d_6$) δ 10.25 (s, 1H), 8.03 (s, 1H), 7.35 (d, J=7.6 Hz, 1H), 7.14 (d, J=8.0 Hz, 1H), 6.97-6.9 (m, 2H), 6.49 (d, J=7.2 Hz, 1H), 5.02 (s, 1H), 4.52 (t, J=7.6 Hz, 1H), 4.39 (t, J=7.6 Hz, 1H), 4.03 (q, 1H), 3.66 (m, 3H), 2.86 (dd, 1H), 2.76 (q, 2H), 2.58-2.44 (m, 3H), 2.21 (s, 1H), 1.76 (d, J=9.6 Hz, 3H), 1.75-1.54 (m, 2H), 1.51 (d, J=8.8 Hz, 3H), 1.14 (d, J=9.2 Hz, 3H).

Example 61

(1S,3R)-2-(bicyclo[1.1.1]pentan-1-yl)-1-(5-((1-(3-fluoropropyl)azetidin-3-yl)oxy)pyrimidin-2-yl)-3-methyl-2,3,4,9-tetrahydro-1H-pyrido[3,4-b]indole (Compound 61)

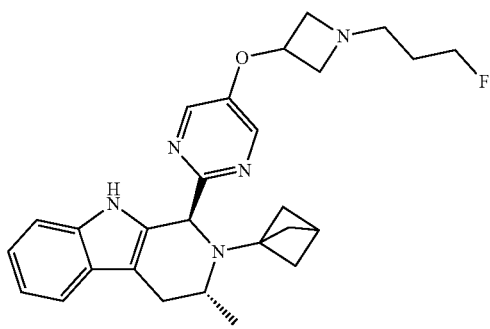 [SMILES: C[C@@H]1Cc2c([nH]c3ccccc23)[C@@H](c2ncc(OC3CN(CCCF)C3)cn2)N1C12CC(C1)C2]

Compound 61 was prepared following a procedure analogous to that described for Example 38. MS (ESI) m/z 460.39 [M−H]−; $^1$H NMR (400 MHz, DMSO-$d_6$) δ 10.31 (s, 1H), 8.41 (s, 1H), 7.37 (d, J=7.6 Hz, 1H), 7.15 (d, J=7.6 Hz, 1H), 6.9-6.99 (m, 2H), 5.15 (s, 1H), 4.93-4.96 (m, 1H), 4.43 (dt, J=47.6 Hz, 6 Hz, 2H), 3.65-3.76 (m, 3H), 2.92-2.97 (m, 1H), 3.05-3.09 (m, 2H), 2.5-2.6 (m, 3H), 1.53-1.76 (m, 8H), 1.14 (d, J=6.8 Hz, 3H).

Example 62

N-(4-((1R,3R)-2-(3-(fluoromethyl)bicyclo[1.1.1]pentan-1-yl)-3-methyl-2,3,4,9-tetrahydro-1H-pyrido[3,4-b]indol-1-yl)phenyl)-1-(3-fluoropropyl)azetidin-3-amine (Compound 62)

Example 63

N-(4-((1S,3S)-2-(3-(fluoromethyl)bicyclo[1.1.1]pentan-1-yl)-3-methyl-2,3,4,9-tetrahydro-1H-pyrido[3,4-b]indol-1-yl)phenyl)-1-(3-fluoropropyl)azetidin-3-amine (Compound 63)

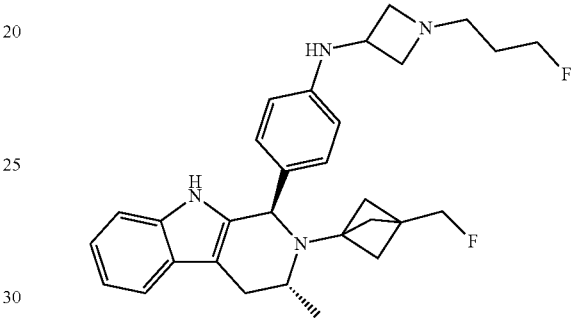

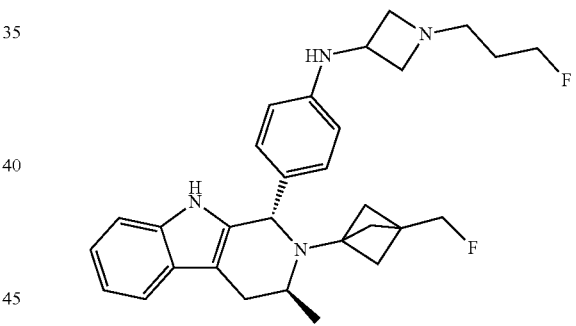

Compounds 62 and 63 were prepared following a procedure analogous to that described for Examples 58 and 59 above. Compound 62: MS (ESI) m/z 489.45 [M−H]+; $^1$H NMR (400 MHz, DMSO-$d_6$) δ 10.19 (s, 1H), 7.35 (d, J=7.2 Hz, 1H), 7.18 (d, J=8.0 Hz, 1H), 7.0-6.88 (m, 4H), 6.43 (d, J=8.4 Hz, 2H), 5.94 (d, J=6.8 Hz, 1H), 4.75 (br s, 1H), 4.52-4.28 (m, 4H), 3.93-3.88 (m, 1H), 3.63-3.59 (m, 2H), 3.50-3.46 (m, 1H), 2.94-2.89 (m, 1H), 2.73-2.69 (m, 2H), 2.56-2.45 (m, 3H), 1.73-1.52 (m, 8H), 1.06 (d, J=6.4 Hz, 3H). Compound 63: MS (LCMS) m/z 470.43 [M−H]+. $^1$H NMR (400 MHz, DMSO-$d_6$) δ 10.25 (s, 1H), 7.36 (d, J=7.6 Hz, 1H), 7.20-7.18 (m, 3H), 6.98-6.89 (m, 2H), 6.73 (d, J=12 Hz, 2H), 4.84 (s, 1H), 4.72 (t, J=6.0 Hz, 1H), 4.32 (t, J=5.6 Hz, 1H), 3.71-3.67 (m, 2H), 3.47-3.46 (m, 1H), 2.90-2.85 (m, 3H), 2.57-2.53 (m, 1H), 2.36 (t, J=7.2, 2H),1.56 (d, J=8.8 Hz, 3H), 1.40 (d, J=9.2 Hz, 3H), 1.31-1.26 (m, 2H), 1.08 (d, J=6.4 Hz, 3H), 0.83 (t, J=7.2 Hz, 3H). The absolute stereochemistry was arbitrarily assigned for Compound 62 and Compound 63.

Example 64

1-allyl-N-(4-((1R,3R)-2-(bicyclo[1.1.1]pentan-1-yl)-3-methyl-2,3,4,9-tetrahydro-1H-pyrido[3,4-b]indol-1-yl)phenyl)azetidin-3-amine (Compound 64)

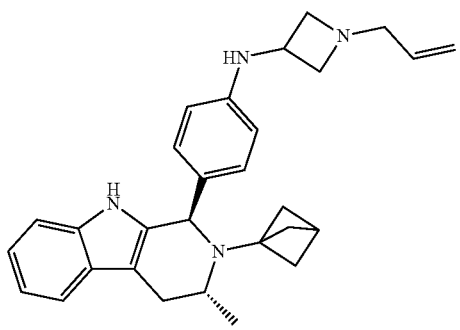 [SMILES: C=CCN1CC(Nc2ccc([C@@H]3c4[nH]c5ccccc5c4C[C@@H](C)N3C34CC(C3)C4)cc2)C1]

Compound 64 was prepared following a procedure analogous to that described for Example 49. MS (ESI) m/z 439.49 [M+H]$^+$; $^1$H NMR (400 MHz, DMSO-d$_6$) δ 10.24 (s, 1H), 7.35 (d, J=7.6 Hz, 1H), 7.18 (d, J=8.0 Hz, 1H), 6.98-6.88 (m, 4H), 6.42 (d, J=8.4 Hz, 2H), 5.92 (d, J=7.2 Hz, 1H), 5.76-5.66 (m, 1H), 5.17-5.12 (m, 2H), 4.76 (s, 1H), 3.91-3.88 (m, 1H), 3.61-3.58 (m, 2H), 3.45-3.43 (m, 1H), 3.01 (d, J=6.0 Hz, 1H), 2.89-2.85 (m, 1H), 2.76-2.72 (m, 2H), 2.57-2.49 (m, 1H), 2.19 (s, 1H), 1.72 (d, J=9.6 Hz, 3H), 1.58 (d, J=9.2 Hz, 3H), 1.09 (d, J=6.8 Hz, 3H).

Example 65

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(prop-2-yn-1-yl)azetidin-3-amine (Compound 65)

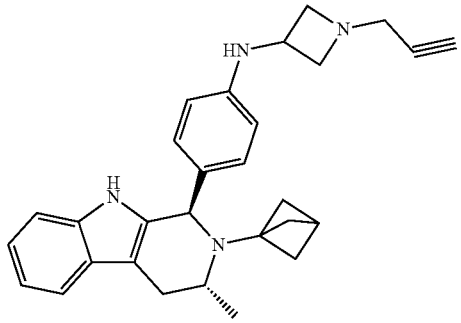 [SMILES: C#CCN1CC(Nc2ccc([C@@H]3c4[nH]c5ccccc5c4C[C@@H](C)N3C34CC(C3)C4)cc2)C1]

Compound 65 was prepared following a procedure analogous to that described for Example 49. MS (ESI) m/z 435.46 [M–H]$^-$; $^1$H NMR (400 MHz, DMSO-d$_6$) δ 10.23 (s, 1H), 7.35 (d, J=7.6 Hz, 1H), 7.18 (d, J=7.6 Hz, 1H), 6.99-6.9 (m, 4H), 6.42 (d, J=8.8 Hz, 2H), 5.99 (d, J=6 Hz, 1H), 4.77 (s, 1H), 3.93 (br, 1H), 3.71 (br, 2H), 3.48 (br, 1H), 3.40-3.22 (m, 3H), 3.08 (br, 2H), 2.86 (dd, 1H), 2.55 (br, 1H), 2.21 (s, 1H), 1.76 (d, J=9.6 Hz, 3H), 1.51 (d, J=8.8 Hz, 3H), 1.14 (d, J=9.2 Hz, 3H).

Example 66

(R)-1-(3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (Compound 66)

Example 67

(R)-1-(3-((1S,3S)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (Compound 67)

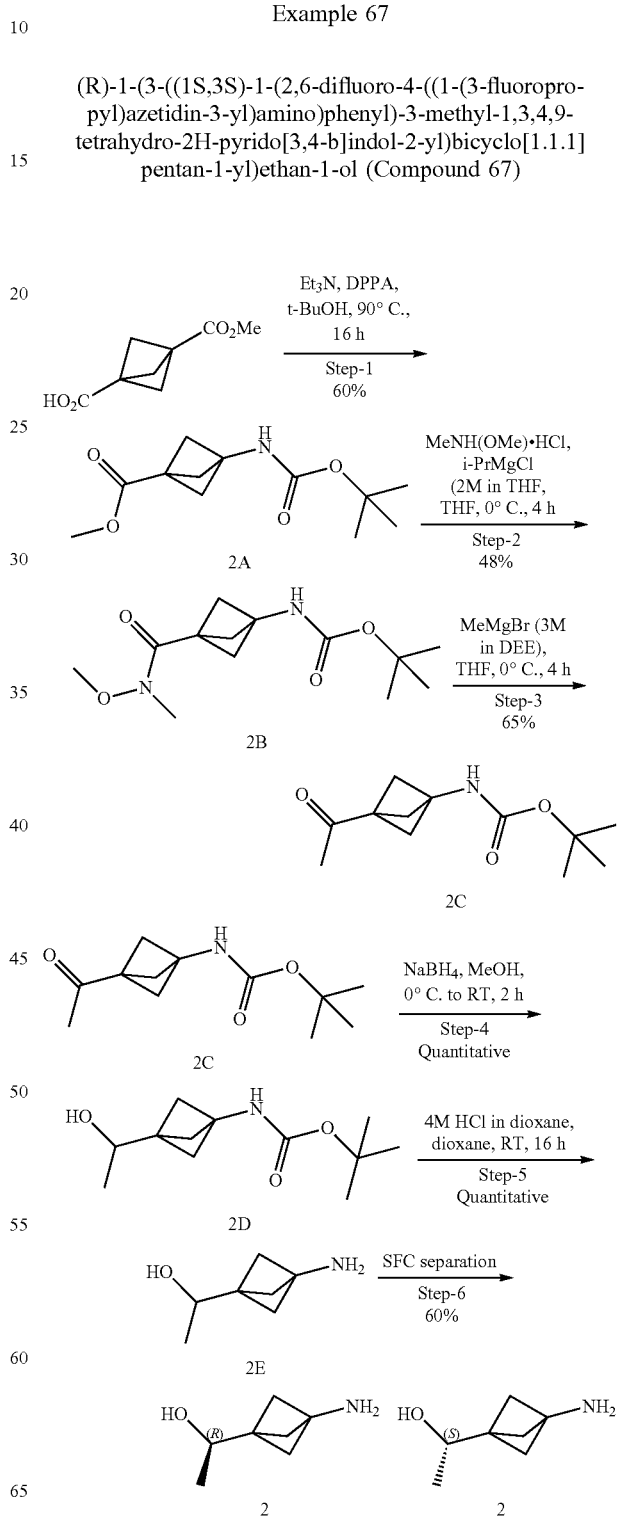

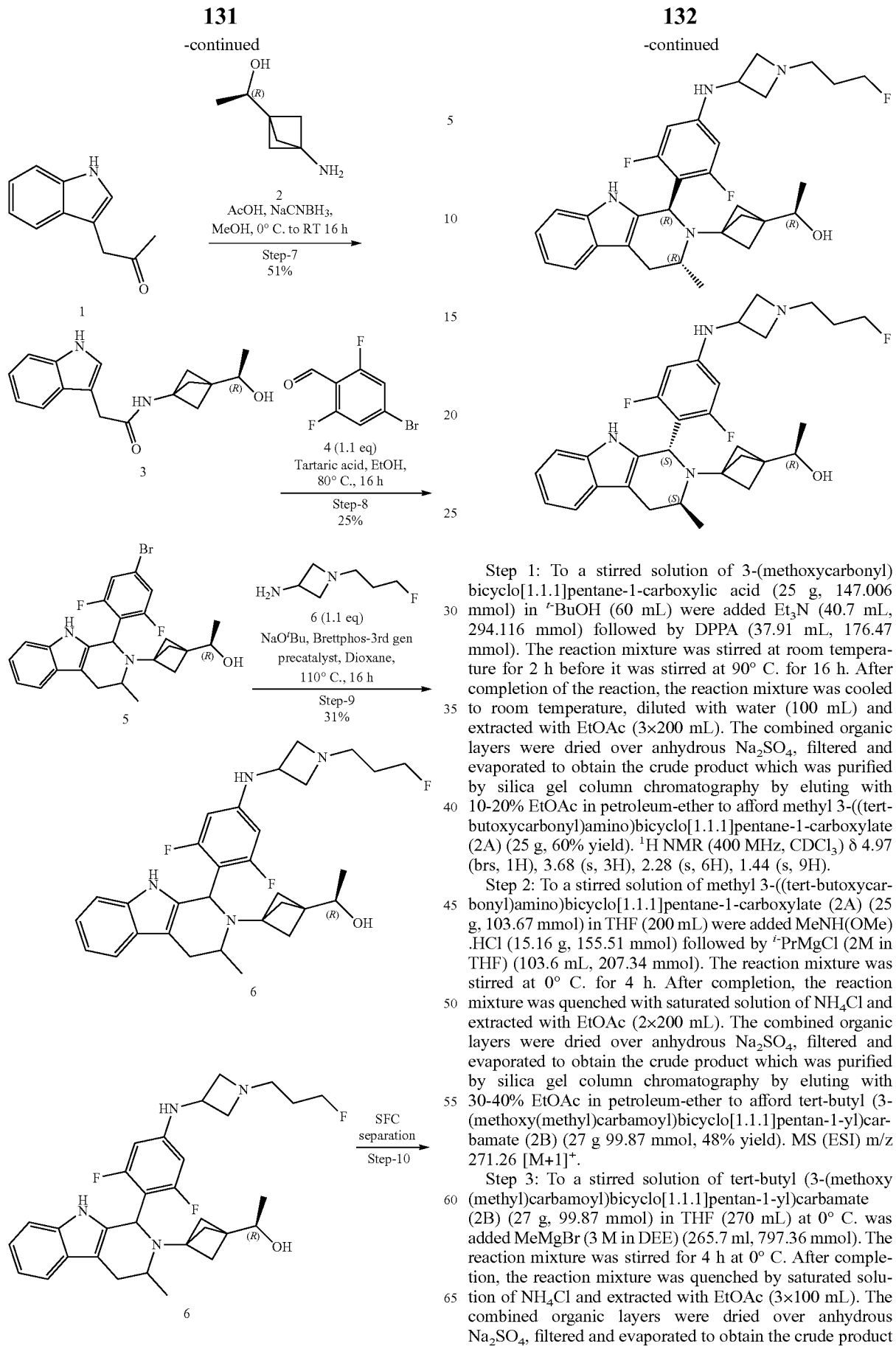

Step 1: To a stirred solution of 3-(methoxycarbonyl)bicyclo[1.1.1]pentane-1-carboxylic acid (25 g, 147.006 mmol) in $^t$BuOH (60 mL) were added Et$_3$N (40.7 mL, 294.116 mmol) followed by DPPA (37.91 mL, 176.47 mmol). The reaction mixture was stirred at room temperature for 2 h before it was stirred at 90° C. for 16 h. After completion of the reaction, the reaction mixture was cooled to room temperature, diluted with water (100 mL) and extracted with EtOAc (3×200 mL). The combined organic layers were dried over anhydrous Na$_2$SO$_4$, filtered and evaporated to obtain the crude product which was purified by silica gel column chromatography by eluting with 10-20% EtOAc in petroleum-ether to afford methyl 3-((tert-butoxycarbonyl)amino)bicyclo[1.1.1]pentane-1-carboxylate (2A) (25 g, 60% yield). $^1$H NMR (400 MHz, CDCl$_3$) δ 4.97 (brs, 1H), 3.68 (s, 3H), 2.28 (s, 6H), 1.44 (s, 9H).

Step 2: To a stirred solution of methyl 3-((tert-butoxycarbonyl)amino)bicyclo[1.1.1]pentane-1-carboxylate (2A) (25 g, 103.67 mmol) in THF (200 mL) were added MeNH(OMe).HCl (15.16 g, 155.51 mmol) followed by $^i$PrMgCl (2M in THF) (103.6 mL, 207.34 mmol). The reaction mixture was stirred at 0° C. for 4 h. After completion, the reaction mixture was quenched with saturated solution of NH$_4$Cl and extracted with EtOAc (2×200 mL). The combined organic layers were dried over anhydrous Na$_2$SO$_4$, filtered and evaporated to obtain the crude product which was purified by silica gel column chromatography by eluting with 30-40% EtOAc in petroleum-ether to afford tert-butyl (3-(methoxy(methyl)carbamoyl)bicyclo[1.1.1]pentan-1-yl)carbamate (2B) (27 g 99.87 mmol, 48% yield). MS (ESI) m/z 271.26 [M+1]$^+$.

Step 3: To a stirred solution of tert-butyl (3-(methoxy(methyl)carbamoyl)bicyclo[1.1.1]pentan-1-yl)carbamate (2B) (27 g, 99.87 mmol) in THF (270 mL) at 0° C. was added MeMgBr (3 M in DEE) (265.7 ml, 797.36 mmol). The reaction mixture was stirred for 4 h at 0° C. After completion, the reaction mixture was quenched by saturated solution of NH$_4$Cl and extracted with EtOAc (3×100 mL). The combined organic layers were dried over anhydrous Na$_2$SO$_4$, filtered and evaporated to obtain the crude product which was purified by silica gel column chromatography by eluting with 20-30% EtOAc in petroleum-ether to afford tert-butyl (3-acetylbicyclo[1.1.1]pentan-1-yl)carbamate (2C) (8.6 g, 65% yield). MS (ESI) m/z 170.08 [M−56]$^+$; $^1$H NMR (400 MHz, CDCl$_3$) δ 4.95 (brs, 1H), 2.26 (s, 6H), 2.14 (s, 3H), 1.45 (s, 9H).

Step 4: To a stirred solution of tert-butyl (3-acetylbicyclo[1.1.1]pentan-1-yl)carbamate (2C) (8.6 g, 38.17 mmol) in MeOH (60 mL) was added NaBH$_4$ (2D) (2.9 g, 76.44 mmol) at 0° C. The reaction was then warmed to RT and stirred for 2 h. After completion, the reaction mixture was concentrated under reduced pressure, diluted with water (30 mL) and extracted with EtOAc (2×50 mL). The combined organic layers were dried over anhydrous Na$_2$SO$_4$, filtered and evaporated to obtain the crude product. It was further purified by silica gel column chromatography by eluting with 20-30% EtOAc in petroleum ether to afford tert-butyl (3-(1-hydroxyethyl)bicyclo[1.1.1]pentan-1-yl)carbamate (2D) (4 g, quantitative yield). MS (ESI) m/z 172.08 [M−56]$^+$ (M-$^t$Bu); $^1$H NMR (400 MHz, DMSO-d$_6$) δ 7.37 (brs, 1H), 4.34 (d, J=4.8 Hz, 1H), 3.68-3.62 (m, 1H), 1.72 (d, J=9.2 Hz, 3H), 1.65 (d, J=9.2 Hz, 3H), 1.36 (s, 9H), 0.95 (d, J=6.4 Hz, 3H).

Step 5: To a solution of tert-butyl (3-(1-hydroxyethyl)bicyclo[1.1.1]pentan-1-yl)carbamate (2D) (4 g, 17.59 mmol) in 1,4-dioxane (40 mL) at 0° C. was added 4M HCl in 1,4-dioxane (60 mL) at the same temperature. The reaction mixture was stirred at room temperature for 16 h. After completion, the reaction mixture was evaporated and neutralized by saturated solution of NaHCO$_3$ (30-50 mL). It was then extracted with 10% MeOH/DCM (3×50 mL) and the combined organic layers were dried over anhydrous Na$_2$SO$_4$, filtered and evaporated to obtain the desired product 1-(3-aminobicyclo[1.1.1]pentan-1-yl)ethan-1-ol (2.5 g, quantitative yield). MS (ESI) m/z 128.08 [M+H]$^+$; $^1$H NMR (400 MHz, DMSO-d$_6$) δ 8.13 (brs, 2H), 4.54 (brs, 1H), 3.69 (d, J=6.4 Hz, 1H), 3.16 (s, 1H), 1.71-1.80 (m, 6H), 0.98 (d, J=6.4 Hz, 3H).

Step 6: 1-(3-Aminobicyclo[1.1.1]pentan-1-yl)ethan-1-ol (2E, racemic) (2.5 g, 19.65 mmol) was purified by chiral SFC to afford (R)-1-(3-aminobicyclo[1.1.1]pentan-1-yl)ethan-1-ol (Int-2) (0.670 g, 5.26 mmol, 26.80% yield). $^1$H NMR (400 MHz, DMSO-d$_6$) δ 4.23 (d, J=4.8 Hz, 2H), 3.61 (q, J=4.4 Hz, 1H), 2.02 (s, 2H), 1.52-1.43 (m, 6H), 0.94 (d, J=6.4 Hz, 3H); and (S)-1-(3-aminobicyclo[1.1.1]pentan-1-yl)ethan-1-ol (0.740 g, 5.81 mmol, 29.60% yield). $^1$H NMR (400 MHz, DMSO-d$_6$) δ 4.23 (d, J=4.8 Hz, 2H), 3.61 (q, J=4.4 Hz, 1H), 2.02 (s, 2H), 1.52-1.43 (m, 6H), 0.94 (d, J=6.4 Hz, 3H).

Step 7: To a stirred solution of 1-(1H-indol-3-yl)propan-2-one (1) (1 g, 5.77 mmol) in MeOH (10 mL) were added (R)-1-(3-aminobicyclo[1.1.1]pentan-1-yl)ethan-1-ol (2) (0.670 g, 5.199 mmol) followed by AcOH (1 mL). The reaction mixture was stirred at room temperature for 3 h. NaCNBH$_3$ (0.727 g, 11.54 mmol) was then added, and the resulting reaction mixture was stirred at room temperature for 16 h. After completion, the reaction mixture was diluted with water (15 mL) and extracted with EtOAc (3×30 mL). The combined organic layers were dried over anhydrous Na$_2$SO$_4$, filtered and evaporated to obtain a crude product. The crude was further purified by column chromatography over silica gel eluting with 40-60% EtOAc in petroleum-ether to afford (1R)-1-(3-(((1-(1H-indol-3-yl)propan-2-yl)amino)bicyclo[1.1.1]pentan-1-yl)ethan-1-ol (3) (1.1 g, 51% yield). MS (ESI) m/z 285.71 [M+1]$^+$; $^1$H NMR (400 MHz, DMSO-d$_6$) δ 10.81 (s, 1H), 7.48 (d, J=7.6 Hz, 1H), 7.32 (d, J=8.0 Hz, 1H), 7.11 (s, 1H), 7.05 (t, J=7.2 Hz, 1H), 6.96 (t, J=7.6 Hz, 1H), 4.30 (d, J=4.0 Hz, 1H), 4.08 (s, 1H), 3.16 (s, 2H), 3.65 (t, J=5.6 Hz, 1H), 2.99 (brs, 1H), 2.84 (dd, J=14.0, 4.8 Hz, 1H), 2.56 (d, J=7.6 Hz, 1H), 1.90 (s, 1H), 1.62-1.49 (m, 6H), 0.98-0.93 (m, 6H).

Step 8: To a stirred solution of (1R)-1-(3-((1-(1H-indol-3-yl)propan-2-yl)amino)bicyclo[1.1.1]pentan-1-yl)ethan-1-ol (3) (1.1 g, 3.51 mmol) in EtOH 10 mL) were added 4-bromo-2,6-difluorobenzaldehyde (5) (0.694 g, 3.16 mmol) followed by tartaric acid (0.789 mg, 5.265 mmol). The reaction mixture was stirred at 80° C. for 16 h. After completion, the reaction mixture was cooled to room temperature, and was neutralized by saturated solution of NaHCO$_3$ and extracted with 10% MeOH in DCM (2×50 mL). The combined organic layers were dried over anhydrous Na$_2$SO$_4$, filtered and evaporated obtain a crude product. The crude was further purified by silica gel column chromatography by eluting with 50-70% EtOAc in petroleum ether to afford (1R)-1-(3-(1-(4-bromo-2,6-difluorophenyl)-3-methyl-1,3,4,9-tetrahydro-2H-pyrido[3,4-b]indol-2-yl)bicyclo[1.1.1]pentan-1-yl)ethan-1-ol (5) (600 mg 1.23 mmol, 25% yield). MS (ESI) m/z 489.25 [M+1]$^+$; $^1$H NMR (400 MHz, DMSO-d$_6$) δ 10.51 (s, 1H), 7.39 (t, J=8.8 Hz, 3H), 7.30 (d, J=7.2 Hz, 1H), 7.17 (d, J=8.0 Hz, 1H), 7.01-6.92 (m, 3H), 5.27 (s, 1H), 4.27 (t, J=3.2 Hz, 1H), 3.64-3.55 (m, 1H), 3.29 (d, J=6.4 Hz, 1H), 3.01-2.93 (m, 1H), 2.81-2.57 (m, 1H), 1.62-1.53 (m, 4H), 1.38 (dd, J=28 Hz, 9.2 Hz, 3H), 1.19-1.16 (m, 2H), 1.1-1.00 (m, 7H), 0.99-0.89 (m, 3H).

Step 9: To a stirred solution of (1R)-1-(3-(1-(4-bromo-2,6-difluorophenyl)-3-methyl-1,3,4,9-tetrahydro-2H-pyrido[3,4-b]indol-2-yl)bicyclo[1.1.1]pentan-1-yl)ethan-1-ol (5) (600 mg, 1.23 mmol) in 1,4-dioxane (10 mL) were added 1-(3-fluoropropyl)azetidin-3-amine (6) (350 mg, 2.46 mmol) and NaOt-Bu (236 mg, 2.46 mmol). The reaction mixture was then degassed under argon atmosphere for 30 min. Later, Brettphos-3rd gen precatalyst (112 mg, 0.123 mmol) was added and the reaction mixture was again degassed for 30 min before heated at 110° C. for 16 h. After completion of the reaction, it was cooled to room temperature and filtered through a bed of celite. The filtrate was diluted with water (10 mL) and extracted with 10% MeOH in DCM (2×30 mL). The combined organic layers were dried over anhydrous Na$_2$SO$_4$, filtered and evaporated. The crude product was purified by reverse phase prep-HPLC to afford (1R)-1-(3-(1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (230 mg, 31% yield) (6).

Step 10: (1R)-1-(3-(1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (6) (230 mg, 0.426 mmol,) was purified by chiral SFC to afford (R)-1-(3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (Compound 66) (55 mg, 0.102 mmol, 24% yield). MS (ESI) m/z 537.42 [M−H]$^-$; $^1$H NMR (400 MHz, DMSO-d$_6$) δ 10.36 (s, 1H), 7.34 (d, J=7.6 Hz, 1H), 7.17 (d, J=8.0 Hz, 1H), 6.97-6.88 (m, 2H), 6.60 (d, J=6.8 Hz, 1H), 6.08 (d, J=12.0 Hz, 1H), 5.12 (s, 1H), 4.50 (t, J=6.0 Hz, 1H), 4.38 (t, J=6.0 Hz, 1H), 4.24 (d, J=4.4 Hz, 1H), 3.93 (q, 1H), 3.63-3.54 (brm, 1H), 2.91 (dd, J=8.0, 3.6 Hz, 1H), 2.73 (t, J=6.4 Hz, 1H), 2.51-2.43 (m, 3H), 1.69-1.57 (m, 5H), 1.35 (d, J=9.2 Hz, 3H), 1.04 (d, J=6.4 Hz, 3H), 0.89 (d, J=6.4 Hz, 3H). UPLC: 95.82%, LCMS: 97.59% and chiral SFC: 99.87%; and (R)-1-(3-((1S,3S)-1-(2,6-difluoro-4-((1-(3-fluoropropyl)azetidin-3-yl)amino)phenyl)-3- methyl-1,3,4,9-tetrahydro-2H-pyrido[3,4-b]indol-2-yl)bicyclo[1.1.1]pentan-1-yl)ethan-1-ol (Compound 67) (60 mg, 26% yield). MS (ESI) m/z 537.42 [M–H]⁻; ¹H NMR (400 MHz, DMSO-d₆) δ 10.36 (s, 1H), 7.34 (d, J=7.6 Hz, 1H), 7.17 (d, J=8.0 Hz, 1H), 6.97-6.88 (m, 2H), 6.60 (d, J=6.8 Hz, 1H), 6.08 (d, J=12.0 Hz, 1H), 5.12 (s, 1H), 4.50 (t, J=6.0 Hz, 1H), 4.38 (t, J=6.0 Hz, 1H), 4.24 (d, J=4.4 Hz, 1H), 3.93 (q, 1H), 3.63-3.54 (m, 1H), 2.91 (dd, J=14.0, 3.6 Hz, 1H), 2.73 (t, J=6.4 Hz, 1H), 2.51-2.43 (m, 3H), 1.61-1.68 (m, 5H), 1.42 (d, J=9.2 Hz, 3H), 1.05 (d, J=6.4 Hz, 3H), 0.895 (d, J=6.4 Hz, 3H). HPLC: 95.02%, LCMS: 95.48% and chiral SFC: 99.70%. The absolute stereochemistry was arbitrarily assigned for Compound 66 and Compound 67.

Example 68

(S)-1-(3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (Compound 68)

Example 69

(S)-1-(3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentan-1-yl)ethan-1-ol (Compound 69)

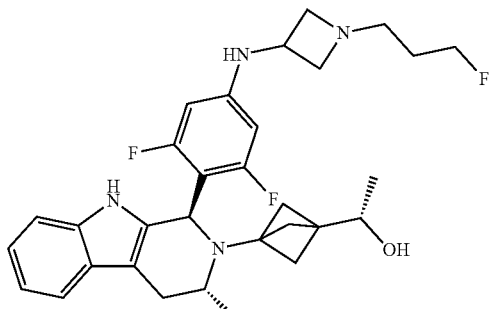

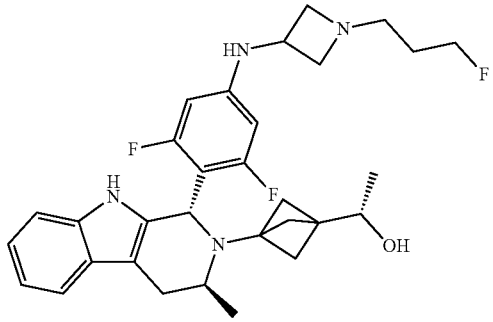

Compounds 68 and 69 were prepared following a procedure analogous to that described for Examples 66 and 67 above. Compound 68: MS (ESI) m/z 537.42 [M–H]⁻; ¹H NMR (400 MHz, DMSO-d₆) δ 10.36 (s, 1H), 7.34 (d, J=7.6 Hz, 1H), 7.17 (d, J=8.0 Hz, 1H), 6.95 (t, J=6.8 Hz, 1H), 6.90 (t, J=7.6 Hz, 1H), 6.60 (d, J=6.8 Hz, 1H), 6.08 (d, J=12.0 Hz, 1H), 5.12 (s, 1H), 4.50 (t, J=6.0 Hz, 1H), 4.38 (t, J=6.0 Hz, 1H), 4.24 (d, J=4.4 Hz, 1H), 3.93 (q, 1H), 3.63-3.54 (m, 1H), 2.91 (dd, J=14.0, 3.6 Hz, 1H), 2.73 (t, J=6.4 Hz, 1H), 2.51-2.43 (m, 3H), 1.69-1.57 (m, 5H), 1.35 (d, J=9.2 Hz, 3H), 1.04 (d, J=6.4 Hz, 3H), 0.89 (d, J=6.4 Hz, 3H). UPLC: 96.55% LCMS: 97.73%, Chiral SFC: 99.79%; Compound 69: MS (ESI) m/z 537.52 [M–H]⁻; ¹H NMR (400 MHz, DMSO-d₆) δ 10.36 (s, 1H), 7.34 (d, J=7.6 Hz, 1H), 7.17 (d, J=8.0 Hz, 1H), 6.95 (t, J=6.8 Hz, 1H), 6.90 (t, J=7.6 Hz, 1H), 6.60 (d, J=6.8 Hz, 1H), 6.08 (d, J=12.0 Hz, 1H), 5.12 (s, 1H), 4.50 (t, J=6.0 Hz, 1H), 4.38 (t, J=6.0 Hz, 1H), 4.24 (d, J=4.4 Hz, 1H), 3.93 (q, 1H), 3.63-3.54 (m, 1H), 2.91 (dd, J=14.0, 3.6 Hz, 1H), 2.73 (t, J=6.4 Hz, 1H), 2.51-2.43 (m, 3H), 1.69-1.57 (m, 5H), 1.35 (d, J=9.2 Hz, 3H), 1.04 (d, J=6.4 Hz, 3H), 0.89 (d, J=6.4 Hz, 3H). HPLC: 95.59% LCMS: 97.09%, Chiral SFC: 99.80%. The absolute stereochemistry was arbitrarily assigned for Compound 68 and Compound 69.

Example 70

(3-((1R,3R)-1-(2,6-difluoro-4-(((S)-1-(3-fluoropropyl)pyrrolidin-3-yl)amino)phenyl)-3-methyl-1,3,4,9-tetrahydro-2H-pyrido[3,4-b]indol-2-yl)bicyclo[1.1.1]pentan-1-yl)methanol (Compound 70)

Example 71

(3-((1S,3S)-1-(2,6-difluoro-4-(((S)-1-(3-fluoropropyl)pyrrolidin-3-yl)amino)phenyl)-3-methyl-1,3,4,9-tetrahydro-2H-pyrido[3,4-b]indol-2-yl)bicyclo[1.1.1]pentan-1-yl)methanol (Compound 71)

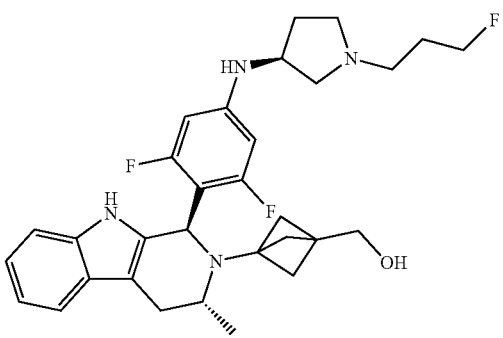

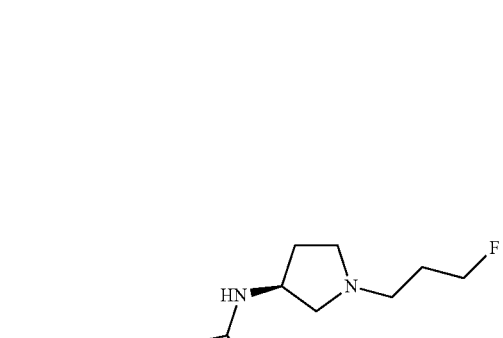

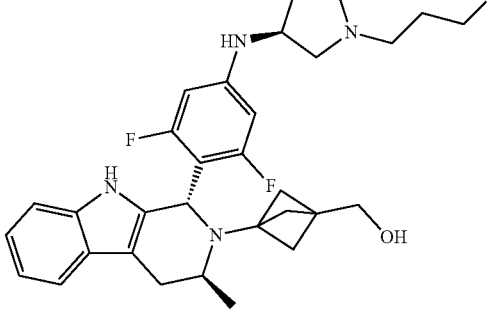

Compounds 70 and 71 were prepared following a procedure analogous to that described for 66 and 67 above. Compound 70: MS (ESI) m/z 539.3 [M+H]+; $^1$H NMR (400 MHz, DMSO-$d_6$) δ 10.45 (s, 1H), 7.34 (d, J=7.6 Hz, 1H), 7.17 (d, J=8.0 Hz, 1H), 6.88-6.97 (m, 2H), 6.31 (d, J=6.8 Hz, 1H), 6.12 (d, J=12 Hz, 2H), 5.20 (S, 1H), 4.52-4.56 (t, J=12.0 Hz, 1H), 4.34-4.43 (m, 2H), 3.80 (bs, 1H), 3.60 (bs, 1H), 3.40 (m, 2H), 2.99 (m, 1H), 2.75 (m, 1H), 2.61 (m, 1H), 2.40-2.50 (m, 4H), 2.30 (m, 1H), 1.76-1.82 (m, 2H), 1.50-1.52 (m, 4H), 1.44 (d, J=9.2 Hz, 3H), 1.04 (d, J=6.8 Hz, 3H); Compound 71: MS (ESI) m/z 539.3 [M+H]+; $^1$H NMR (400 MHz, DMSO-$d_6$) δ 10.45 (s, 1H), 7.34 (d, J=7.6 Hz, 1H), 7.18 (d, J=7.6 Hz, 1H), 6.89-6.97 (m, 2H), 6.32 (d, J=6.8 Hz, 1H), 6.12 (d, J=12 Hz, 2H), 5.15 (S, 1H), 4.41-4.56 (m, 2H), 4.35 (m, 1H), 3.8 (bs, 1H), 3.6 (bs, 1H), 3.32-3.35 (m, 2H), 2.99 (m, 1H), 2.74-2.77 (t, J= 6.8 Hz, 1H), 2.61 (m, 1H), 2.41-2.45 (m, 5H), 2.21 (m, 1H), 1.78-1.84 (m, 2H), 1.61 (d, J=9.2 Hz, 4H), 1.42 (d, J=9.2 Hz, 3H), 1.23 (s, 2H), 1.04 (d, J=6.8 Hz, 3H). The absolute stereochemistry was arbitrarily assigned for Compound 70 and Compound 71.

Example 72

(S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-1-propylpyrrolidin-3-amine (Compound 72)

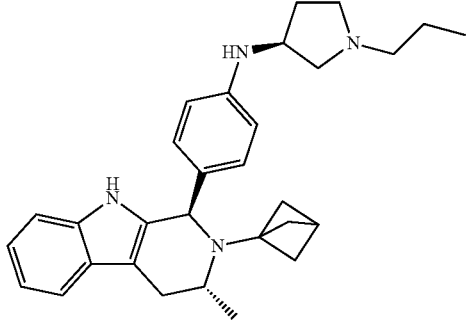 [SMILES: CCCN1CC[C@H](Nc2ccc([C@@H]3c4[nH]c5ccccc5c4C[C@@H](C)N3C34CC(C3)C4)cc2)C1]

Compound 72 was prepared following a procedure analogous to that described for Example 49. MS (ESI) m/z 455.3 [M+H]+; $^1$H NMR (400 MHz, DMSO-$d_6$) δ 10.23 (s, 1H), 7.36 (d, J=7.6 Hz, 1H), 7.19 (d, J=8.0 Hz, 1H), 6.96-6.90 (m, 4H), 6.46 (d, J=8.8 Hz, 2H), 5.58 (d, J=6.8 Hz, 1H), 4.76 (s, 1H), 3.85 (br s, 1H), 3.48-3.31 (m, 1H), 2.89-2.78 (m, 1H), 2.76-2.74 (m, 1H), 2.52-2.49 (m, 2H), 2.45-2.41 (m, 1H), 2.33-2.27 (m, 3H), 2.20-2.10 (m, 2H), 1.73 (d, J=9.6 Hz, 3H), 1.60-1.52 (m, 4H), 1.44-1.38 (m, 2H), 1.10 (d, J=6.8 Hz, 3H), 0.85 (t, J=7.2 Hz, 3H).

Example 73

(3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-(3-fluoropropyl)pyrrolidin-3-amine (Compound 73)

Example 74

(3S,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-(3-fluoropropyl)pyrrolidin-3-amine (Compound 74)

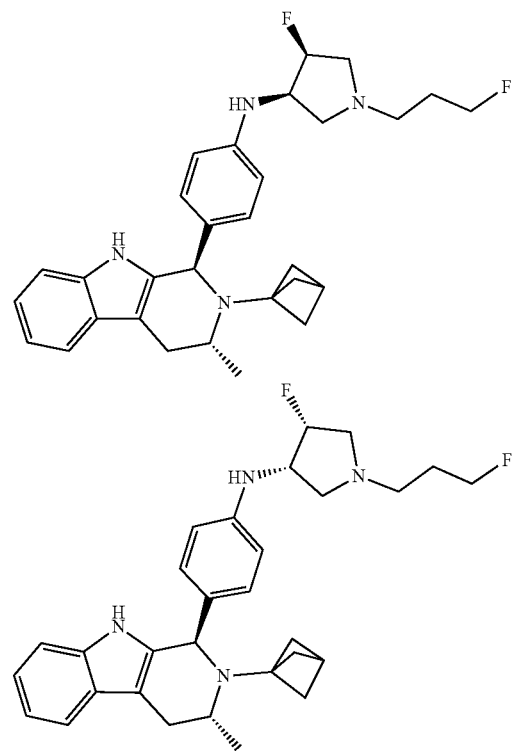

Compounds 73 and 74 were prepared following a procedure analogous to that described for Examples 66 and 67 above. Compound 73 (110 mg, 20% yield). MS (ESI) m/z 489.42 [M−H]−, $^1$H NMR (400 MHz, DMSO-$d_6$) δ 10.25 (s, 1H), 7.36 (d, J=8 Hz, 1H), 7.19 (d, J=8 Hz, 1H), 6.89-6.98 (m, 4H), 6.62 (d, J=8.4 Hz, 2H), 5.59 (d, J=8.4 Hz, 1H), 5.05-5.19 (m, 1H), 4.78 (s, 1H), 4.53 (t, J=6 Hz, 1H), 4.42 (t, J=6 Hz, 1H), 3.9-4.0 (m, 1H), 3.44-3.46 (m, 1H), 3.1-3.15 (m, 1H), 2.86-2.98 (m, 2H), 2.52-2.72 (m, 3H), 2.41-2.46 (m, 2H), 2.12 (s, 1H), 1.72-1.84 (m, 5H), 1.59 (d, J=9.2 Hz, 3H), 1.1 (d, J=6.8 Hz, 3H). Compound 74 (134 mg, 24% yield). MS (ESI) m/z 489.49 [M−H]−, $^1$H NMR (400 MHz, DMSO-$d_6$) δ 10.25 (s, 1H), 7.36 (d, J=8 Hz, 1H), 7.19 (d, J=8 Hz, 1H), 6.89-6.98 (m, 4H), 6.62 (d, J=8.4 Hz, 2H), 5.59 (d, J=8.4 Hz, 1H), 5.05-5.19 (m, 1H), 4.78 (s, 1H), 4.53 (t, J=6 Hz, 1H), 4.42 (t, J=6 Hz, 1H), 3.9-4.0 (m, 1H), 3.44-3.46 (m, 1H), 3.1-3.15 (m, 1H), 2.86-2.98 (m, 2H), 2.52-2.72 (m, 3H), 2.41-2.46 (m, 2H), 2.12 (s, 1H), 1.72-1.84 (m, 5H), 1.59 (d, J=9.2 Hz, 3H), 1.23 (s, 1H), 1.1 (d, J=6.8 Hz, 3H). The absolute stereochemistry was arbitrarily assigned for Compound 73 and Compound 74.

Example 75

(3R,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-(3-fluoropropyl)pyrrolidin-3-amine (Compound 75)

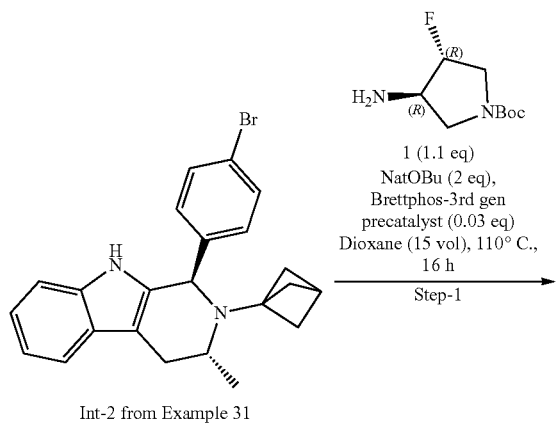

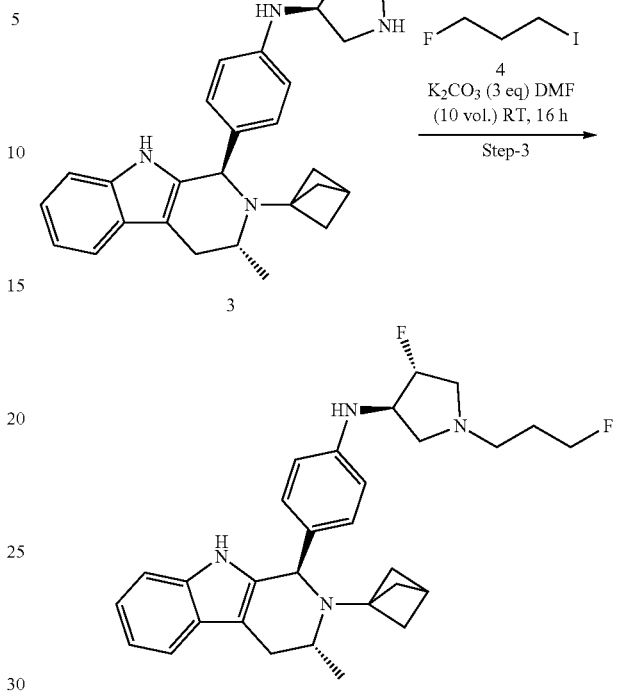

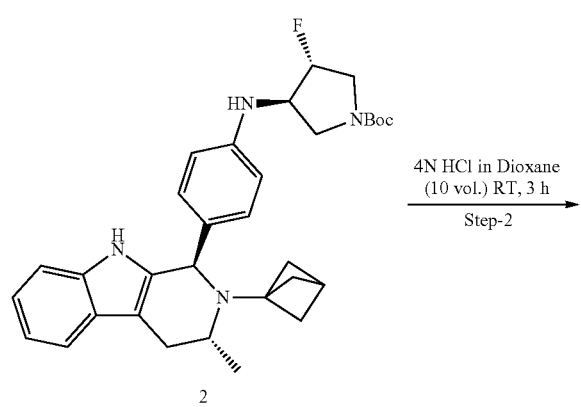

Step 1: To a stirred solution of (1R,3R)-2-(bicyclo[1.1.1]pentan-1-yl)-1-(4-bromophenyl)-3-methyl-2,3,4,9-tetrahydro-1H-pyrido[3,4-b]indole (Int-2, Example 31) (500 mg, 1.13 mmol) in 1,4-dioxane (10 mL) were added tert-butyl (3R,4R)-3-amino-4-fluoropyrrolidine-1-carboxylate (1) (276.6 mg, 1.35 mmol) and NaOt-Bu (217.1 mg, 2.26 mmol). The reaction mixture was degassed under argon for 30 min. Later Brettphos-3rd gen precatalyst (30.73 mg, 0.03 mmol) was added and the reaction mixture was again degassed for 30 min. It was then heated at 110° C. for 16 h. After completion of the reaction, it was cooled to room temperature and filtered through a bed of celite. The filtrate was diluted with water (50 mL) and extracted with EtOAc (2×10 mL). The combined organic layers were dried over Na$_2$SO$_4$, filtered and evaporated. The crude product was purified by RP prep-HPLC to afford tert-butyl (3R,4R)-3-((4-((1R,3R)-2-(bicyclo[1.1.1]pentan-1-yl)-3-methyl-2,3,4,9-tetrahydro-1H-pyrido[3,4-b]indol-1-yl)phenyl) amino)-4-fluoropyrrolidine-1-carboxylate (2) (440 mg, 0.847 mmol, 67% yield). MS (ESI) m/z 531.46 [M+H]$^+$; $^1$H NMR (400 MHz, DMSO-d$_6$) δ 10.26 (s, 1H), 7.36 (d, J=7.6 Hz, 1H), 7.19 (d, J=8.4 Hz, 1H), 7.04 (d, J=7.6 Hz, 2H), 6.98-6.88 (m, 2H), 6.54 (d, J=8.4 Hz, 2H), 5.89 (q, 1H), 5.08-4.92 (d, 1H), 4.82 (s, 1H), 4.04 (q, 1H), 3.68-3.40 (m, 4H), 2.88-2.86 (dd, 1H), 2.60-2.50 (m, 1H), 2.20 (s, 1H), 1.73 (d, J=9.6 Hz, 3H), 1.56 (d, J=8.4 Hz, 3H), 1.42 (s, 9H), 1.11 (d, J=9.2 Hz, 3H).

Step 2: To a solution of tert-butyl (3R,4R)-3-((4-((1R,3R)-2-(bicyclo[1.1.1]pentan-1-yl)-3-methyl-2,3,4,9-tetrahydro-1H-pyrido[3,4-b]indol-1-yl)phenyl)amino)-4-fluoropyrrolidine-1-carboxylate (2) (440 mg, 0.829 mmol) in dioxane (2 mL) was added 4N HCl in dioxane (2 ml) at 0° C. It was then stirred at room temperature for 3 h. Progress of the reaction was monitored by TLC and LCMS. After completion, the reaction mixture was evaporated under reduced pressure to obtained a crude which was then triturated with diethyl ether (15 mL) to afford (3R,4R)—N-(4-

((1R,3R)-2-(bicyclo[1.1.1]pentan-1-yl)-3-methyl-2,3,4,9-tetrahydro-1H-pyrido[3,4b]indol-1-yl)phenyl)-4-fluoropyrrolidin-3-amine (3) (350 mg, 0.812 mmol, 90%). MS (ESI) m/z 431.4 [M+H]⁺; ¹H NMR (400 MHz, DMSO-d₆) δ 10.26 (s, 1H), 7.37 (d, J=7.6 Hz, 1H), 7.19 (d, J=8.4 Hz, 1H), 7.04 (d, J=7.6 Hz, 2H), 6.98-6.88 (m, 2H), 6.54 (d, J=8.4 Hz, 2H), 5.63 (d, J=6.0 Hz, 1H), 4.78 (t, J=7.6 Hz, 2H), 3.82-3.67 (q, 1H), 3.46 (m, 1H), 3.04-2.86 (m, 4H), 2.62-2.50 (m, 2H), 2.20 (s, 1H), 1.73 (d, J=9.6 Hz, 3H), 1.57 (d, J=8.8 Hz, 3H), 1.08 (d, J=9.2 Hz, 3H).

Step 3: To a solution of (3R,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoropyrrolidin-3-amine (3) (350 mg, 0.812 mmol) in DMF (3 mL) were added 1-fluoro-3-iodopropane (4) (183.1 mg, 0.974 mmol) and K₂CO₃ (168.3 mg, 1.21 mmol) at room temperature. The reaction mixture was stirred at room temperature for 16 h. After completion of the reaction, it was diluted with water (5 mL) and extracted with EtOAc (2×10 mL). The combined organic layer was collected, dried over Na₂SO₄, filtered and evaporated. The crude product was purified by RP prep-HPLC to afford (3R,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-(3-fluoropropyl)pyrrolidin-3-amine (Compound 75) (89.8 mg, 0.18 mmol, 29%). MS (ESI) m/z 489.48 [M+H]⁻; ¹H NMR (400 MHz, DMSO-d₆) δ 10.25 (s, 1H), 7.36 (d, J=7.6 Hz, 1H), 7.19 (d, J=8.0 Hz, 1H), 7.02 (d, J=7.6 Hz, 2H), 6.98-6.9 (m, 2H), 6.54 (d, J=7.6 Hz, 2H), 5.76 (d, J=6.0 Hz, 1H), 4.78 (t, J=7.6 Hz, 2H), 4.56 (t, J=7.6 Hz, 1H), 4.44 (t, J=7.6 Hz, 1H), 3.92-3.86 (m, 1H), 3.46 (m, 1H), 3.04-2.86 (m, 2H), 2.76-2.50 (m, 4H), 2.21 (s, 1H), 2.12 (m, 1H), 1.73 (d, J=9.6 Hz, 3H), 1.58 (d, J=8.8 Hz, 3H), 1.14 (d, J=9.2 Hz, 3H).

Example 76

3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentane-1-carboxamide (Compound 76)

Example 77

3-((1S,3S)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)bicyclo[1.1.1]pentane-1-carboxamide (Compound 77)

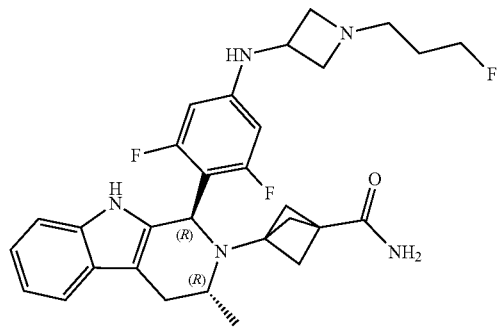

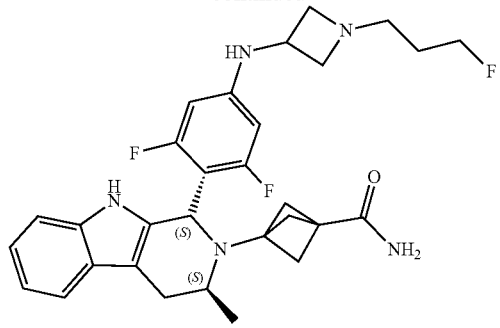

Compounds 76 and 77 were prepared following a procedure analogous to that described for Examples 58 and 59 above. Compound 76: MS (ESI) m/z 536.40 [M–H]⁻; ¹H NMR (400 MHz, DMSO-d₆) δ 7.35 (d, J=7.2 Hz, 1H), 7.17 (m, 2H), 6.98-6.89 (m, 2H), 6.83 (s, 1H), 6.65 (d, J=6.8 Hz, 1H), 6.1 (d, J=12 Hz, 2H), 5.12 (s, 1H), 4.5 (dt, J=47, 6 Hz, 2H), 3.94 (q, J=6.8 Hz, 1H), 3.56-3.64 (m, 3H), 2.94-2.89 (m, 1H), 2.73 (t, J=7.2 Hz, 2H), 2.54-2.46 (m, 3H), 1.89 (d, J=8.8 Hz, 3H), 1.81 (s, 1H), 1.73-1.6 (m, 5H), 1.05 (d, J=6.8 Hz, 3H). HPLC: 96.32%, LCMS: 99.11%, Chiral SFC: 99.94%. Compound 77: MS (ESI) m/z 538.36 [M+H]⁺; ¹H NMR (400 MHz, DMSO-d₆) δ 7.36 (d, J=7.2 Hz, 1H), 7.17 (m, 2H), 6.98-6.89 (m, 2H), 6.83 (s, 1H), 6.65 (d, J=6.8 Hz, 1H), 6.1 (d, J=12 Hz, 2H), 5.12 (s, 1H), 4.5 (dt, J=47, 6 Hz, 2H), 3.94 (q, J=6.8 Hz, 1H), 3.56-3.64 (m, 3H), 2.94-2.89 (m, 1H), 2.73 (t, J=7.2 Hz, 2H), 2.54-2.46 (m, 3H), 1.89 (d, J=8.8 Hz, 3H), 1.81 (s, 1H), 1.73-1.6 (m, 5H), 1.05 (d, J=6.8 Hz, 3H). HPLC: 97.10%, LCMS: 98.08%, Chiral SFC: 96.81%. The absolute stereochemistry was arbitrarily assigned for Compound 76 and Compound 77.

Example 78

(3S,4R)-4-((4-((1R,3R)-2-(bicyclo[1.1.1]pentan-1-yl)-3-methyl-2,3,4,9-tetrahydro-1H-pyrido[3,4-b]indol-1-yl)phenyl)amino)-1-(3-fluoropropyl)pyrrolidin-3-ol (Compound 78)

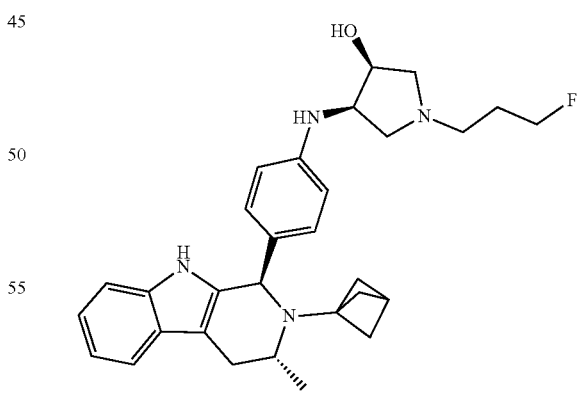

Compound 78 was prepared following a procedure analogous to that described for Example 49 with LCMS purity: 97.96%, UPLC purity: 95.06% and Chiral purity: 96.53%. MS (ESI) m/z 489.4 [M+H]⁺. ¹H NMR (400 MHz, DMSO-d₆) δ 10.22 (s, 1H), 7.39 (d, J=7.2 Hz, 1H), 7.21 (d, J=7.6 Hz, 1H), 6.97-6.89 (m, 4H), 6.55-6.53 (d, J=8 Hz, 2H), 5.12-5.11 (d, J=4 Hz, 1H), 4.921 (bs, 1H), 4.79 (s, 1H), 4.53-4.38 (dt, $J_1$=47.6 Hz, $J_2$=6.0 Hz, 2H), 4.18 (brs, 1H), 3.71-3.69 (m, 1H), 3.45-3.44 (m, 1H), 3.03-2.97 (m, 2H), 2.86 (m, 1H), 2.57-2.44 (m, 3H), 2.33-2.29 (d, 3H), 1.81-1.72 (m, 5H), 1.11-1.09 (d, J=8.0 Hz 3H)

Example 79

(3S,4S)-4-((4-((1R,3R)-2-(bicyclo[1.1.1]pentan-1-yl)-3-methyl-2,3,4,9-tetrahydro-1H-pyrido[3,4-b]indol-1-yl)phenyl)amino)-1-(3-fluoropropyl)pyrrolidin-3-ol (Compound 79)

Example 80

(3R,4R)-4-((4-((1R,3R)-2-(bicyclo[1.1.1]pentan-1-yl)-3-methyl-2,3,4,9-tetrahydro-1H-pyrido[3,4-b]indol-1-yl)phenyl)amino)-1-(3-fluoropropyl)pyrrolidin-3-ol (Compound 80)

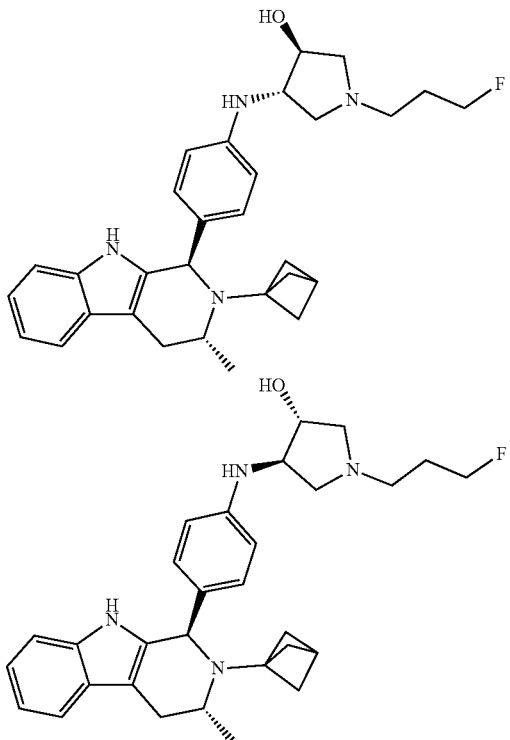

Compounds 79 and 80 were prepared following a procedure analogous to that described for Examples 66 and 67 above. Compound 79. MS (LCMS) m/z 489.4 [M+H]⁺. ¹H NMR (400 MHz, DMSO-d₆) δ 10.21 (s, 1H), 7.35 (d, J=7.6 Hz, 1H), 7.193 (d, J=8 Hz, 1H), 6.98-6.89 (m, 4H), 6.54 (d, J=8.4 Hz, 2H), 5.59 (d, J=6 Hz, 1H), 4.77 (s, 1H), 4.41-4.51 (dt, J=47.2 Hz, 2H), 3.87 (brs, 1H), 3.48-3.32 (m, 2H), 2.93-2.76 (m, 2H), 2.91-2.75 (m, 1H), 2.50-2.30 (m, 5H), 2.19 (s, 1H), 1.81-1.71 (m, 5H), 1.58 (d, J=9.2 Hz, 3H), 1.08 (d, J=6.4 Hz, 3H). Compound 80. MS (LCMS) m/z 489.3 [M+H]⁺. ¹H NMR (400 MHz, DMSO-d₆) δ 10.21 (s, 1H), 7.35 (d, J=7.6 Hz, 1H), 7.193 (d, J=8 Hz, 1H), 6.98-6.89 (m, 4H), 6.54 (d, J=8.4 Hz, 2H), 5.59 (d, J=6 Hz, 1H), 4.77 (s, 1H), 4.41-4.51 (dt, J=47.2 Hz, 2H), 3.87 (brs, 1H), 3.48-3.32 (m, 2H), 2.93-2.76 (m, 2H), 2.91-2.75 (m, 1H), 2.50-2.30 (m, 5H), 2.19 (s, 1H), 1.81-1.71 (m, 5H), 1.58 (d, J=9.2 Hz, 3H), 1.08 (d, J=6.4 Hz, 3H). The absolute stereochemistry was arbitrarily assigned for Compound 79 and Compound 80.

Example 81

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(2-fluoroethyl)azetidin-3-amine (Compound 81)

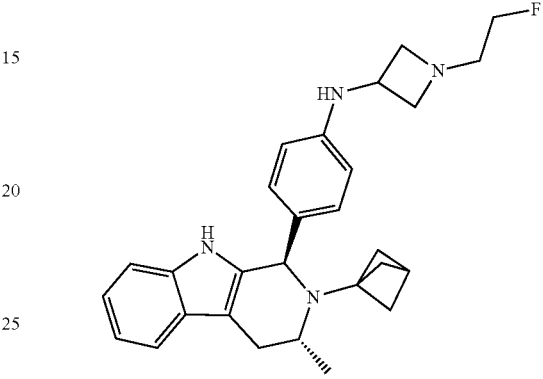

Compound 81 was prepared following a procedure analogous to that described for Example 49. MS (ESI) m/z 443.5 [M+H]⁻; ¹H NMR (400 MHz, DMSO-d₆) δ 10.22 (s, 1H), 7.35 (d, J=7.6 Hz, 1H), 7.18 (d, J=8.0 Hz, 1H), 6.98-6.9 (m, 4H), 6.42 (d, J=8.8 Hz, 2H), 5.94 (d, J=6.8 Hz, 1H), 4.76 (s, 1H), 4.45 (t, J=7.6 Hz, 1H), 4.36 (t, J=7.6 Hz, 1H), 3.92 (q, 1H), 3.68 (m, 2H), 3.45 (br, 1H), 2.84 (m, 3H), 2.73 (t, J=7.6 Hz, 1H), 2.66 (t, J=7.6 Hz, 1H), 2.51 (s, 1H), 2.22 (s, 1H), 1.73 (d, J=9.2 Hz, 3H), 1.56 (d, J=8.4 Hz, 3H), 1.09 (d, J=9.2 Hz, 3H).

Example 82

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-((R)-2-fluoropropyl)azetidin-3-amine (Compound 82)

Example 83

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-((S)-2-fluoropropyl)azetidin-3-amine (Compound 83)

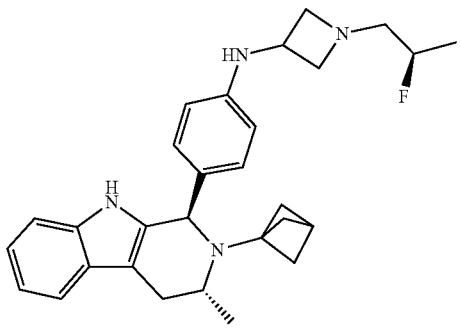

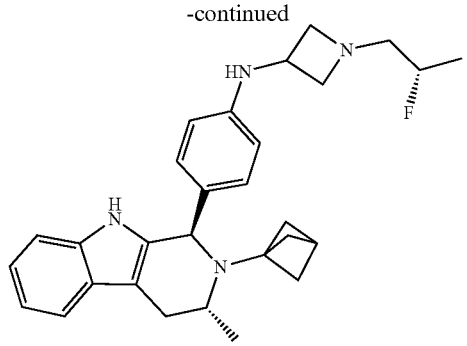

Compounds 82 and 83 were prepared following a procedure analogous to that described for Examples 66 and 67 above. Compound 82 MS (ESI) m/z 457.3 [M+H]$^-$, $^1$H NMR (400 MHz, DMSO-d$_6$) δ 10.22 (s, 1H), 7.35 (d, J=7.6 Hz, 1H), 7.18 (d, J=7.6 Hz, 1H), 6.98-6.89 (m, 4H), 6.42 (d, J=8.4 Hz, 2H), 5.95 (d, J=3.6 Hz, 1H), 4.77 (s, 1H), 4.21 (br, 1H), 3.98 (q, 1H), 3.76 (br, 1H), 3.42 (q, 1H), 2.93 (br, 3H), 2.55 (m, 3H), 2.19 (s, 1H), 1.73 (d, J=7.6 Hz, 3H), 1.59 (d, J=9.2 Hz, 3H), 1.27-1.19 (m, 3H), 1.22 (d, J=8.4 Hz, 3H). Compound 83. MS (ESI) m/z 459.4 [M+H]$^+$, $^1$H NMR (400 MHz, DMSO-d$_6$) δ 10.22 (s, 1H), 7.35 (d, J=7.6 Hz, 1H), 7.18 (d, J=7.6 Hz, 1H), 6.99-6.89 (m, 4H), 6.43 (d, J=8.0 Hz, 2H), 5.99 (br, 1H), 4.67 (s, 1H), 4.05 (br, 1H), 3.88 (q, 2H), 3.44 (q, 1H), 2.93 (br, 3H), 2.55 (m, 3H), 2.19 (s, 1H), 1.73 (d, J=7.6 Hz, 3H), 1.59 (d, J=9.2 Hz, 3H), 1.27-1.19 (m, 3H), 1.22 (d, J=8.4 Hz, 3H). The absolute stereochemistry was arbitrarily assigned for Compound 82 and Compound 83.

Example 84

(3R,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-1-butyl-4-fluoropyrrolidin-3-amine (Compound 84)

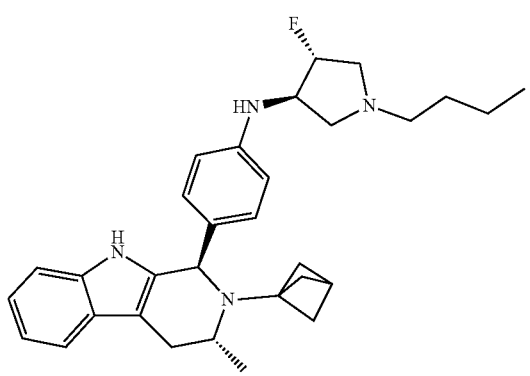 [SMILES: CCCCN1C[C@@H](F)[C@H](Nc2ccc([C@@H]3c4[nH]c5ccccc5c4C[C@@H](C)N3C34CC(C3)C4)cc2)C1]

Compound 84 was prepared following a procedure analogous to that described for Example 49. MS (ESI) m/z 487.3 [M+H]$^+$; $^1$H NMR (400 MHz, DMSO-d$_6$) δ 10.23 (s, 1H), 7.36 (d, J=7.6 Hz, 1H), 7.18 (d, J=8.0 Hz, 1H), 7.02 (d, J=8.0 Hz, 2H), 6.98-6.89 (m, 2H), 6.53 (d, J=8.4 Hz, 2H), 5.75 (d, J=6.0 Hz, 1H), 4.78 (t, J=7.6 Hz, 2H), 3.47-3.28 (m, 1H), 3.46 (q, 1H), 3.28 (m, 1H), 3.0-2.86 (m, 2H), 2.56 (m, 2H), 2.36 (br, 2H), 2.21 (s, 1H), 2.08 (br, 1H), 1.72 (d, J=7.6 Hz, 3H), 1.56 (d, J=8.4 Hz, 1H), 1.43 (m, 2H), 1.31 (m, 2H), 1.11 (d, J=7.6 Hz, 3H), 0.88 (t, J=7.2 Hz, 3H).

Example 85

(3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (Compound 85)

Example 86

(3S,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (Compound 86)

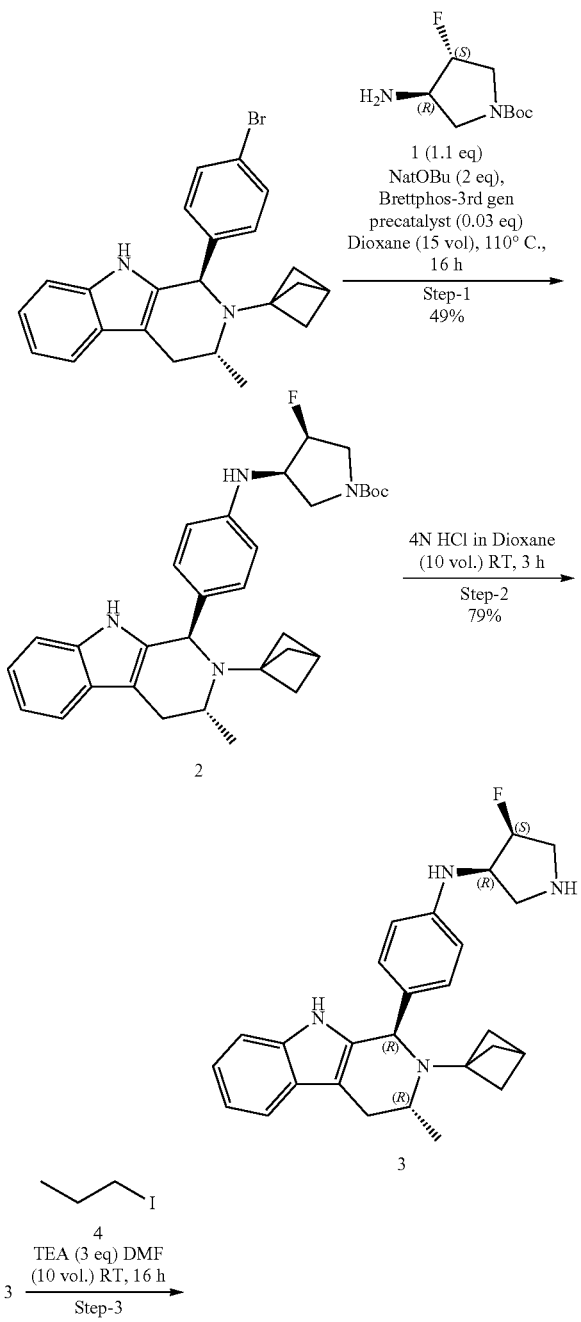

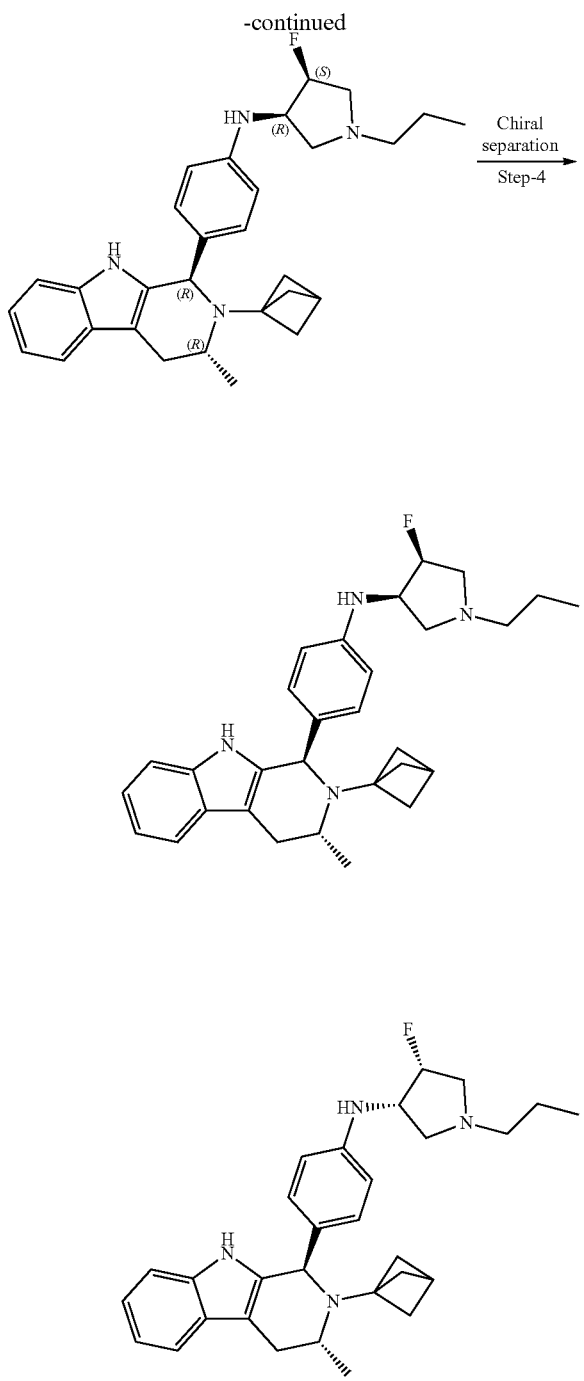

Step 1: To a stirred solution of (1R,3R)-2-(bicyclo[1.1.1]pentan-1-yl)-1-(4-bromophenyl)-3-methyl-2,3,4,9-tetrahydro-1H-pyrido[3,4-b]indole (800 mg, 1.9607 mmol) in 1,4-dioxane (10 mL) were added tert-butyl (3R,4S)-3-amino-4-fluoropyrrolidine-1-carboxylate (1) (435 mg, 2.1568 mmol) and NaOt-Bu (752.0 mg, 7.8431 mmol). The reaction mixture was degassed under argon for 30 min. Later Brettphos-3rd gen precatalyst (53 mg, 0.0588 mmol) was added and the reaction mixture was again degassed for 30 min and then heated at 110° C. for 16 h. After completion, the reaction mixture was cooled to room temperature and filtered through a bed of celite. The filtrate was diluted with water (50 mL) and extracted with EtOAc (2×10 mL). The combined organic layers were dried over anhydrous Na$_2$SO$_4$, filtered and evaporated. The crude product was purified by RP prep-HPLC to afford tert-butyl (3R,4S)-3-((4-((1R,3R)-2-(bicyclo[1.1.1]pentan-1-yl)-3-methyl-2,3,4,9-tetrahydro-1H-pyrido[3,4-b]indol-1-yl)phenyl)amino)-4-fluoropyrrolidine-1-carboxylate (2) (550 mg, 52% yield). MS (ESI) m/z 531.6[M+H]

Step 2: To a solution of tert-butyl (3R,4S)-3-((4-((1R,3R)-2-(bicyclo[1.1.1]pentan-1-yl)-3-methyl-2,3,4,9-tetrahydro-1H-pyrido[3,4-b]indol-1-yl)phenyl)amino)-4-fluoropyrrolidine-1-carboxylate (2) (550 mg, 0.001039 mmol) in dioxane (5 mL) at 0° C. was added 4N HCl in dioxane (2 ml) at 0° C. The reaction was stirred at room temperature for 2 h. Progress of the reaction was monitored by TLC and LCMS. After completion, the reaction mixture was evaporated under reduced pressure to obtained crude which was triturated with diethyl ether (15 mL) to afford (3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoropyrrolidin-3-amine (3) (300 mg, 71%). MS (ESI) m/z 431.51[M+H].

Step 3: To a solution of (3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoropyrrolidin-3-amine (3) (700 mg, 1.6269 mmol) in DMF (5 mL) were added 3-iodopropane (4) (183.1 mg, 1.9523 mmol) and TEA (0.67 ml, 4.8807 mmol) at room temperature. The reaction was stirred at room temperature for 16 h. After completion, the reaction mixture was cooled to room temperature, diluted with water (5 mL) and extracted with EtOAc (2×10 mL). The combined organic layer was collected, dried over Na$_2$SO$_4$, filtered and evaporated to afford a crude residue. The crude was purified by RP prep-HPLC to afford (3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (500 mg, 1.0586 mmol, 65%). MS (ESI) m/z 473.61[M+H]

Step 4: (3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (500 mg, 1.0586 mmol) was purified by chiral SFC to afford (3R,4S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (Compound 85) (0.0566 g, 1.1983 mmol, 11%), and (3S,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (Compound 86) (0.1537 g, 30%). Compound 85: MS (ESI) m/z 471.40 [M−H]: 1H NMR (400 MHz, DMSO-d6) δ 10.24 (s, 1H), 7.35 (d, J=7.6 Hz, 1H), 7.19 (d, J=8.0 Hz, 1H), 6.98-6.9 (m, 4H), 6.61 (d, J=8.4 Hz, 2H), 5.56 (d, J=8.8 Hz, 1H), 5.01-5.03 (m, 1H), 4.78 (s, 1H), 3.46-3.44 (m, 1H), 2.93-2.86 (m, 2H), 2.85-2.66 (m, 2H), 2.43-2.34 (m, 3H), 2.19 (s, 1H), 1.74 (m, 3H), 1.59 (d, J=8 Hz, 3H), 1.44-1.38 (q, J=16 Hz, 2H), 1.09 (d, J=4 Hz, 3H), 0.85 (t, J=9.6 Hz, 3H). Compound 86: MS (ESI) m/z 471.40 [M−H]⁻; 1H NMR (400 MHz, DMSO-d6) δ 10.24 (s, 1H), 7.35 (d, J=8.8 Hz, 1H), 7.19 (d, J=8.0 Hz, 1H), 6.98-6.89 (m, 4H), 6.62 (d, J=8.4 Hz, 2H), 5.17 (s, 1H), 4.78 (brs, 1H), 4.1-3.8 (m, 1H), 3.45 (d, J=6.4 Hz, 2H), 3.2 (dd, 1H), 2.95 (t, J=8.0 Hz, 1H), 2.86 (dd, J=4.8 Hz, 1H), 2.72-2.75 (m, 2H), 2.48-2.3 (m, 3H), 2.20 (s, 1H), 1.73, (d, J=8.8 Hz, 3H), 1.59 (d, J=9.2 Hz, 3H), 1.44-1.41 (q, J=7.6 2H), 1.10 (d, J=6.4 Hz, 3H), 0.87-0.83 (t, J=7.2, 3H). The absolute stereochemistry was arbitrarily assigned for Compound 85 and Compound 86.

Example 87

(3R,4R)—N-(4-((1R,3R)-2-(bicyclo[1.1.1]pentan-1-yl)-3-methyl-2,3,4,9-tetrahydro-1H-pyrido[3,4-b]indol-1-yl)phenyl)-4-fluoro-1-propylpyrrolidin-3-amine (Compound 87)

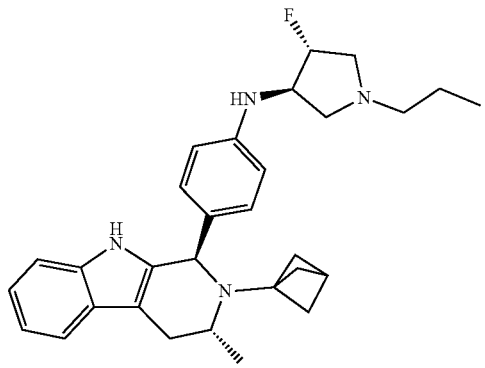 [SMILES: CCCN1C[C@@H](F)[C@H](Nc2ccc([C@@H]3c4[nH]c5ccccc5c4C[C@@H](C)N3C34CC(C3)C4)cc2)C1]

Compound 87 was prepared following a procedure analogous to that described for Example 49. MS (ESI) m/z 473.37 [M+H]$^+$; $^1$H NMR (400 MHz, DMSO-d$_6$) δ 10.25 (s, 1H), 7.36 (d, J=7.6 Hz, 1H), 7.19 (d, J=8.0 Hz, 1H), 7.02 (d, J=8.0 Hz, 2H), 6.98-6.9 (m, 2H), 6.53 (d, J=7.6 Hz, 2H), 5.75 (d, J=6.0 Hz, 1H), 4.78 (t, J=7.6 Hz, 2H), 3.92-3.78 (m, 1H), 3.44 (q, 1H), 3.33 (m, 1H), 2.92-2.86 (m, 2H), 2.56-2.38 (m, 2H), 2.38 (q, 2H), 2.12 (m, 1H), 2.09 (q, 1H), 1.74 (d, J=9.6 Hz, 3H), 1.59 (d, J=8.8 Hz, 3H), 1.39 (q, 2H), 1.14 (d, J=9.2 Hz, 3H), 0.86 (t, 3H).

Example 88

N-(4-((1R,3R)-2-(bicyclo[1.1.1]pentan-1-yl)-3-methyl-2,3,4,9-tetrahydro-1H-pyrido[3,4-b]indol-1-yl)phenyl)-1-(2,2-difluoropropyl)azetidin-3-amine (Compound 88)

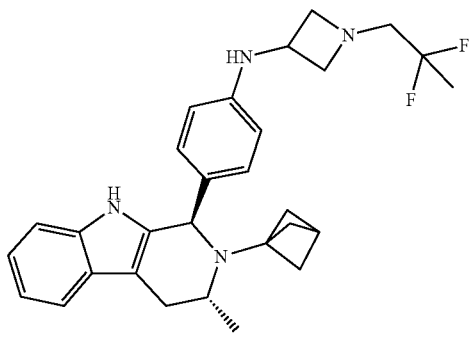 [SMILES: C[C@@H]1Cc2c([nH]c3ccccc23)[C@@H](c2ccc(NC3CN(CC(C)(F)F)C3)cc2)N1C12CC(C1)C2]

Compound 88 was prepared following a procedure analogous to that described for Example 49. MS (ESI) m/z 477.3 [M+H]$^+$; $^1$H NMR (400 MHz, DMSO-d$_6$) δ 10.21 (s, 1H), 7.35 (d, J=7.6 Hz, 1H), 7.18 (d, J=8.0 Hz, 1H), 6.98-6.88 (m, 4H), 6.42 (d, J=8.4 Hz, 2H), 5.94 (d, J=6.8 Hz, 1H), 4.77 (s, 1H), 3.96 (q, J=6.4 Hz, 1H), 3.72 (t, J=6.8 Hz, 2H), 3.46-3.42 (m, 1H), 2.95-2.85 (m, 3H), 2.79 (t, J=14.0 Hz, 2H), 2.57-2.49 (m, 1H), 2.19 (s, 1H), 1.75-1.52 (m, 9H), 1.10 (d, J=6.4 Hz, 3H).

Example 89

(3S,5S)—N-(4-((1R,3R)-2-(bicyclo[1.1.1]pentan-1-yl)-3-methyl-2,3,4,9-tetrahydro-1H-pyrido[3,4-b]indol-1-yl)phenyl)-5-methyl-1-propylpyrrolidin-3-amine (Compound 89)

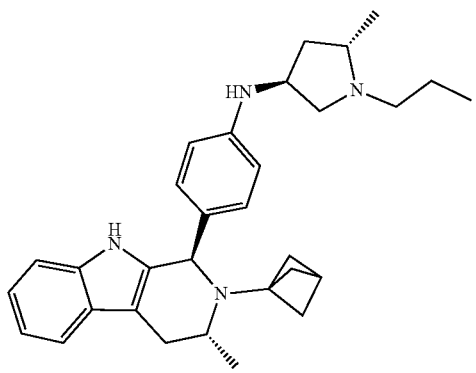 [SMILES: CCCN1C[C@@H](Nc2ccc([C@@H]3c4[nH]c5ccccc5c4C[C@@H](C)N3C34CC(C3)C4)cc2)C[C@@H]1C]

Compound 89 was prepared following a procedure analogous to that described for Example 49. MS (LCMS) m/z 469.4 [M+H], 1H NMR (400 MHz, DMSO-d$_6$) δ 10.21 (s, 1H), 7.35 (d, J=7.6 Hz, 1H), 7.21 (d, J=7.6 Hz, 1H), 6.97-6.89 (m, 4H), 6.46 (d, J=8.40 Hz, 2H), 5.54 (d, J=6.8 Hz, 1H), 4.76 (s, 1H), 3.75 (q, J=6.4 Hz, 1H), 3.45 (t, J=9.2 Hz 1H), 2.89-2.85 (m, 1H), 2.64 (d, J=11.6 Hz, 2H), 2.57-2.49 (m, 2H), 2.45 (s, 1H), 2.19 (s, 1H), 1.98-1.96 (m, 1H), 1.92-1.88 (m, 1H), 1.73-1.68 (m, 5H), 1.59 (d, J=9.2 Hz, 3H), 1.10-1.09 (d, J=6.0 Hz, 3H), 1.05-1.04 (d, J=6.40 Hz, 3H), 0.85 (t, J=7.2 Hz, 3H)

Example 90

3-((1S,3S)-1-(2,6-difluoro-4-(((S)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 90)

Example 91

3-((1S,3S)-1-(2,6-difluoro-4-(((R)-1-(3-fluoropropyl)pyrrolidin-3-yl)oxy)phenyl)-3-methyl-1,3,4,9-tetrahydro-2H-pyrido[3,4-b]indol-2-yl)bicyclo[1.1.1]pentane-1-carbonitrile (Compound 91)

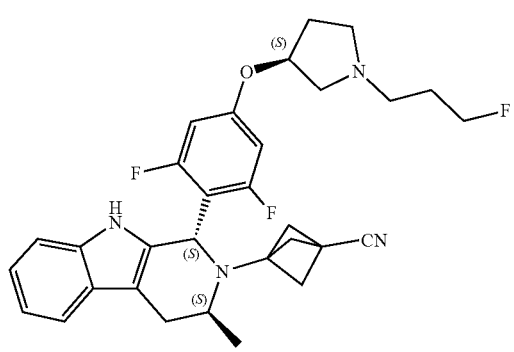

-continued

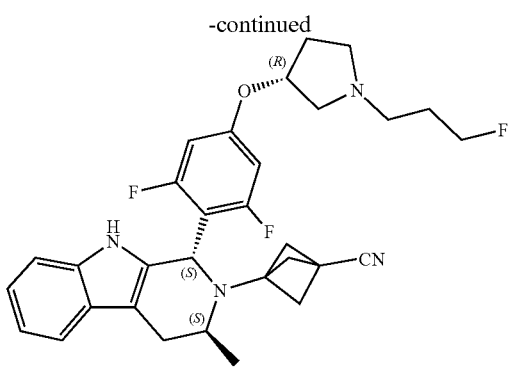

Compounds 90 and 91 were prepared following a procedure analogous to that described for Examples 32 and 33 above. Compound 90: MS (ESI) m/z 533.41 [M−H]⁻; ¹H NMR (400 MHz, DMSO-d₆) δ 10.51 (s, 1H), 7.37 (d, J=7.6 Hz, 1H), 7.18 (d, J=8.0 Hz, 1H), 6.98 (dt, J=46 Hz, 7.6 Hz, 2H), 6.62 (d, J=11.2 Hz, 1H), 5.22 (s, 1H), 4.89 (s, 1H), 4.48 (dt, J=47 Hz, 6 Hz, 2H), 3.53 (brs, 1H), 2.91-2.85 (m, 1H), 2.83-2.81 (m, 1H), 2.71-2.56 (m, 3H), 2.50-2.24 (m, 7H), 2.07 (d, J=8.8 Hz, 3H), 1.86-1.74 (m, 3H), 1.07 (d, J=6.4 Hz, 3H). HPLC: 98.77%, LCMS: 99.78% and chiral SFC: 99.89%. Compound 91: MS (ESI) m/z 533.38 [M−H]⁻; ¹H NMR (400 MHz, DMSO-d₆) δ 10.51 (s, 1H), 7.37 (d, J=7.6 Hz, 1H), 7.18 (d, J=8.0 Hz, 1H), 6.90 (t, J=6.8 Hz, 1H), 6.93 (t, J=7.2 Hz, 1H), 6.62 (d, J=10.8 Hz, 1H), 5.22 (s, 1H), 4.89 (s, 1H), 4.54 (t, J=6 Hz, 1H), 4.41 (t, J=6 Hz, 1H), 3.53 (brs, 1H), 2.91-2.85 (m, 1H), 2.83-2.81 (m, 1H), 2.71-2.49 (m, 3H), 2.50-2.24 (m, 7H), 2.07 (d, J=8.8 Hz, 3H), 1.86-1.74 (m, 3H), 1.07 (d, J=6.4 Hz, 3H). HPLC: 98.94%, LCMS: 99.74% and chiral SFC: 99.90%. The absolute stereochemistry was arbitrarily assigned for Compound 90 and Compound 91.

Example 92

N-(4-((1R,3R)-2-(bicyclo[1.1.1]pentan-1-yl)-3-methyl-2,3,4,9-tetrahydro-1H-pyrido[3,4-b]indol-1-yl)-3-fluoro-5-methoxyphenyl)-1-(3-fluoropropyl)azetidin-3-amine (Compound 92)

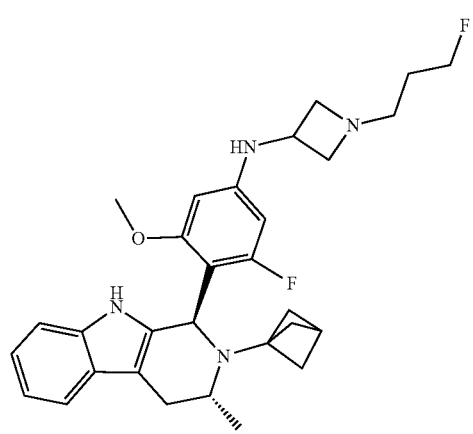 [SMILES: COc1cc(NC2CN(CCCF)C2)cc(F)c1[C@@H]1c2[nH]c3ccccc3c2C[C@@H](C)N1C12CC(C1)C2]

Compound 92 was prepared following a procedure analogous to that described for Example 49. MS (ESI) m/z 507.30 [M+1]⁺; ¹H NMR (400 MHz, DMSO-d₆) δ 10.16 (s, 1H), 7.31 (d, J=7.2 Hz, 1H), 7.16 (d, J=7.6 Hz, 1H), 6.9-6.86 (m, 2H), 6.31 (d, J=6.8 Hz, 1H), 6.02 (s, 1H), 5.72 (dd, J=14 Hz, 3.6 Hz, 1H), 5.32 (s, 1H), 4.52-4.37 (dt, J₁=47.6 Hz, J₂=6.0 Hz, 2H), 3.95-3.92 (m, 1H) 3.77 (s, 3H), 3.65-3.60 (m, 3H), 2.89-2.85 (m, 1H), 2.74-2.69 (m, 2H), 2.47-2.44 (m, 3H), 2.17 (s, 1H), 1.74-1.55 (m, 8H), 1.23 (m, 1H), 1.05 (d, J=6.4 Hz, 3H).

Example 93

N-((1-(4-(((1R,3R)-2-(bicyclo[1.1.1]pentan-1-yl)-3-methyl-2,3,4,9-tetrahydro-1H-pyrido[3,4-b]indol-1-yl)phenyl)piperidin-4-yl)methyl)propan-1-amine (Compound 93)

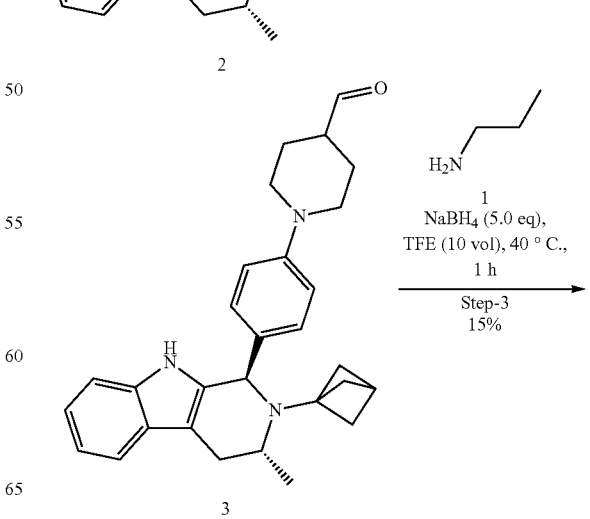

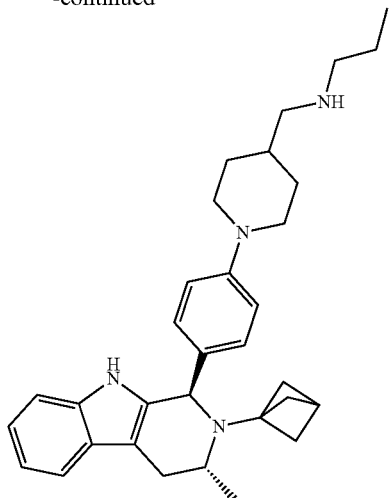

Step 1: To a stirred solution of (1R,3R)-2-(bicyclo[1.1.1]pentan-1-yl)-1-(4-bromophenyl)-3-methyl-2,3,4,9-tetrahydro-1H-pyrido[3,4-b]indole (Example 31, Intermediate 2) (1 g, 2.46 mmol) in Toluene (10 mL) were added 4-(dimethoxymethyl)piperidine (0.58 g, 3.69 mmol) and NaO$^t$Bu (0.7 g, 7.39 mmol). The reaction mixture was degassed under argon for 15 min. Later Pd$_2$(dba)$_3$ (0.22 g, 0.246 mmol) and X-Phos (0.23 g, 0.49 mmol) were added, and the reaction mixture was again degassed for 10 min. It was then heated at 110° C. for 16 h. After the completion, the reaction mixture was cooled to room temperature and filtered through a celite pad. The filtrate was diluted with water (50 mL) and extracted with EtOAc (2×50 mL). The combined organic layers were dried over anhydrous Na$_2$SO$_4$, filtered and evaporated. The crude product was purified by column chromatography (40-45% EtOAc:petroleum ether) to afford (1R,3R)-2-(bicyclo[1.1.1]pentan-1-yl)-1-(4-(4-(dimethoxymethyl)piperidin-1-yl)phenyl)-3-methyl-2,3,4,9-tetrahydro-1H-pyrido[3,4-b]indole (0.7 g, 0.11 mmol, 58% yield). MS (ESI) m/z 486.66 [M+H]$^+$;

Step 2: To a solution of (1R,3R)-2-(bicyclo[1.1.1]pentan-1-yl)-1-(4-(4-(dimethoxymethyl)piperidin-1-yl)phenyl)-3-methyl-2,3,4,9-tetrahydro-1H-pyrido[3,4-b]indole (2) (1.6 g, 3.298 mmol) in THF (16 mL) was added 2N H$_2$SO$_4$ (66 ml, 40V) at 0° C. The reaction mixture was further stirred at RT for 1 h. After the completion of reaction, the reaction mixture was carefully quenched with 5 M NaOH (30 mL) and extracted with (10% MeOH:DCM) (2×50 mL). The combined organic layer was washed with brine (50 mL), dried over sodium sulfate, filtered and concentrated under reduced pressure to afford 1-(4-((1R,3R)-2-(bicyclo[1.1.1]pentan-1-yl)-3-methyl-2,3,4,9-tetrahydro-1H-pyrido[3,4-b]indol-1-yl)phenyl)piperidine-4-carbaldehyde (0.8 g, 55% yield) (3). The crude product was directly taken next step without purification.

Step 3: To a stirred solution of 1-(4-((1R,3R)-2-(bicyclo[1.1.1]pentan-1-yl)-3-methyl-2,3,4,9-tetrahydro-1H-pyrido[3,4-b]indol-1-yl)phenyl)piperidine-4-carbaldehyde (300 mg, 0.6829 mmol) in trifluoroethanol (3 mL) at 40° C. was added propan-1-amine (3) (403 mg, 6.8296 mmol). The reaction mixture was stirred at same temperature for 5 min followed by addition of NaBH$_4$ (129 mg, 3.4145 mmol) and was stirred for another 1 h. Reaction was monitored by TLC (10% MeOH:DCM). The reaction mixture was cooled to room temperature, filtered through celite, and the filtrate was concentrated. The residue was purified by RP-Prep HPLC to afford N-((1-(4-((1R,3R)-2-(bicyclo[1.1.1]pentan-1-yl)-3-methyl-2,3,4,9-tetrahydro-1H-pyrido[3,4-b]indol-1-yl)phenyl)piperidin-4-yl)methyl)propan-1-amine (Compound 93) (52.3 mg, 0.1078 mmol, Yield: 15%), with HPLC purity: 99.12%, LCMS purity: 99.21%, Chiral SFC: 99.38%. MS (ESI) m/z 481.63 [M−H]$^+$; $^1$H NMR (400 MHz, DMSO-d$_6$) δ 10.3 (s, 1H), 7.37-7.35 (d, J=7.6 Hz, 1H), 7.20-7.18 (d, J=7.6 Hz, 1H), 7.10-7.08 (d, J=8.8 Hz, 2H), 6.98-6.89 (m, 2H), 6.85-6.83 (d, J=8.8 Hz, 2H), 4.85 (s, 1H), 3.62 (d, J=12.4 Hz, 2H), 3.49-3.45 (m, 1H), 2.95-2.90 (dd, J=4.4 Hz, J=14.8 Hz, 1H), 2.58 (t, J=14.8 Hz, 3H), 2.47-2.39 (m, 4H), 2.21 (s, 1H), 1.74 (t, J=10 Hz, 5H), 1.58 (d, J=9.2 Hz, 4H), 1.43 (q, J=7.6 Hz, J=14.8 Hz, 2H), 1.18 (d, J=2.8 Hz, 2H), 1.10 (d, J=6.8 Hz, 3H), 0.83-0.87 (t, J=7.2 Hz, 3H), Example 94

6-((1S,3R)-2-(bicyclo[1.1.1]pentan-1-yl)-3-methyl-2,3,4,9-tetrahydro-1H-pyrido[3,4-b]indol-1-yl)-N-(1-(3-fluoropropyl)azetidin-3-yl)-5-methoxypyridin-3-amine (Compound 94)

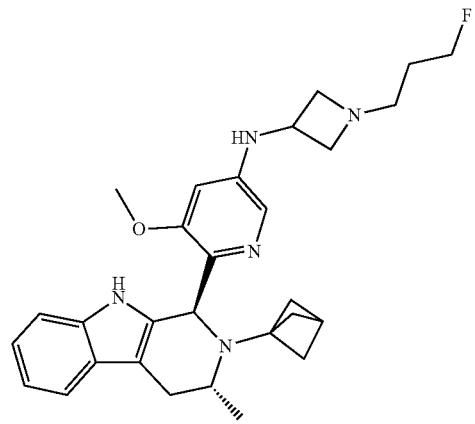 [SMILES: COc1cc(NC2CN(CCCF)C2)cnc1[C@@H]1c2[nH]c3ccccc3c2C[C@@H](C)N1C12CC(C1)C2]

Compound 94 was prepared following a procedure analogous to that described for Example 49 (47.4 mg, 0.0969 mmol, 14.23%) with HPLC purity: 97.60%, LCMS: 97.99%, and Chiral SFC: 97.99%. MS (ESI) m/z 488.40 [M−H]$^+$; $^1$H NMR (400 MHz, DMSO-d$_6$) δ 10.34 (s, 1H), 7.34 (d, J=7.2 Hz, 1H), 7.23 (d, J=2 Hz, 1H), 7.13 (d J=7.6 Hz, 1H), 6.97-6.87 (m, 2H), 6.53 (d, J=2 Hz, 1H), 6.21 (d, J=7.2 Hz, 1H), 6.51 (d, J=2.0 Hz, 1H), 5.41 (s, 1H), 3.59 (s, 1H), 4.50-4.37 (dt, J$_1$=47.2 Hz, J$_2$=6.0 Hz, 1H), 3.99 (t, J=6.8 Hz, 1H), 3.80 (d, J=7.6 Hz, 3H), 3.66 (t, J=6.8 Hz, 2H), 2.79-2.72 (m, 4H), 2.58-2.47 (m, 2H), 2.20 (s, 1H), 1.79-1.60 (m, 8H) 1.15 (d, J=7.2 Hz, 3H),

Example 95

(3R,4R)-4-(4-((1R,3R)-2-(bicyclo[1.1.1]pentan-1-yl)-3-methyl-2,3,4,9-tetrahydro-1H-pyrido[3,4-b]indol-1-yl)phenoxy)-1-(3-fluoropropyl)pyrrolidin-3-ol (Compound 95)

Example 96

(3S,4S)-4-(4-((1R,3R)-2-(bicyclo[1.1.1]pentan-1-yl)-3-methyl-2,3,4,9-tetrahydro-1H-pyrido[3,4-b]indol-1-yl)phenoxy)-1-(3-fluoropropyl)pyrrolidin-3-ol (Compound 96)

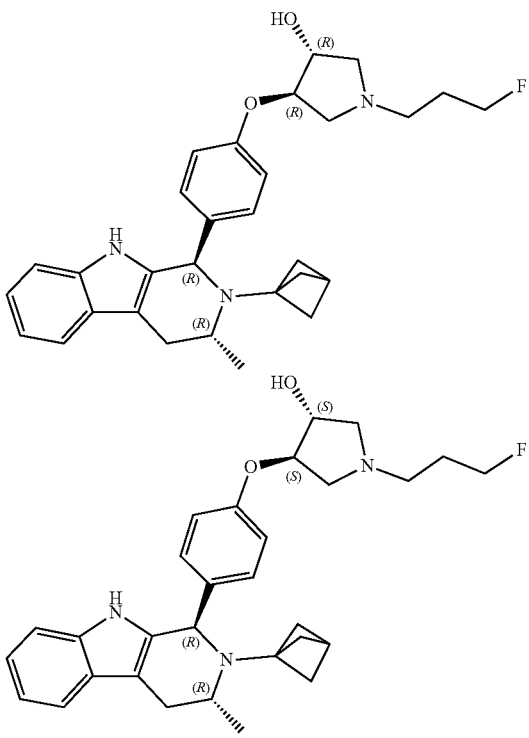

Compounds 95 and 96 were prepared following a procedure analogous to that described for Examples 32 and 33 above. Compound 95: MS (LCMS) m/z 490.3 [M+H]$_+$ $^1$H NMR (400 MHz, DMSO-d$_6$)) δ 10.32 (s, 1H), 7.37 (d, J=7.6 Hz, 1H), 7.19 (dd, J$_1$=7.6 Hz, J$_2$=2.4 Hz, 3H), 6.99-6.89 (m, 2H), 6.86 (d, J=8.8 Hz, 2H), 5.31 (brs, 1H), 4.89 (s, 1H), 4.54-4.39 (m, 3H), 3.49 (q, 1H), 4.07 (s, 1H), 2.94-2.88 (m, 3H), 2.61-2.50 (m, 2H), 2.50-2.44 (m, 2H), 2.30 (t, J=5.2 Hz, 1H), 2.20 (s, 1H), 1.80-1.72 (m, 5H), 1.59-1.52 (m, 3H),) 1.11 (d, J=6.4 Hz, 3H). 99.48% of LCMS purity (chiral HPLC: 99.92%). Compound 96: MS (LCMS) m/z 490.30 [M+H]$_+$ $^1$H NMR (400 MHz, DMSO-d$_6$) δ 10.35 (s, 1H), 7.37 (d, J=7.6 Hz, 1H), 7.20 (m, 3H), 7.01-6.92 (m, 2H), 6.86 (d, J=8.8 Hz, 2H), 5.30 (brs, 1H), 4.89 (s, 1H), 4.53-4.39 (dt, J$_1$=47.2 Hz, J$_2$=6 Hz, 2H), 4.47-4.49 (m, 1H), 4.10 (s, 1H), 3.46 (s, 1H), 2.96-2.88 (m, 3H), 2.61-2.52 (m, 2H), 2.52-2.45 (m, 2H), 2.31 (q, J$_1$=9.6 Hz, J$_2$=5.2 Hz 1H), 2.21 (s, 1H), 1.80-1.72 (m, 5H), 1.57 (d, J=9.2 Hz, 3H), 1.10 (d, J=6.8 Hz, 3H). 99.69% of LCMS purity (chiral HPLC: 99.69%). The absolute stereochemistry was arbitrarily assigned for Compound 95 and Compound 96.

Example A

Breast Cancer Cell Proliferation Assay (MCF-7)

MCF7 was expanded and maintained in the medium (Phenol red free DMEM/F12 (Hyclone SH30272.01) NEAA (Gibco11140-050) Na-pyruvate (Gibco 11360-070) and Re-stripped Charcoal stripped FBS (Gemini 100-119)). The cells were adjusted to a concentration of 3,000 cells per mL in the above media, and the cells were incubated (37° C., 5% CO$_2$). The following day a 10-point, serial dilution of compounds was added to the cells at a final concentration ranging from 10-0.000005 μM for test compounds (17β-estradiol was used as a control). Additional cells were plated in 30 wells to serve as the day 1 (pretreatment) comparison. After 5 days of compound exposure, Cell Titer-Glo reagent was added to the cells and the relative luminescence units (RLUs) of each well was determined. Cell Titer-Glo was also added to 32 μL of medium without cells to obtain a background value. The plates were allowed to incubate at room temperature for 10 minutes to stabilize luminescent signal and the luminescence signal was recorded with EnSpire. The relative increase in cell number of each sample is determined as follows: (RLU sample-RLU background/RLU estrogen only treated cells-RLU background)×100=% inhibition. Results are summarized in Table 2.

Example B

ER Degradation Determination by Western Blot

MCF-7 cells were plated at 0.3 million cells/mL (3 mL/well) in 6-well plates in experiment media and incubated at 37° C., 5% CO2 for 48 hours. Next day, 10× solution of compounds were made in DMSO and added the solution to the cells to achieve a final concentration of 10 μM. A DMSO control was included to enable a determination of the relative efficacy of test compounds. Fulvestrant was used as a positive control for ER-alpha degradation, and 4-OH tamoxifen as a control for receptor stabilization. After incubating cells with compounds for 18-24 hours, cell lysates were prepared (2× Cell lysis buffer:100 mM Tris, pH 8, 300 mM NaCl, 2% NP40, 1% Na deoxycholate, 0.04% SDS, 2 mM EDTA) and mixed thoroughly and incubated on ice. The protein concentration was quantified using BCA kit. Protein was separated on 4%-20% NuPAGE Novex 4-12% Bis-Tris Protein Gels using 1×MES running buffer. The gel was then transferred onto a nitrocellulose membrane. The blots were probed with antibodies against ESR1 protein (Santa Cruz, sc-8005). GAPDH protein was used as an internal control. Results are summarized in Table 2.

TABLE 2

| Compound | MCF7 IC$_{50}$ (nM) | ERα % degradation |
|---|---|---|
| fulvestrant | A | A |
| AZD9833 | A | A |
| GDC9545 | A | A |
| 1 | A | A |
| 2 | A | A |
| 3 | A | ND |
| 4 | B | ND |
| 5 | B | ND |
| 6 | A | A |
| 7 | B | ND |
| 8 | A | ND |
| 9 | B | ND |

TABLE 2-continued

| Compound | MCF7 IC$_{50}$ (nM) | ERα % degradation |
|---|---|---|
| 10 | A | A |
| 11 | C | ND |
| 12 | B | ND |
| 13 | A | ND |
| 14 | A | ND |
| 15 | A | A |
| 16 | A | A |
| 17 | C | ND |
| 18 | A | A |
| 19 | A | A |
| 20 | A | A |
| 21 | D | ND |
| 22 | B | ND |
| 23 | A | A |
| 24 | A | ND |
| 25 | A | ND |
| 26 | C | ND |
| 28 | C | ND |
| 29 | C | ND |
| 30 | C | A |
| 31 | A | A |
| 32 | C | ND |
| 33 | C | ND |
| 34 | B | ND |
| 35 | A | ND |
| 36 | C | ND |
| 37 | A | ND |
| 38 | A | A |
| 39 | A | A |
| 40 | A | A |
| 41 | C | ND |
| 42 | A | A |
| 43 | B | ND |
| 44 | C | ND |
| 46 | C | ND |
| 47 | A | ND |
| 48 | A | ND |
| 49 | C | ND |
| 50 | A | A |
| 51 | B | ND |
| 52 | A | A |
| 53 | B | ND |
| 54 | A | ND |
| 55 | C | ND |
| 56 | A | ND |
| 57 | B | ND |
| 58 | A | A |
| 59 | B | ND |
| 60 | C | ND |
| 61 | C | ND |
| 62 | C | ND |
| 63 | A | ND |
| 64 | A | ND |
| 65 | A | ND |
| 70 | A | A |
| 71 | A | ND |
| 72 | A | A |
| 73 | A | ND |
| 75 | A | A |
| 76 | B | ND |
| 77 | C | ND |
| 78 | A | ND |
| 79 | B | ND |
| 80 | A | ND |
| 91 | A | ND |
| 92 | A | ND |
| 83 | A | ND |
| 84 | A | ND |
| 85 | A | ND |
| 86 | B | ND |
| 87 | A | ND |
| 88 | B | ND |
| 89 | B | ND |
| 90 | C | ND |
| 91 | C | ND |
| 92 | A | ND |
| 93 | A | ND |
| 94 | C | ND |

IC$_{50}$: A = a single IC$_{50}$ ≤25 nM; B = a single IC$_{50}$ ≥25 nM and ≤250 nM; C = a single IC$_{50}$ ≥250 nM.
ND: Not determined.

Example C

Pharmacokinetic Determination

Grouping female CD-1 mice weighing 20-30 g randomly to three groups; one group was administered with test compound at a dose of 3.0 mg/kg by intravenous injection, the other two groups were administered with test compound at a dose of 10.0 mg/kg by oral. The formulation for IV groups is DMSO/PEG400/30% HP-β-CD (5/20/75) and the formulation for PO groups is 25% HP-β-CD in 25 mM citrate buffer (pH3.0). After administering, blood samples of intravenous injection group were collected at time points of predose, 0.0833, 0.25, 0.5, 1, 2, 4, 8, 12 and 24 h; blood samples of oral group were collected at time points of predose, 0.25, 0.5, 1, 2, 4, 8, 12, and 24 h. Both blood samples and brain samples were collected at 2 hours post dosing for the second PO group. Standard curve was plotted based on concentrations of the samples in a suitable range, the concentrations of test compounds in plasma samples and brain samples were determined by using LC-MS/MS. Pharmacokinetic parameters were calculated according to drug concentration-time curve using a noncompartmental method by WinNonLin (Phoenix™, version 6.1) or other similar software. Results are summarized in Table 3.

TABLE 3

Mouse PK

| Compound | Dose method | AUC$_{last}$ (μM*h) | Cl (ml·min$^{-1}$·kg$^{-1}$) | V$_{dss}$ (L/Kg) | C$_{max}$ (μM) | T$_{max}$ (h) | T$_{1/2}$ (h) | F(%) | B/P ratio |
|---|---|---|---|---|---|---|---|---|---|
| AZD9833 | IV | ND | ND | ND | ND | ND | ND | ND | ND |
|  | PO | 4.19 | ND | ND | 0.649 | 2 | 2.34 | ND | 0.23 |
| GDC9545 | IV | ND | ND | ND | ND | ND | ND | ND | ND |
|  | PO | 13.3 | ND | ND | 0.96 | 4 | 8.66 | ND | 0.17 |
| 1 | IV | 2.79 | 24.2 | 31.9 | ND | ND | 18 | ND | ND |
|  | PO | 4.88 | ND | ND | 0.466 | 2 | 10.5 | 52.4 | 11.0 |
| 2 | IV | 1.74 | 55.8 | 31.9 | ND | ND | 8.78 | ND | ND |
|  | PO | 2.51 | ND | ND | 0.358 | 1 | 7.23 | 43.3 | 2.87 |
| 5 | IV | 2.93 | 30.2 | 16.7 | ND | ND | 9.10 | ND | ND |
|  | PO | 4.84 | ND | ND | 0.61 | 1 | 9.40 | 49.5 | 7.07 |

TABLE 3-continued

| | | Mouse PK | | | | | | | |
|---|---|---|---|---|---|---|---|---|---|
| Compound | Dose method | $AUC_{last}$ (μM*h) | Cl (ml · min$^{-1}$ · kg$^{-1}$) | $V_{dss}$ (L/Kg) | $C_{max}$ (μM) | $T_{max}$ (h) | $T_{1/2}$ (h) | F(%) | B/P ratio |
| 6 | IV | 2.93 | 30.2 | 16.7 | ND | ND | 9.1 | ND | ND |
|   | PO | 4.84 | ND | ND | 0.611 | 1 | 9.4 | 49.5 | 4.42 |
| 10 | IV | 1.03 | 101 | 12.8 | ND | ND | 2.19 | ND | ND |
|   | PO | 0.527 | ND | ND | 0.178 | 0.5 | 2.12 | 15.3 | 7.51 |
| 15 | IV | 0.892 | 100.4 | 66.4 | ND | ND | 10 | ND | ND |
|   | PO | 1.45 | ND | ND | 0.2 | 1 | 9.2 | 47.3 | 10.8 |
| 16 | IV | 2.08 | 53.5 | 11.8 | ND | ND | 3.85 | ND | ND |
|   | PO | 2.73 | ND | ND | 0.59 | 1 | 3.24 | 39.5 | ND |
| 19 | IV | 2.15 | 47.6 | 23.2 | ND | ND | 6.58 | ND | ND |
|   | PO | 5.00 | ND | ND | 0.44 | 1 | 8.50 | 69.8 | 12.3 |
| 21 | IV | 0.59 | ND | ND | ND | ND | ND | ND | ND |
|   | PO | 0.10 | ND | ND | 0.06 | 0.25 | 1.01 | 5.03 | ND |
| 31 | IV | 1.03 | ND | ND | ND | ND | ND | ND | ND |
|   | PO | 3.00 | ND | ND | 0.24 | 2 | ND | 87.7 | 12 |
| 39 | IV | 1.33 | 85 | 16 | ND | ND | 5.13 | ND | ND |
|   | PO | 1.31 | ND | ND | 0.224 | 0.5 | 3.95 | 29.6 | 11.4 |
| 40 | IV | 1.47 | 64.2 | 49.6 | ND | ND | 11.5 | ND | ND |
|   | PO | 3.46 | ND | ND | 0.261 | 1 | ND | 70.5 | 13.5 |
| 42 | IV | 1.51 | 40.0 | ND | ND | ND | ND | ND | ND |
|   | PO | 2.79 | ND | ND | 0.22 | 1 | ND | 55.4 | 29.4 |
| 58 | IV | 1.04 | 92.0 | 42.3 | ND | ND | 7.08 | ND | ND |
|   | PO | 1.10 | ND | ND | 0.08 | 2 | 5.56 | 31.8 | ND |
| 70 | IV | 2.46 | 36.1 | 12.2 | ND | ND | 6.51 | ND | ND |
|   | PO | 2.09 | ND | ND | 0.21 | 2 | 5.25 | 21.4 | ND |
| 72 | IV | 2.17 | ND | ND | ND | ND | ND | ND | ND |
|   | PO | 3.73 | ND | ND | 0.24 | 4 | ND | 51.5 | 8.82 |
| 75 | IV | 1.49 | 66.1 | 17.9 | ND | ND | 7.29 | ND | ND |
|   | PO | 2.94 | ND | ND | 0.84 | 0.5 | 7.38 | 59.2 | 6.84 |

ND: Not determined
B/P ratio: Brain concentration vs plasma concentration at 2 hours post dosing Example D Efficacy Study on MCF-7 Human Breast Cancer Orthotopic Model The MCF-7 tumor cell line were maintained in vitro as monolayer culture in DMEM Medium supplemented with 15% heat inactivated fetal bovine serum at 37° C. in an atmosphere of 5% $CO_2$ in air. The medium were renewed every 2 to 3 days and tumor cells were routinely subcultured at a confluence of 80%-90% by trypsin-EDTA, not to exceed 4-5 passages. The cells growing in an exponential growth phase were harvested and counted for tumor inoculation.

Each mouse was inoculated subcutaneously on the 2$^{nd}$ right mammary fat pad with the single cell suspension of 95% viable tumor cells ($1.5 \times 10^7$) in 200 μL DMEM Matrigel mixture (1:1 ratio) without serum for the tumor development. The treatments were started when mean tumor size reached 195 mm$^3$.

The measurement of tumor size was conducted twice a week with a caliper and the tumor volume (mm$^3$) was estimated using the formula: $TV = a \times b^2/2$ throughout the study, where "a" and "b" was long and short diameters of a tumor, respectively. The TVs were used for calculation of the tumor growth inhibition (TGI, an indicator of antitumor effectiveness) value using the formula: $(1-(T_d-T_0)/(C_d-C_0)) \times 100\%$. $T_d$ and $C_d$ are the mean tumor volumes of the treated and control animals, and $T_0$ and $C_0$ are the mean tumor volumes of the treated and control animals at the start of the experiment. The tumor regression was defined as individual tumor volume decrease (terminal TV compares to initial TV). The percent tumor regression was calculated using the formula: $(1-(T_d/T_0)) \times 100\%$.

Plasma samples were collected with seven time points (0.25 h, 0.5 h, 1 h, 2 h, 4 h, 8 h, and 24 h) post final dosing for PK analysis. Tumor samples were collected with three time points (2 h, 8 h and 24 h) post final dosing for PK analysis.

Tumor growth inhibition and PK data are summarized in Table 4.

TABLE 4

| | In vivo efficacy | | | |
|---|---|---|---|---|
| Compound | Plasma AUC (h * ng/mL) | Tumor AUC (h * ng/mL) | Tumor/Plasma ratio | TGI |
| GDC9545 | 10530 | 183743 | 17.5 | 130 |
| 31 | 6783 | 360399 | 53.1 | 106 |
| 42 | 5306 | 296719 | 55.9 | 106 |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

What is claimed is:
1. A method of treatment, comprising
   identifying a subject that is in need of treatment for a disease or condition that is estrogen receptor alpha dependent and/or estrogen receptor alpha mediated; and administering to said subject an effective amount of a compound of Formula (I), or a pharmaceutically acceptable salt thereof, having the structure:

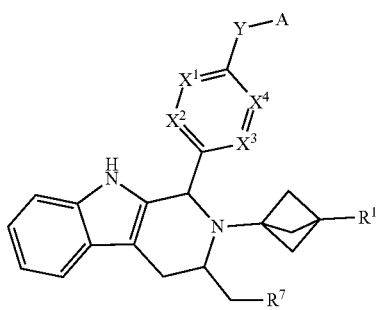

wherein:
each $X^1$, $X^2$, $X^3$ and $X^4$ is independently N or $CR^2$;
Y is a bond, alkenyl, —O($CR^3R^4$)$_m$—, or —NH($CR^5R^6$)$_n$—;
$R^1$ is selected from H, F, OH, CN, alkyl, haloalkyl, alkoxy, amide, or hydroxyalkyl;
each $R^2$, $R^3$, $R^4$, $R^5$ and $R^6$ is independently H, halogen, alkoxy, or alkyl;
$R^7$ is H or halogen;
m and n are each 0, 1 or 2; and
A is a heterocyclyl optionally substituted with 1 or more substituents selected from halogen, CN, OH, alkyl, alkenyl, alkynyl, cycloalkyl, haloalkyl, haloalkylamino, haloalkoxy, hydroxyalkyl, or cyanoalkyl;
wherein the disease or condition is selected from the group consisting of breast cancer, gynecological cancer, endometrial cancer, ovarian cancer, and cervical cancer.

2. The method of claim 1, wherein the disease or condition is breast cancer.

3. The method of claim 2, wherein the breast cancer is a metastatic breast cancer.

4. The method of claim 3, wherein the metastatic breast cancer is a breast cancer that has metastasized to at least one organ selected from brain, liver, bone and lung.

5. The method of claim 4, wherein the metastatic breast cancer is a breast cancer that has metastasized to brain.

6. The method of claim 1, wherein said administering to said subject comprises an intravenous administration.

7. The method of claim 1, wherein said administering to said subject comprises an oral administration.

8. The method of claim 1, wherein said administering to said subject comprises an intramuscular administration.

9. The method of claim 1, wherein said administering to said subject comprises a subcutaneous administration.

10. The method of claim 1, wherein said administering to said subject comprises a topical administration.

11. The method of claim 1, wherein $X^1$, $X^2$, $X^3$ and $X^4$ are each $CR^2$.

12. The method of claim 1, wherein $R^1$ is H or $C_{1-6}$haloalkyl.

13. The method of claim 1, wherein $R^2$ is H, F, Cl or Br.

14. The method of claim 1, wherein Y is —O($CR^3R^4$)$_m$—.

15. The method of claim 1, wherein Y is —NH($CR^5R^6$)$_n$—.

16. The method of claim 1, wherein A is 3-6 membered N-containing heterocyclyl that is substituted with F, CN, $C_{1-3}$ alkyl, $C_{3-6}$ cycloalkyl, $C_{1-3}$ fluoroalkyl, $C_{1-3}$ fluoroalkylamino, $C_{1-3}$ fluoroalkoxy, $C_{1-3}$ hydroxyalkyl, or $C_{1-3}$ cyanoalkyl.

17. The method of claim 1, wherein the compound of Formula (I) has a structure selected from Compound Structure Nos. 1-96 as set forth in the following table:

| No. | Compound Structure |
| --- | --- |
| 1 | 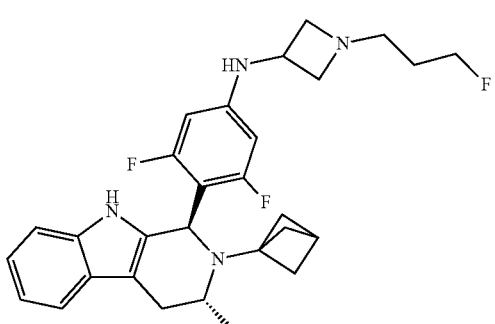 |
| 2 | 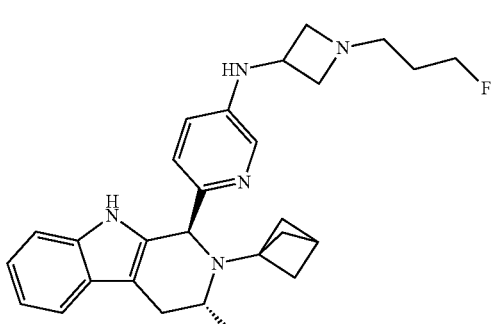 |
| 3 | 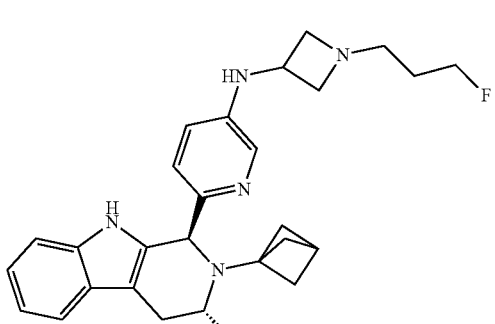 |
| 4 | 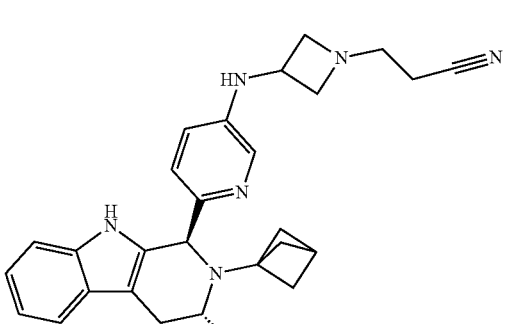 |

| No. | Compound Structure |
|---|---|
| 5 | 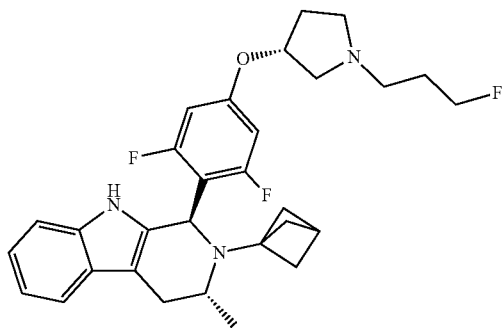 [SMILES: C[C@@H]1Cc2c([nH]c3ccccc23)[C@@H](c2c(F)cc(O[C@@H]3CCN(CCCF)C3)cc2F)N1C12CC(C1)C2] |
| 6 | 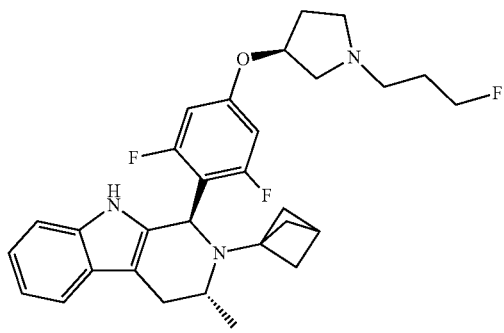 [SMILES: C[C@@H]1Cc2c([nH]c3ccccc23)[C@@H](c2c(F)cc(O[C@H]3CCN(CCCF)C3)cc2F)N1C12CC(C1)C2] |
| 7 | 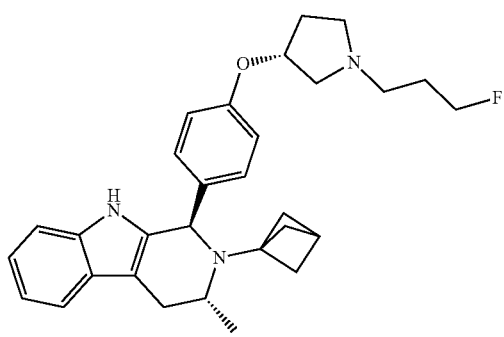 [SMILES: C[C@@H]1Cc2c([nH]c3ccccc23)[C@@H](c2ccc(O[C@@H]3CCN(CCCF)C3)cc2)N1C12CC(C1)C2] |
| 8 | 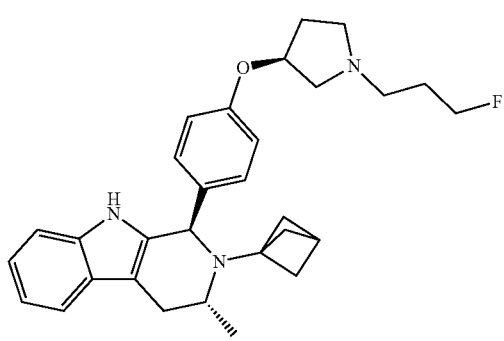 [SMILES: C[C@@H]1Cc2c([nH]c3ccccc23)[C@@H](c2ccc(O[C@H]3CCN(CCCF)C3)cc2)N1C12CC(C1)C2] |
| No. | Compound Structure |
|---|---|
| 9 | 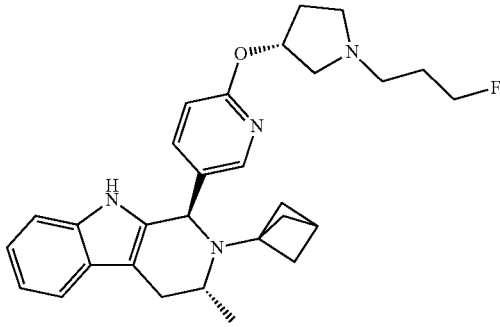 [SMILES: C[C@@H]1Cc2c([nH]c3ccccc23)[C@@H](c2ccc(O[C@@H]3CCN(CCCF)C3)nc2)N1C12CC(C1)C2] |
| 10 | 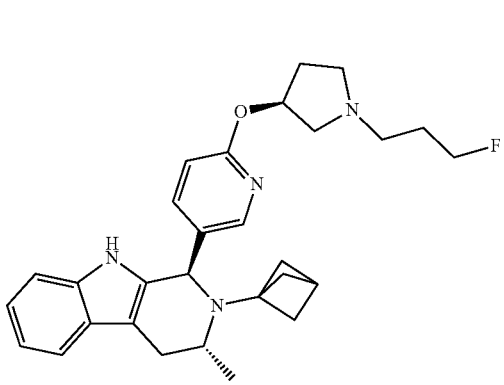 [SMILES: C[C@@H]1Cc2c([nH]c3ccccc23)[C@@H](c2ccc(O[C@H]3CCN(CCCF)C3)nc2)N1C12CC(C1)C2] |
| 11 | 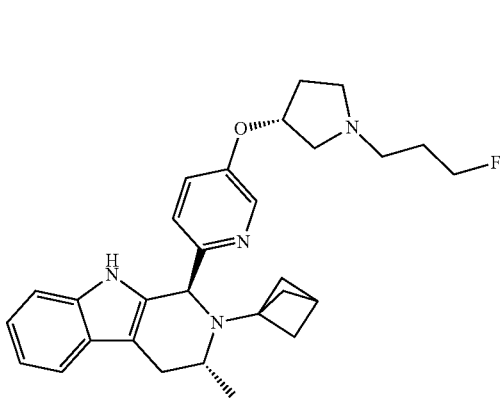 [SMILES: C[C@@H]1Cc2c([nH]c3ccccc23)[C@@H](c2ccc(O[C@@H]3CCN(CCCF)C3)cn2)N1C12CC(C1)C2] |
| 12 | 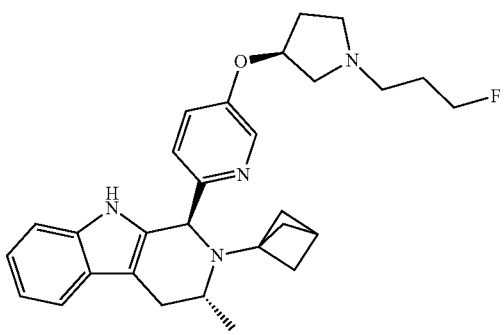 [SMILES: C[C@@H]1Cc2c([nH]c3ccccc23)[C@@H](c2ccc(O[C@H]3CCN(CCCF)C3)cn2)N1C12CC(C1)C2] |

-continued
| No. | Compound Structure |
|---|---|
| 13 | 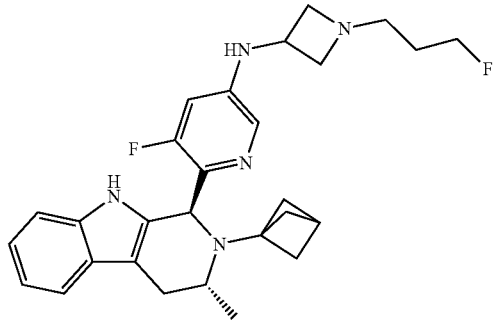 [SMILES: C[C@@H]1Cc2c([nH]c3ccccc23)[C@@H](c2ncc(NC3CN(CCCF)C3)cc2F)N1C12CC(C1)C2] |
| 14 | 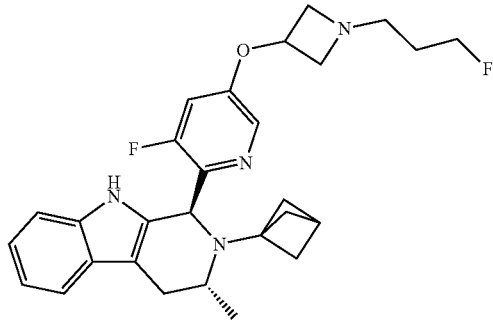 [SMILES: C[C@@H]1Cc2c([nH]c3ccccc23)[C@@H](c2ncc(OC3CN(CCCF)C3)cc2F)N1C12CC(C1)C2] |
| 15 | 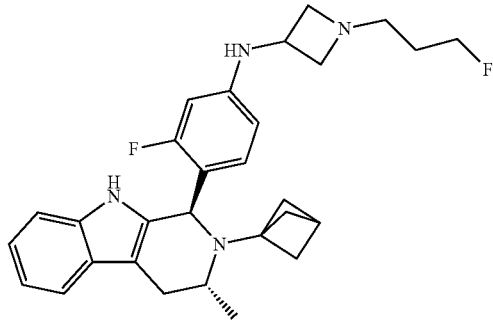 [SMILES: C[C@@H]1Cc2c([nH]c3ccccc23)[C@@H](c2ccc(NC3CN(CCCF)C3)cc2F)N1C12CC(C1)C2] |
| 16 | 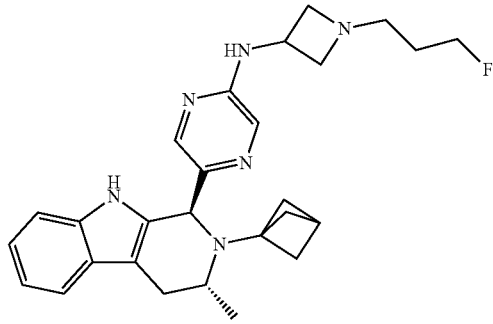 |
-continued
| No. | Compound Structure |
|---|---|
| 17 | 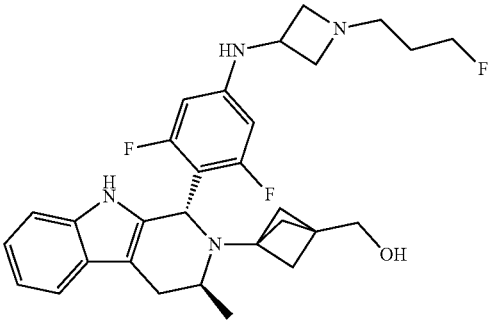 [SMILES: C[C@H]1Cc2c([nH]c3ccccc23)[C@H](c2c(F)cc(NC3CN(CCCF)C3)cc2F)N1C12CC(CO)(C1)C2] |
| 18 | 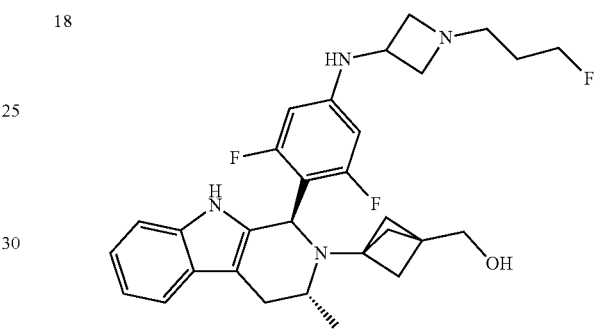 |
| 19 | 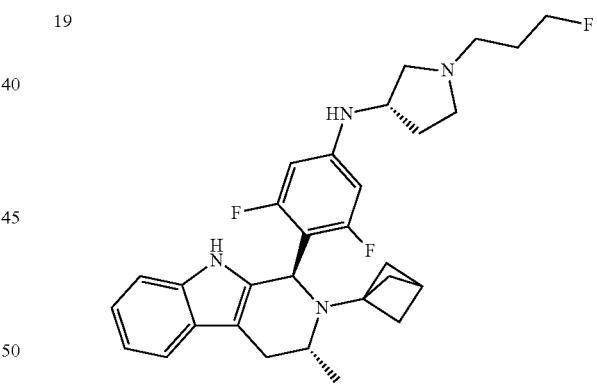 |
| 20 | 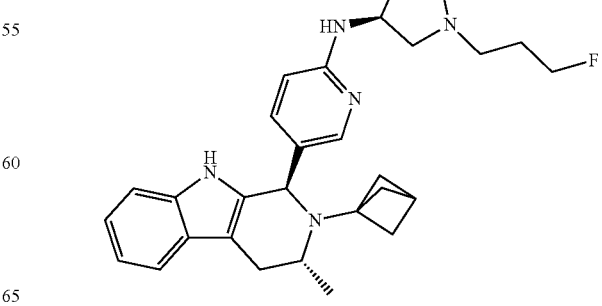 |

| No. | Compound Structure |
|---|---|
| 21 | 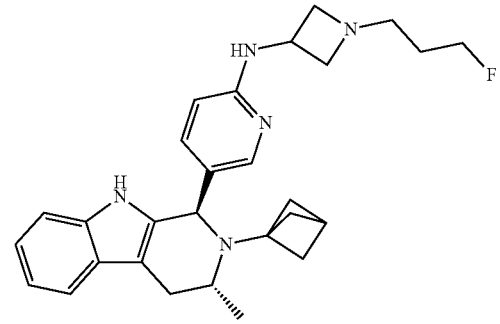 [SMILES: C[C@@H]1Cc2c([nH]c3ccccc23)[C@@H](c2ccc(NC3CN(CCCF)C3)nc2)N1C12CC(C1)C2] |
| 22 | 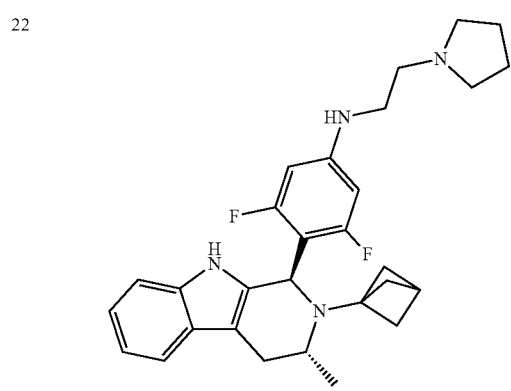 |
| 23 | 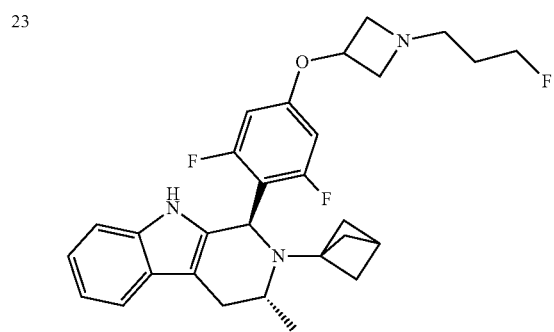 |
| 24 | 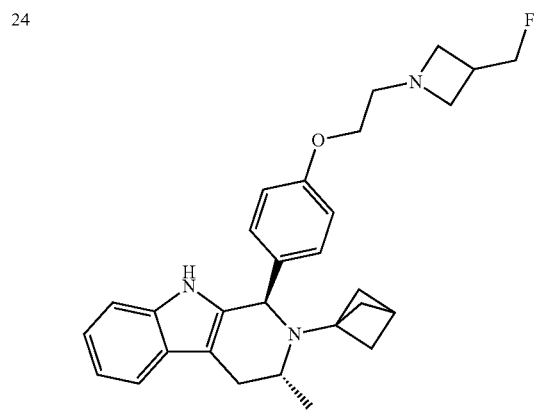 |
| No. | Compound Structure |
|---|---|
| 25 | 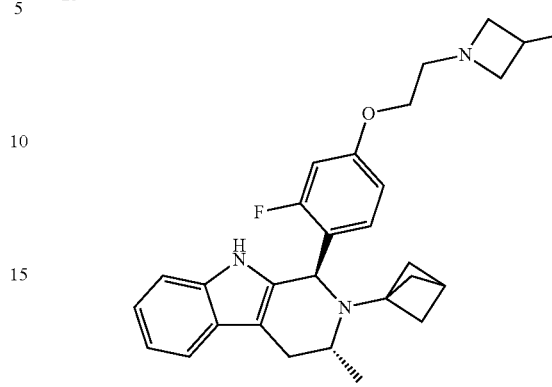 |
| 26 | 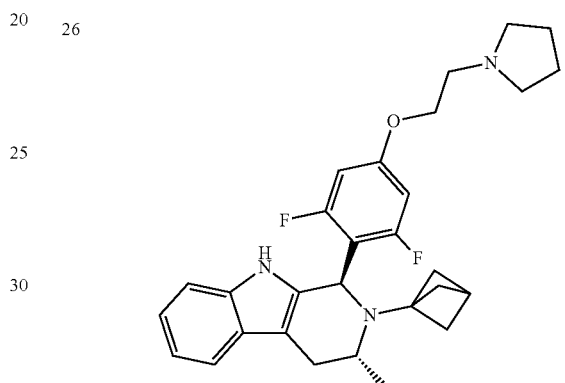 |
| 27 | 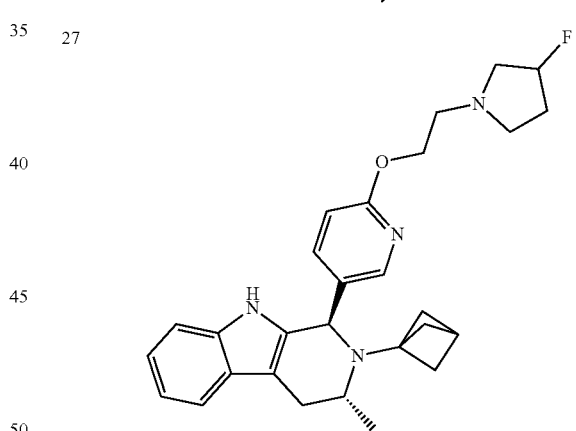 |
| 28 | 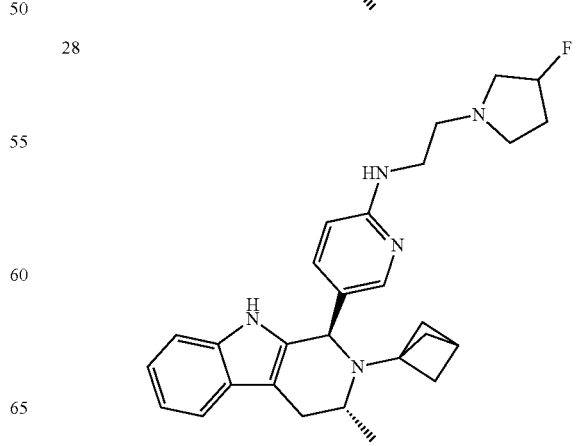 |

| No. | Compound Structure |
|---|---|
| 29 | 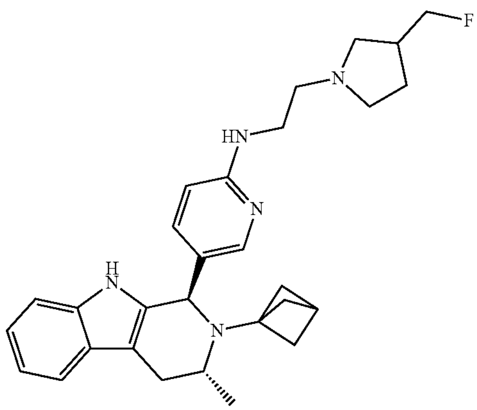 [SMILES: C[C@@H]1Cc2c([nH]c3ccccc23)[C@@H](c2ccc(NCCN3CCC(CF)C3)nc2)N1C12CC(C1)C2] |
| 30 | 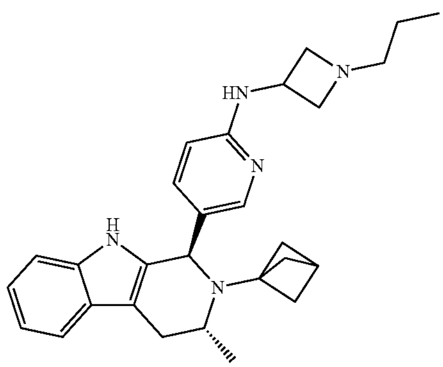 [SMILES: CCCN1CC(Nc2ccc([C@@H]3c4[nH]c5ccccc5c4C[C@@H](C)N3C34CC(C3)C4)cn2)C1] |
| 31 | 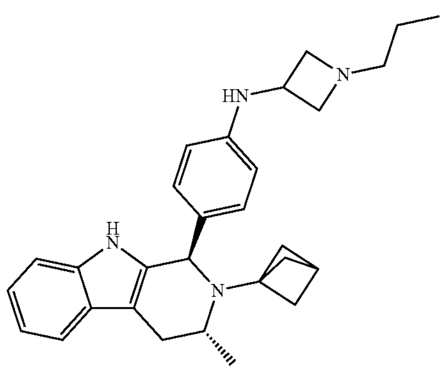 |
| 32 | 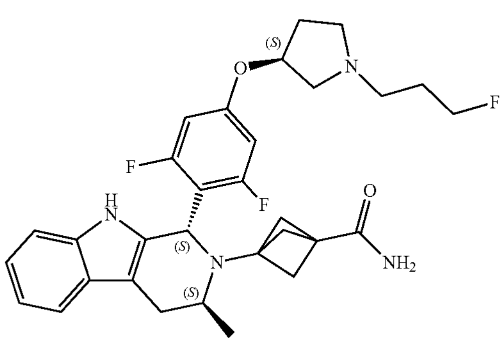 |

| No. | Compound Structure |
|---|---|
| 33 | 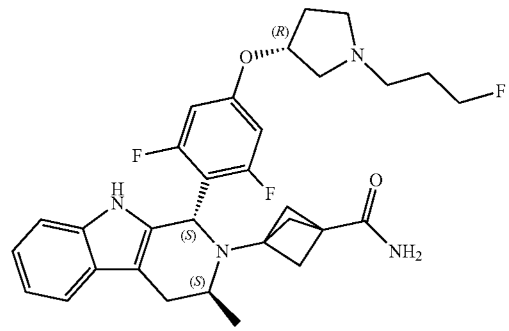 |
| 34 | 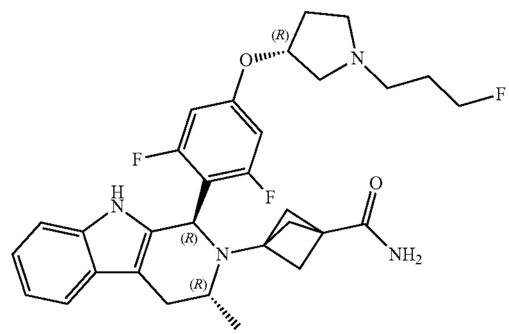 |
| 35 | 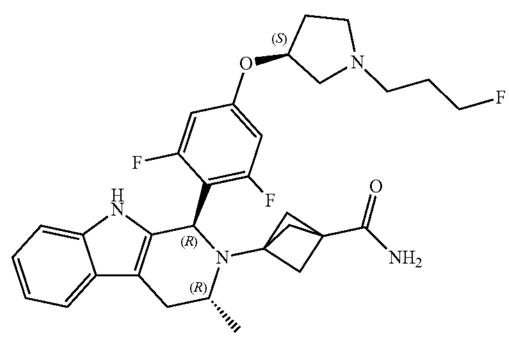 |
| 36 | 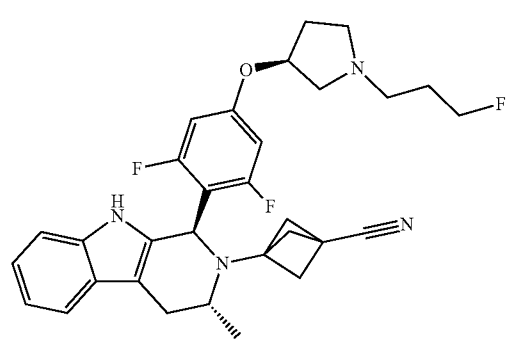 [SMILES: C[C@@H]1Cc2c([nH]c3ccccc23)[C@@H](c2c(F)cc(O[C@H]3CCN(CCCF)C3)cc2F)N1C12CC(C#N)(C1)C2] |

| No. | Compound Structure |
|---|---|
| 37 | 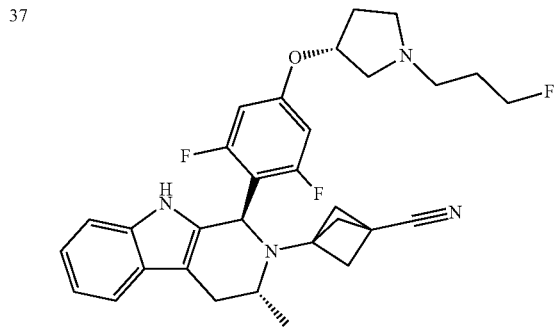 |
| 38 | 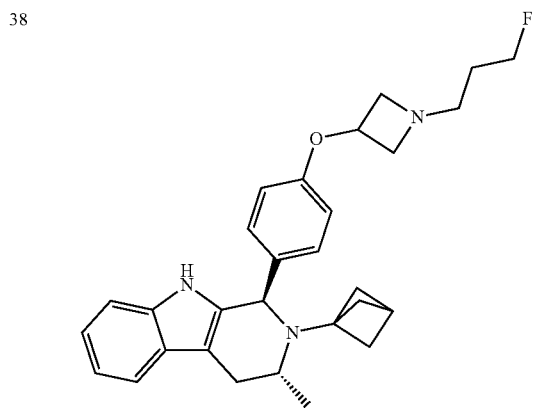 |
| 39 | 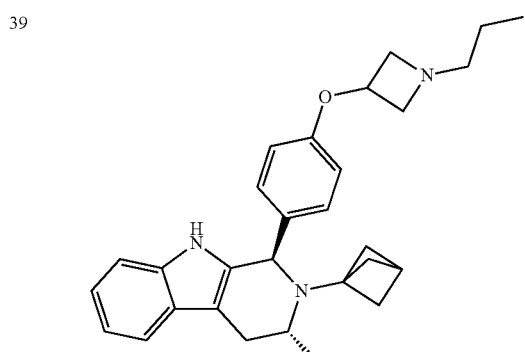 |
| 40 | 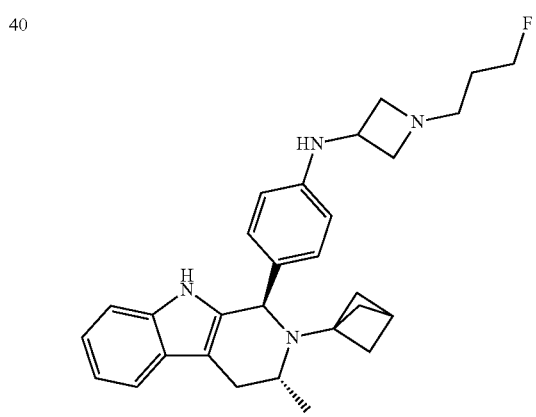 |
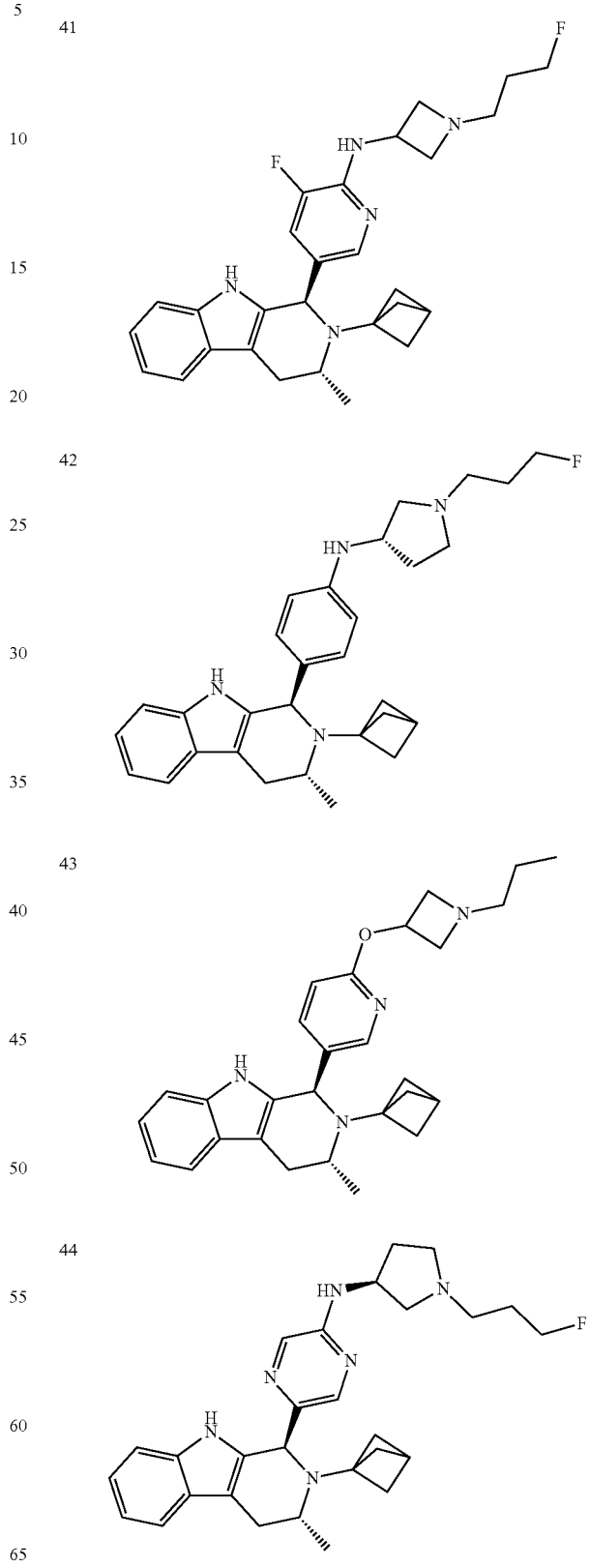

-continued
| No. | Compound Structure |
|---|---|
| 45 | 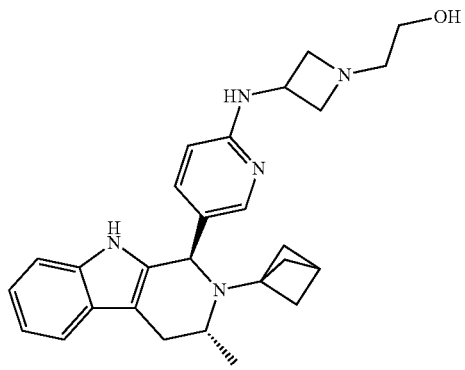 [SMILES: C[C@@H]1Cc2c([nH]c3ccccc23)[C@@H](c2ccc(NC3CN(CCO)C3)nc2)N1C12CC(C1)C2] |
| 46 | 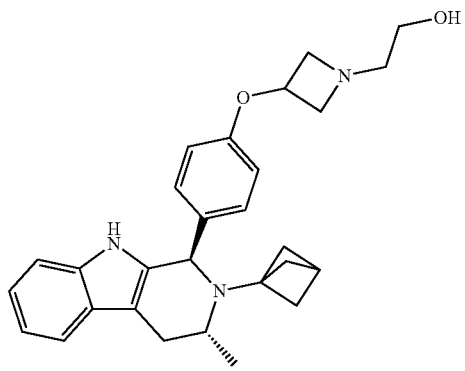 [SMILES: C[C@@H]1Cc2c([nH]c3ccccc23)[C@@H](c2ccc(OC3CN(CCO)C3)cc2)N1C12CC(C1)C2] |
| 47 | 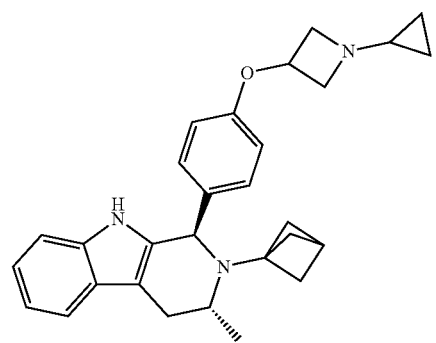 [SMILES: C[C@@H]1Cc2c([nH]c3ccccc23)[C@@H](c2ccc(OC3CN(C4CC4)C3)cc2)N1C12CC(C1)C2] |
| 48 | 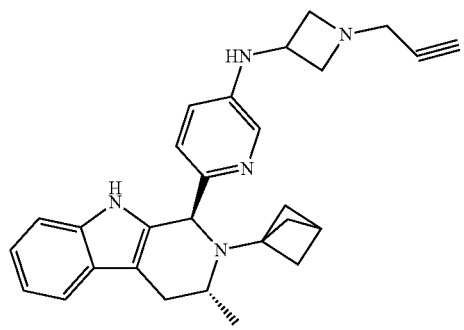 [SMILES: C#CCN1CC(Nc2ccc([C@@H]3c4[nH]c5ccccc5c4C[C@@H](C)N3C34CC(C3)C4)nc2)C1] |
-continued
| No. | Compound Structure |
|---|---|
| 49 | 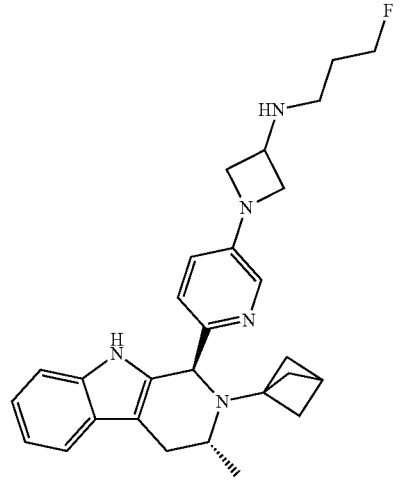 [SMILES: C[C@@H]1Cc2c([nH]c3ccccc23)[C@@H](c2ccc(N3CC(NCCCF)C3)cn2)N1C12CC(C1)C2] |
| 50 | 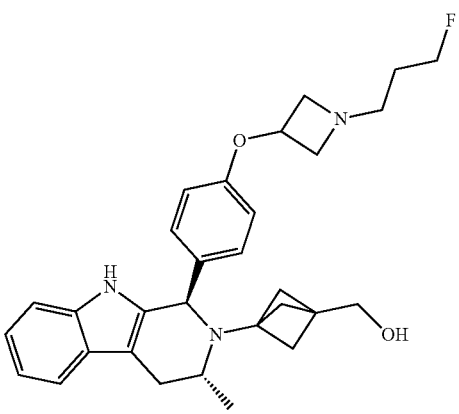 [SMILES: C[C@@H]1Cc2c([nH]c3ccccc23)[C@@H](c2ccc(OC3CN(CCCF)C3)cc2)N1C12CC(CO)(C1)C2] |
| 51 | 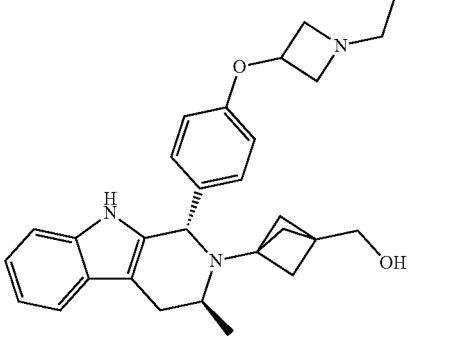 |

| No. | Compound Structure |
|---|---|
| 52 | 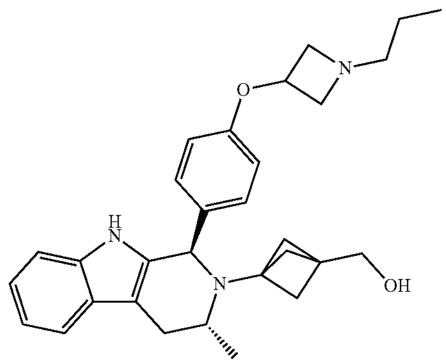 [SMILES: CCCN1CC(Oc2ccc([C@@H]3c4[nH]c5ccccc5c4C[C@@H](C)N3C34CC(CO)(C3)C4)cc2)C1] |
| 53 | 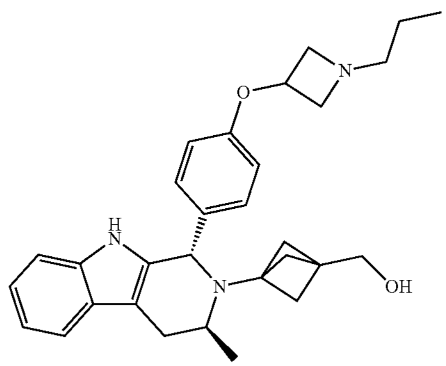 [SMILES: CCCN1CC(Oc2ccc([C@H]3c4[nH]c5ccccc5c4C[C@H](C)N3C34CC(CO)(C3)C4)cc2)C1] |
| 54 | 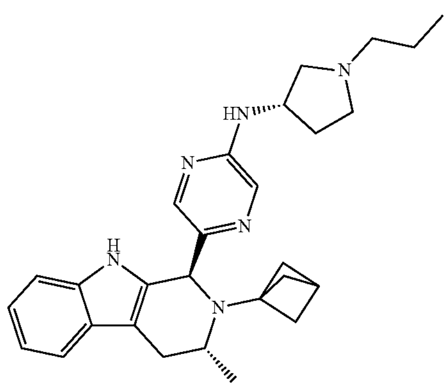 [SMILES: CCCN1CC[C@H](Nc2cnc([C@@H]3c4[nH]c5ccccc5c4C[C@@H](C)N3C34CC(C3)C4)cn2)C1] |
| 55 | 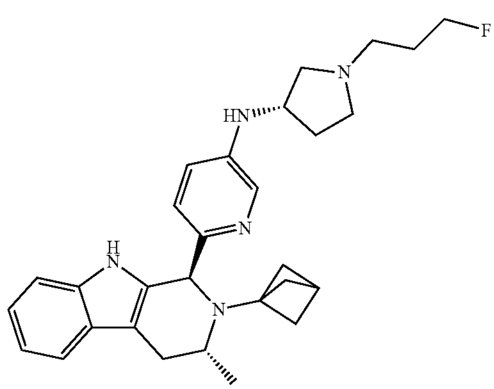 [SMILES: C[C@@H]1Cc2c([nH]c3ccccc23)[C@@H](c2ccc(N[C@H]3CCN(CCCF)C3)cn2)N1C12CC(C1)C2] |

| No. | Compound Structure |
|---|---|
| 56 | |
| 57 | |
| 58 | |
| 59 | |

| No. | Compound Structure |
|---|---|
| 60 | 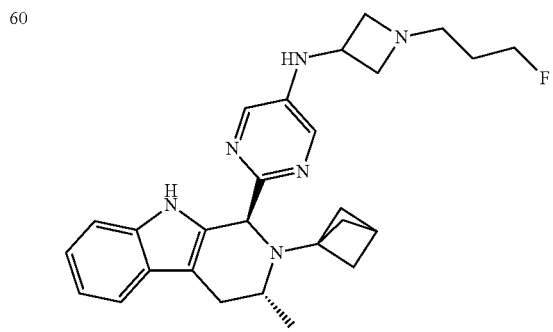 |
| 61 | 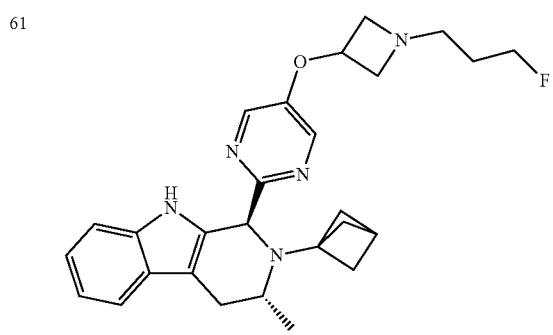 |
| 62 | 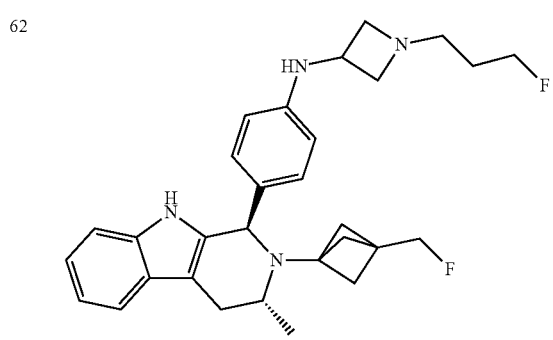 |
| 63 | 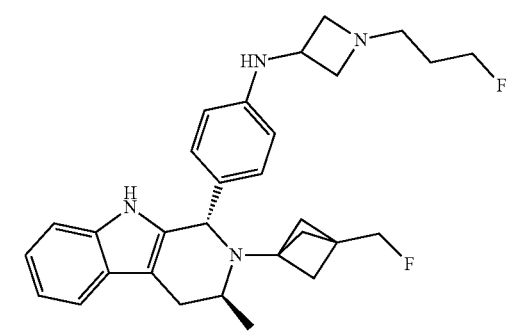 [SMILES: C[C@H]1Cc2c([nH]c3ccccc23)[C@H](c2ccc(NC3CN(CCCF)C3)cc2)N1C12CC(CF)(C1)C2] |
| No. | Compound Structure |
|---|---|
| 64 | 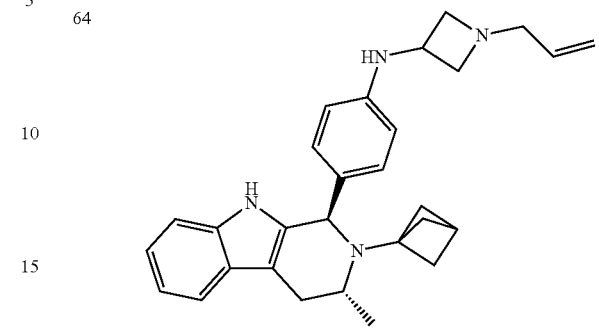 |
| 65 | 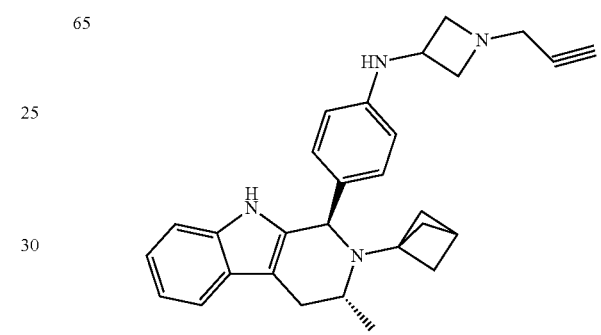 |
| 66 | 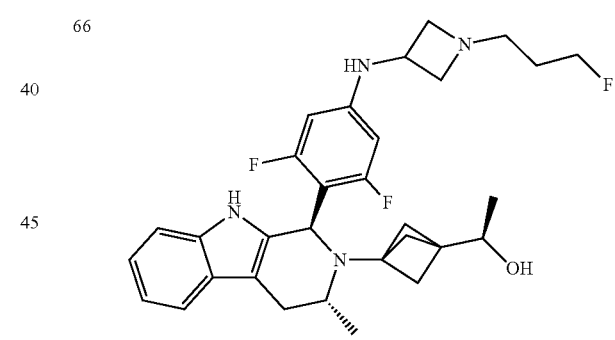 |
| 67 | 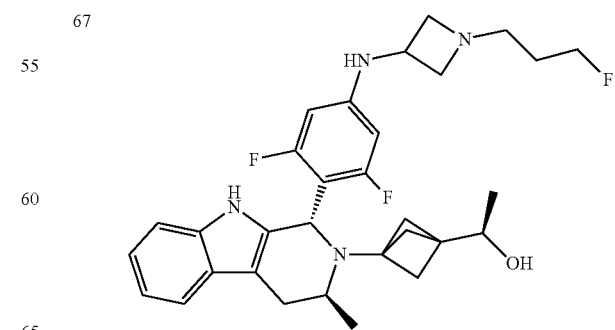 |

-continued
| No. | Compound Structure |
|---|---|
| 68 | 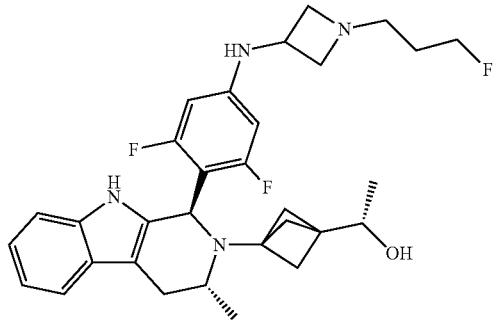 [SMILES: C[C@@H]1Cc2c([nH]c3ccccc23)[C@@H](c2c(F)cc(NC3CN(CCCF)C3)cc2F)N1C12CC([C@H](C)O)(C1)C2] |
| 69 | 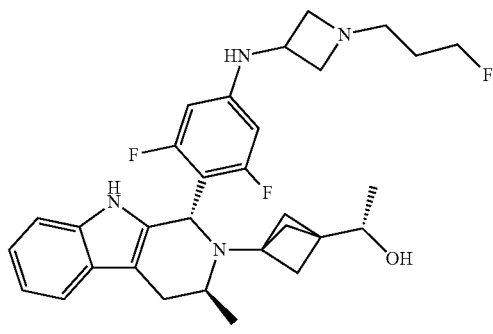 [SMILES: C[C@H](O)C12CC(N3[C@@H](c4c(F)cc(NC5CN(CCCF)C5)cc4F)c4[nH]c5ccccc5c4C[C@@H]3C)(C1)C2] |
| 70 | 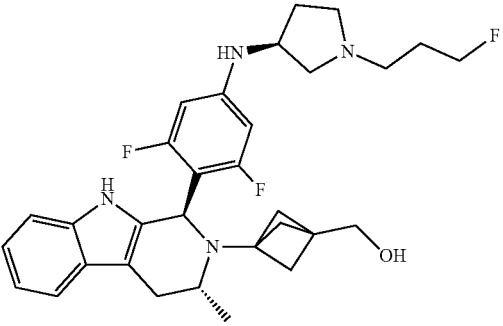 [SMILES: C[C@@H]1Cc2c([nH]c3ccccc23)[C@@H](c2c(F)cc(N[C@H]3CCN(CCCF)C3)cc2F)N1C12CC(CO)(C1)C2] |
| 71 | 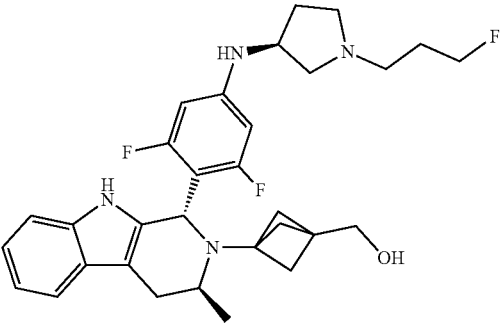 [SMILES: C[C@H]1Cc2c([nH]c3ccccc23)[C@H](c2c(F)cc(N[C@H]3CCN(CCCF)C3)cc2F)N1C12CC(CO)(C1)C2] |
-continued
| No. | Compound Structure |
|---|---|
| 72 | 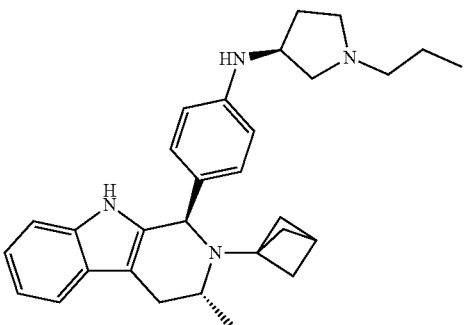 |
| 73 | 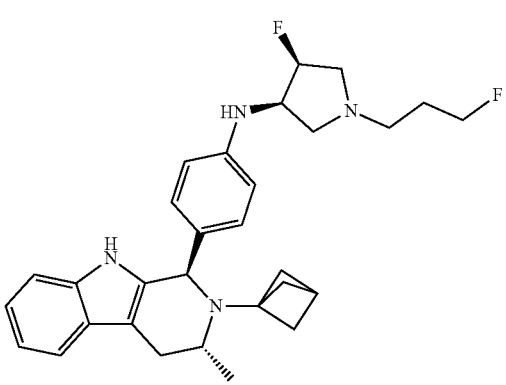 [SMILES: C[C@@H]1Cc2c([nH]c3ccccc23)[C@@H](c2ccc(N[C@@H]3CN(CCCF)C[C@@H]3F)cc2)N1C12CC(C1)C2] |
| 74 | 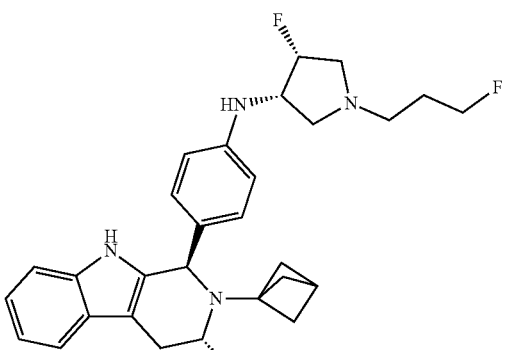 |
| 75 | 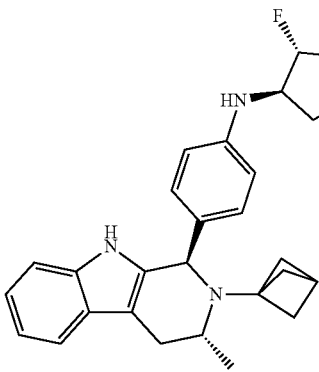 |

| No. | Compound Structure |
|---|---|
| 76 | 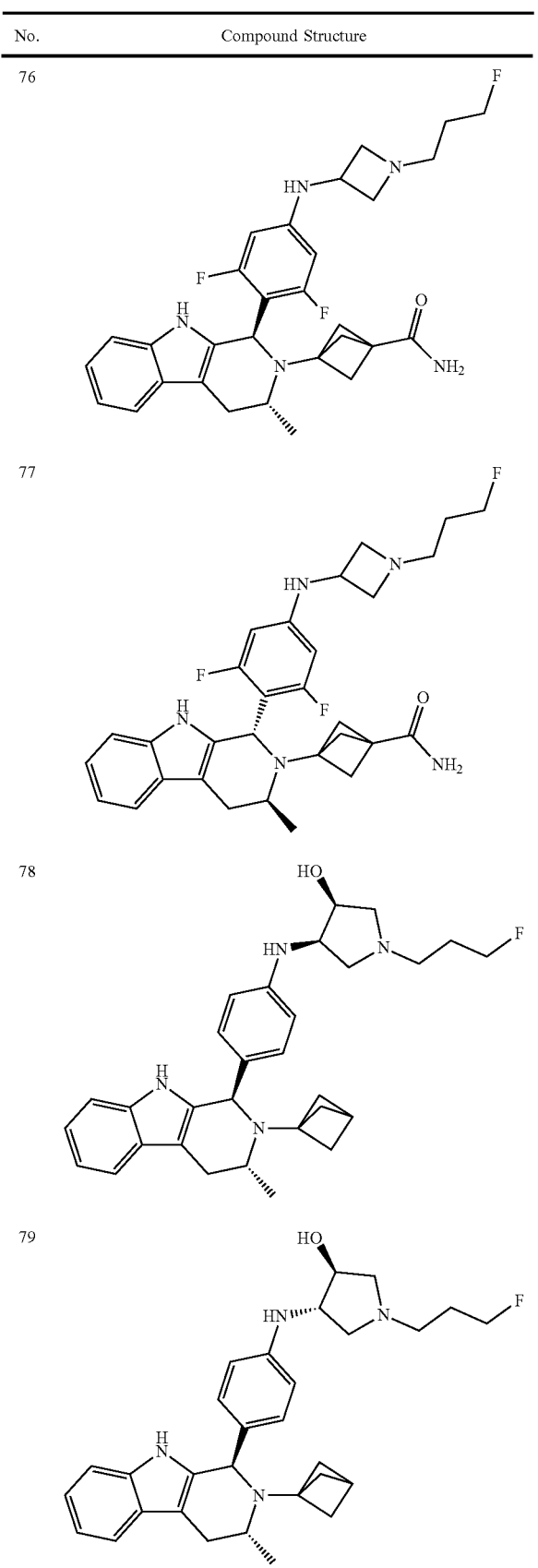 |
| 77 | |
| 78 | |
| 79 | |
| No. | Compound Structure |
|---|---|
| 80 | 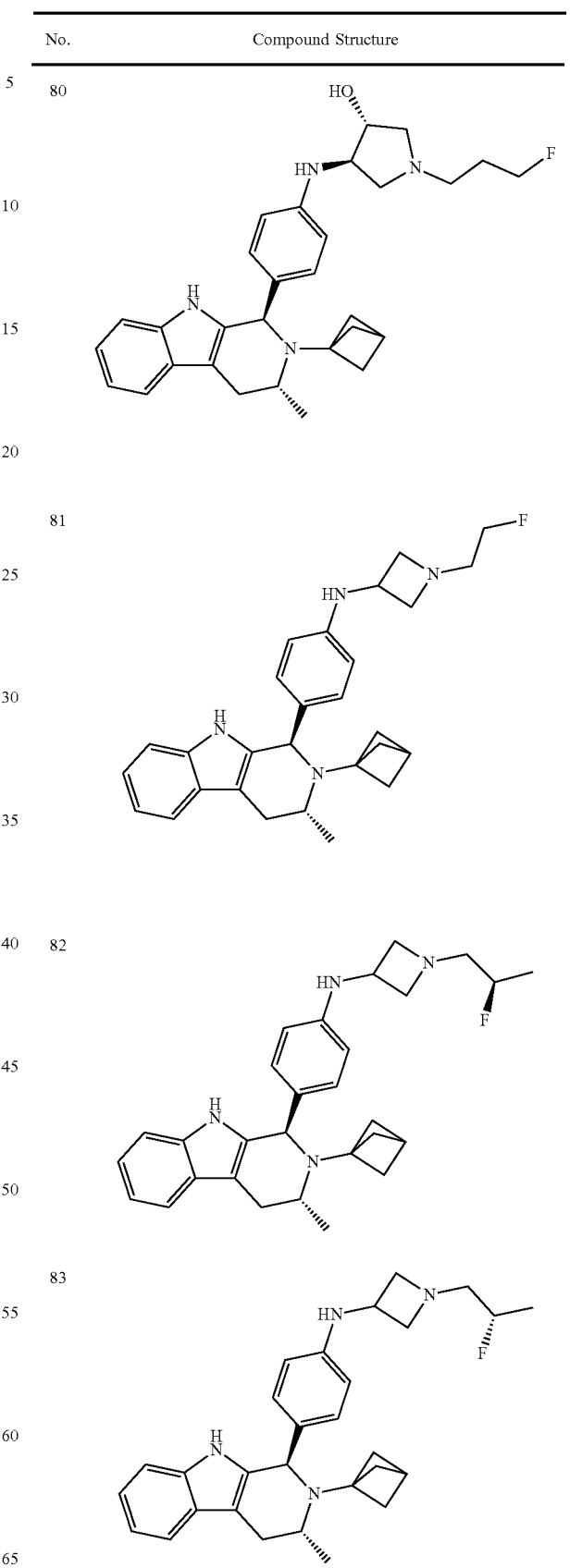 |
| 81 | |
| 82 | |
| 83 | |

-continued

| No. | Compound Structure |
|---|---|
| 84 | 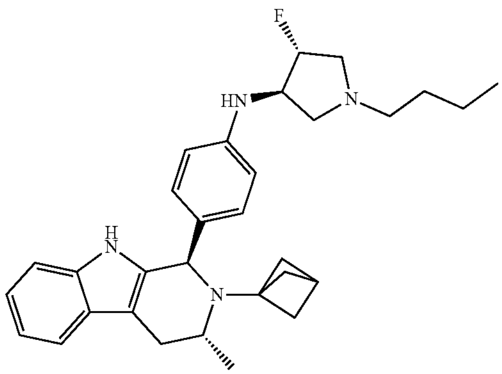 [SMILES: CCCCN1C[C@@H](F)[C@H](Nc2ccc([C@@H]3c4[nH]c5ccccc5c4C[C@@H](C)N3C34CC(C3)C4)cc2)C1] |
| 85 | 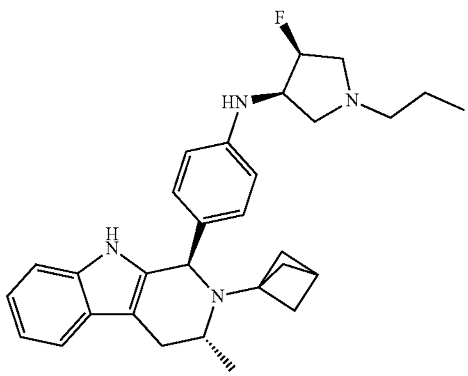 [SMILES: CCCN1C[C@H](F)[C@H](Nc2ccc([C@@H]3c4[nH]c5ccccc5c4C[C@@H](C)N3C34CC(C3)C4)cc2)C1] |
| 86 | 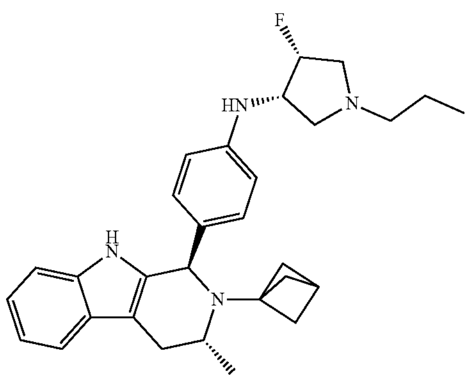 [SMILES: CCCN1C[C@@H](F)[C@@H](Nc2ccc([C@@H]3c4[nH]c5ccccc5c4C[C@@H](C)N3C34CC(C3)C4)cc2)C1] |
| 87 | 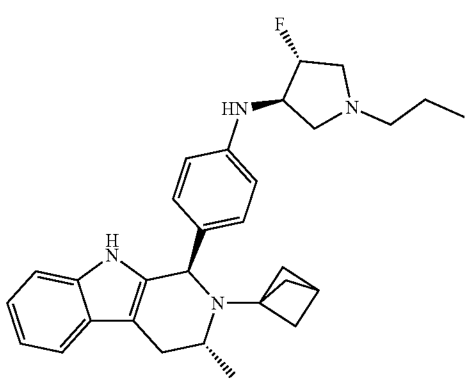 [SMILES: CCCN1C[C@@H](F)[C@H](Nc2ccc([C@@H]3c4[nH]c5ccccc5c4C[C@@H](C)N3C34CC(C3)C4)cc2)C1] |
| 88 | |
| 89 | |
| 90 | |
| 91 | |

| No. | Compound Structure |
|---|---|
| 92 | 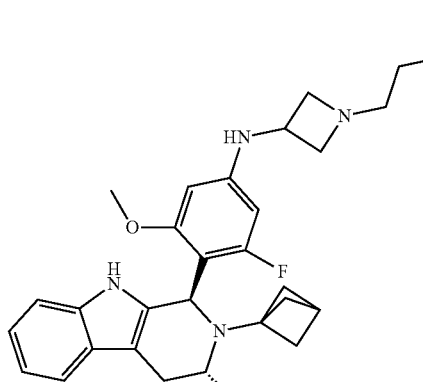 |
| 93 | |
| 94 | |
| No. | Compound Structure |
|---|---|
| 95 | |
| 96 | |
18. The method of claim 1, wherein the compound of Formula (I) has a structure selected from Compound Structure Nos. 1, 2, 6, 10, 15, 16, 18, 19, 20, 23, 31, 38, 39, 40, 42, 50, 52, 58, 70, 72, and 75 as set forth in the following table:
| No. | Compound Structure |
|---|---|
| 1 | 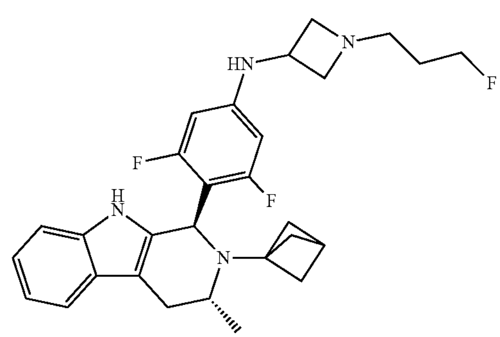 [SMILES: C[C@@H]1Cc2c([nH]c3ccccc23)[C@@H](c2c(F)cc(NC3CN(CCCF)C3)cc2F)N1C12CC(C1)C2] |

| No. | Compound Structure |
|---|---|
| 2 | 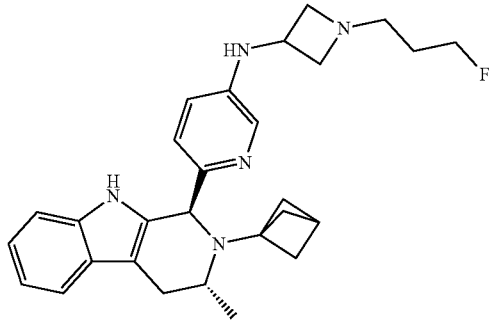 [SMILES: C[C@@H]1Cc2c([nH]c3ccccc23)[C@@H](c2ccc(NC3CN(CCCF)C3)cn2)N1C12CC(C1)C2] |
| 6 | 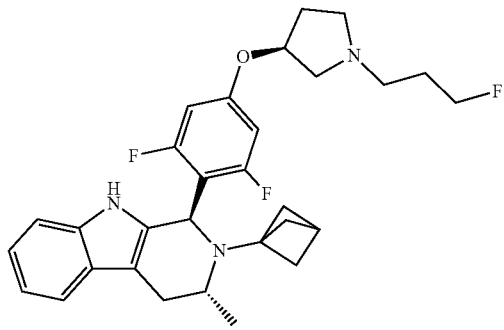 [SMILES: C[C@@H]1Cc2c([nH]c3ccccc23)[C@@H](c2c(F)cc(O[C@H]3CCN(CCCF)C3)cc2F)N1C12CC(C1)C2] |
| 10 | 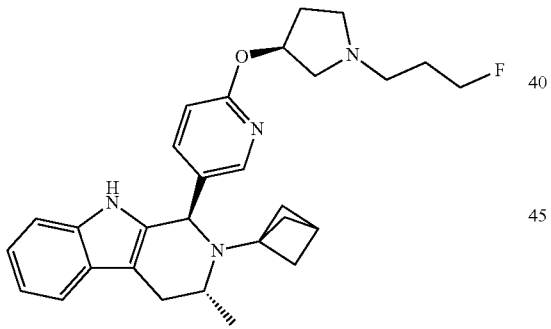 |
| 15 | 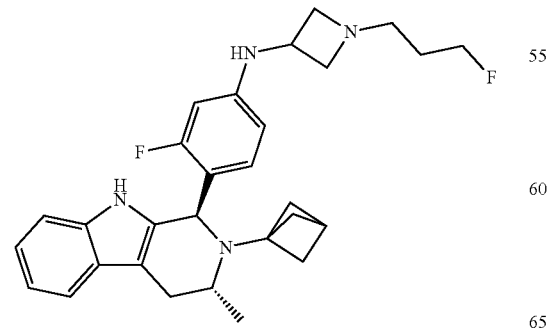 |
| No. | Compound Structure |
|---|---|
| 16 | 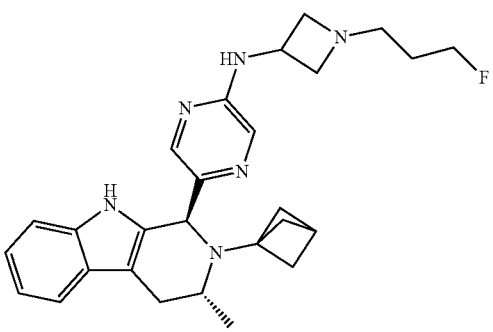 [SMILES: C[C@@H]1Cc2c([nH]c3ccccc23)[C@@H](c2cnc(NC3CN(CCCF)C3)cn2)N1C12CC(C1)C2] |
| 18 | 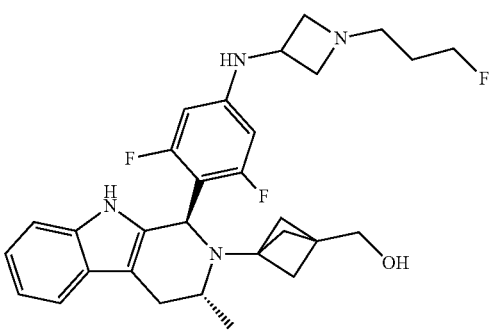 [SMILES: C[C@@H]1Cc2c([nH]c3ccccc23)[C@@H](c2c(F)cc(NC3CN(CCCF)C3)cc2F)N1C12CC(CO)(C1)C2] |
| 19 | 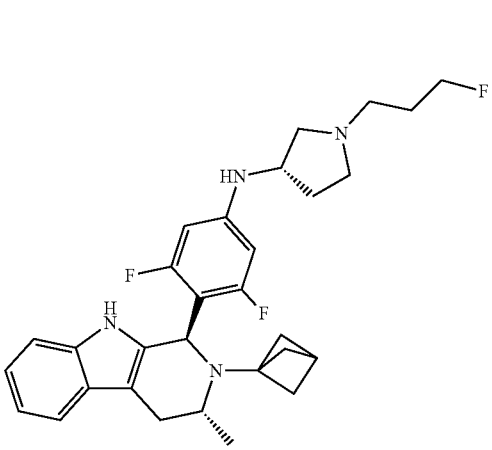 [SMILES: C[C@@H]1Cc2c([nH]c3ccccc23)[C@@H](c2c(F)cc(N[C@H]3CCN(CCCF)C3)cc2F)N1C12CC(C1)C2] |
| 20 | 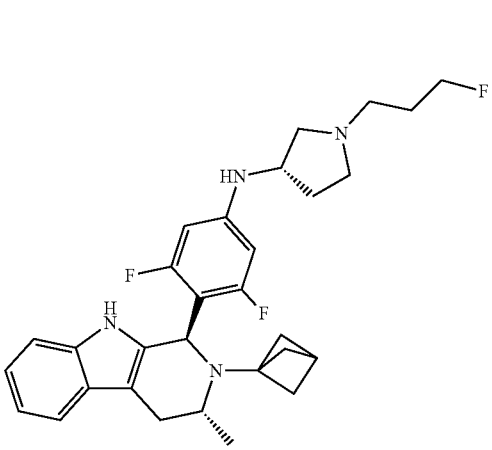 [SMILES: C[C@@H]1Cc2c([nH]c3ccccc23)[C@@H](c2c(F)cc(N[C@H]3CCN(CCCF)C3)cc2F)N1C12CC(C1)C2] |

-continued
| No. | Compound Structure |
|---|---|
| 23 | 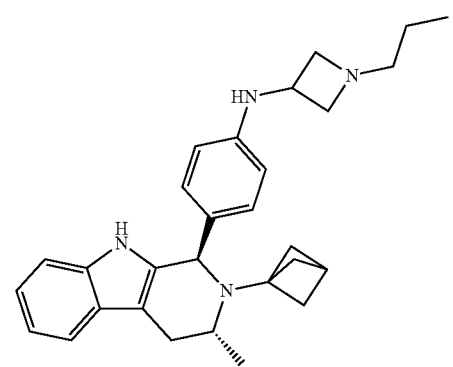 [SMILES: CCCN1CC(Nc2ccc([C@@H]3c4[nH]c5ccccc5c4C[C@@H](C)N3C34CC(C3)C4)cc2)C1] |
| 31 | 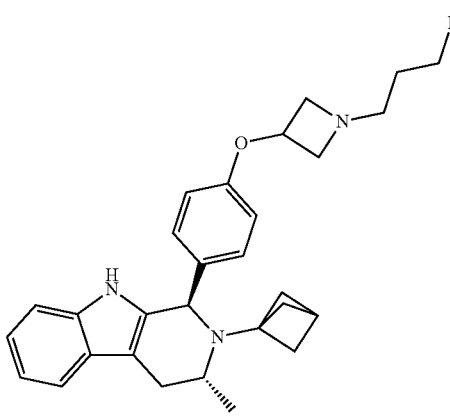 |
| 38 | 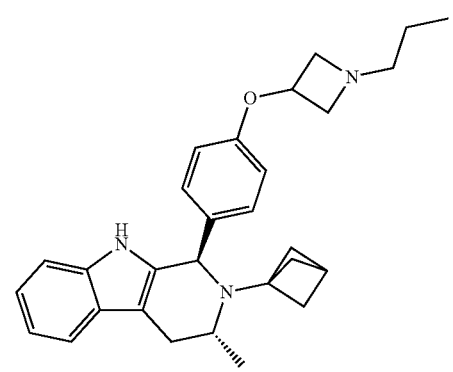 [SMILES: CCCN1CC(Oc2ccc([C@@H]3c4[nH]c5ccccc5c4C[C@@H](C)N3C34CC(C3)C4)cc2)C1] |
| 39 | (structure shown) |
-continued
| No. | Compound Structure |
|---|---|
| 40 | 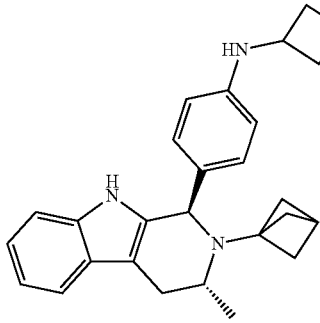 |
| 42 | 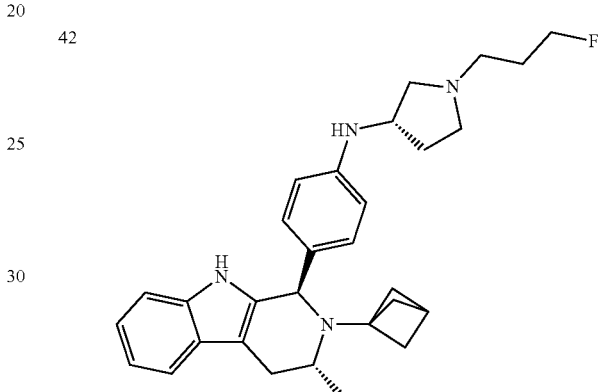 |
| 50 | 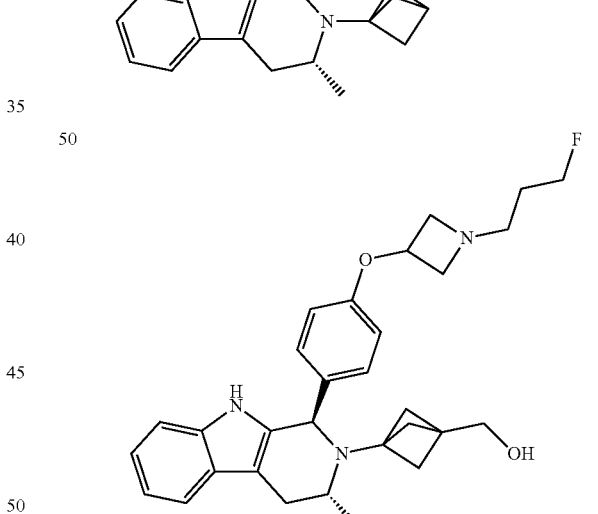 |
| 52 | (structure shown) |

-continued
| No. | Compound Structure |
|---|---|
| 58 | 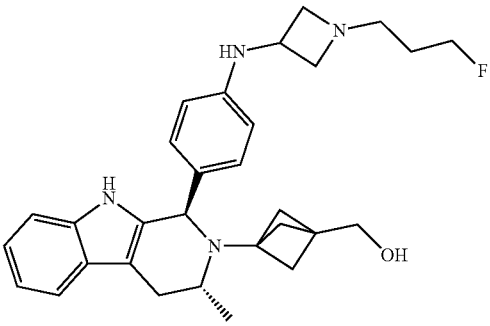 |
| 70 | 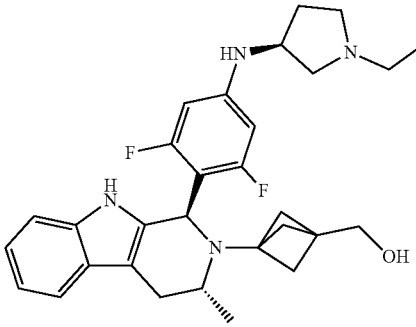 |
-continued
| No. | Compound Structure |
|---|---|
| 72 | 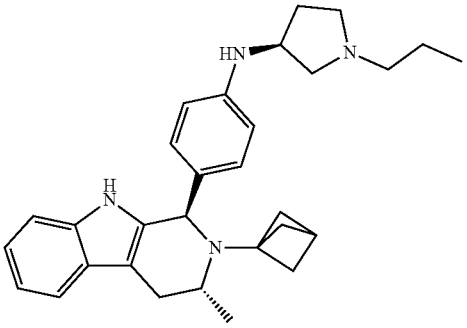 [SMILES: CCCN1CC[C@H](Nc2ccc([C@@H]3c4[nH]c5ccccc5c4C[C@@H](C)N3C34CC(C3)C4)cc2)C1] |
| 75 | 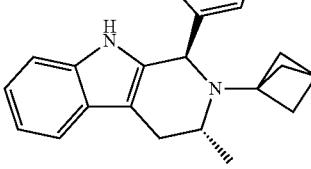 |
* * * * *